US012522658B2

(12) United States Patent
Ganesan et al.

(10) Patent No.: US 12,522,658 B2
(45) Date of Patent: Jan. 13, 2026

(54) ANTI-CD79 CHIMERIC ANTIGEN RECEPTORS, CAR-T CELLS, AND USES THEREOF

(71) Applicant: Janssen Biotech, Inc., Horsham, PA (US)

(72) Inventors: Rajkumar Ganesan, Blue Bell, PA (US); Elena Lasorsa, Antwerp (BE); Ulrike Philippar, Antwerp (BE)

(73) Assignee: Janssen Biotech, Inc., Horsham, PA (US)

( * ) Notice: Subject to any disclaimer, the term of this patent is extended or adjusted under 35 U.S.C. 154(b) by 651 days.

(21) Appl. No.: 16/950,296

(22) Filed: Nov. 17, 2020

(65) Prior Publication Data

US 2021/0145878 A1 May 20, 2021

Related U.S. Application Data

(60) Provisional application No. 62/936,662, filed on Nov. 18, 2019.

(51) Int. Cl.
*C07K 16/28* (2006.01)
*A61K 40/11* (2025.01)
*A61K 40/31* (2025.01)
*A61K 40/42* (2025.01)
*A61P 35/00* (2006.01)

(52) U.S. Cl.
CPC .......... *C07K 16/2815* (2013.01); *A61K 40/11* (2025.01); *A61K 40/31* (2025.01); *A61K 40/421* (2025.01); *A61P 35/00* (2018.01); *C07K 16/2809* (2013.01); *C07K 16/2878* (2013.01); *A61K 2239/31* (2023.05); *A61K 2239/38* (2023.05)

(58) Field of Classification Search
CPC ........................................................ A61K 37/17
See application file for complete search history.

(56) References Cited

U.S. PATENT DOCUMENTS

| | | | |
|---|---|---|---|
| 3,832,253 | A | 8/1974 | Di Palma |
| 3,854,480 | A | 12/1974 | Zaffaroni |
| 4,452,775 | A | 6/1984 | Kent |
| 4,667,014 | A | 5/1987 | Nestor, Jr. et al. |
| 4,748,034 | A | 5/1988 | de Rham |
| 5,075,109 | A | 12/1991 | Tice et al. |
| 5,225,539 | A | 7/1993 | Winter |
| 5,239,660 | A | 8/1993 | Ooi |
| 5,545,806 | A | 8/1996 | Lonberg et al. |
| 5,569,825 | A | 10/1996 | Lonberg et al. |
| 5,585,089 | A | 12/1996 | Queen et al. |
| 5,639,641 | A | 6/1997 | Pedersen et al. |
| 5,693,761 | A | 12/1997 | Queen et al. |
| 5,714,352 | A | 2/1998 | Jakobovits |
| 6,265,150 | B1 | 7/2001 | Terstappen et al. |
| 7,695,936 | B2 | 4/2010 | Carter et al. |
| 12,180,278 | B2 * | 12/2024 | Bednar ................ C07K 16/468 |
| 2002/0197266 | A1 | 12/2002 | Debinski |
| 2007/0004909 | A1 | 1/2007 | Johnson et al. |
| 2007/0287170 | A1 | 12/2007 | Davis et al. |
| 2009/0060910 | A1 | 3/2009 | Johnson et al. |
| 2009/0182127 | A1 | 7/2009 | Kjaergaard et al. |
| 2010/0015133 | A1 | 1/2010 | Igawa et al. |
| 2010/0286374 | A1 | 11/2010 | Kannan et al. |
| 2011/0123532 | A1 | 5/2011 | Gurney et al. |
| 2012/0149876 | A1 | 6/2012 | Von Kreudenstein et al. |
| 2016/0362472 | A1 | 12/2016 | Bitter et al. |
| 2018/0371081 | A1 | 12/2018 | Corbin et al. |
| 2019/0248902 | A1 | 8/2019 | Nioi et al. |
| 2021/0145878 | A1 | 5/2021 | Ganesan et al. |

FOREIGN PATENT DOCUMENTS

| | | | |
|---|---|---|---|
| CN | 109265565 A | | 1/2019 |
| EP | 0239400 B1 | | 8/1994 |
| GB | 2188638 B | | 4/1987 |
| WO | WO 2004/003144 A2 | | 1/2004 |
| WO | WO 2004/111233 A1 | | 12/2004 |
| WO | WO 2006/081139 A2 | | 8/2006 |
| WO | WO 2008/119353 A1 | | 10/2008 |
| WO | WO 2009/063970 A1 | | 5/2009 |
| WO | WO 2009/085462 A1 | | 7/2009 |
| WO | WO 2010/011860 A1 | | 1/2010 |
| WO | WO 2010/019656 A1 | | 2/2010 |
| WO | WO 2010/059543 A1 | | 5/2010 |
| WO | WO 2010/141249 A2 | | 12/2010 |
| WO | WO 2011/056997 A1 | | 5/2011 |
| WO | WO 2011/131746 A2 | | 10/2011 |
| WO | WO 2011/143545 A1 | | 11/2011 |
| WO | WO 2015/166105 A2 | | 11/2015 |
| WO | WO 2016/164937 A2 | | 10/2016 |
| WO | WO 2017/049038 A2 | | 3/2017 |
| WO | 2017/186928 A1 | | 11/2017 |
| WO | WO 2018/226958 A1 | | 12/2018 |

(Continued)

OTHER PUBLICATIONS

Ormhøj et al. (Clin. Cancer Res. Dec. 1, 2019; 25 (23): 7046-57; author manuscript; pp. 1-23).*
Gussow et al. (Methods in Enzymology. 1991; 203: 99-121).*
Rudikoff et al. (Proc. Natl. Acad. Sci. USA. 1982; 79 (6): 1979-1983).*
Winkler et al. (J. Immunol. Oct. 15, 2000; 165 (8): 4505-4514).*
Mariuzza et al. (Annu. Rev. Biophys. Biophys. Chem. 1987; 16: 139-159).*
Giusti et al. (Proc. Natl. Acad. Sci. USA. May 1987; 84 (9): 2926-30).*
Chien et al. (Proc. Natl. Acad. Sci. USA. Jul. 1989; 86 (14): 5532-5536).*
Caldas et al. (Mol. Immunol. May 2003; 39 (15): 941-952).*
Bridgeman et al. (J.Immunol. Jun. 15, 2010; 184 (12): 6938-49).*
Ma et al. (Prostate. Sep. 15, 2004; 61 (1): 12-25).*
Hudecek et al. (Clin. Cancer Res. Jun. 15, 2013; 19 (12): 3153-64).*

(Continued)

*Primary Examiner* — Peter J Reddig

(57) ABSTRACT

The present disclosure provides for chimeric antigen receptors (CARs) that specifically target a Cluster of Differentiation 79b protein (CD79b), and immunoresponsive cells comprising such CARs, for the treatment of cancer.

12 Claims, 69 Drawing Sheets

Specification includes a Sequence Listing.

(56) References Cited

FOREIGN PATENT DOCUMENTS

| | | | |
|---|---|---|---|
| WO | WO 2019/060695 | A1 | 3/2019 |
| WO | WO 2019/092451 | A1 | 5/2019 |
| WO | WO 2019/164891 | A1 | 8/2019 |
| WO | WO 2019/220109 | A1 | 11/2019 |
| WO | WO 2019/220110 | A1 | 11/2019 |
| WO | WO 2019/241688 | A1 | 12/2019 |
| WO | WO 2020/124021 | A1 | 6/2020 |
| WO | 2021/099944 | A1 | 5/2021 |

OTHER PUBLICATIONS

Long et al. (Nat. Med. Jun. 2015; 21 (6): 581-90).*
Künkele et al. (Cancer Immunol. Res. Apr. 2015; 3 (4): 368-79).*
Fujiwara et al. (Cells. May 9, 2020; 9 (5): 1182; pp. 1-17).*
Alfarano et al. (Blood. Apr. 1, 1999; 93 (7): 2327-35).*
Atwell et al. (Protein Eng. Jul. 1999; 12 (7): 597-604).*
Long et al. (J. Biol. Chem. Jun. 8, 2018; 293 (23): 9030-40).*
Lazar et al. (Molecular and Cellular Biology, 1988, 8: 1247-1252).*
Guo et al. (Proc. Natl. Acad. Sci. USA. Jun. 22, 2004; 101 (25): 9205-10).*
Knappik et al., (2000) J Mol Biol 296:57-86.
Shi et al., (2010) J Mol Biol 397:385-96.
Chan et al., *Fmoc Solid Phase Peptide Synthesis*, Oxford University Press, Oxford, United Kingdom, 2000.
Sambrook et al., *Molecular Cloning: A Laboratory Manual*, 3rd ed., Cold Spring Harbor Press, Cold Spring Harbor, N.Y. 2001.
Hudecz, F., *Methods Mol. Biol.* 298: 209-223 (2005).
Kirin et al., *Inorg Chem.* 44(15): 5405-5415 (2005)).
Köhler and Milstein, *Eur. J. Immunol.*, 5, 511-519 (1976).
C. A. Janeway et al. (eds.), *Immunobiology*, 5th Ed., Garland Publishing, New York, N.Y. (2001).
Haskard and Archer, J. *Immunol. Methods*, 74(2), 361-67 (1984).
Roder et al., *Methods Enzymol.*, 121, 140-67 (1986).
Huse et al., *Science*, 246, 127581 (1989).
Pedersen et al., J. Mol. Biol., 235, 959-973 (1994).
Wu and Kabat, J Exp Med 132:211-50, 1970.
Chothia and Lesk, Mol Biol 196:901-17, 1987.
Lefranc et al., Dev Comparat Immunol 27:55-77, 2003.
Houston et al., 1988, *Proc. Natl. Acad. Sci. USA* 85:5879-5883.
Bird et al., 1988, *Science* 242:423-426.
Rosenberg et al., *New Eng. J. of Med.* 319:1676, 1988.
Kochenderfer, J.N. et al. Chemotherapy-refractory diffuse large B-cell lymphoma and indolent B-cell malignancies can be effectively treated with autologous T cells expressing an anti-CD19 chimeric antigen receptor. *J Clin Oncol* 33, 540-549 (2015).
Schuster, S.J. et al. Chimeric Antigen Receptor T Cells in Refractory B-Cell Lymphomas. *N Engl J Med* 377, 2545-2554 (2017).
Shalabi, H. et al. Sequential loss of tumor surface antigens following chimeric antigen receptor T-cell therapies in diffuse large B-cell lymphoma. *Haematologica* 103, e215-e218 (2018).
Sotillo, E. et al. Convergence of Acquired Mutations and Alternative Splicing of CD19 Enables Resistance to CART-19 Immunotherapy. *Cancer Discov* 5, 1282-1295 (2015).
Packard, T.A. & Cambier, J.C. B lymphocyte antigen receptor signaling: initiation, amplification, and regulation. *F1000Prime Rep* 5, 40 (2013).
Puri, K.D., Di Paolo, J.A. & Gold, M.R. B-cell receptor signaling inhibitors for treatment of autoimmune inflammatory diseases and B-cell malignancies. *Int Rev Immunol* 32, 397-427 (2013).
Polson, A.G. et al. Antibody-drug conjugates targeted to CD79 for the treatment of non-Hodgkin lymphoma. *Blood* 110, 616-623 (2007).
Palanca-Wessels, M.C.A. et al. Safety and activity of the anti-CD79B antibody-drug conjugate polatuzumab vedotin in relapsed or refractory B-cell non-Hodgkin lymphoma and chronic lymphocytic leukaemia: a phase 1 study. *The Lancet Oncology* 16, 704-715 (2015).
Astsaturov, I.A. et al. Differential expression of B29 (CD79b) and mb-1 (CD79a) proteins in acute lymphoblastic leukaemia. *Leukemia* 10, 769-773 (1996).
Written Opinion of the International Searching Authority, issued May 17, 2022, in related PCT Appl. No. IB2020/060826.
Jiang Dongpeng et al: "T cells redirected against Ig[beta] for the immunotherapy of B cell lymphoma", Blood Cancer Journal, Nature Publishing Group UK, London, vol. 34, No. 3, Oct. 17, 2019 (Oct. 17, 2019), pp. 821-830, XP037046034.
Database Geneseq [Online] Oct. 3, 2019 (Oct. 3, 2019), "Anti-ASGRI antibody VH region, Seq 28200.",XP002802590, retrieved from EBI accession No. GSP:BGR1 4297 Database accession No. BGR1 4297.
Database Geneseq [Online] Apr. 22, 2004 (Apr. 22, 2004), "Reg IV-specific single chain antibody fragment (scFv) #27.",XP002802591, retrieved from EBI accession No. GSP:AD158068 Database accession No. AD158068.
Database Geneseq [Online] Jul. 11, 2019 (Jul. 11, 2019), "Anti-CDI 37 single domain antibody VH chain (1.81) polypeptide SEQ: 324.",XP002802592, retrieved from EBI accession No. GSP:BGJ15O91 Database accession No. BGJ15O91.
Database Geneseq [Online] Apr. 1, 2010 (Apr. 1, 2010), "Human rearranged VKA1 7 protein sequence, SEQ ID 63.",XP002802593, retrieved from EBI accession No. GSP:AXV20924 Database accession No. AXV20924.
Database Geneseq [Online] Oct. 17, 2019 (Oct. 17, 2019), "Anti-BCM,4 antibody 320111 heavy chain variable region, SEQ 6.",XP002802594, retrieved from EBI accession No. GSP:BGR34255 Database accession No. BGR34255.
Database EMBL [Online] Feb. 4, 2016 (Feb. 4, 2016), "*Homo sapiens* (human) partial immunoglobulin heavy chain variable region ID-AMB38434; SV 1; linear; mRNA; STD; HUM; 367 BP.", XP002802595, retrieved from EBI accession No. EMBL:AMB38434.
Sarah F Andrews et al: "Immune history profoundly affects broadly protective B cell responses to influenza", Science Translational Medicine, vol. 7, No. 316,Dec. 2, 2015 (Dec. 2, 2015), pp. 1-14, XP055596886, DOI: 10.11 26/scitranslmed.aad0522.
Database Geneseq [Online] Dec. 1, 2016 (Dec. 1, 2016), "Human anti-IL-2 antibody VL sequence, SEQ ID 1 85.",XP002802596, retrieved from EBI accession No. GSP:BDH53338 Database accession No. BDH53338.
Database Geneseq [Online] Jun. 25, 2009 (Jun. 25, 2009), "Murine antiGPR49 mAb 2U2E-2 heavy chain variable region SEQ 24.",XP002802597, retrieved from EBI accession No. GSP:AWV20653 Database accession No. AWV20653.
Database Geneseq [Online] Oct. 5, 2006 (Oct. 5, 2006), "Human IL-1 beta mAb VL chain, SEQ ID No. 76.",XP002802598, retrieved from EBI accession No. GSP:AEJ44985 Database accession No. AEJ44985.
Database Geneseq [Online] Apr. 15, 2010 (Apr. 15, 2010), "Anti-RAGE antibody XT-M4 single chain (ScFv) fragment protein SEQ ID:5.",XP002802599,retrieved from EBI accession No. GSP:AXV64027 Database accession No. AXV64027.
Database Geneseq [Online] Aug. 5, 2010 (Aug. 5, 2010), "Human antiNotchl antibody light chain protein SEQ ID:91 7.",XP002802600, retrieved from EBI accession No. GSP:AYC40706 Database accession No. AYC40706.
Database Geneseq [Online] Feb. 21, 2019 (Feb. 21, 2019), "Anti-INSR mAb heavy chain variable region Clone XPA. 15.047, SEQ ID No. 180.",XP002802601 , retrieved from EBI accession No. GSP:BFY64437 Database accession No. BFY64437.
Database EMBL [Online] May 15, 2017 (May 15, 2017), "*Mus musculus* (house mouse) partial immunoglobulin kappa light chain variable region ID—AR078943; SV 1; linear; genomic DNA; STD; TGN; 238 BP." XP002802602, retrieved from EBI accession No. EMBL:AR078943.
Longo Nancy S. et al: "Mechanisms That Shape Human Antibody Repertoire Development in Mice Transgenic for Human Ig H and L Chain Loci", The Journal of Immunology, vol. 198, No. 10, Apr. 24, 2017 (Apr. 24, 2017), pp. 3963-3977, XP055792695.
Database EMBL [Online] Jun. 1, 2012 (Jun. 1, 2012), "*Homo sapiens* (human) partial immunoglobulin alpha heavy chain variable

(56) References Cited

OTHER PUBLICATIONS region ID—AEZ52222; SV 1; linear; mRNA; STD; HUM; 294 BP.",XP002802603, retrieved from EBI accession No. EMBL:AEZ52222.

Database Geneseq [Online] Feb. 17, 2011(Feb. 17, 2011), "Human anti-Notch3 antibody VH sequence, Seq ID 837.", XP002802604, retrieved from EBI accession No. GSP:AYM93881 Database accession No. AYM93881.

Database Geneseq [Online] Jul. 7, 2011(Jul. 7, 2011), "Exemplary variable heavy chain antibody SEQ ID:1 975.",XP002802605, retrieved from EBI accession No. GSP:AZ138804 Database accession No. AZ138804.

Database EMBL [Online] Apr. 20, 2007 (Apr. 20, 2007), "*Homo sapiens* (human) partial immunoglobulin lambda light chain variable region ID—ABP4821 9; SV 1; linear; genomic DNA; STD; HUM; 259 BP.", XP002802606, retrieved from EBI accession No. EMBL:ABP48219.

Richl P et al: "The lambda gene immunoglobulin repertoire of human neonatal B cells", Molecular Immunology, vol. 45, No. 2 , pp. 320-327, Jun. 8, 2007; XP028783262, ISSN: 0161-5890, DOI: 10.1016/ J.MOLIMM.2007.06.I 55.

Database Geneseq [Online] May 4, 2017 (May 4, 2017), "Anti-CD 1 15 mAb CCL-204A heavy chain variable region, SEQ 159.", XP002802607, retrieved from EBI accession No. GSP:BD562600 Database accession No. BD562600.

Database Geneseq [Online] Dec. 17, 2015 (Dec. 17, 2015), "Human anti-P2X4 antibody (292) light chain variable region, SEQ ID 479.", XP002802608, retrieved from EBI accession No. GSP:BCG82956 Database accession No. BCG82956.

Database EMBL [Online] Apr. 24, 2015 (Apr. 24, 2015), "*Homo sapiens* (human) partial immunoglobulin heavy chain variable region ID—CEF94269; SV 1; linear; genomic DNA; STD; HUM; 318 BP.", XP002802609, retrieved from EBI accession No. EMBL:CEF94269.

Hansen Tina Østergaard et al: "Sterile DJ H Rearrangements Reveal that Distance Between Gene Segments on the Human Ig H Chain Locus Influences Their Ability to Rearrange", The Journal of Immunology, vol. 194, No. 3, Jan. 2, 2015 (Jan. 2, 2015), pp. 973-982, XP055792811.

D. Dornan et al: "Therapeutic potential of an anti-CD79b antibody-drug conjugate, anti-CD79b-vc-MMAE, for the treatment of non-Hodgkin lymphoma", Blood, vol. 114, No. 13, Sep. 24, 2009 (Sep. 24, 2009), pp. 2721-2729, XP055075268, ISSN: 0006-4971, DOI: 10.1182/ blood-2009-02-205500.

Dornan David et al: "Supplementary Figure 1 to: Therapeutic potential of an anti-CD79b antibody-drug conjugate, anti-CD79b-vc-MMAE, for the treatment of non-Hodgkin lymphoma", Blood, Sep. 24, 2009 (Sep. 24, 2009), XP055793085, Retrieved from the Internet: U RL:https://ash.silverchair-cdn .com/ash/content_public/journal/blood! 114/13/10.11 82_blood-2009-02-205500/4/zh2721 -sup-figuresi .jpeg? Expires=1 620101985&Signature= YH59hV55aeEwEmqhylpwjqRZoVxfClw 81 jkOz361-y6ZPMHkfRBbllxa7OyLAWEhon6zEEagzH RYnXwzxh5j-bQi iSn REYoocibtuq RfFJ PrhS-X4BZwLmk4WYN DDu82U Lcx6tSbKjqz [retrieved on Apr. 7, 2021].

* cited by examiner

ANTI-CD79 CHIMERIC ANTIGEN RECEPTORS, CAR-T CELLS, AND USES THEREOF

CROSS-REFERENCE TO RELATED APPLICATIONS

This application claims priority to U.S. Provisional Application No. 62/936,662, filed Nov. 18, 2019, the disclosure of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Nov. 9, 2020, is named JBI6171USNP1_SL.txt and is 482,230 bytes in size.

TECHNICAL FIELD

The invention relates to CD79b-targeting chimeric antigen receptors (CARs) comprising CD79b-targeting single-chain variable fragments and engineered CD79b-targeting immune cells expressing the CARs. Also provided are nucleic acids and expression vectors encoding the CARs, recombinant cells containing the vectors, and compositions comprising the engineered immune cells expressing the CD79b-targeting CARs. Methods of making the CARs, and engineered immune cells, and methods of using the engineered immune cells to treat conditions including cancer are also provided.

BACKGROUND

T cell therapy utilizes isolated T cells that have been genetically modified to enhance their specificity for a specific tumor associated antigen. Genetic modification may involve the expression of a chimeric antigen receptor (CAR) or an exogenous T cell receptor to provide new antigen specificity onto the T cell. T cells expressing chimeric antigen receptors (CAR-T cells) can induce tumor immunoreactivity. There is a need for better cancer therapies utilizing CAR-T cells.

Non-Hodgkin lymphoma (NHL) accounts for about 4% of all cancers. Despite improvements in available therapies, relapsed/refractory (r/r) NHLs are characterized by a uniformly poor prognosis. Adoptive immunotherapy using T cells genetically engineered to express a chimeric antigen receptor (CAR), has shown promising results for the treatment of CD19-positive B cell malignancies However, even with an initial overall response rate of approximately 60-80%, only 40% of patients achieve long-term complete remission [1, 2]. Clinical data reporting disease relapse due to CD19 antigen loss in both acute lymphoblastic leukemia (ALL) and diffuse large B-cell lymphoma (DLBCL) patients are now emerging, highlighting an unmet clinical need for targeting novel surface antigens [2, 4].

B cells (B lymphocytes) are central components of the adaptive immunity, responding to several different pathogens by producing antibodies, performing the role of antigen-presenting cells, secreting cytokines, and developing into memory B cells after activation [5]. B cells circulate in the blood and lymphatic systems. In the lymphoid organs they encounter its cognate antigen, and together with an additional signal from a T helper cell, it can differentiate into effector plasma cells. These cells secrete specific antibodies that will circulate in the blood to target and eliminate antigens or pathogens [6].

To detect the antigen or pathogen, B cells have B cell receptors (BCRs) on the cell surface, which is a multicomponent receptor composed of a transmembrane immunoglobulin molecule (mIg) and a disulfide linked heterodimer of CD79a (Igα) and CD79b (Igθ). CD79b is highly expressed in a wide range of B-cell lymphomas. Its expression has been shown to be critical for cancer cell viability of most DLBCL tumor models. Therefore, the development of resistance to CD79b targeted agents through antigen loss may be less likely, making it an attractive target for the development of novel immunotherapeutic approaches. In the clinic, Polatuzumab (Polivy™), an antibody-drug conjugate (ADC) molecule targeting CD79b, has recently been approved for the treatment of r/r DLBCL[7]. Polatuzumab treatments results in an increase in complete response (CR) and duration of response (DOR) rates when combined with standard of care treatments (bendamustine and Rituximab), validating CD79b as a valuable clinical target [8].

Accordingly, there is a need for developing CD79b-targeting CAR-T therapy.

SUMMARY

Disclosed herein are chimeric antigen receptors (CARs), e.g., CARs that target a Cluster of Differentiation 79B protein (CD79b), cells comprising the CARs, vectors encoding the CARs, e.g., recombinant expression vectors, and nucleic acid molecules encoding the CARs, methods of making the CARs, compositions, polypeptides, proteins, nucleic acids, host cells, populations of cells and methods of treating disorders, e.g., cancer, using the disclosed CARs.

In one aspect is provided a chimeric antigen receptor (CAR) comprising:

(a) an extracellular domain comprising an scFv that specifically binds to the Cluster of Differentiation 79B protein (CD79b) antigen, (b) a transmembrane domain, and (c) an intracellular signaling domain optionally comprising at least one co-stimulatory domain.

In some embodiments, the CAR further comprises (d) a CD8a-hinge region, wherein the transmembrane domain comprises a CD8a transmembrane region (CD8a-TM) polypeptide; and wherein the intracellular signaling domain comprises a co-stimulatory domain comprising a TNF receptor superfamily member 9 (CD137) component and a primary signaling domain comprising a T-cell surface glycoprotein CD3 zeta chain (CD3z) component.

In some embodiments, the CD8a-hinge region comprises an amino acid sequence that is at least 90% identical to SEQ ID NO: 38;

the transmembrane domain comprises an amino acid sequence that is at least 90% identical to SEQ ID NO: 39; and/or the intracellular signaling domain comprises a co-stimulatory domain having an amino acid sequence that is at least 90% identical to SEQ ID NO: 40, and a primary signaling domain having an amino acid sequence that is at least 90% identical to SEQ ID NO: 41.

In another aspect is provided a chimeric antigen receptor (CAR) comprising an extracellular antigen-binding domain, a transmembrane domain and an intracellular signaling domain, where the extracellular antigen-binding domain comprises:

a heavy chain complementarity determining region 1 (CDR1) having the amino acid sequence of SEQ ID NO: 208, a heavy chain CDR2 having the amino acid sequence of SEQ ID NO: 209, and a heavy chain CDR3 having the amino acid sequence of SEQ ID NO: 210;

a heavy chain CDR1 having the amino acid sequence of SEQ ID NO: 216, a heavy chain CDR2 having the amino acid sequence of SEQ ID NO: 217, and a heavy chain CDR3 having the amino acid sequence of SEQ ID NO: 218;

a heavy chain CDR1 having the amino acid sequence of SEQ ID NO: 222, a heavy chain CDR2 having the amino acid sequence of SEQ ID NO: 223, and a heavy chain CDR3 having the amino acid sequence of SEQ ID NO: 224;

a heavy chain CDR1 having the amino acid sequence of SEQ ID NO: 228, a heavy chain CDR2 having the amino acid sequence of SEQ ID NO: 217, and a heavy chain CDR3 having the amino acid sequence of SEQ ID NO: 229;

a heavy chain CDR1 having the amino acid sequence of SEQ ID NO: 232, a heavy chain CDR2 having the amino acid sequence of SEQ ID NO: 233, and a heavy chain CDR3 having the amino acid sequence of SEQ ID NO: 234;

a heavy chain CDR1 having the amino acid sequence of SEQ ID NO: 238, a heavy chain CDR2 having the amino acid sequence of SEQ ID NO: 239, and a heavy chain CDR3 having the amino acid sequence of SEQ ID NO: 240;

a heavy chain CDR1 having the amino acid sequence of SEQ ID NO: 242, a heavy chain CDR2 having the amino acid sequence of SEQ ID NO: 243, and a heavy chain CDR3 having the amino acid sequence of SEQ ID NO: 244;

a heavy chain CDR1 having the amino acid sequence of SEQ ID NO: 248, a heavy chain CDR2 having the amino acid sequence of SEQ ID NO: 249, and a heavy chain CDR3 having the amino acid sequence of SEQ ID NO: 250;

a heavy chain CDR1 having the amino acid sequence of SEQ ID NO: 253, a heavy chain CDR2 having the amino acid sequence of SEQ ID NO: 254, and a heavy chain CDR3 having the amino acid sequence of SEQ ID NO: 255;

a heavy chain CDR1 having the amino acid sequence of SEQ ID NO: 257, a heavy chain CDR2 having the amino acid sequence of SEQ ID NO: 258, and a heavy chain CDR3 having the amino acid sequence of SEQ ID NO: 259;

a heavy chain CDR1 having the amino acid sequence of SEQ ID NO: 263, a heavy chain CDR2 having the amino acid sequence of SEQ ID NO: 243, and a heavy chain CDR3 having the amino acid sequence of SEQ ID NO: 264;

a heavy chain CDR1 having the amino acid sequence of SEQ ID NO: 268, a heavy chain CDR2 having the amino acid sequence of SEQ ID NO: 269, and a heavy chain CDR3 having the amino acid sequence of SEQ ID NO: 270; or a heavy chain CDR1 having the amino acid sequence of SEQ ID NO: 274, a heavy chain CDR2 having the amino acid sequence of SEQ ID NO: 275, and a heavy chain CDR3 having the amino acid sequence of SEQ ID NO: 276;

where the extracellular antigen-binding domain binds the CD79b antigen.

In another aspect is provided a chimeric antigen receptor (CAR) comprising an extracellular antigen-binding domain, a transmembrane domain and an intracellular signaling domain, where the extracellular antigen-binding domain comprises:

a light chain CDR1 having the amino acid sequence of SEQ ID NO: 211, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 214, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 215, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 219, a light chain CDR2 having the amino acid sequence of SEQ ID NO: 220, and a light chain CDR3 having the amino acid sequence of SEQ ID NO: 221;

a light chain CDR1 having the amino acid sequence of SEQ ID NO: 225, a light chain CDR2 having the amino acid sequence of SEQ ID NO: 226, and a light chain CDR3 having the amino acid sequence of SEQ ID NO: 227;

a light chain CDR1 having the amino acid sequence of SEQ ID NO: 230, a light chain CDR2 having the amino acid sequence of SEQ ID NO: 231, and a light chain CDR3 having the amino acid sequence of SEQ ID NO: 221;

a light chain CDR1 having the amino acid sequence of SEQ ID NO: 235, a light chain CDR2 having the amino acid sequence of SEQ ID NO: 236, and a light chain CDR3 having the amino acid sequence of SEQ ID NO: 237;

a light chain CDR1 having the amino acid sequence of SEQ ID NO: 241, a light chain CDR2 having the amino acid sequence of SEQ ID NO: 226, and a light chain CDR3 having the amino acid sequence of SEQ ID NO: 227;

a light chain CDR1 having the amino acid sequence of SEQ ID NO: 245, a light chain CDR2 having the amino acid sequence of SEQ ID NO: 246, and a light chain CDR3 having the amino acid sequence of SEQ ID NO: 247;

a light chain CDR1 having the amino acid sequence of SEQ ID NO: 251, a light chain CDR2 having the amino acid sequence of SEQ ID NO: 236, and a light chain CDR3 having the amino acid sequence of SEQ ID NO: 252;

a light chain CDR1 having the amino acid sequence of SEQ ID NO: 251, a light chain CDR2 having the amino acid sequence of SEQ ID NO: 236, and a light chain CDR3 having the amino acid sequence of SEQ ID NO: 256;

a light chain CDR1 having the amino acid sequence of SEQ ID NO: 260, a light chain CDR2 having the amino acid sequence of SEQ ID NO: 261, and a light chain CDR3 having the amino acid sequence of SEQ ID NO: 262;

a light chain CDR1 having the amino acid sequence of SEQ ID NO: 265, a light chain CDR2 having the amino acid sequence of SEQ ID NO: 266, and a light chain CDR3 having the amino acid sequence of SEQ ID NO: 267;

a light chain CDR1 having the amino acid sequence of SEQ ID NO: 271, a light chain CDR2 having the amino acid sequence of SEQ ID NO: 272, and a light chain CDR3 having the amino acid sequence of SEQ ID NO: 273; or a light chain CDR1 having the amino acid sequence of SEQ ID NO: 277, a light chain CDR2 having the amino acid sequence of SEQ ID NO: 266, and a light chain CDR3 having the amino acid sequence of SEQ ID NO: 278;

where the extracellular antigen-binding domain binds the CD79b antigen.

In some embodiments, the extracellular antigen-binding domain further comprises: a light chain CDR1 having the amino acid sequence of SEQ ID NO: 211, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 214, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 215, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 219, a light chain CDR2 having the amino acid sequence of SEQ ID NO: 220, and a light chain CDR3 having the amino acid sequence of SEQ ID NO: 221;

a light chain CDR1 having the amino acid sequence of SEQ ID NO: 225, a light chain CDR2 having the amino acid sequence of SEQ ID NO: 226, and a light chain CDR3 having the amino acid sequence of SEQ ID NO: 227;

a light chain CDR1 having the amino acid sequence of SEQ ID NO: 230, a light chain CDR2 having the amino acid sequence of SEQ ID NO: 231, and a light chain CDR3 having the amino acid sequence of SEQ ID NO: 221;

a light chain CDR1 having the amino acid sequence of SEQ ID NO: 235, a light chain CDR2 having the amino acid sequence of SEQ ID NO: 236, and a light chain CDR3 having the amino acid sequence of SEQ ID NO: 237;

a light chain CDR1 having the amino acid sequence of SEQ ID NO: 241, a light chain CDR2 having the amino acid sequence of SEQ ID NO: 226, and a light chain CDR3 having the amino acid sequence of SEQ ID NO: 227;

a light chain CDR1 having the amino acid sequence of SEQ ID NO: 245, a light chain CDR2 having the amino acid sequence of SEQ ID NO: 246, and a light chain CDR3 having the amino acid sequence of SEQ ID NO: 247;

a light chain CDR1 having the amino acid sequence of SEQ ID NO: 251, a light chain CDR2 having the amino acid sequence of SEQ ID NO: 236, and a light chain CDR3 having the amino acid sequence of SEQ ID NO: 252;

a light chain CDR1 having the amino acid sequence of SEQ ID NO: 251, a light chain CDR2 having the amino acid sequence of SEQ ID NO: 236, and a light chain CDR3 having the amino acid sequence of SEQ ID NO: 256;

a light chain CDR1 having the amino acid sequence of SEQ ID NO: 260, a light chain CDR2 having the amino acid sequence of SEQ ID NO: 261, and a light chain CDR3 having the amino acid sequence of SEQ ID NO: 262;

a light chain CDR1 having the amino acid sequence of SEQ ID NO: 265, a light chain CDR2 having the amino acid sequence of SEQ ID NO: 266, and a light chain CDR3 having the amino acid sequence of SEQ ID NO: 267;

a light chain CDR1 having the amino acid sequence of SEQ ID NO: 271, a light chain CDR2 having the amino acid sequence of SEQ ID NO: 272, and a light chain CDR3 having the amino acid sequence of SEQ ID NO: 273; or a light chain CDR1 having the amino acid sequence of SEQ ID NO: 277, a light chain CDR2 having the amino acid sequence of SEQ ID NO: 266, and a light chain CDR3 having the amino acid sequence of SEQ ID NO: 278. In another aspect is provided a chimeric antigen receptor (CAR), comprising an extracellular antigen-binding domain, a transmembrane domain and an intracellular signaling domain, wherein the extracellular antigen-binding domain comprises the heavy chain CDR1 having the amino acid sequence of SEQ ID NOs: 208, 216, 222, 228, 232, 238, 242, 248, 253, 257, 263, 268, or 274, the heavy chain CDR2 having the amino acid sequence of SEQ ID NOs: 209, 217, 223, 233, 239, 243, 249, 254, 258, 269, or 275, the heavy chain CDR3 having the amino acid sequence of SEQ ID NOs: 210, 218, 224, 229, 234, 240, 244, 250, 255, 259, 264, 270, or 276, the light chain CDR1 having the amino acid sequence of SEQ ID NOs: 211, 214, 215, 219, 225, 230, 235, 241, 245, 251, 260, 265, 271, or 277, the light chain CDR2 having the amino acid sequence of SEQ ID NOs: 212, 220, 226, 231, 236, 246, 261, 266, or 272, and the light chain CDR3 having the amino acid sequence of SEQ ID NOs: 213, 221, 227, 237, 247, 252, 256, 262, 267, 273, or 278.

In some embodiments, the extracellular antigen-binding domain comprises the heavy chain CDR1, the heavy chain CDR2, the heavy chain CDR3, the light chain CDR1, the light chain CDR2 and the light chain CDR3 having the amino acid sequence of a) SEQ ID NOs: 208, 209, 210, 211, 212, and 213, respectively;

b) SEQ ID NOs: 208, 209, 210, 214, 212, and 213, respectively;

c) SEQ ID NOs: 208, 209, 210, 215, 212, and 213, respectively;

d) SEQ ID NOs: 216, 217, 218, 219, 220, and 221, respectively;

e) SEQ ID NOs: 222, 223, 224, 225, 226, and 227, respectively;

f) SEQ ID NOs: 228, 217, 229, 230, 231, and 221, respectively;

g) SEQ ID NOs: 232, 233, 234, 235, 236, and 237, respectively;

h) SEQ ID NOs: 238, 239, 240, 241, 226, and 227, respectively;

i) SEQ ID NOs: 242, 243, 244, 245, 246, and 247, respectively;

j) SEQ ID NOs: 248, 249, 250, 251, 236, and 252, respectively;
k) SEQ ID NOs: 253, 254, 255, 251, 236, and 256, respectively;
l) SEQ ID NOs: 257, 258, 259, 260, 261, and 262, respectively;
m) SEQ ID NOs: 263, 243, 264, 265, 266, and 267, respectively;
n) SEQ ID NOs: 268, 269, 270, 271, 272, and 273, respectively; or
o) SEQ ID NOs: 274, 275, 276, 277, 266, and 278, respectively.

In some embodiments, the extracellular antigen-binding domain comprises:

a heavy chain variable region comprising an amino acid sequence that is at least 90% identical to SEQ ID NO: 1 and a light chain variable region comprising an amino acid sequence that is at least 90% identical to SEQ ID NO: 19;
a heavy chain variable region comprising an amino acid sequence that is at least 90% identical to SEQ ID NO: 1 and a light chain variable region comprising an amino acid sequence that is at least 90% identical to SEQ ID NO: 20;
a heavy chain variable region comprising an amino acid sequence that is at least 90% identical to SEQ ID NO: 2 and a light chain variable region comprising an amino acid sequence that is at least 90% identical to SEQ ID NO: 19;
a heavy chain variable region comprising an amino acid sequence that is at least 90% identical to SEQ ID NO: 2 and a light chain variable region comprising an amino acid sequence that is at least 90% identical to SEQ ID NO: 20;
a heavy chain variable region comprising an amino acid sequence that is at least 90% identical to SEQ ID NO: 3 and a light chain variable region comprising an amino acid sequence that is at least 90% identical to SEQ ID NO: 20;
a heavy chain variable region comprising an amino acid sequence that is at least 90% identical to SEQ ID NO: 4 and a light chain variable region comprising an amino acid sequence that is at least 90% identical to SEQ ID NO: 19;
a heavy chain variable region comprising an amino acid sequence that is at least 90% identical to SEQ ID NO: 5 and a light chain variable region comprising an amino acid sequence that is at least 90% identical to SEQ ID NO: 22;
a heavy chain variable region comprising an amino acid sequence that is at least 90% identical to SEQ ID NO: 5 and a light chain variable region comprising an amino acid sequence that is at least 90% identical to SEQ ID NO: 23;
a heavy chain variable region comprising an amino acid sequence that is at least 90% identical to SEQ ID NO: 6 and a light chain variable region comprising an amino acid sequence that is at least 90% identical to SEQ ID NO: 24;
a heavy chain variable region comprising an amino acid sequence that is at least 90% identical to SEQ ID NO: 7 and a light chain variable region comprising an amino acid sequence that is at least 90% identical to SEQ ID NO: 26;
a heavy chain variable region comprising an amino acid sequence that is at least 90% identical to SEQ ID NO: 8 and a light chain variable region comprising an amino acid sequence that is at least 90% identical to SEQ ID NO: 25;
a heavy chain variable region comprising an amino acid sequence that is at least 90% identical to SEQ ID NO: 9 and a light chain variable region comprising an amino acid sequence that is at least 90% identical to SEQ ID NO: 27;
a heavy chain variable region comprising an amino acid sequence that is at least 90% identical to SEQ ID NO: 10 and a light chain variable region comprising an amino acid sequence that is at least 90% identical to SEQ ID NO: 28;
a heavy chain variable region comprising an amino acid sequence that is at least 90% identical to SEQ ID NO: 11 and a light chain variable region comprising an amino acid sequence that is at least 90% identical to SEQ ID NO: 29;
a heavy chain variable region comprising an amino acid sequence that is at least 90% identical to SEQ ID NO: 12 and a light chain variable region comprising an amino acid sequence that is at least 90% identical to SEQ ID NO: 30;
a heavy chain variable region comprising an amino acid sequence that is at least 90% identical to SEQ ID NO: 13 and a light chain variable region comprising an amino acid sequence that is at least 90% identical to SEQ ID NO: 31;
a heavy chain variable region comprising an amino acid sequence that is at least 90% identical to SEQ ID NO: 14 and a light chain variable region comprising an amino acid sequence that is at least 90% identical to SEQ ID NO: 32;
a heavy chain variable region comprising an amino acid sequence that is at least 90% identical to SEQ ID NO: 15 and a light chain variable region comprising an amino acid sequence that is at least 90% identical to SEQ ID NO: 33;
a heavy chain variable region comprising an amino acid sequence that is at least 90% identical to SEQ ID NO: 16 and a light chain variable region comprising an amino acid sequence that is at least 90% identical to SEQ ID NO: 34;
a heavy chain variable region comprising an amino acid sequence that is at least 90% identical to SEQ ID NO: 16 and a light chain variable region comprising an amino acid sequence that is at least 90% identical to SEQ ID NO: 35;
a heavy chain variable region comprising an amino acid sequence that is at least 90% identical to SEQ ID NO: 17 and a light chain variable region comprising an amino acid sequence that is at least 90% identical to SEQ ID NO: 33; or
a heavy chain variable region comprising an amino acid sequence that is at least 90% identical to SEQ ID NO: 18 and a light chain variable region comprising an amino acid sequence that is at least 90% identical to SEQ ID NO: 36.

In some embodiments, the extracellular antigen-binding domain comprises:

a heavy chain variable region comprising an amino acid sequence of SEQ ID NO: 1 and a light chain variable region comprising an amino acid sequence of SEQ ID NO: 19;

a heavy chain variable region comprising an amino acid sequence of SEQ ID NO: 1 and a light chain variable region comprising an amino acid sequence of SEQ ID NO: 20;

a heavy chain variable region comprising an amino acid sequence of SEQ ID NO: 2 and a light chain variable region comprising an amino acid of SEQ ID NO: 19;

a heavy chain variable region comprising an amino acid sequence of SEQ ID NO: 2 and a light chain variable region comprising an amino acid sequence of SEQ ID NO: 20;

a heavy chain variable region comprising an amino acid sequence of SEQ ID NO: 3 and a light chain variable region comprising an amino acid sequence of SEQ ID NO: 20;

a heavy chain variable region comprising an amino acid sequence of SEQ ID NO: 4 and a light chain variable region comprising an amino acid sequence of SEQ ID NO: 19;

a heavy chain variable region comprising an amino acid sequence of SEQ ID NO: 5 and a light chain variable region comprising an amino acid sequence of SEQ ID NO: 22;

a heavy chain variable region comprising an amino acid sequence of SEQ ID NO: 5 and a light chain variable region comprising an amino acid sequence of SEQ ID NO: 23;

a heavy chain variable region comprising an amino acid sequence of SEQ ID NO: 6 and a light chain variable region comprising an amino acid sequence of SEQ ID NO: 24;

a heavy chain variable region comprising an amino acid sequence of SEQ ID NO: 7 and a light chain variable region comprising an amino acid sequence of SEQ ID NO: 26;

a heavy chain variable region comprising an amino acid sequence of SEQ ID NO: 8 and a light chain variable region comprising an amino acid sequence of SEQ ID NO: 25;

a heavy chain variable region comprising an amino acid sequence of SEQ ID NO: 9 and a light chain variable region comprising an amino acid sequence of SEQ ID NO: 27;

a heavy chain variable region comprising an amino acid sequence of SEQ ID NO: 10 and a light chain variable region comprising an amino acid sequence of SEQ ID NO: 28;

a heavy chain variable region comprising an amino acid sequence of SEQ ID NO: 11 and a light chain variable region comprising an amino acid sequence of SEQ ID NO: 29;

a heavy chain variable region comprising an amino acid sequence of SEQ ID NO: 12 and a light chain variable region comprising an amino acid sequence of SEQ ID NO: 30;

a heavy chain variable region comprising an amino acid sequence of SEQ ID NO: 13 and a light chain variable region comprising an amino acid sequence of SEQ ID NO: 31;

a heavy chain variable region comprising an amino acid sequence of SEQ ID NO: 14 and a light chain variable region comprising an amino acid sequence of SEQ ID NO: 32;

a heavy chain variable region comprising an amino acid sequence of SEQ ID NO: 15 and a light chain variable region comprising an amino acid sequence of SEQ ID NO: 33;

a heavy chain variable region comprising an amino acid sequence of SEQ ID NO: 16 and a light chain variable region comprising an amino acid sequence of SEQ ID NO: 34;

a heavy chain variable region comprising an amino acid sequence of SEQ ID NO: 16 and a light chain variable region comprising an amino acid sequence of SEQ ID NO: 35;

a heavy chain variable region comprising an amino acid sequence of SEQ ID NO: 17 and a light chain variable region comprising an amino acid sequence of SEQ ID NO: 33; or a heavy chain variable region comprising an amino acid sequence of SEQ ID NO: 18 and a light chain variable region comprising an amino acid sequence of SEQ ID NO: 36.

In some embodiments, the extracellular antigen-binding domain comprises:

a heavy chain variable region comprising an amino acid sequence that is at least 90% identical to SEQ ID NO: 14 and a light chain variable region comprising an amino acid sequence that is at least 90% identical to SEQ ID NO: 32.

In some embodiments, the extracellular antigen-binding domain comprises:

a heavy chain variable region comprising an amino acid sequence of SEQ ID NO: 14 and a light chain variable region comprising an amino acid sequence of SEQ ID NO: 32.

In some embodiments, the extracellular antigen-binding domain comprises a single-chain variable fragment (scFv). In some embodiments, the scFv comprises a linker polypeptide between the light chain variable region (VL) and the heavy chain variable region (VH). In some embodiments, the linker polypeptide comprises an amino acid sequence that is at least 90% identical to SEQ ID NO: 42. In some embodiments, the linker polypeptide comprises an amino acid sequence of SEQ ID NO: 42. In some embodiments, the scFv comprises an amino acid sequence that is at least 90% identical to a sequence selected from the group consisting of SEQ ID NOS: 75-118. In some embodiments, the scFv comprises an amino acid sequence that is selected from the group consisting of SEQ ID NOS: 75-118. In some embodiments, the extracellular antigen-binding domain comprises a signal polypeptide. In some embodiments, the signal polypeptide comprises an amino acid sequence that is at least 90% identical to SEQ ID NO: 37. In some embodiments, the signal polypeptide comprises an amino acid sequence of SEQ ID NO: 37.

In some embodiments, the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member component, and a combination thereof. In some embodiments, the CD137 component comprises an amino acid sequence that is at least 90% identical to SEQ ID NO: 40. In some embodiments, the CD137 component comprises an amino acid sequence of SEQ ID NO: 40. In some embodiments, the CD3z component comprises an amino acid sequence that is at least 90% identical to SEQ ID NO: 41. In some embodiments, the CD3z component comprises an amino acid sequence of SEQ ID NO: 41. In some embodiments, the intracellular signaling domain comprises an amino acid sequence that is at least 90% identical to SEQ ID NO: 163. In some embodiments, the intracellular signaling domain comprises an amino acid sequence of SEQ ID NO: 163. In some embodiments, the transmembrane domain comprises a CD8a transmembrane region (CD8a-TM) polypeptide. In some embodiments, the CD8a-TM polypeptide comprises an amino acid sequence that is at least 90% identical to SEQ ID NO: 39. In some embodiments, the CD8a-TM polypeptide comprises an amino acid sequence of SEQ ID NO: 39.

In various embodiments, the CAR further comprises a hinge region linking the transmembrane domain to the extracellular antigen-binding domain. In some embodiments, the hinge region is a CD8a-hinge region. In some embodiments, the CD8a-hinge region comprises an amino acid sequence that is at least 90% identical to SEQ ID NO: 38. In some embodiments, the CD8a-hinge region comprises an amino acid sequence of SEQ ID NO: 38.

In some embodiments, the extracellular antigen-binding domain comprises an amino acid sequence that is at least 90% identical to a sequence selected from the group consisting of SEQ ID NOS: 119-162. In some embodiments, the extracellular antigen-binding domain comprises an amino acid sequence selected from the group consisting of SEQ ID NOS: 119-162.

In some embodiments, the CAR comprises an amino acid sequence that is at least 90% identical to a sequence selected from the group consisting of SEQ ID NOS: 164-207. In some embodiments, the CAR comprises an amino acid sequence selected from the group consisting of SEQ ID NOS: 164-207.

In another aspect is provided a chimeric antigen receptor (CAR), comprising an extracellular antigen-binding domain, a transmembrane domain and an intracellular signaling domain, wherein the extracellular antigen-binding domain comprises:

a heavy chain complementarity determining region 1 (CDR1) having the amino acid sequence of SEQ ID NO: 257, a heavy chain CDR2 having the amino acid sequence of SEQ ID NO: 258, and a heavy chain CDR3 having the amino acid sequence of SEQ ID NO: 259.

In another aspect is provided a chimeric antigen receptor (CAR), comprising an extracellular antigen-binding domain, a transmembrane domain and an intracellular signaling domain, wherein the extracellular antigen-binding domain comprises:

a light chain CDR1 having the amino acid sequence of SEQ ID NO: 260, a light chain CDR2 having the amino acid sequence of SEQ ID NO: 261, and a light chain CDR3 having the amino acid sequence of SEQ ID NO: 262.

In some embodiments, the extracellular antigen-binding domain may comprise the heavy chain CDR1, the heavy chain CDR2, the heavy chain CDR3, the light chain CDR1, the light chain CDR2 and the light chain CDR3 having the amino acid sequence SEQ ID NOs: 257, 258, 259, 260, 261, 262, respectively.

In another aspect is provided a chimeric antigen receptor (CAR), comprising an extracellular antigen-binding domain, a transmembrane domain and an intracellular signaling domain, wherein the extracellular antigen-binding domain comprises:

a heavy chain variable region (VH) having the amino acid sequence that is at least 90% identical to SEQ ID NO: 14 and a light chain variable region (VL) having the amino acid sequence that is at least 90% identical to SEQ ID NO: 32, and wherein the extracellular antigen-binding domain binds the CD79b antigen.

In another aspect is provided a chimeric antigen receptor (CAR), comprising an extracellular antigen-binding domain, a transmembrane domain and an intracellular signaling domain, wherein the extracellular antigen-binding domain comprises:

a heavy chain variable region (VH) having the amino acid sequence of SEQ ID NO: 14 and a light chain variable region (VL) having the amino acid sequence of SEQ ID NO: 32, and wherein the extracellular antigen-binding domain binds the CD79b antigen.

In various embodiments, the extracellular antigen-binding domain comprises a single-chain variable fragment (scFv), the scFv comprising the heavy chain variable region (VH) and a light chain variable region (VL). The scFv may also comprise a linker polypeptide between the heavy chain variable region (VH) and the light chain variable region (VL). In certain embodiments, the linker polypeptide may comprise an amino acid sequence that is at least 90% identical to SEQ ID NO: 42. In certain embodiments, the linker polypeptide may comprise an amino acid sequence of SEQ ID NO: 42.

In certain embodiments, the scFv may comprise an amino acid sequence that is at least 90% identical to SEQ ID NO: 113. In certain embodiments, the scFv may comprise an amino acid sequence of SEQ ID NO: 113.

In some embodiments, the extracellular antigen-binding domain may comprise a signal polypeptide. In such embodiments, the signal polypeptide may comprise an amino acid sequence that is at least 90% identical to SEQ ID NO: 37. In such embodiments, the signal polypeptide may comprise an amino acid sequence of SEQ ID NO: 37.

In some embodiments, the intracellular signaling domain may comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member component, and a combination thereof. As a non-limiting example, the CD137 component may comprise an amino acid sequence that is at least 90% identical to SEQ ID NO: 40; the CD3z component may comprise an amino acid sequence that is at least 90% identical to SEQ ID NO: 41; and, the intracellular signaling domain may comprise an amino acid sequence that is at least 90% identical to SEQ ID NO: 163. As another non-limiting example, the CD137 component may comprise an amino acid sequence of SEQ ID NO: 40; the CD3z component may comprise an amino acid sequence of SEQ ID NO: 41; and, the intracellular signaling domain may comprise an amino acid sequence of SEQ ID NO: 163.

In certain embodiments, the intracellular signaling domain may comprise an amino acid sequence that is at least 90% identical to SEQ ID NO: 163. In certain embodiments, the intracellular signaling domain may comprise an amino acid sequence of SEQ ID NO: 163.

In some embodiments, the transmembrane domain may comprise a CD8a transmembrane region (CD8a-TM) polypeptide. In such embodiments, the CD8a-TM polypeptide may comprise an amino acid sequence that is at least 90% identical to SEQ ID NO: 39. In such embodiments, the CD8a-TM polypeptide may comprise an amino acid sequence of SEQ ID NO: 39.

In some embodiments, the CARs disclosed herein may further comprise a hinge region linking the transmembrane domain to the extracellular antigen-binding domain. In certain embodiments, the hinge region may be a CD8a-hinge region. In such embodiments, the CD8a-hinge region may comprise an amino acid sequence that is at least 90% identical to SEQ ID NO: 38. In such embodiments, the CD8a-hinge region may comprise an amino acid sequence of SEQ ID NO: 38.

In some embodiments, the extracellular antigen-binding domain comprises an amino acid sequence that is at least 90% identical to SEQ ID NO: 157. In some embodiments, the extracellular antigen-binding domain comprises an amino acid sequence of SEQ ID NO: 157.

In some embodiments, the CARs disclosed herein may comprise an amino acid sequence that is at least 90% identical to SEQ ID NO: 202. In some embodiments, the CARs disclosed herein may comprise an amino acid sequence of SEQ ID NO: 202. In another aspect is provided an isolated lymphocyte expressing any of the above-described CARs. In some embodiments, the lymphocyte is a T lymphocyte. In some embodiments, the lymphocyte is a natural killer (NK) cell.

Also provided is an isolated nucleic acid molecule encoding any of the above-described CARs. Also provided is a vector comprising the nucleic acid molecule. In addition, a cell expressing the nucleic acid molecule is also provided.

Further provided is a pharmaceutical composition comprising an effective amount of any of the above lymphocytes, and a pharmaceutically acceptable excipient.

In another aspect is provided a method of treating a subject having cancer. The method comprises administering a therapeutically effective amount of any of the above lymphocytes or the above pharmaceutical composition to a subject in need thereof, whereby the lymphocyte induces killing of cancer cells in the subject. In some embodiments, the cancer is B-cell lymphoma. In some embodiments, the cancer is a non-Hodgkin lymphoma. In some embodiments, the cancer is a diffuse large B-cell lymphoma (DLBCL), mantle cell lymphoma (MCL), follicular lymphoma (FL), marginal zone lymphoma (MZ), acute lymphoblastic leukemia (ALL), chronic lymphocytic leukemia (CLL), multiple myeloma (MM), mucosa-associated lymphoid tissue (MALT) lymphoma, Hodgkin's lymphoma, Burkitt's lymphoma, hairy-cell leukemia, or Plasmacytoma.

In another aspect is provided a method of targeted killing of a cancer cell, the method comprising contacting the cancer cell with any of the above lymphocytes, whereby the lymphocyte induces killing of the cancer cell. In some embodiments, the cancer cell is a malignant B cell. In some embodiments, the cancer cell is a cell of a non-Hodgkin lymphoma.

In some embodiments, the cancer cell is a cell of diffuse large B-cell lymphoma (DLBCL), mantle cell lymphoma (MCL), follicular lymphoma (FL), marginal zone lymphoma (MZ), acute lymphoblastic leukemia (ALL), chronic lymphocytic leukemia (CLL), multiple myeloma (MM), mucosa-associated lymphoid tissue (MALT) lymphoma, Hodgkin's lymphoma, Burkitt's lymphoma, hairy-cell leukemia or Plasmacytoma.

In another aspect is provided a method of detecting the presence of cancer in a subject, comprising:

(a) contacting a cell sample obtained from the subject with any of the above CARs, thereby forming a CAR-cell complex, and
(b) detecting the complex, wherein detection of the complex is indicative of the presence of cancer in the subject.

BRIEF DESCRIPTION OF THE DRAWINGS

The foregoing will be apparent from the following more particular description of example embodiments, as illustrated in the accompanying drawings.

In FIGS. 2A-AC and 2E, all SN8 (CD9W) constructs are in the LH orientation.

In FIGS. 3A-3D, all SN8 (CD9W) constructs are in the LH orientation. In FIG. 3E-3F, the HL or LH orientation is indicated with the first letter.

In FIG. 4A-4C, all SN8 (CD9W) constructs are in the LH orientation. In FIG. 4D, the HL or LH orientation is indicated with the first letter.

In FIGS. 5A-5C, all SN8 (CD9W) constructs are in the LH orientation. In FIG. 5C, the HL or LH orientation is indicated with the first letter.

In FIG. 6, all SN8 (CD9W) constructs are in the LH orientation.

Figure 12A:
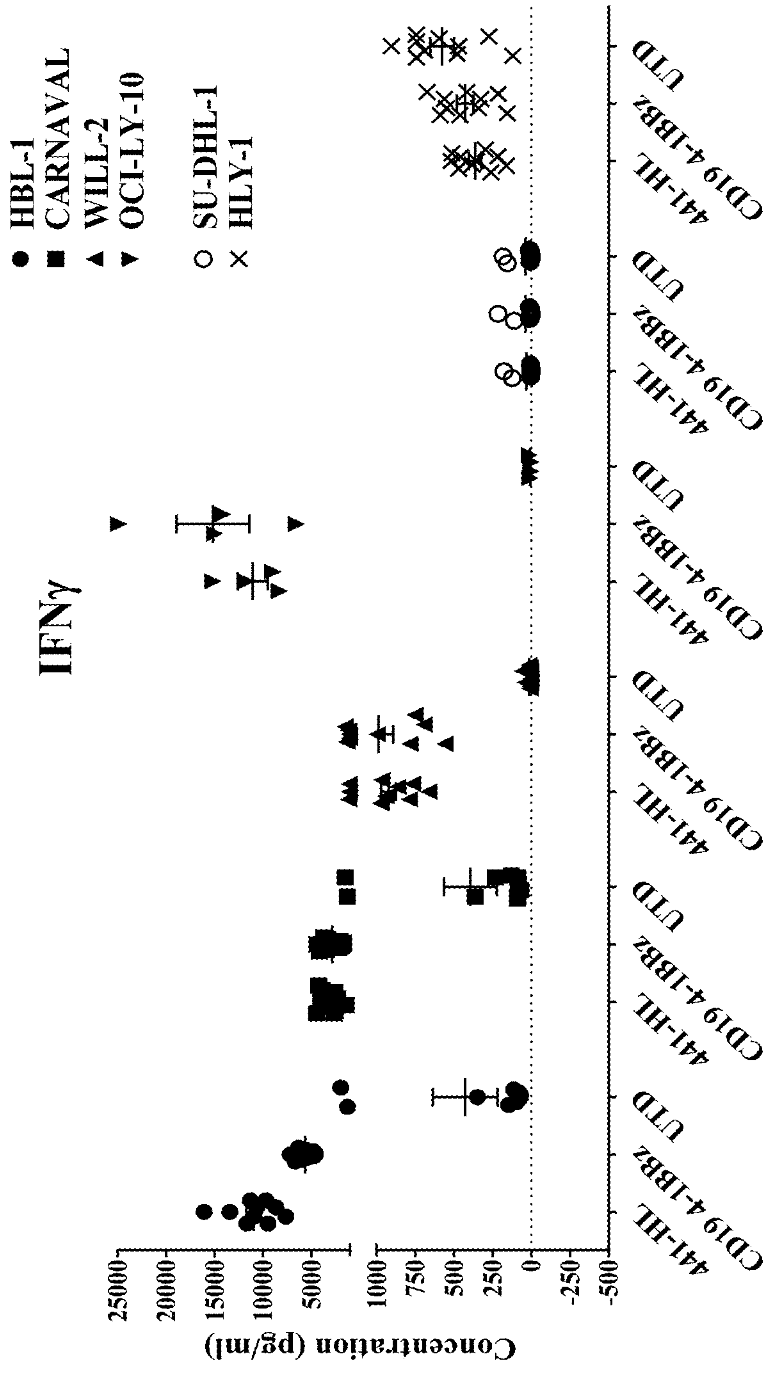
FIGS. 12A-12J show antigen-specific production of pro-inflammatory cytokines by 441-HL CAR-T cells. Supernatants from four CD79b/CD19+(HBL-1, OCI-LY-10, CARNAVAL, WILL-2) and two CD79b/CD19−(HLY-1 and SU-DHL-1) cell lines were collected during the flow cytometry-based killing assay and tested by Meso Scale Discovery (MSD). Data analysis was performed and results for each cytokine were plotted as individual values for each the five donors (two independent experiments), as well as an average value for each treatment group. Plots of INFγ, IL-2, TNFα, IL-6 levels (pg per mL) detected in supernatants of 441-HL CAR-T, CD19 CAR-T and UTD cells collected for each donor, as well as merged across donors (mean±SEM) are shown in FIGS. 12A-12D. Plots of IL-4, IL-10, IL10 and IL12p70 (pg per mL) detected in supernatants of 441-HL CAR-T, CD19 CAR-T and UTD cells collected for each donor, as well as merged across donors (mean±SEM) are shown in FIGS. 12E-12H. Plots of IL-13 and IL-8 (pg per mL) detected in supernatants of 441-HL CAR-T, CD19
Figure 12B:
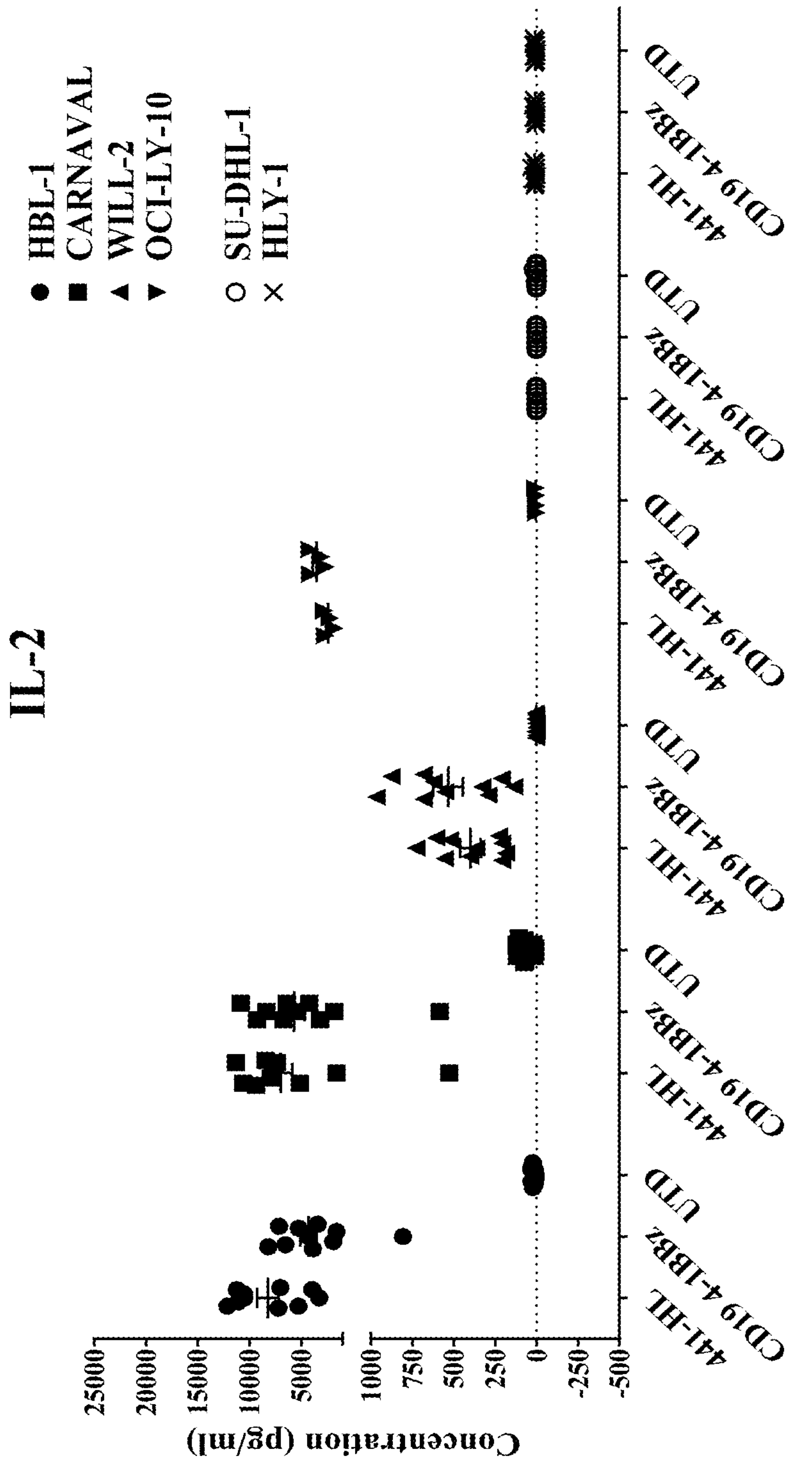
Figure 12C:
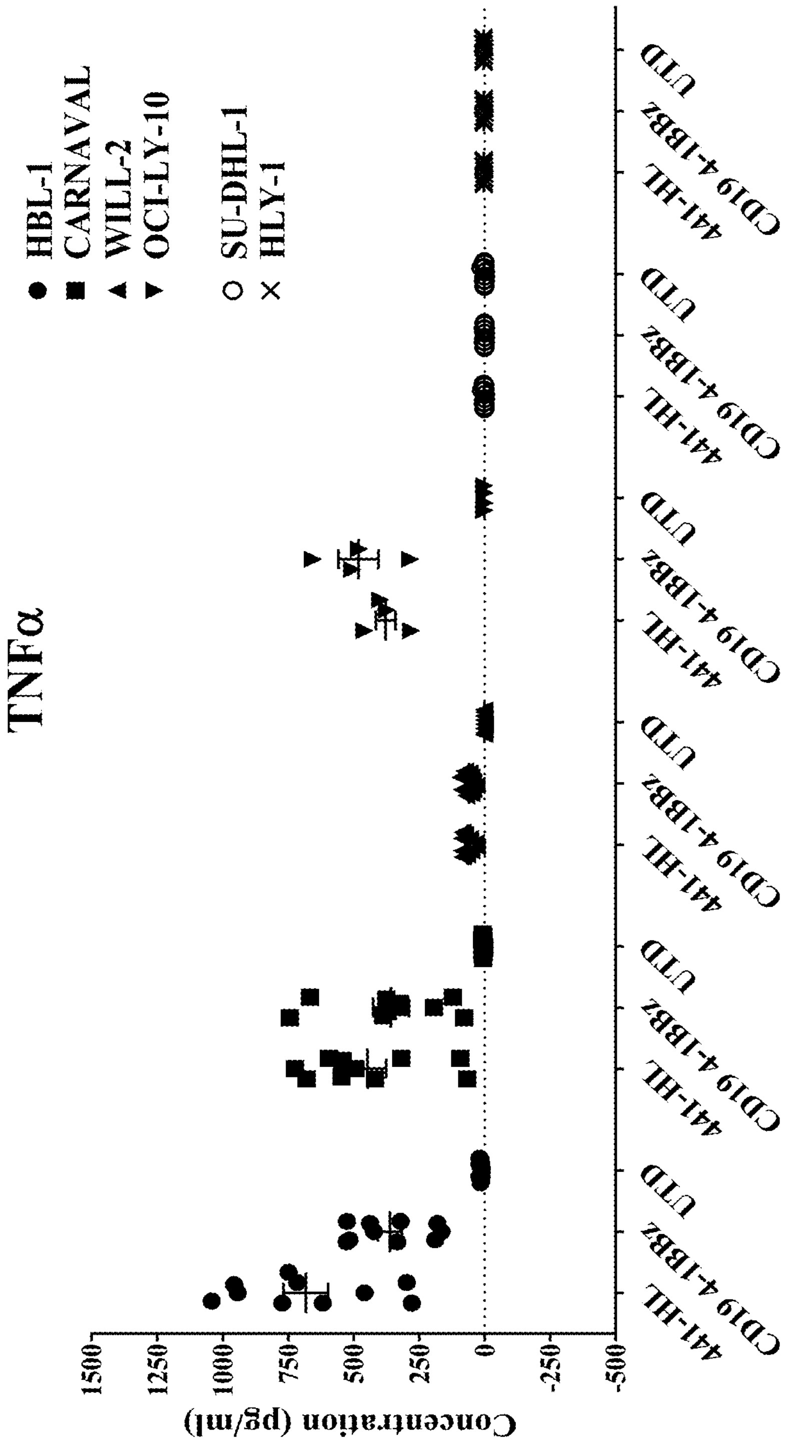
Figure 12D:
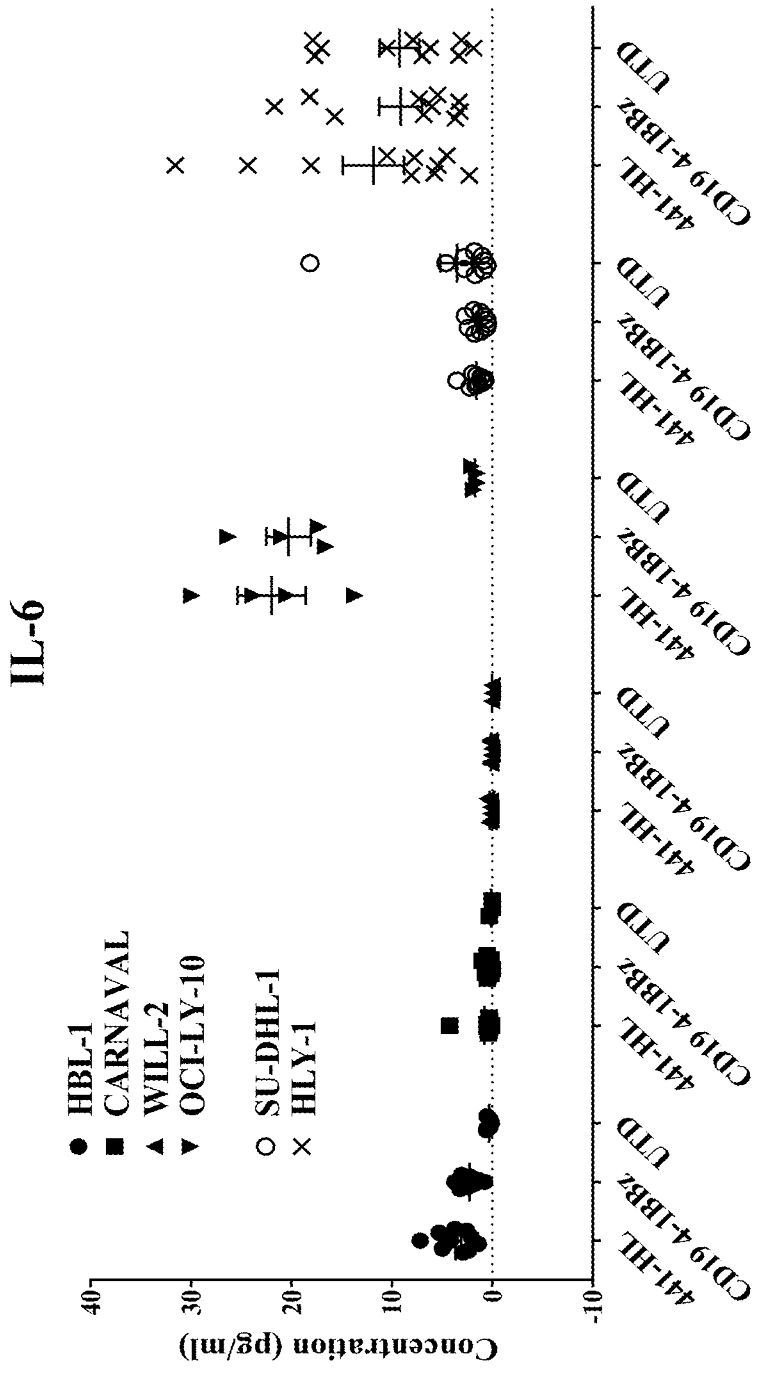
Figure 12E:
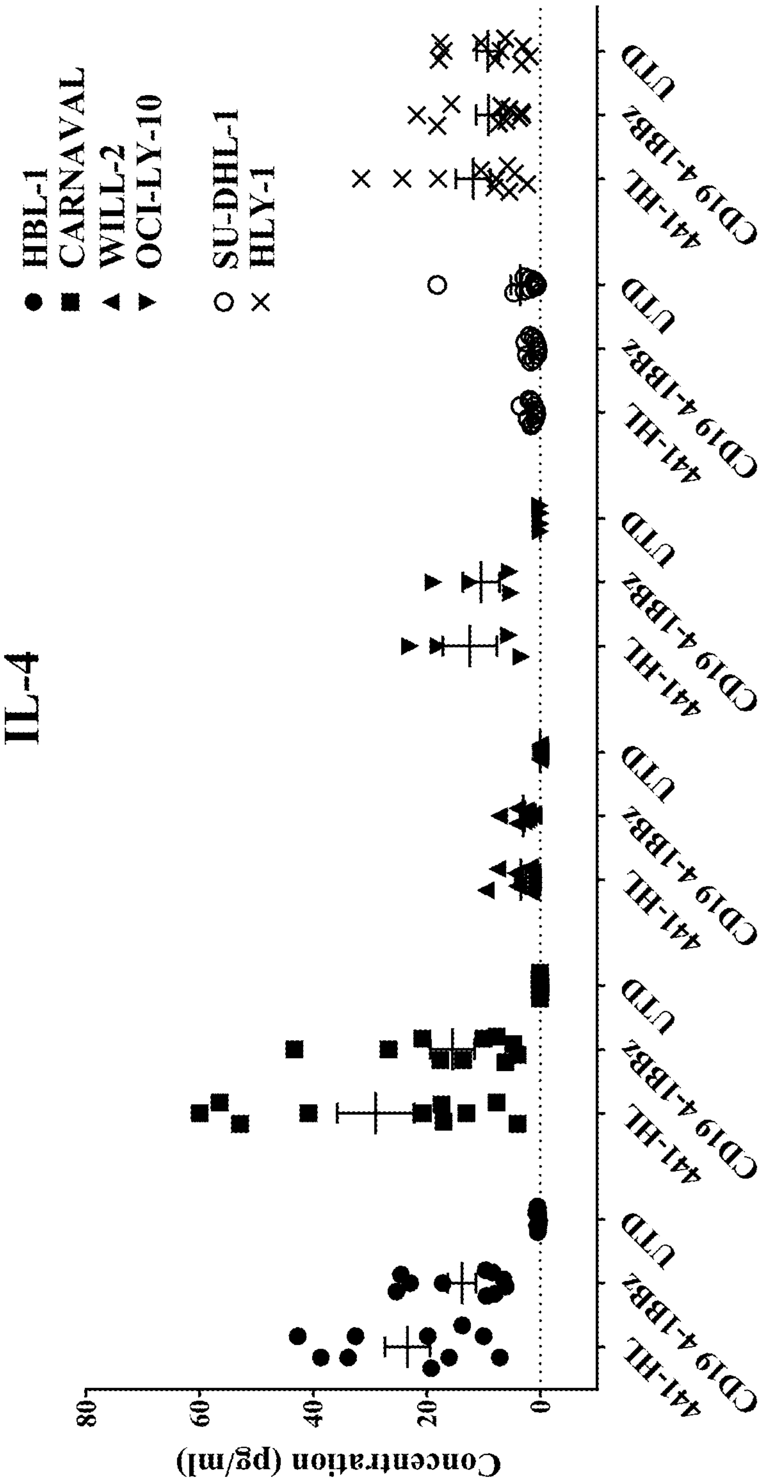
Figure 12F:
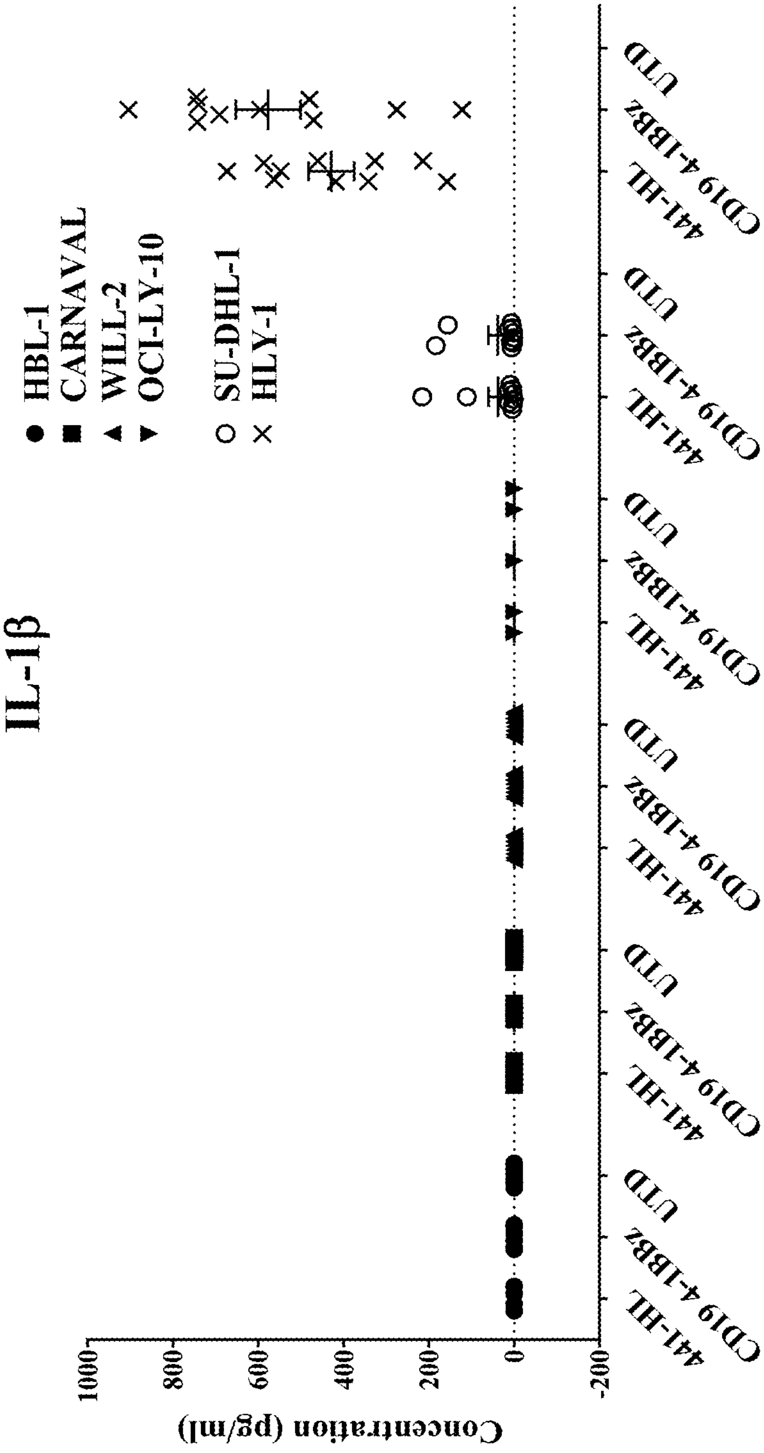
Figure 12G:
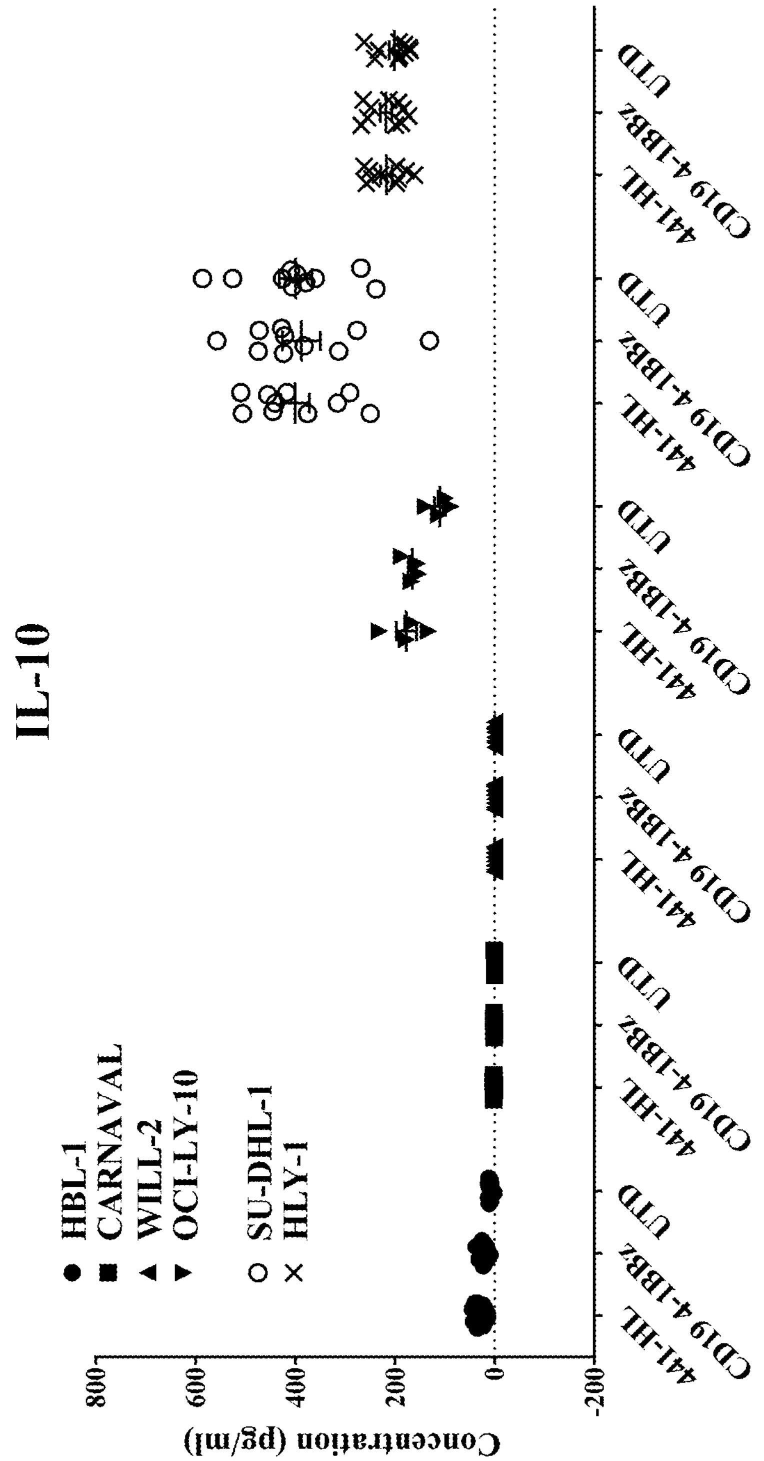
Figure 12H:
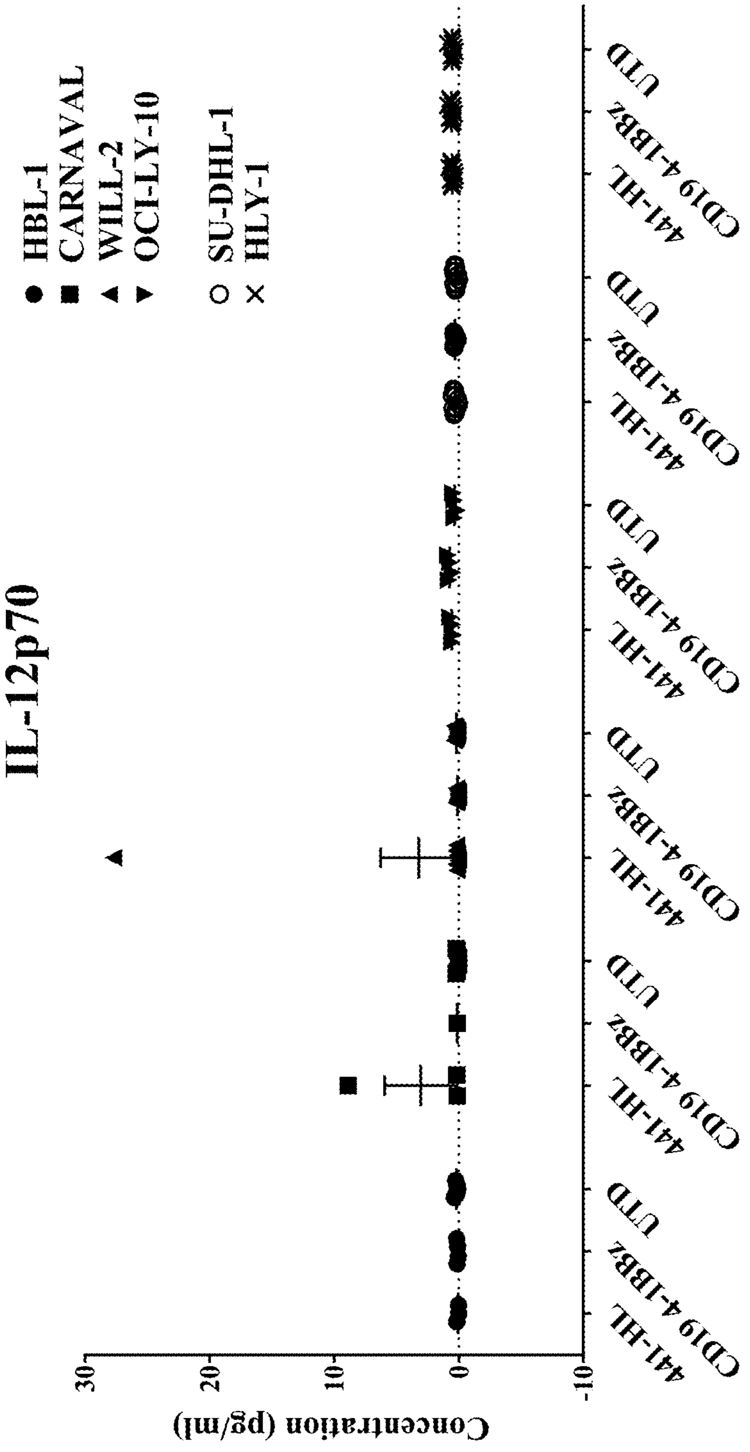
Figure 12I:
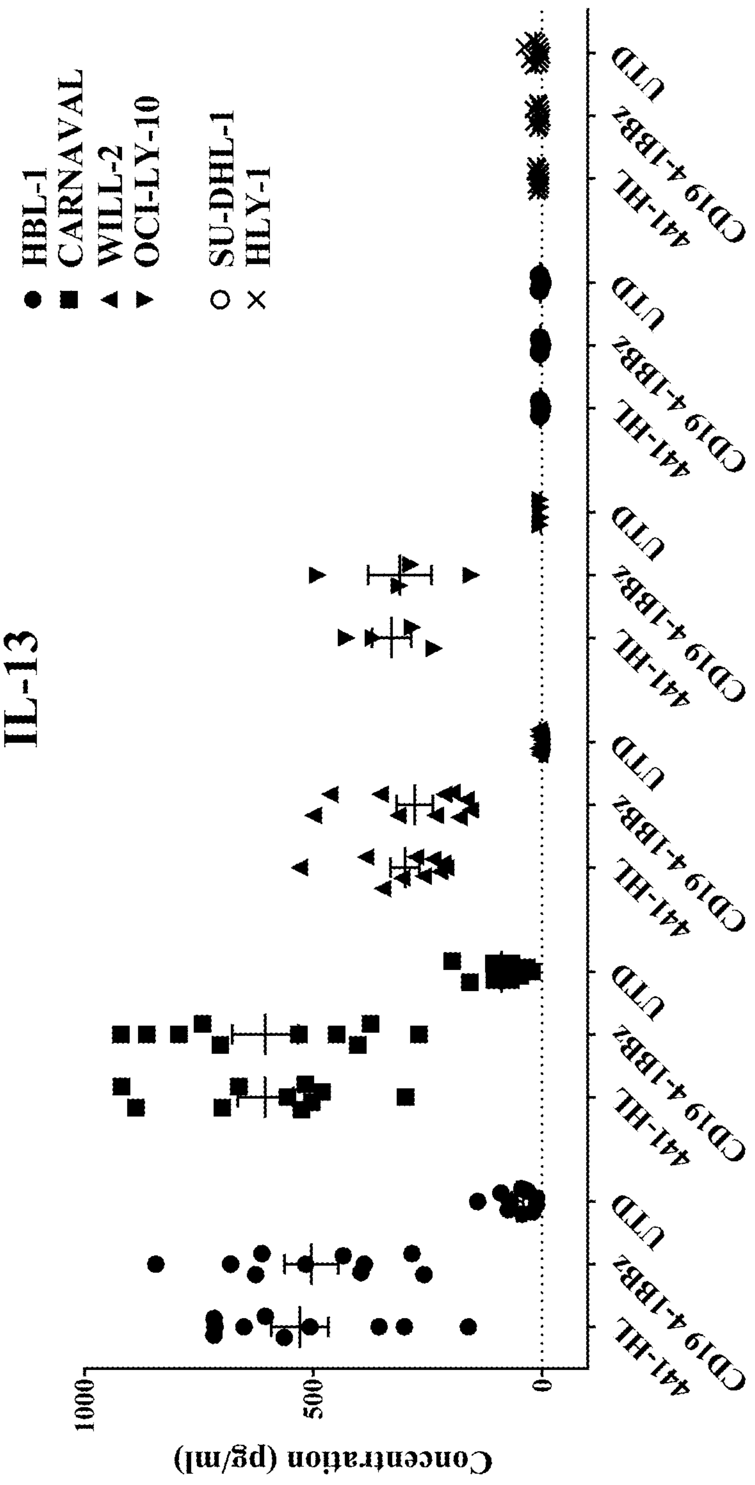
Figure 12J:
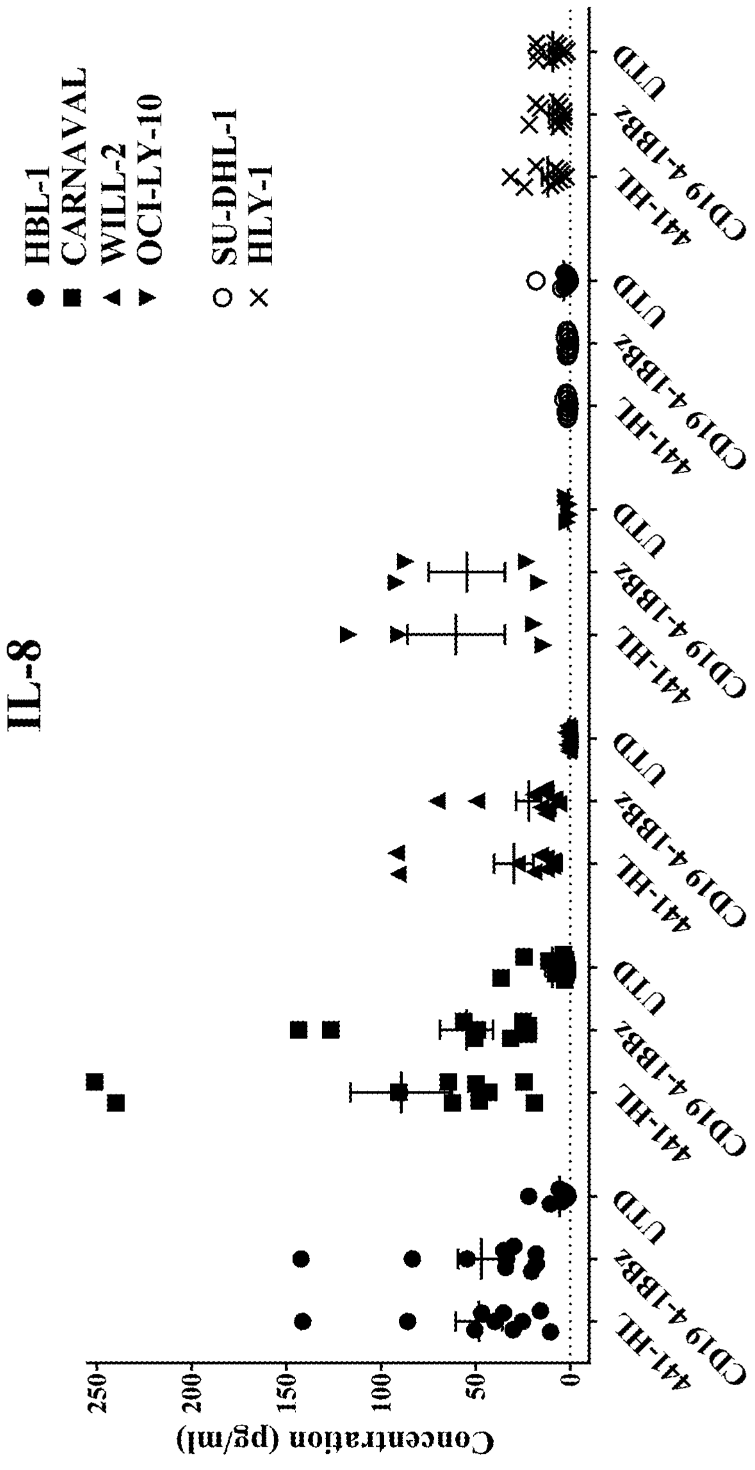

CAR-T and UTD cells collected for each donor, as well as merged across donors (mean±SEM) are shown in FIGS. 12I-12J.

Figure 13A:
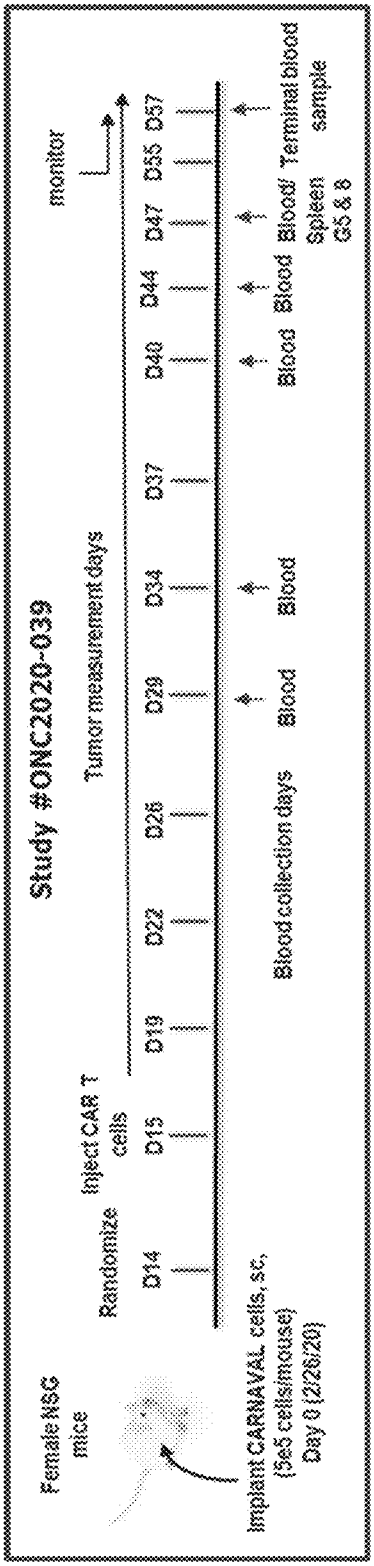
Figure 13B:
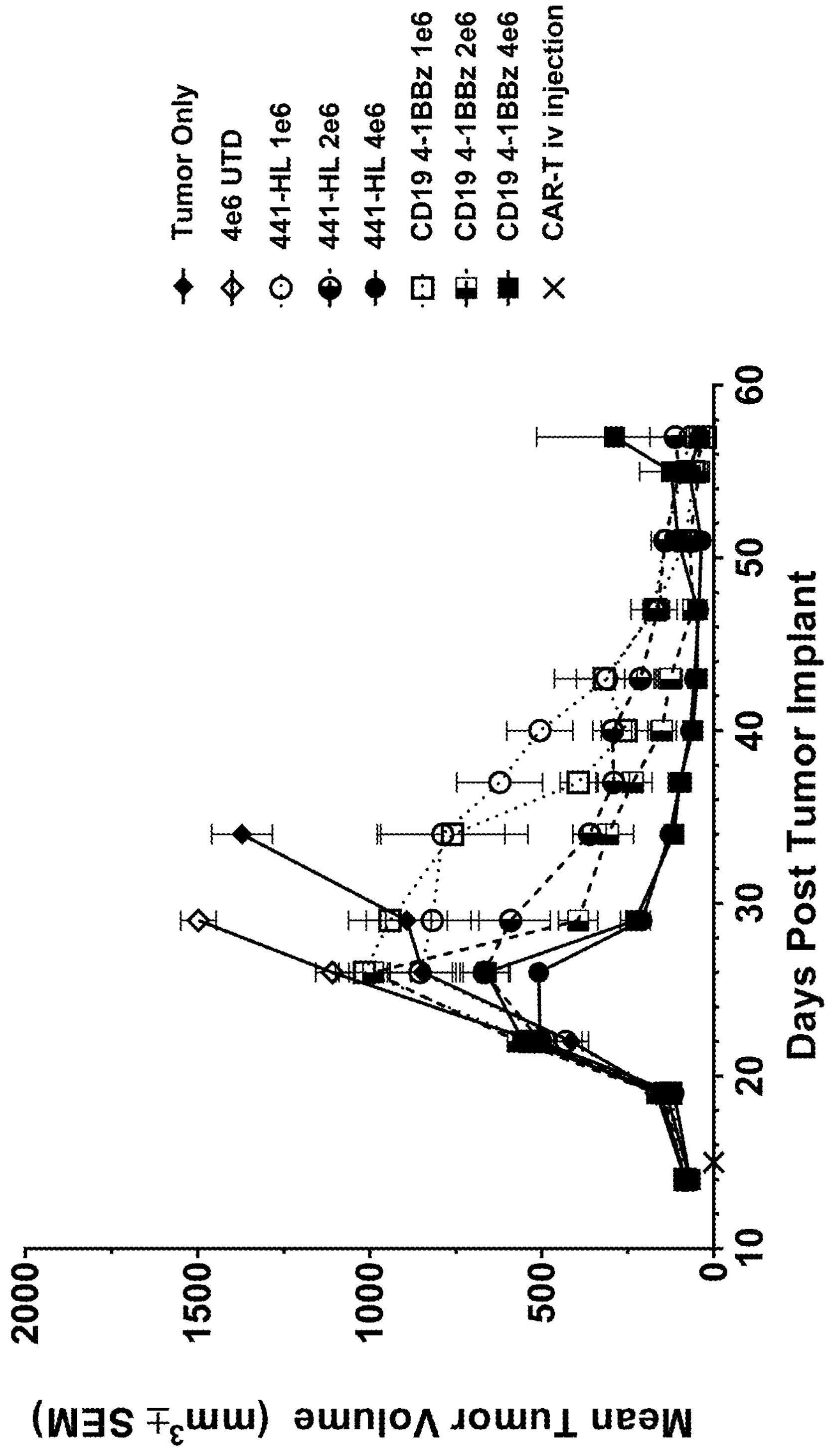
Figure 13C:
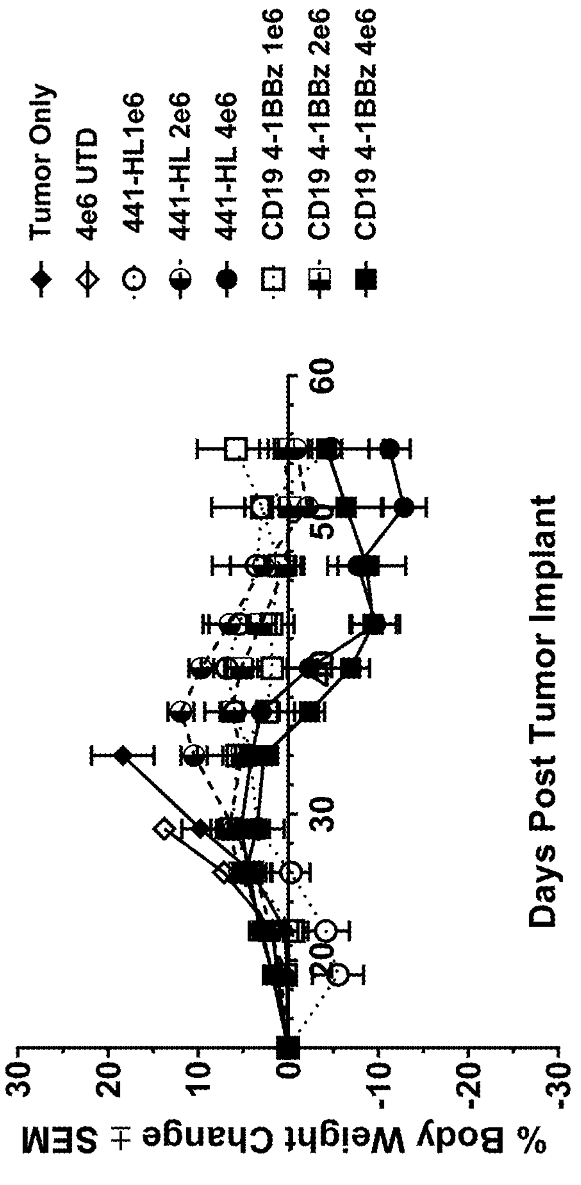

FIGS. 13A-13C show dose-dependent inhibition of tumor growth by CD79b CAR-T cells in CARNAVAL xenograft model. FIG. 13A shows a schematic representation of the experimental paradigm used to investigate in vivo efficacy of CD79b CAR-T cells in CARNAVAL xenograft model. CARNAVAL cells ($5\times10^5$) in logarithmic growth phase were implanted subcutaneously in NOD/scid/IL-2Rg−/− (NSG) mice on Day 0. When mean group tumor volume reached approximately 50-100 $mm^3$/mouse (14 days post-implant), doses of CAR+ T cells as described herein were injected intravenously. Tumor volume and body weight were recorded, and blood samples collected at regular intervals. Average tumor volume ($mm^2$±SEM) across days post tumor implant is shown in FIG. 13B. Average percent body weight change (%±SEM) across days post tumor implant is shown in FIG. 13C.

DETAILED DESCRIPTION

A description of example embodiments follows.

The present disclosure provides chimeric antigen receptors (CARs) that target Cluster of Differentiation 79B protein (CD79b), cells comprising such CARs, and methods of treating cancer (e.g., B-cell lymphoma) using the CARs described herein.

The CARs of the invention have antigen specificity for CD79b. The phrases "have antigen specificity" and "elicit antigen-specific response" as used herein mean that the CAR can specifically bind to and immunologically recognize an antigen, such that binding of the CAR to the CD79b antigen elicits an immune response. Methods of testing the CARs for antigen specificity and for the ability to recognize target cells are known in the art.

The disclosure also provides related nucleic acids, recombinant expression vectors, host cells, populations of cells, antibodies, or antigen binding portions thereof, and pharmaceutical compositions relating to the CARs of the invention.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly-used dictionaries, should be interpreted as having a meaning that is consistent with their meaning in the context of the relevant art and/or as otherwise defined herein.

Definitions

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

The terminology used herein is for the purpose of describing particular embodiments only and is not intended to be limiting. As used herein, the indefinite articles "a", "an" and "the" should be understood to include plural reference unless the context clearly indicates otherwise.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

"Activation" or "stimulation" means to induce a change in the cells' biologic state by which the cells (e.g., T cells and NK cells) express activation markers, produce cytokines, proliferate and/or become cytotoxic to target cells. All these changes can be produced by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to T cell and/or NK cell proliferation and/or upregulation or downregulation of key molecules.

"Bispecific" refers to a molecule (such as an antibody) that specifically binds two distinct antigens or two distinct epitopes within the same antigen. The bispecific molecule may have cross-reactivity to other related antigens, for example to the same antigen from other species (homologs), such as human or monkey, for example *Macaca* cynomolgus (cynomolgus, cyno) or Pan troglodytes, or may bind an epitope that is shared between two or more distinct antigens.

The term "chimeric antigen receptor" or "CAR" as used herein is defined as a cell-surface receptor comprising an extracellular target-binding domain, a transmembrane domain and an intracellular signaling domain, all in a combination that is not naturally found together on a single protein. This particularly includes receptors wherein the extracellular domain and the intracellular signaling domain are not naturally found together on a single receptor protein. The chimeric antigen receptors of the present invention are intended primarily for use with lymphocyte such as T cells and natural killer (NK) cells.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

"Heterologous" refers to two or more polynucleotides or two or more polypeptides that are not found in the same relationship to each other in nature.

"Heterologous polynucleotide" refers to a non-naturally occurring polynucleotide that encodes two or more neoantigens as described herein.

"Heterologous polypeptide" refers to a non-naturally occurring polypeptide comprising two or more neoantigen polypeptides as described herein.

"Host cell" refers to any cell that contains a heterologous nucleic acid. An exemplary heterologous nucleic acid is a vector (e.g., an expression vector).

The terms "T cell" and "T lymphocyte" are interchangeable and used synonymously herein. As used herein, T cell includes thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD8+ T cell), CD4+CD8+ T cell, or any other subset of T cells. Other illustrative populations of T cells suitable for use in particular embodiments include naive T cells and memory T cells. Also included are "NKT cells", which refer to a specialized population of T cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (τδ T cells)," which refer to a specialized population that to a small subset of T cells possessing a distinct TCR on their surface, and unlike the majority of T cells in which the TCR is composed of two glycoprotein chains designated α- and β-TCR chains, the TCR in 76 T cells is made up of a 7-chain and a 6-chain. γδ T cells can play a role in immunosurveillance and immunoregulation, and were found to be an important source of IL-17 and to induce robust CD8+ cytotoxic T cell response. Also included are "regulatory T cells" or "Tregs" which refer to T cells that suppress an abnormal or excessive immune response and play a role in immune tolerance. Tregs cells are typically transcription factor Foxp3-positive CD4+ T cells and can also include transcription factor Foxp3-negative regulatory T cells that are IL-10-producing CD4+ T cells.

The terms "natural killer cell" and "NK cell" are interchangeable and used synonymously herein. As used herein, NK cell refers to a differentiated lymphocyte with a CD 16+CD56+ and/or CD57+ TCR-phenotype. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

As used herein, the term "antigen" refers to any agent (e.g., protein, peptide, polysaccharide, glycoprotein, glycolipid, nucleic acid, portions thereof, or combinations thereof) molecule capable of being bound by a T-cell receptor. An antigen is also able to provoke an immune response. An example of an immune response may involve, without limitation, antibody production, or the activation of specific immunologically competent cells, or both. A skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components, organisms, subunits of proteins/antigens, killed or inactivated whole cells or lysates.

"Antigen-binding fragment" or "Antigen-binding domain" refers to a portion of the protein that binds an antigen. Antigen-binding domain may be synthetic, enzymatically obtainable or genetically engineered polypeptides and include portions of an immunoglobulin that bind an antigen, such as VH, the VL, the VH and the VL, Fab, Fab', $F(ab')_2$, Fd and Fv fragments, domain antibodies (dAb) consisting of one VH domain or one VL domain, shark variable IgNAR domains, camelized VH domains, VHH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3, alternative scaffolds that bind an antigen, and multispecific proteins comprising the antigen-binding fragments. Antigen-binding fragments (such as VH and VL) may be linked together via a synthetic linker to form various types of single antibody designs where the VH/VL domains may pair intramolecularly, or intermolecularly in those cases when the VH and VL domains are expressed by separate single chains, to form a monovalent antigen-binding domain, such as single chain Fv (scFv) or diabody. Antigen-binding fragments may also be conjugated to other antibodies, proteins, antigen-binding fragments or alternative scaffolds which may be monospecific or multispecific to engineer bispecific and multispecific proteins.

The terms "antibody" and "antibodies" refer to monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), intrabodies, minibodies, diabodies and anti-idiotypic (anti-Id) antibodies (including, e.g., anti-Id antibodies to antigen-specific TCR), and epitope-binding fragments of any of the above. The terms "antibody" and "antibodies" also refer to covalent diabodies such as those disclosed in U.S. Pat. Appl. Pub. 2007/0004909 and Ig-DARTS such as those disclosed in U.S. Pat. Appl. Pub. 2009/0060910. Antibodies useful as a TCR-binding molecule include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgM1, IgM2, IgA1 and IgA2) or subclass.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or a synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody".

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Specifically binds," "specific binding," "specifically binding" or "binds" refer to a proteinaceous molecule binding to an antigen or an epitope within the antigen with greater affinity than for other antigens. Typically, the proteinaceous molecule binds to the antigen or the epitope within the antigen with an equilibrium dissociation constant ($K_D$) of about $1\times10^{-7}$ M or less, for example about $5\times10^{-8}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, typically with the $K_D$ that is at least one hundred fold less than its $K_D$ for binding to a non-specific antigen (e.g., BSA, casein). In the context of the CD79b antigen described here, "specific binding" refers to binding of the proteinaceous molecule to the CD79b antigen without detectable binding to a wild-type protein the neoantigen is a variant of.

The term "host cell" means any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5a, JM109, and KCB, SURE® Competent Cells (*E. coli* cells), and SOLOPACK Gold Cells, can be used as host cells for vector replication and/or expression. Additionally, bacterial cells such as *E. coli* LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, CHO, Saos, and PC12.

Host cells of the present disclosure include T cells and natural killer cells that contain DNA or RNA sequences encoding the CAR and that express the CAR on the cell surface. Host cells may be used for enhancing T cell activity, natural killer cell activity, treatment of cancer, and treatment of autoimmune disease.

The term "proliferation" refers to an increase in cell division, either symmetric or asymmetric division of cells. The term "expansion" refers to the outcome of cell division and cell death.

The term "differentiation" refers to a method of decreasing the potency or proliferation of a cell or moving the cell to a more developmentally restricted state.

The terms "express" and "expression" mean allowing or causing the information in a gene or DNA sequence to become produced, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or transmembrane.

The term "transfection" means the introduction of a "foreign" (i.e., extrinsic or extracellular) nucleic acid into a cell using recombinant DNA technology. The term "genetic modification" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences operably linked to polynucleotide encoding the chimeric antigen receptor, such as start, stop, promoter, signal, secretion, or other sequences used by a cell's genetic machinery. The gene or sequence may include nonfunctional sequences or sequences with no known function. A host cell that receives and expresses introduced DNA or RNA has been "genetically engineered." The DNA or RNA introduced to a host cell can come from any source, including cells of the same genus or species as the host cell, or from a different genus or species.

The term "transduction" means the introduction of a foreign nucleic acid into a cell using a viral vector.

The term "regulatory element" refers to any cis-acting genetic element that controls some aspect of the expression of nucleic acid sequences. In some embodiments, the term "promoter" comprises essentially the minimal sequences required to initiate transcription. In some embodiments, the term "promoter" includes the sequences to start transcription, and in addition, also include sequences that can upregulate or downregulate transcription, commonly termed "enhancer elements" and "repressor elements", respectively.

As used herein, the term "operatively linked," "operably linked" and similar phrases, when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

The terms "treat" or "treatment" refer to therapeutic treatment wherein the object is to slow down (lessen) an undesired physiological change or disease, or provide a beneficial or desired clinical outcome during treatment. Beneficial or desired clinical outcomes include alleviation of symptoms, diminishment of extent of disease, stabilized (i.e., not worsening) state of disease, delay or slowing of disease progression, amelioration or palliation of the disease state, and/or remission (whether partial or total), whether detectable or undetectable. "Treatment" can also mean prolonging survival as compared to expected survival if a subject was not receiving treatment. Those in need of treatment include those subjects already with the undesired physiological change or disease as well as those subjects prone to have the physiological change or disease.

As used herein, the term "subject" refers to an animal. The terms "subject" and "patient" may be used interchangeably herein in reference to a subject. As such, a "subject" includes a human that is being treated for a disease, or prevention of a disease, as a patient. The methods described herein may be used to treat an animal subject belonging to any classification. Examples of such animals include mammals. Mammals include, but are not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). In one embodiment, the mammal is a human.

By "enhance" or "promote," or "increase" or "expand" or "improve" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, effector function, persistence, and/or an increase in cancer cell death killing ability, among others apparent from the understanding in the art and the description herein. In certain embodiments, an "increased" or "enhanced" amount can be a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. In certain embodiments, a "decrease" or "reduced" amount can be a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response (reference response) produced by vehicle, a control composition, or the response in a particular cell lineage.

"Cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor.

"Relapsed" refers to the return of a disease or the signs and symptoms of a disease after a period of improvement after prior treatment with a therapeutic.

"Refractory" refers to a disease that does not respond to a treatment. A refractory disease can be resistant to a treatment before or at the beginning of the treatment, or a refractory disease can become resistant during a treatment.

A "tumor cell" or a "cancer cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid, uptake of exogenous nucleic acid or it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The terms "prevent," "preventing," "prevention," or "prophylaxis" of a disease or disorder mean preventing that a disorder occurs in a subject.

A "therapeutically effective amount" or "effective amount", used interchangeably herein, refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Example indicators of an effective therapeutic or combination of therapeutics that include, for example, improved well-being of the patient, reduction of a tumor burden, arrested or slowed growth of a tumor, and/or absence of metastasis of cancer cells to other locations in the body.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "protein" is used herein encompasses all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "nucleic acid", "nucleotide", and "polynucleotide" encompass both DNA and RNA unless specified otherwise. By a "nucleic acid sequence" or "nucleotide sequence" is meant the nucleic acid sequence encoding an amino acid; these terms may also refer to the nucleic acid sequence including the portion coding for any amino acids added as an artifact of cloning, including any amino acids coded for by linkers.

"Isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E.W. Martin.

"Cluster of Differentiation 79B protein" or "CD79b" refers to a known protein which is also called B-Cell-Specific Glycoprotein B29, Ig-Beta, or AGM6. The B lymphocyte antigen receptor is a multimeric complex that includes the antigen-specific component, surface immunoglobulin (Ig), which non-covalently associates with Ig-alpha and Ig-beta. CD79b is the Ig-beta protein of the B-cell antigen component. All CD79b isoforms and variants are encompassed in "CD79b". The amino acid sequences of the various isoforms are retrievable from GenBank®, the Genetic Sequence Data Bank containing publicly available nucleotide sequences, accession numbers AAH32651.1, EAW94232.1, AAH02975.2, NP_000617.1, and NP_001035022.1 The amino acid sequence of a full length CD79b sequence is shown below. The sequence includes the extracellular domain (residues 29-159) and the cytoplasmic domain (residues 181-229).

```
                                        (SEQ ID NO: 282)
MARLALSPVPSHWMVALLLLLSAEPVPAARSEDRYRNPKGSACSRIWQSP

RFIARKRGFTVKMHCYMNSASGNVSWLWKQEMDENPQQLKLEKGRMEESQ

NESLATLTIQGIRFEDNGIYFCQQKCNNTSEVYQGCGTELRVMGFSTLAQ

LKQRNTLKDGIIMIQTLLIILFIIVPIFLLLDKDDSKAGMEEDHTYEGLD

IDQTATYEDIVTLRTGEVKWSVGEHPGQE
```

Chimeric Antigen Receptors

The present invention relates generally to the use of T cells genetically modified to stably express a desired chimeric antigen receptor. A chimeric antigen receptor (CAR) is an artificially constructed hybrid protein or polypeptide containing the antigen-binding domains of an antibody (scFv) linked to T-cell signaling domains. Characteristics of CARs can include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigens independent of antigen processing, thus bypassing a major mechanism of tumor evasion. Moreover, when expressed in T-cells, CARs advantageously do not dimerize with endogenous T cell receptor (TCR) alpha and beta chains.

The CARs described herein provide recombinant polypeptide constructs comprising at least an extracellular antigen-binding domain, a transmembrane domain and an intracellular signaling domain (also referred to herein as "a cytoplasmic signaling domain") comprising a functional signaling domain derived from a stimulatory molecule as defined below. T cells expressing a CAR are referred to herein as CAR T cells, CAR-T cells or CAR modified T cells, and these terms are used interchangeably herein. The cell can be genetically modified to stably express an antibody binding domain on its surface, conferring novel antigen specificity that is MHC independent.

In some instances, the T cell is genetically modified to stably express a CAR that combines an antigen recognition domain of a specific antibody with an intracellular domain of the CD3-zeta chain or FcγRI protein into a single chimeric protein. In one embodiment, the stimulatory molecule is the zeta chain associated with the T cell receptor complex.

An "intracellular signaling domain," as the term is used herein, refers to an intracellular portion of a molecule. It is the functional portion of the protein which acts by transmitting information within the cell to regulate cellular activity via defined signaling pathways by generating second messengers or functioning as effectors by responding to such messengers. The intracellular signaling domain generates a signal that promotes an immune effector function of the CAR containing cell, e.g., a CAR-T cell. Examples of immune effector function, e.g., in a CAR-T cell, include cytolytic activity and helper activity, including the secretion of cytokines.

In an embodiment, the intracellular signaling domain can comprise a primary intracellular signaling domain. Example primary intracellular signaling domains include those derived from the molecules responsible for primary stimulation, or antigen dependent simulation. In an embodiment, the intracellular signaling domain can comprise a co-stimulatory intracellular domain. Example co-stimulatory intracellular signaling domains include those derived from molecules responsible for co-stimulatory signals, or antigen independent stimulation. For example, in the case of a CAR-T, a primary intracellular signaling domain can comprise a cytoplasmic sequence of a T cell receptor, and a co-stimulatory intracellular signaling domain can comprise cytoplasmic sequence from co-receptor or co-stimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3-zeta, FcR gamma, FcR beta, CD3 gamma, CD3 delta, CD3 epsilon, CD5, CD22, CD79a, CD79b, and CD66d DAP10 and DAP12.

The term "zeta" or alternatively "zeta chain", "CD3-zeta" or "TCR-zeta" is defined as the protein provided as GenBank® Acc. No. BAG36664.1, or the equivalent residues from a nonhuman species, e.g., murine, rabbit, primate, mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect, the cytoplasmic domain of zeta comprises residues 52 through 164 of GenBank® Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO: 28, or a sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 41.

The term "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules are cell surface molecules other than antigen receptors or their ligands that are required for an efficient immune response. Co-stimulatory molecules include, but are not limited to an MHC class 1 molecule, BTLA and a Toll ligand receptor, as well as OX40, CD2, CD27, CD28, CDS, ICAM-1, LFA-1 (CD11a/CD18) and 4-1BB (CD137).

A co-stimulatory intracellular signaling domain can be the intracellular portion of a co-stimulatory molecule. A co-stimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, MyD88, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment thereof.

The term "4-1BB" or alternatively "CD137" refers to a member of the TNFR superfamily with an amino acid sequence provided as GenBank® Acc. No. AAA62478.2, or the equivalent residues from a nonhuman species, e.g., mouse, rodent, monkey, ape and the like; and a "4-1BB co-stimulatory domain" is defined as amino acid residues 214-255 of GenBank® accession no. AAA62478.2, or the equivalent residues from a non-human species, e.g., mouse, rodent, monkey, ape and the like. In one aspect, the "4-1BB co-stimulatory domain" or "CD137 co-stimulatory domain" is the sequence provided as SEQ ID NO: 27 or the equivalent residues from a non-human species, e.g., mouse, rodent, monkey, ape and the like, or a sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 40.

In one embodiment, a transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In one example embodiment, the transmembrane domain comprises the CD8a hinge domain.

In some embodiments, the cytoplasmic signaling domain further comprises one or more functional signaling domains derived from at least one co-stimulatory molecule as defined herein. In one embodiment, the co-stimulatory molecule is chosen from 4-1BB (i.e., CD137), CD27, CD3-zeta and/or CD28. CD28 is a T cell marker important in T cell co-stimulation. CD27 is a member of the tumor necrosis factor receptor superfamily and acts as a co-stimulatory immune checkpoint molecule. 4-1BB transmits a potent co-stimulatory signal to T cells, promoting differentiation and enhancing long-term survival of T lymphocytes. CD3-zeta associates with TCRs to produce a signal and contains immunoreceptor tyrosine-based activation motifs (ITAMs). In another embodiment, the co-stimulatory molecule is MyD88 or CD40.

In one embodiment, the CAR comprises an intracellular hinge domain comprising CD8 and an intracellular T cell receptor signaling domain comprising CD28, 4-1BB, and CD3-zeta. In another embodiment, the CAR comprises an intracellular hinge domain and an intracellular T cell receptor signaling domain comprising CD28, 4-1BB, and CD3-zeta, wherein the hinge domain comprises all or part of the extracellular region of CD8, CD4 or CD28; all or part of an antibody constant region; all or part of the FcγRIIIa receptor, an IgG hinge, an IgM hinge, an IgA hinge, an IgD hinge, an IgE hinge, or an Ig hinge. The IgG hinge may be from IgG1, IgG2, IgG3, IgG4, IgM1, IgM2, IgA1, IgA2, IgD, IgE, or a chimera thereof.

CARs described herein provide recombinant polypeptide constructs comprising at least an extracellular antigen-binding domain, a transmembrane domain and an intracellular signaling domain (also referred to herein as "a cytoplasmic signaling domain") comprising, e.g., a functional signaling domain derived from a stimulatory molecule as defined below.

In one embodiment, the CAR comprises a chimeric fusion protein comprising an extracellular antigen recognition domain, a transmembrane domain and an intracellular signaling domain comprising a functional signaling domain derived from a stimulatory molecule. In one embodiment, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one embodiment, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule.

The CARs of the invention can be designed to comprise the CD28 and/or 4-1BB signaling domain by itself or be combined with any other desired cytoplasmic domain(s) useful in the context of the CARs of the invention. In one embodiment, the cytoplasmic domain of the CAR can further comprise the signaling domain of CD3-zeta. For example, the cytoplasmic domain of the CAR can include but is not limited to CD3-zeta, 4-1BB and CD28 signaling modules and combinations thereof. Accordingly, the invention provides CAR T cells and methods of their use for adoptive therapy.

The disclosure further provides variants, e.g., functional variants, of the CARs, nucleic acids, polypeptides, and proteins described herein. "Variant" refers to a polypeptide or a polynucleotide that differs from a reference polypeptide or a reference polynucleotide by one or more modifications for example, substitutions, insertions or deletions. The term "functional variant" as used herein refers to a CAR, polypeptide, or protein having substantial or significant sequence identity or similarity to a parent CAR, polypeptide, or protein, which functional variant retains the biological activity of the CAR, polypeptide, or protein for which it is a variant. Functional variants encompass, e.g., those variants of the CAR, polypeptide, or protein described herein (the parent CAR, polypeptide, or protein) that retain the ability to recognize target cells to a similar extent, the same extent, or to a higher extent, as the parent CAR, polypeptide, or protein. In reference to the parent CAR, polypeptide, or protein, the functional variant can, for example, be at least about 30%, about 40%, about 50%, about 60%, about 75%, about 80%, about 85%, about 90%, about 91%, about 92%, about 93%, about 94%, about 95%, about 96%, about 97%, about 98%, about 99% or more identical in amino acid sequence to the parent CAR, polypeptide, or protein.

A functional variant can, for example, comprise the amino acid sequence of the parent CAR, polypeptide, or protein with at least one conservative amino acid substitution. In another embodiment, the functional variants can comprise the amino acid sequence of the parent CAR, polypeptide, or protein with at least one non-conservative amino acid substitution. In this case, the non-conservative amino acid substitution may not interfere with or inhibit the biological activity of the functional variant. The non-conservative amino acid substitution may enhance the biological activity of the functional variant such that the biological activity of the functional variant is increased as compared to the parent CAR, polypeptide, or protein.

Amino acid substitutions of the inventive CARs may be conservative amino acid substitutions. Conservative amino acid substitutions are known in the art, and include amino acid substitutions in which one amino acid having certain physical and/or chemical properties is exchanged for another amino acid that has the same or similar chemical or physical properties. For example, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The CAR, polypeptide, or protein can consist essentially of the specified amino acid sequence or sequences described herein, such that other components e.g., other amino acids, do not materially change the biological activity of the functional variant.

The CARs, polypeptides, and proteins of embodiments of the disclosure (including functional portions and functional variants) can be of any length, i.e., can comprise any number of amino acids, provided that the CARs, polypeptides, or proteins (or functional portions or functional variants thereof) retain their biological activity, e.g., the ability to specifically bind to an antigen, detect diseased cells (e.g., cancer cells) in a host, or treat or prevent disease in a host, etc. For example, the polypeptide can be about 50 to about 5000 amino acids long, such as about 50, about 70, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000 or more amino acids in length. The polypeptides of the invention also include oligopeptides.

The CARs, polypeptides, and proteins of embodiments of the invention (including functional portions and functional variants of the invention) can comprise synthetic amino acids in place of one or more naturally occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, α-(2-amino-2-norbornane)-carboxylic acid, α,γ-diaminobutyric acid, α,β-diaminopropionic acid, homophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, indoline-2-carboxylic acid, 1,2,3,4-tetrahydroisoquinoline-3-carboxylic acid, aminomalonic acid, aminomalonic acid monoamide, and α-tert-butylglycine.

The CARs, polypeptides, and proteins of embodiments of the invention (including functional portions and functional variants) can be subject to post-translational modifications. They can be glycosylated, esterified, N-acylated, amidated, carboxylated, phosphorylated, esterified, cyclized via, e.g., a disulfide bridge, or converted into an acid addition salt. In some embodiments, they are dimerized or polymerized, or conjugated.

The CARs, polypeptides, and/or proteins of embodiments of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; and *Epitope Mapping*, ed. Westwood et al., Oxford University Press, Oxford, United Kingdom, 2001. Also, polypeptides and proteins can be recombinantly produced using the nucleic acids described herein using standard recombinant methods. See, for instance, Sambrook et al., *Molecular Cloning: A Laboratory Manual,* 3rd ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the CARs, polypeptides, and proteins of the invention (including functional portions and functional variants thereof) can be isolated and/or purified from a source, such as a plant, a bacterium, an insect, a mammal, etc. Methods of isolation and purification are known in the art. Alternatively, the CARs, polypeptides, and/or proteins described herein (including functional portions and functional variants thereof) can be commercially synthesized. In this respect, the CARs, polypeptides, and proteins can be synthetic, recombinant, isolated, and/or purified.

Examples of modified nucleotides that can be used to generate the recombinant nucleic acids utilized to produce the polypeptides described herein include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, carboxymethylaminomethyl-2-thiouridine, 5-carboxymethylaminomethyluracil, dihydrouracil, $N^6$-substituted adenine, 7-methylguanine, 5-methylaminomethyluracil, 5-methoxyaminomethyl-2-thiouracil, beta-D-mannosylqueosine, 5"-methoxycarboxymethyluracil, 5-methoxyuracil, 2-methylthio-$N^6$-isopentenyladenine, uracil-5-oxyacetic acid (v), wybutoxosine, pseudouracil, queuosine, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

The nucleic acid can comprise any isolated or purified nucleotide sequence which encodes any of the CARs, polypeptides, or proteins, or functional portions or functional variants thereof. Alternatively, the nucleotide sequence can comprise a nucleotide sequence which is degenerate to any of the sequences or a combination of degenerate sequences.

Some embodiments of the invention also provide an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-12 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the CARs described herein. It is generally appreciated that conditions can be rendered more stringent by the addition of increasing amounts of formamide.

In an embodiment, the nucleic acids of the invention can be incorporated into a recombinant expression vector. The present disclosure provides recombinant expression vectors comprising any of the nucleic acids of the invention. As used herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors described herein are not naturally-occurring as a whole; however, parts of the vectors can be naturally-occurring. The described recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. The non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λEMBL4, and λNM1149, λZapII (Stratagene) can be used. Examples of plant expression vectors include pBI01, pBI01.2, pBI121, pBI101.3, and pBIN19 (Clontech). Examples of animal expression vectors include pEUK-Cl, pMAM, and pMAMneo (Clontech). The recombinant expression vector may be a viral vector, e.g., a retroviral vector, e.g., a gamma retroviral vector.

In an embodiment, the recombinant expression vectors of the invention are prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, SV40, 2μ plasmid, λ, bovine papilloma virus, and the like.

The recombinant expression vector may comprise regulatory sequences, such as transcription and translation initiation and termination codons, which are specific to the type of host (e.g., bacterium, plant, fungus, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the described expression vectors include, for instance, neomycin/G418 resistance genes, histidinol x resistance genes, histidinol resistance genes, tetracycline resistance genes, and ampicillin resistance genes.

The recombinant expression vector can comprise a native or normative promoter operably linked to the nucleotide sequence encoding the CAR, polypeptide, or protein (including functional portions and functional variants thereof), or to the nucleotide sequence which is complementary to or which hybridizes to the nucleotide sequence encoding the CAR, polypeptide, or protein. The selection of promoters, e.g., strong, weak, tissue-specific, inducible and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an RSV promoter, an SV40 promoter, or a promoter found in the long-terminal repeat of the murine stem cell virus.

The recombinant expression vector can comprise one or more additional regulatory elements, such as enhancer elements, 5' and 3' UTR, or terminator sequences, operably linked to the nucleotide sequence encoding the CAR, polypeptide, or protein (including functional portions and functional variants thereof), or to the nucleotide sequence which is complementary to or which hybridizes to the nucleotide sequence encoding the CAR, polypeptide, or protein.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, and nitroreductase.

Included in the scope of the invention are conjugates, e.g., bioconjugates, comprising any of the CARs, polypeptides, or proteins (including any of the functional portions or variants thereof), host cells, nucleic acids, recombinant expression vectors, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., Inorg Chem. 44(15): 5405-5415 (2005)).

An embodiment of the invention further provides an antibody, or antigen binding portion thereof, which binds, e.g., specifically binds, to an epitope of the CARs of the invention.

The antibody can be any type of immunoglobulin that is known in the art. Immunoglobulins may be assigned to five major classes, IgA, IgD, IgE, IgG and IgM. IgA and IgG are further classified as the isotypes IgA1, IgA2, IgG1, IgG2, IgG3 and IgG4. Antibody light chains of vertebrate species can be assigned to one of two types, kappa (κ) and lambda (λ), based on the amino acid sequences of their constant domains. The antibody can be of any class or isotype.

The antibodies include immunoglobulin molecules including monoclonal antibodies including murine, human, humanized and chimeric monoclonal antibodies, polyclonal, antigen-binding fragments, bispecific or multispecific antibodies, monomeric, dimeric, tetrameric or multimeric antibodies, single chain antibodies, domain antibodies and any other modified configuration of the immunoglobulin molecule that comprises an antigen binding site of the required specificity. The antibody can be a naturally-occurring antibody, e.g., an antibody isolated and/or purified from a mammal, e.g., a murine, primate, mouse, rabbit, goat, horse, chicken, hamster, human, etc. Alternatively, the antibody can be an engineered (e.g., genetically-engineered) antibody.

Humanized antibodies have antigen binding sites derived from non-human species and the variable region frameworks are derived from human immunoglobulin sequences. Human antibodies have heavy and light chain variable regions in which both the framework and the antigen binding site are derived from sequences of human origin.

Also, the antibody can have any level of affinity or avidity for the functional portion of the CAR. In some embodiments, the antibody may bind the CD79b antigen with a range of affinities ($K_D$). In one embodiment according to the invention, and in some embodiments of each and every one of the numbered embodiments listed below, the antibody binds to the CD79b antigen with high affinity, for example, with a $K_D$ equal to or less than about $10^{-7}$ M, such as but not limited to, 1-9.9 (or any range or value therein, such as 1, 2, 3, 4, 5, 6, 7, 8, or 9)$\times10^{-8}$M, $10^{-9}$ M, $10^{-10}$ M, $10^{-11}$ M, $10^{-12}$ M, $10^{-13}$ M, $10^{-14}$ M, $10^{-15}$ M or any range or value therein, as determined by surface plasmon resonance or the Kinexa method, as practiced by those of skill in the art. One example affinity is equal to or less than $1\times10^{-8}$ M. Another example affinity is equal to or less than $1\times10^{-9}$ M.

Methods of testing antibodies for the ability to bind to any functional portion of the CARs are known in the art and include any antibody-antigen binding assay, such as, for example, radioimmunoassay (RIA), Western blot, enzyme-linked immunosorbent assay (ELISA), immunoprecipitation, and competitive inhibition assays.

Suitable methods of making antibodies are known in the art. For instance, standard hybridoma methods are described in, e.g., Köhler and Milstein, *Eur. J. Immunol.,* 5, 511-519 (1976), Harlow and Lane (eds.), *Antibodies: A Laboratory Manual*, CSH Press (1988), and C. A. Janeway et al. (eds.), *Immunobiology,* 5th Ed., Garland Publishing, New York, N.Y. (2001)). Alternatively, other methods, such as EBV-hybridoma methods (Haskard and Archer, J. *Immunol. Methods,* 74(2), 361-67 (1984), and Roder et al., *Methods Enzymol.,* 121, 140-67 (1986)), and bacteriophage vector expression systems (see, e.g., Huse et al., *Science,* 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display can also be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen (i.e., CD79b), and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are known in the art and are described in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235, 959-973 (1994).

Antibodies, as utilized herein, can be multiple or single chain, or intact immunoglobulins, and may be derived from natural sources or from recombinant sources. Antibodies can be tetramers of immunoglobulin molecules.

In some embodiments, the antibody is a bispecific antibody. The VL and/or the VH regions of existing antibodies or the VL and VH regions identified de novo as described herein may be engineered into bispecific full-length antibodies. Such bispecific antibodies may be made by modulating the CH3 interactions in antibody Fc to form bispecific antibodies using technologies such as those described in U.S. Pat. No. 7,695,936; Int. Pat. Publ. No. WO04/111233; U.S. Pat. Publ. No. 2010/0015133; U.S. Pat. Publ. No. 2007/0287170; Int. Pat. Publ. No. WO2008/119353; U.S. Pat. Publ. No. 2009/0182127; U.S. Pat. Publ. No. 2010/0286374; U.S. Pat. Publ. No. 2011/0123532; Int. Pat. Publ. No. WO2011/131746; Int. Pat. Publ. No. WO2011/143545; or U.S. Pat. Publ. No. 2012/0149876. For example, bispecific antibodies of the invention may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody and the second monospecific bivalent antibody are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Example reducing agents that may be used are 2-mercapto-ethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

The term "antibody fragment" refers to at least one portion of an intact antibody, or recombinant variants thereof, that retains the antigen binding properties of the parental full length antibody. It refers to, for example, the antigen-binding domain, e.g., an antigenic determining variable region of an intact antibody, that is sufficient to confer recognition and binding, e.g., specific binding of the antibody fragment to a target, such as an antigen. "Antigen-binding fragment" refers to a portion of an immunoglobulin molecule Examples of antibody fragments include, but are not limited to, Fab, Fab', $F(ab')_2$, and Fv fragments, single chain antibodies (scFv), linear antibodies, single domain antibodies such as sdAb (either VL or VH), camelid VHH domains, and multi-specific antibodies formed from antibody fragments.

The term "scFv" refers to a protein comprising at least one antibody fragment comprising a variable region of a light chain and at least one antibody fragment comprising a variable region of a heavy chain. In some embodiments, the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

VH and the VL domains identified herein may be incorporated into a scFv format and the binding and thermostability of the resulting scFv to CD79b may be assessed using known methods. Binding may be assessed using a surface plasmon resonance system such as ProteOn™ XPR36 or Biacore™ 3000 or KinExA® instrumentation (kinetic exclusion assay instrumentation), ELISA or competitive binding assays known to those skilled in the art. Binding may be evaluated using purified scFvs or *E. coli* supernatants or lysed cells containing the expressed scFv. The measured affinity of a test scFv to CD79b may vary if measured under different conditions (e.g., osmolarity, pH). Thus, measurements of affinity and other binding parameters (e.g., $K_D$, $K_{on}$, $K_{off}$) are typically made with standardized conditions and standardized buffers. Thermostability may be evaluated by heating the test scFv at elevated temperatures, such as at 50° C., 55° C. or 60° C. for a period of time, such as 5 minutes (min), 10 min, 15 min, 20 min, 25 min or 30 min and measuring binding of the test scFv to CD79b. The scFvs retaining comparable binding to CD79b when compared to a non-heated scFv sample are referred to as being thermostable.

The cD79b antigen-binding domain may comprise sequences encoding variants demonstrating improved thermostability when compared to the parent antibody SN8. The positions engineered which may confer improved thermostability comprise residues M12, I20, R40, and A79 in the VH (residue numbering according to the SN8_VH of SEQ ID NO: 283) and L4, D32, F51, V82, and A87 in the VL (residue numbering according to the SN8_VL of SEQ ID NO: 284).

In recombinant expression systems, the linker is a peptide linker and may include any naturally occurring amino acid. Exemplary amino acids that may be included into the linker are Gly, Ser Pro, Thr, Glu, Lys, Arg, Ile, Leu, His and The. The linker should have a length that is adequate to link the VH and the VL in such a way that they form the correct conformation relative to one another so that they retain the desired activity, such as binding to CD79b.

The linker may be about 5-50 amino acids long. In some embodiments, the linker is about 10-40 amino acids long. In some embodiments, the linker is about 10-35 amino acids long. In some embodiments, the linker is about 10-30 amino acids long. In some embodiments, the linker is about 10-25 amino acids long. In some embodiments, the linker is about 10-20 amino acids long. In some embodiments, the linker is about 15-20 amino acids long. In some embodiments, the linker is 6 amino acids long. In some embodiments, the linker is 7 amino acids long. In some embodiments, the linker is 8 amino acids long. In some embodiments, the linker is 9 amino acids long. In some embodiments, the linker is 10 amino acids long. In some embodiments, the linker is 11 amino acids long. In some embodiments, the linker is 12 amino acids long. In some embodiments, the linker is 13 amino acids long. In some embodiments, the linker is 14 amino acids long. In some embodiments, the linker is 15 amino acids long. In some embodiments, the linker is 16 amino acids long. In some embodiments, the linker is 17 amino acids long. In some embodiments, the linker is 18 amino acids long. In some embodiments, the linker is 19 amino acids long. In some embodiments, the linker is 20 amino acids long. In some embodiments, the linker is 21 amino acids long. In some embodiments, the linker is 22 amino acids long. In some embodiments, the linker is 23 amino acids long. In some embodiments, the linker is 24 amino acids long. In some embodiments, the linker is 25 amino acids long. In some embodiments, the linker is 26 amino acids long. In some embodiments, the linker is 27 amino acids long. In some embodiments, the linker is 28 amino acids long. In some embodiments, the linker is 29 amino acids long. In some embodiments, the linker is 30 amino acids long. In some embodiments, the linker is 31 amino acids long. In some embodiments, the linker is 32 amino acids long. In some embodiments, the linker is 33 amino acids long. In some embodiments, the linker is 34 amino acids long. In some embodiments, the linker is 35 amino acids long. In some embodiments, the linker is 36 amino acids long. In some embodiments, the linker is 37 amino acids long. In some embodiments, the linker is 38 amino acids long. In some embodiments, the linker is 39 amino acids long. In some embodiments, the linker is 40 amino acids long. Exemplary linkers that may be used are Gly rich linkers, Gly and Ser containing linkers, Gly and Ala containing linkers, Ala and Ser containing linkers, and other flexible linkers.

Other linker sequences may include portions of immunoglobulin hinge area, CL or CH1 derived from any immunoglobulin heavy or light chain isotype. Exemplary linkers that may be used are shown in Table 1. Additional linkers are described for example in Int. Pat. Publ. No. WO2019/060695.

In some embodiments, the scFv comprises, from the N- to C-terminus, a VH, a linker and a VL (VH-Linker-VL).

In some embodiments, the scFv comprises, from the N- to C-terminus, the VL, the linker and the VH (VL-Linker-VH).

In some embodiments, the linker comprises the amino acid sequence of SEQ ID NO: 42.

In some embodiments, the linker comprises the amino acid sequence of SEQ ID NO: 43.

In some embodiments, the linker comprises the amino acid sequence of SEQ ID NO: 44.

In some embodiments, the linker comprises the amino acid sequence of SEQ ID NO: 45.

In some embodiments, the linker comprises the amino acid sequence of SEQ ID NO: 46.

In some embodiments, the linker comprises the amino acid sequence of SEQ ID NO: 47.

In some embodiments, the linker comprises the amino acid sequence of SEQ ID NO: 48.

In some embodiments, the linker comprises the amino acid sequence of SEQ ID NO: 49.

In some embodiments, the linker comprises the amino acid sequence of SEQ ID NO: 50.

In some embodiments, the linker comprises the amino acid sequence of SEQ ID NO: 51.

In some embodiments, the linker comprises the amino acid sequence of SEQ ID NO: 52.

In some embodiments, the linker comprises the amino acid sequence of SEQ ID NO: 53.

In some embodiments, the linker comprises the amino acid sequence of SEQ ID NO: 54.

In some embodiments, the linker comprises the amino acid sequence of SEQ ID NO: 55.

In some embodiments, the linker comprises the amino acid sequence of SEQ ID NO: 56.

In some embodiments, the linker comprises the amino acid sequence of SEQ ID NO: 57.

In some embodiments, the linker comprises the amino acid sequence of SEQ ID NO: 58.

In some embodiments, the linker comprises the amino acid sequence of SEQ ID NO: 59.

In some embodiments, the linker comprises the amino acid sequence of SEQ ID NO: 60.

In some embodiments, the linker comprises the amino acid sequence of SEQ ID NO: 61.

In some embodiments, the linker comprises the amino acid sequence of SEQ ID NO: 62.

In some embodiments, the linker comprises the amino acid sequence of SEQ ID NO: 63.

In some embodiments, the linker comprises the amino acid sequence of SEQ ID NO: 64.

In some embodiments, the linker comprises the amino acid sequence of SEQ ID NO: 65.

In some embodiments, the linker comprises the amino acid sequence of SEQ ID NO: 66.

In some embodiments, the linker comprises the amino acid sequence of SEQ ID NO: 67.

In some embodiments, the linker comprises the amino acid sequence of SEQ ID NO: 68.

In some embodiments, the linker comprises the amino acid sequence of SEQ ID NO: 69.

In some embodiments, the linker comprises the amino acid sequence of SEQ ID NO: 70.

In some embodiments, the linker comprises the amino acid sequence of SEQ ID NO: 71.

In some embodiments, the linker comprises the amino acid sequence of SEQ ID NO: 72.

In some embodiments, the linker comprises the amino acid sequence of SEQ ID NO: 73.

In some embodiments, the linker comprises the amino acid sequence of SEQ ID NO: 74.

TABLE 1

| Linker name | Amino acid sequence | SEQ ID NO: |
|---|---|---|
| Linker 1 | GGSEGKSSGSGSESKSTGGS | 42 |
| Linker 2 | GGGSGGGS | 43 |
| Linker 3 | GGGSGGGSGGGS | 44 |
| Linker 4 | GGGSGGGSGGGSGGGS | 45 |
| Linker 5 | GGGSGGGSGGGSGGGSGGGS | 46 |
| Linker 6 | GGGGSGGGGSGGGGS | 47 |
| Linker 7 | GGGGSGGGGSGGGGSGGGGS | 48 |
| Linker 8 | GGGGSGGGGSGGGGSGGGGSGGGGS | 49 |
| Linker 9 | GSTSGSGKPGSGEGSTKG | 50 |
| Linker 10 | IRPRAIGGSKPRVA | 51 |
| Linker 11 | GKGGSGKGGSGKGGS | 52 |
| Linker 12 | GGKGSGGKGSGGKGS | 53 |
| Linker 13 | GGGKSGGGKSGGGKS | 54 |
| Linker 14 | GKGKSGKGKSGKGKS | 55 |
| Linker 15 | GGGKSGGKGSGKGGS | 56 |
| Linker 16 | GKPGSGKPGSGKPGS | 57 |
| Linker 17 | GKPGSGKPGSGKPGSGKPGS | 58 |
| Linker 18 | GKGKSGKGKSGKGKSGKGKS | 59 |
| Linker 19 | STAGDTHLGGEDFD | 60 |
| Linker 20 | GEGGSGEGGSGEGGS | 61 |
| Linker 21 | GGEGSGGEGSGGEGS | 62 |
| Linker 22 | GEGESGEGESGEGES | 63 |
| Linker 23 | GGGESGGEGSGEGGS | 64 |
| Linker 24 | GEGESGEGESGEGESGEGES | 65 |

TABLE 1-continued

| Linker name | Amino acid sequence | SEQ ID NO: |
|---|---|---|
| Linker 25 | GSTSGSGKPGSGEGSTKG | 66 |
| Linker 26 | PRGASKSGSASQTGSAPGS | 67 |
| Linker 27 | GTAAAGAGAAGGAAAGAAG | 68 |
| Linker 28 | GTSGSSGSGSGGSGSGGGG | 69 |
| Linker 29 | GKPGSGKPGSGKPGSGKPGS | 70 |
| Linker 30 | GSGS | 71 |
| Linker 31 | APAPAPAPAP | 72 |
| Linker 32 | APAPAPAPAPAPAPAPAPAP | 73 |
| Linker 33 | AEAAAKEAAAKEAAAAKEAAAAKEAAAAK AAA | 74 |

An embodiment of the invention also provides antigen binding portions of any of the antibodies described herein. The antigen binding portion can be any portion that has at least one antigen binding site, such as Fab, F(ab')2, dsFv, sFv, diabodies, and triabodies.

In some embodiments, antigen-binding fragments are heavy chain complementarity determining regions (HCDR) 1, 2 and/or 3, light chain complementarity determining regions (LCDR) 1, 2 and/or 3, a heavy chain variable region (VH), or a light chain variable region (VL), Fab, F(ab')2, Fd and Fv fragments and domain antibodies (dAb) comprising (e.g., consisting of) either one VH domain or one VL domain. VH and VL domains may be linked together via a linker, e.g., a synthetic linker.

"Complementarity determining regions (CDR)" are antigen binding sites in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk, Mol Biol 196:901-17, 1987). The International ImMunoGeneTics (IMGT) database (http://imgt_org) provides a standardized numbering and definition of antigen-binding sites. The correspondence between CDRs, HVs and IMGT delineations is described in Lefranc et al., Dev Comparat Immunol 27:55-77, 2003. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, scintillates, avidin, streptavidin, protein A, protein G, antibodies or fragments thereof, polyhistidine, Ni2+, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases, the detectable label emits a signal as a result of being stimulated by an external field. Suitable dyes include any commercially available dyes such as, for example, 5(6)-carboxyfluorescein, IRDye® (near-infrared fluorescent dye) 680RD maleimide or IRDye® (near-infrared fluorescent dye) 800CW, ruthenium polypyridyl dyes, and the like. Suitable fluorophores are fluorescein isothiocyanate (FITC), fluorescein thiosemicarbazide, rhodamine, Texas Red, CyDye™ (fluorophores designed for a broad range of applications, e.g., Cy3, Cy5, Cy5.5), Alexa Fluor® (fluorescent dyes, e.g., Alexa488, Alexa555, Alexa594; Alexa647), near infrared (NIR) (700-900 nm) fluorescent dyes, and carbocyanine and aminostyryl dyes.

Also provided by the present disclosure is a nucleic acid comprising a nucleotide sequence encoding any of the CARs, polypeptides, or proteins described herein (including functional portions and functional variants thereof).

The portion of the CAR comprising an antibody or antibody fragment thereof may exist in a variety of forms where the antigen-binding domain is expressed as part of a contiguous polypeptide chain including, for example, a single domain antibody fragment (sdAb), a scFv and a human chimeric or humanized antibody (Harlow et al., 1999, In: Using *Antibodies: A Laboratory Manual*, Cold Spring Harbor Laboratory Press, N.Y.; Harlow et al., 1989, In: *Antibodies: A Laboratory Manual*, Cold Spring Harbor, N.Y.; Houston et al., 1988, *Proc. Natl. Acad. Sci. USA* 85:5879-5883; Bird et al., 1988, Science 242:423-426). In one aspect, the antigen-binding domain of a CAR composition of the invention comprises an antibody fragment. In one aspect, the CAR comprises an antibody fragment that comprises a scFv.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and known in the art.

The term "antigen" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is apparent that the present disclosure includes, but is not limited to, the use of partial nucleotide sequences of more than one gene and that these nucleotide sequences are arranged in various combinations to encode polypeptides that elicit the desired immune response.

In one aspect, the disclosure provides a CAR, comprising an extracellular antigen-binding domain, a transmembrane domain and an intracellular signaling domain, wherein the extracellular antigen-binding domain binds the CD79b antigen.

In one aspect, the disclosure provides a CAR, comprising an extracellular antigen-binding domain, a transmembrane domain and an intracellular signaling domain, wherein the extracellular antigen-binding domain comprises: In one embodiment, the extracellular antigen-binding domain comprises:

a) a heavy chain CDR1, a CDR2 and a CDR3 of a heavy chain variable region (VH) of SEQ ID NO: 1 and a light chain CDR1, a CDR2 and a CDR3 of a light chain variable region (VL) of SEQ ID NO: 19;
b) a heavy chain CDR1, a CDR2 and a CDR3 of a heavy chain variable region (VH) of SEQ ID NO: 1 and a light chain CDR1, a CDR2 and a CDR3 of a light chain variable region (VL) of SEQ ID NO: 20;
c) a heavy chain CDR1, a CDR2 and a CDR3 of a heavy chain variable region (VH) of SEQ ID NO: 2 and a light chain complementarity determining region (CDR) 2, a CDR2 and a CDR3 of a light chain variable region (VL) of SEQ ID NO: 19;
d) a heavy chain CDR1, a CDR2 and a CDR3 of a heavy chain variable region (VH) of SEQ ID NO: 2 and a light chain CDR1, a CDR2 and a CDR3 of a light chain variable region (VL) of SEQ ID NO: 20;
e) a heavy chain CDR1, a CDR2 and a CDR3 of a heavy chain variable region (VH) of SEQ ID NO: 3 and a light chain CDR1, a CDR2 and a CDR3 of a light chain variable region (VL) of SEQ ID NO: 20;
f) a heavy chain CDR1, a CDR2 and a CDR3 of a heavy chain variable region (VH) of SEQ ID NO: 4 and a light chain CDR1, a CDR2 and a CDR3 of a light chain variable region (VL) of SEQ ID NO: 19;
g) a heavy chain CDR1, a CDR2 and a CDR3 of a heavy chain variable region (VH) of SEQ ID NO: 5 and a light chain CDR1, a CDR2 and a CDR3 of a light chain variable region (VL) of SEQ ID NO: 22;
h) a heavy chain CDR1, a CDR2 and a CDR3 of a heavy chain variable region (VH) of SEQ ID NO: 5 and a light chain CDR1, a CDR2 and a CDR3 of a light chain variable region (VL) of SEQ ID NO: 23;
i) a heavy chain CDR1, a CDR2 and a CDR3 of a heavy chain variable region (VH) of SEQ ID NO: 6 and a light chain CDR1, a CDR2 and a CDR3 of a light chain variable region (VL) of SEQ ID NO: 24;
j) a heavy chain CDR1, a CDR2 and a CDR3 of a heavy chain variable region (VH) of SEQ ID NO: 7 and a light chain CDR1, a CDR2 and a CDR3 of a light chain variable region (VL) of SEQ ID NO: 26;
k) a heavy chain CDR1, a CDR2 and a CDR3 of a heavy chain variable region (VH) of SEQ ID NO: 8 and a light chain CDR1, a CDR2 and a CDR3 of a light chain variable region (VL) of SEQ ID NO: 25;
l) a heavy chain CDR1, a CDR2 and a CDR3 of a heavy chain variable region (VH) of SEQ ID NO: 9 and a light chain CDR1, a CDR2 and a CDR3 of a light chain variable region (VL) of SEQ ID NO: 27;

m) a heavy chain CDR1, a CDR2 and a CDR3 of a heavy chain variable region (VH) of SEQ ID NO: 10 and a light chain CDR1, a CDR2 and a CDR3 of a light chain variable region (VL) of SEQ ID NO: 28;
n) a heavy chain CDR1, a CDR2 and a CDR3 of a heavy chain variable region (VH) of SEQ ID NO: 11 and a light chain CDR1, a CDR2 and a CDR3 of a light chain variable region (VL) of SEQ ID NO: 29;
o) a heavy chain CDR1, a CDR2 and a CDR3 of a heavy chain variable region (VH) of SEQ ID NO: 12 and a light chain CDR1, a CDR2 and a CDR3 of a light chain variable region (VL) of SEQ ID NO: 30;
p) a heavy chain CDR1, a CDR2 and a CDR3 of a heavy chain variable region (VH) of SEQ ID NO: 13 and a light chain CDR1, a CDR2 and a CDR3 of a light chain variable region (VL) of SEQ ID NO: 31;
q) a heavy chain CDR1, a CDR2 and a CDR3 of a heavy chain variable region (VH) of SEQ ID NO: 14 and a light chain CDR1, a CDR2 and a CDR3 of a light chain variable region (VL) of SEQ ID NO: 32;
r) a heavy chain CDR1, a CDR2 and a CDR3 of a heavy chain variable region (VH) of SEQ ID NO: 15 and a light chain CDR1, a CDR2 and a CDR3 of a light chain variable region (VL) of SEQ ID NO: 33;
s) a heavy chain CDR1, a CDR2 and a CDR3 of a heavy chain variable region (VH) of SEQ ID NO: 16 and a light chain CDR1, a CDR2 and a CDR3 of a light chain variable region (VL) of SEQ ID NO: 34;
t) a heavy chain CDR1, a CDR2 and a CDR3 of a heavy chain variable region (VH) of SEQ ID NO: 16 and a light chain CDR1, a CDR2 and a CDR3 of a light chain variable region (VL) of SEQ ID NO: 35;
u) a heavy chain CDR1, a CDR2 and a CDR3 of a heavy chain variable region (VH) of SEQ ID NO: 17 and a light chain CDR1, a CDR2 and a CDR3 of a light chain variable region (VL) of SEQ ID NO: 33; or
v) a heavy chain CDR1, a CDR2 and a CDR3 of a heavy chain variable region (VH) of SEQ ID NO: 18 and a light chain CDR1, a CDR2 and a CDR3 of a light chain variable region (VL) of SEQ ID NO: 36.

In one embodiment, the extracellular antigen-binding domain comprises:

a heavy chain CDR1, a CDR2 and a CDR3 of a heavy chain variable region (VH) of SEQ ID NO: 14 and a light chain CDR1, a CDR2 and a CDR3 of a light chain variable region (VL) of SEQ ID NO: 32.

In one aspect, the disclosure provides a CAR, comprising an extracellular antigen-binding domain, a transmembrane domain and an intracellular signaling domain, wherein the extracellular antigen-binding domain comprises:

a heavy chain CDR1 having an amino acid sequence selected from the group consisting of SEQ ID NOs: 208, 216, 222, 228, 232, 238, 242, 248, 253, 257, 263, 268, and 274, and conservative modifications thereof, wherein the extracellular antigen-binding domain binds the CD79b antigen.

In one aspect, the disclosure provides a CAR, comprising an extracellular antigen-binding domain, a transmembrane domain and an intracellular signaling domain, wherein the extracellular antigen-binding domain comprises:

a heavy chain CDR2 having an amino acid sequence selected from the group consisting of SEQ ID NOs: 209, 217, 223, 233, 239, 243, 249, 254, 258, 269, and 275, and conservative modifications thereof, wherein the extracellular antigen-binding domain binds the CD79b antigen.

In one aspect, the disclosure provides a CAR, comprising an extracellular antigen-binding domain, a transmembrane domain and an intracellular signaling domain, wherein the extracellular antigen-binding domain comprises:

a heavy chain CDR3 having an amino acid sequence selected from the group consisting of SEQ ID NOs: 210, 218, 224, 229, 234, 240, 244, 250, 255, 259, 264, 270, and 276, and conservative modifications thereof, wherein the extracellular antigen-binding domain binds the CD79b antigen.

In one aspect, the disclosure provides a CAR, comprising an extracellular antigen-binding domain, a transmembrane domain and an intracellular signaling domain, wherein the extracellular antigen-binding domain comprises:

a heavy chain complementarity determining region 1 (CDR1) having the amino acid sequence of SEQ ID NO: 208, a heavy chain CDR2 having the amino acid sequence of SEQ ID NO: 209, and a heavy chain CDR3 having the amino acid sequence of SEQ ID NO: 210;
a heavy chain CDR1 having the amino acid sequence of SEQ ID NO: 216, a heavy chain CDR2 having the amino acid sequence of SEQ ID NO: 217, and a heavy chain CDR3 having the amino acid sequence of SEQ ID NO: 218;
a heavy chain CDR1 having the amino acid sequence of SEQ ID NO: 222, a heavy chain CDR2 having the amino acid sequence of SEQ ID NO: 223, and a heavy chain CDR3 having the amino acid sequence of SEQ ID NO: 224;
a heavy chain CDR1 having the amino acid sequence of SEQ ID NO: 228, a heavy chain CDR2 having the amino acid sequence of SEQ ID NO: 217, and a heavy chain CDR3 having the amino acid sequence of SEQ ID NO: 229;
a heavy chain CDR1 having the amino acid sequence of SEQ ID NO: 232, a heavy chain CDR2 having the amino acid sequence of SEQ ID NO: 233, and a heavy chain CDR3 having the amino acid sequence of SEQ ID NO: 234;
a heavy chain CDR1 having the amino acid sequence of SEQ ID NO: 238, a heavy chain CDR2 having the amino acid sequence of SEQ ID NO: 239, and a heavy chain CDR3 having the amino acid sequence of SEQ ID NO: 240;
a heavy chain CDR1 having the amino acid sequence of SEQ ID NO: 242, a heavy chain CDR2 having the amino acid sequence of SEQ ID NO: 243, and a heavy chain CDR3 having the amino acid sequence of SEQ ID NO: 244;
a heavy chain CDR1 having the amino acid sequence of SEQ ID NO: 248, a heavy chain CDR2 having the amino acid sequence of SEQ ID NO: 249, and a heavy chain CDR3 having the amino acid sequence of SEQ ID NO: 250;
a heavy chain CDR1 having the amino acid sequence of SEQ ID NO: 253, a heavy chain CDR2 having the amino acid sequence of SEQ ID NO: 254, and a heavy chain CDR3 having the amino acid sequence of SEQ ID NO: 255;
a heavy chain CDR1 having the amino acid sequence of SEQ ID NO: 257, a heavy chain CDR2 having the amino acid sequence of SEQ ID NO: 258, and a heavy chain CDR3 having the amino acid sequence of SEQ ID NO: 259;
a heavy chain CDR1 having the amino acid sequence of SEQ ID NO: 263, a heavy chain CDR2 having the amino acid sequence of SEQ ID NO: 243, and a heavy chain CDR3 having the amino acid sequence of SEQ ID NO: 264;

a heavy chain CDR1 having the amino acid sequence of SEQ ID NO: 268, a heavy chain CDR2 having the amino acid sequence of SEQ ID NO: 269, and a heavy chain CDR3 having the amino acid sequence of SEQ ID NO: 270; or a heavy chain CDR1 having the amino acid sequence of SEQ ID NO: 274, a heavy chain CDR2 having the amino acid sequence of SEQ ID NO: 275, and a heavy chain CDR3 having the amino acid sequence of SEQ ID NO: 276;

wherein the extracellular antigen-binding domain binds the CD79b antigen.

In one embodiment, the CAR of the disclosure comprises an extracellular antigen-binding domain, a transmembrane domain and an intracellular signaling domain, wherein the extracellular antigen-binding domain comprises:

a heavy chain CDR1 having the amino acid sequence of SEQ ID NO: 257, a heavy chain CDR2 having the amino acid sequence of SEQ ID NO: 258, and a heavy chain CDR3 having the amino acid sequence of SEQ ID NO: 259.

In one aspect, the disclosure provides a CAR, comprising an extracellular antigen-binding domain, a transmembrane domain and an intracellular signaling domain, wherein the extracellular antigen-binding domain comprises:

a light chain CDR1 having an amino acid sequence selected from the group consisting of SEQ ID NOs: 211, 214, 215, 219, 225, 230, 235, 241, 245, 251, 260, 265, 271, and 277, and conservative modifications thereof, wherein the extracellular antigen-binding domain binds the CD79b antigen.

In one aspect, the disclosure provides a CAR, comprising an extracellular antigen-binding domain, a transmembrane domain and an intracellular signaling domain, wherein the extracellular antigen-binding domain comprises:

a light chain CDR2 having an amino acid sequence selected from the group consisting of SEQ ID NOs: 212, 220, 226, 231, 236, 246, 261, 266, and 272, and conservative modifications thereof, wherein the extracellular antigen-binding domain binds the CD79b antigen.

In one aspect, the disclosure provides a CAR, comprising an extracellular antigen-binding domain, a transmembrane domain and an intracellular signaling domain, wherein the extracellular antigen-binding domain comprises:

a light chain CDR3 having an amino acid sequence selected from the group consisting of SEQ ID NOs: 213, 221, 227, 237, 247, 252, 256, 262, 267, 273, or 278, and conservative modifications thereof, wherein the extracellular antigen-binding domain binds the CD79b antigen.

In one aspect, the disclosure provides a CAR, comprising an extracellular antigen-binding domain, a transmembrane domain and an intracellular signaling domain, wherein the extracellular antigen-binding domain comprises:

a light chain CDR1 having the amino acid sequence of SEQ ID NO: 211, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 214, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 215, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 219, a light chain CDR2 having the amino acid sequence of SEQ ID NO: 220, and a light chain CDR3 having the amino acid sequence of SEQ ID NO: 221;

a light chain CDR1 having the amino acid sequence of SEQ ID NO: 225, a light chain CDR2 having the amino acid sequence of SEQ ID NO: 226, and a light chain CDR3 having the amino acid sequence of SEQ ID NO: 227;

a light chain CDR1 having the amino acid sequence of SEQ ID NO: 230, a light chain CDR2 having the amino acid sequence of SEQ ID NO: 231, and a light chain CDR3 having the amino acid sequence of SEQ ID NO: 221;

a light chain CDR1 having the amino acid sequence of SEQ ID NO: 235, a light chain CDR2 having the amino acid sequence of SEQ ID NO: 236, and a light chain CDR3 having the amino acid sequence of SEQ ID NO: 237;

a light chain CDR1 having the amino acid sequence of SEQ ID NO: 241, a light chain CDR2 having the amino acid sequence of SEQ ID NO: 226, and a light chain CDR3 having the amino acid sequence of SEQ ID NO: 227;

a light chain CDR1 having the amino acid sequence of SEQ ID NO: 245, a light chain CDR2 having the amino acid sequence of SEQ ID NO: 246, and a light chain CDR3 having the amino acid sequence of SEQ ID NO: 247;

a light chain CDR1 having the amino acid sequence of SEQ ID NO: 251, a light chain CDR2 having the amino acid sequence of SEQ ID NO: 236, and a light chain CDR3 having the amino acid sequence of SEQ ID NO: 252;

a light chain CDR1 having the amino acid sequence of SEQ ID NO: 251, a light chain CDR2 having the amino acid sequence of SEQ ID NO: 236, and a light chain CDR3 having the amino acid sequence of SEQ ID NO: 256;

a light chain CDR1 having the amino acid sequence of SEQ ID NO: 260, a light chain CDR2 having the amino acid sequence of SEQ ID NO: 261, and a light chain CDR3 having the amino acid sequence of SEQ ID NO: 262;

a light chain CDR1 having the amino acid sequence of SEQ ID NO: 265, a light chain CDR2 having the amino acid sequence of SEQ ID NO: 266, and a light chain CDR3 having the amino acid sequence of SEQ ID NO: 267;

a light chain CDR1 having the amino acid sequence of SEQ ID NO: 271, a light chain CDR2 having the amino acid sequence of SEQ ID NO: 272, and a light chain CDR3 having the amino acid sequence of SEQ ID NO: 273; or a light chain CDR1 having the amino acid sequence of SEQ ID NO: 277, a light chain CDR2 having the amino acid sequence of SEQ ID NO: 266, and a light chain CDR3 having the amino acid sequence of SEQ ID NO: 278;

wherein the extracellular antigen-binding domain binds the CD79b antigen.

In one embodiment, the CAR of the disclosure comprises an extracellular antigen-binding domain, a transmembrane domain and an intracellular signaling domain, wherein the extracellular antigen-binding domain comprises:

a light chain CDR1 having the amino acid sequence of SEQ ID NO: 260, a light chain CDR2 having the amino acid sequence of SEQ ID NO: 261, and a light chain CDR3 having the amino acid sequence of SEQ ID NO: 262.

In one embodiment, the extracellular antigen-binding domain comprises the heavy chain CDR1, the heavy chain CDR2, the heavy chain CDR3, the light chain CDR1, the light chain CDR2 and the light chain CDR3 having the amino acid sequence of a) SEQ ID NOs: 208, 209, 210, 211, 212 and 213, respectively;
b) SEQ ID NOs: 208, 209, 210, 214, 212 and 213, respectively;
c) SEQ ID NOs: 208, 209, 210, 215, 212 and 213, respectively;
d) SEQ ID NOs: 216, 217, 218, 219, 220 and 221, respectively;
e) SEQ ID NOs: 222, 223, 224, 225, 226, and 227, respectively;
f) SEQ ID NOs: 228, 217, 229, 230, 231, and 221, respectively;
g) SEQ ID NOs: 232, 233, 234, 235, 236, and 237, respectively;
h) SEQ ID NOs: 238, 239, 240, 241, 226, and 227, respectively;
i) SEQ ID NOs: 242, 243, 244, 245, 246, and 247, respectively;
j) SEQ ID NOs: 248, 249, 250, 251, 236, and 252, respectively;
k) SEQ ID NOs: 253, 254, 255, 251, 236, and 256, respectively;
l) SEQ ID NOs: 257, 258, 259, 260, 261, and 262, respectively;
m) SEQ ID NOs: 263, 243, 264, 265, 266, and 267, respectively;
n) SEQ ID NOs: 268, 269, 270, 271, 272, and 273, respectively; or
o) SEQ ID NOs: 274, 275, 276, 277, 266, and 278, respectively.

In one embodiment, the extracellular antigen-binding domain comprises the heavy chain CDR1, the heavy chain CDR2, the heavy chain CDR3, the light chain CDR1, the light chain CDR2 and the light chain CDR3 having the amino acid sequence of SEQ ID NOs: 257, 258, 259, 260, 261, and 262, respectively.

In one embodiment, the extracellular antigen-binding domain comprises a heavy chain variable domain (HCVH) comprising an amino acid sequence selected from SEQ ID NOS: 1-18; or a light chain variable domain (LCVL) comprising an amino acid sequence selected from SEQ ID NOS: 19-36, or a combination of a HCVH comprising an amino acid sequence selected from the group consisting of SEQ ID NOS: 1-18, and a LCVL comprising an amino acid sequence selected from the group consisting of SEQ ID NOS: 19-36.

In one embodiment, the extracellular antigen-binding domain comprises:

a heavy chain variable region comprising an amino acid sequence of SEQ ID NO: 1 and a light chain variable region comprising an amino acid sequence of SEQ ID NO: 19;

a heavy chain variable region comprising an amino acid sequence of SEQ ID NO: 1 and a light chain variable region comprising an amino acid sequence of SEQ ID NO: 20;

a heavy chain variable region comprising an amino acid sequence of SEQ ID NO: 2 and a light chain variable region comprising an amino acid sequence of SEQ ID NO: 19;

a heavy chain variable region comprising an amino acid sequence of SEQ ID NO: 2 and a light chain variable region comprising an amino acid sequence of SEQ ID NO: 20;

a heavy chain variable region comprising an amino acid sequence of SEQ ID NO: 3 and a light chain variable region comprising an amino acid sequence of SEQ ID NO: 20;

a heavy chain variable region comprising an amino acid sequence of SEQ ID NO: 4 and a light chain variable region comprising an amino acid sequence of SEQ ID NO: 19;

a heavy chain variable region comprising an amino acid sequence of SEQ ID NO: 5 and a light chain variable region comprising an amino acid sequence of SEQ ID NO: 22;

a heavy chain variable region comprising an amino acid sequence of SEQ ID NO: 5 and a light chain variable region comprising an amino acid sequence of SEQ ID NO: 23;

a heavy chain variable region comprising an amino acid sequence of SEQ ID NO: 6 and a light chain variable region comprising an amino acid sequence of SEQ ID NO: 24;

a heavy chain variable region comprising an amino acid sequence of SEQ ID NO: 7 and a light chain variable region comprising an amino acid sequence of SEQ ID NO: 26;

a heavy chain variable region comprising an amino acid sequence of SEQ ID NO: 8 and a light chain variable region comprising an amino acid sequence of SEQ ID NO: 25;

a heavy chain variable region comprising an amino acid sequence of SEQ ID NO: 9 and a light chain variable region comprising an amino acid sequence of SEQ ID NO: 27;

a heavy chain variable region comprising an amino acid sequence of SEQ ID NO: 10 and a light chain variable region comprising an amino acid sequence of SEQ ID NO: 28;

a heavy chain variable region comprising an amino acid sequence of SEQ ID NO: 11 and a light chain variable region comprising an amino acid sequence of SEQ ID NO: 29;

a heavy chain variable region comprising an amino acid sequence of SEQ ID NO: 12 and a light chain variable region comprising an amino acid sequence of SEQ ID NO: 30;

a heavy chain variable region comprising an amino acid sequence of SEQ ID NO: 13 and a light chain variable region comprising an amino acid sequence of SEQ ID NO: 31;

a heavy chain variable region comprising an amino acid sequence of SEQ ID NO: 14 and a light chain variable region comprising an amino acid sequence of SEQ ID NO: 32;

a heavy chain variable region comprising an amino acid sequence of SEQ ID NO: 15 and a light chain variable region comprising an amino acid sequence of SEQ ID NO: 33;

a heavy chain variable region comprising an amino acid sequence of SEQ ID NO: 16 and a light chain variable region comprising an amino acid sequence of SEQ ID NO: 34;

a heavy chain variable region comprising an amino acid sequence of SEQ ID NO: 16 and a light chain variable region comprising an amino acid sequence of SEQ ID NO: 35;

a heavy chain variable region comprising an amino acid sequence of SEQ ID NO: 17 and a light chain variable region comprising an amino acid sequence of SEQ ID NO: 33; or a heavy chain variable region comprising an amino acid sequence of SEQ ID NO: 18 and a light chain variable region comprising an amino acid sequence of SEQ ID NO: 36.

In one embodiment, the extracellular antigen-binding domain comprises:

a heavy chain variable region comprising an amino acid sequence of SEQ ID NO: 14 and a light chain variable region comprising an amino acid sequence of SEQ ID NO: 32.

In one embodiment, the extracellular antigen-binding domain comprises:

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 1 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 19;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 1 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 20;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 2 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 19;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 2 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 20;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 3 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 20;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 4 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 19;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 5 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 22;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 5 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 23;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 6 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 24;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 7 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 26;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 8 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 25;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 9 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 27;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 10 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 28;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 11 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 29;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 12 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 30;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 13 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 31;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 14 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 32;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 15 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 33;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 16 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 34;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 16 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 35;

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 17 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 33; or a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO:

18 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 36.

In one embodiment, the extracellular antigen-binding domain comprises:

a heavy chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 14 and a light chain variable region comprising an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 32.

In one embodiment, the extracellular antigen-binding domain comprises a scFv. In some embodiments, the scFv comprises a linker polypeptide between the light chain variable region and the heavy chain variable region. In certain embodiments, the extracellular antigen-binding domain is a scFv which comprises an amino acid sequence selected from the group consisting of SEQ ID NOS: 75-118, and specifically binds to a CD79b polypeptide (e.g., a human CD79b polypeptide having the amino acid sequence described herein, or fragments thereof). In some embodiments, the linker polypeptide comprises an amino acid sequence selected from the group consisting of SEQ ID NOS: 42-74.

In one embodiment, the linker polypeptide comprises an amino acid sequence of SEQ ID NO: 42. In one embodiment, the linker polypeptide comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 42.

In one embodiment, the scFv comprises an amino acid sequence selected from the group consisting of SEQ ID NOS: 75-118. In one embodiment, the scFv comprises an amino acid sequence of SEQ ID NO: 75. In one embodiment, the scFv comprises an amino acid sequence of SEQ ID NO: 76. In one embodiment, the scFv comprises an amino acid sequence of SEQ ID NO: 77. In one embodiment, the scFv comprises an amino acid sequence of SEQ ID NO: 78. In one embodiment, the scFv comprises an amino acid sequence of SEQ ID NO: 79. In one embodiment, the scFv comprises an amino acid sequence of SEQ ID NO: 80. In one embodiment, the scFv comprises an amino acid sequence of SEQ ID NO: 81. In one embodiment, the scFv comprises an amino acid sequence of SEQ ID NO: 82. In one embodiment, the scFv comprises an amino acid sequence of SEQ ID NO: 83. In one embodiment, the scFv comprises an amino acid sequence of SEQ ID NO: 84. In one embodiment, the scFv comprises an amino acid sequence of SEQ ID NO: 85. In one embodiment, the scFv comprises an amino acid sequence of SEQ ID NO: 86. In one embodiment, the scFv comprises an amino acid sequence of SEQ ID NO: 87. In one embodiment, the scFv comprises an amino acid sequence of SEQ ID NO: 88. In one embodiment, the scFv comprises an amino acid sequence of SEQ ID NO: 89. In one embodiment, the scFv comprises an amino acid sequence of SEQ ID NO: 90. In one embodiment, the scFv comprises an amino acid sequence of SEQ ID NO: 91. In one embodiment, the scFv comprises an amino acid sequence of SEQ ID NO: 92. In one embodiment, the scFv comprises an amino acid sequence of SEQ ID NO: 93. In one embodiment, the scFv comprises an amino acid sequence of SEQ ID NO: 94. In one embodiment, the scFv comprises an amino acid sequence of SEQ ID NO: 95. In one embodiment, the scFv comprises an amino acid sequence of SEQ ID NO: 96. In one embodiment, the scFv comprises an amino acid sequence of SEQ ID NO: 97. In one embodiment, the scFv comprises an amino acid sequence of SEQ ID NO: 98. In one embodiment, the scFv comprises an amino acid sequence of SEQ ID NO: 99. In one embodiment, the scFv comprises an amino acid sequence of SEQ ID NO: 100. In one embodiment, the scFv comprises an amino acid sequence of SEQ ID NO: 101. In one embodiment, the scFv comprises an amino acid sequence of SEQ ID NO: 102. In one embodiment, the scFv comprises an amino acid sequence of SEQ ID NO: 103. In one embodiment, the scFv comprises an amino acid sequence of SEQ ID NO: 104. In one embodiment, the scFv comprises an amino acid sequence of SEQ ID NO: 105. In one embodiment, the scFv comprises an amino acid sequence of SEQ ID NO: 106. In one embodiment, the scFv comprises an amino acid sequence of SEQ ID NO: 107. In one embodiment, the scFv comprises an amino acid sequence of SEQ ID NO: 108. In one embodiment, the scFv comprises an amino acid sequence of SEQ ID NO: 109. In one embodiment, the scFv comprises an amino acid sequence of SEQ ID NO: 110. In one embodiment, the scFv comprises an amino acid sequence of SEQ ID NO: 111. In one embodiment, the scFv comprises an amino acid sequence of SEQ ID NO: 112. In one embodiment, the scFv comprises an amino acid sequence of SEQ ID NO: 113. In one embodiment, the scFv comprises an amino acid sequence of SEQ ID NO: 114. In one embodiment, the scFv comprises an amino acid sequence of SEQ ID NO: 115. In one embodiment, the scFv comprises an amino acid sequence of SEQ ID NO: 116. In one embodiment, the scFv comprises an amino acid sequence of SEQ ID NO: 117. In one embodiment, the scFv comprises an amino acid sequence of SEQ ID NO: 118.

In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with a sequence selected from the group consisting of SEQ ID NOS: 75-118. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 75. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 76. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 77. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 78. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 79. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 80. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 81. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 82. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 83. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 84. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 85. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 86. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 87. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 88. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 89. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 90. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 91. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 92. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 93. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 94. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 95. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 96. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 97. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 98. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 99. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 100. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 101. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 102. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 103. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 104. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 105. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 106. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 107. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 108. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 109. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 110. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 111. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 112. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 113. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 114. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 115. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 116. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 117. In one embodiment, the scFv comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 118.

In one embodiment, the extracellular antigen-binding domain is a scFv which comprises an amino acid sequence of SEQ ID NO: 113, or an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 113.

In one embodiment, the extracellular antigen-binding domain comprises a signal polypeptide. In some embodiments, the signal polypeptide comprises an amino acid sequence of SEQ ID NO: 37. In one embodiment, the signal polypeptide comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 37.

In one aspect, the disclosure provides a CAR, comprising an extracellular antigen-binding domain, a transmembrane domain and an intracellular signaling domain, wherein the extracellular antigen-binding domain comprises an amino acid sequence selected from the group consisting of SEQ ID NOS: 119-162. Another feature of the CAR having an extracellular antigen-binding domain comprising an amino acid sequence selected from the group consisting of SEQ ID NOS: 119-162 is that the extracellular antigen-binding domain binds the CD79b antigen.

In one embodiment, the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member (such as, e.g., CD28 or inducible T-cell co-stimulator (ICOS)) component, and a combination thereof.

In one embodiment, the CD137 component comprises an amino acid sequence of SEQ ID NO: 40. In one embodiment, the CD137 component comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 40.

In one embodiment, the CD3z component comprises an amino acid sequence of SEQ ID NO: 41. In one embodiment, the CD3z component comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 41.

In one embodiment, the intracellular signaling domain comprises an amino acid sequence of SEQ ID NO: 163. In one embodiment, the intracellular signaling domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 163.

In one embodiment, the transmembrane domain comprises a CD8a transmembrane region (CD8a-TM) polypeptide. In some embodiments, the CD8a-TM polypeptide comprises an amino acid sequence of SEQ ID NO: 39. In some embodiments, the CD8a-TM polypeptide comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 39.

In one embodiment, the transmembrane domain comprises at least the transmembrane region(s) of) the α, β or ζ chain of the T-cell receptor, CD28, CD3 epsilon, CD45, CD4, CD5, CD8, CD8a, CD9, CD16, CD22, CD33, CD37, CD40, CD64, CD80, CD86, CD134, CD137, CD154. In another embodiment, the transmembrane domain comprises at least the transmembrane domain of, ζ, η or FcFR1γ and -β, MB1 (Igα), B29 or CD3-γ, ζ, or η. In another embodiment, the transmembrane domain is synthetic, e.g., comprising predominantly hydrophobic residues such as leucine and valine, a triplet of phenylalanine, or tryptophan.

In one embodiment, the CAR further comprises a hinge region linking the transmembrane domain to the extracellular antigen-binding domain. In some embodiments, the hinge region is a CD8a-hinge region. In some embodiments, CD8a-hinge region comprises an amino acid sequence of SEQ ID NO: 38. In some embodiments, the CD8a-hinge region comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 38. In some embodiments, the hinge region comprises the sequence EPKSCDKTHTCPPCP (SEQ ID NO: 285), or comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with EPKSCDKTHTCPPCP (SEQ ID NO: 285). In some embodiments, the hinge region comprises the sequence ERKCCVECPPCP (SEQ ID NO: 286), or comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with ERKCCVECPPCP (SEQ ID NO: 286). In some embodiments, the hinge region comprises the sequence ELKTPLGDTTHTCPRCP $(EPKSCDTPPPCPRCP)_3$ (SEQ ID NO: 287), or comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with ELKTPLGDTTHTCPRCP$(EPKSCDTPPPCPRCP)_3$ (SEQ ID NO: 287). In some embodiments, the hinge region comprises the sequence ESKYGPPCPSCP (SEQ ID NO: 288), or comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with ESKYGPPCPSCP (SEQ ID NO: 288).

In one embodiment, the extracellular antigen-binding domain comprises an amino acid sequence selected from the group consisting of SEQ ID NOS: 119-162. In one embodiment, the extracellular antigen-binding domain comprises an amino acid sequence of SEQ ID NO: 119. In one embodiment, the extracellular antigen-binding domain comprises an amino acid sequence of SEQ ID NO: 120. In one embodiment, the extracellular antigen-binding domain comprises an amino acid sequence of SEQ ID NO: 121. In one embodiment, the extracellular antigen-binding domain comprises an amino acid sequence of SEQ ID NO: 122. In one embodiment, the extracellular antigen-binding domain comprises an amino acid sequence of SEQ ID NO: 123. In one embodiment, the extracellular antigen-binding domain comprises an amino acid sequence of SEQ ID NO: 124. In one embodiment, the extracellular antigen-binding domain comprises an amino acid sequence of SEQ ID NO: 125. In one embodiment, the extracellular antigen-binding domain comprises an amino acid sequence of SEQ ID NO: 126. In one embodiment, the extracellular antigen-binding domain comprises an amino acid sequence of SEQ ID NO: 127. In one embodiment, the extracellular antigen-binding domain comprises an amino acid sequence of SEQ ID NO: 128. In one embodiment, the extracellular antigen-binding domain comprises an amino acid sequence of SEQ ID NO: 129. In one embodiment, the extracellular antigen-binding domain comprises an amino acid sequence of SEQ ID NO: 130. In one embodiment, the extracellular antigen-binding domain comprises an amino acid sequence of SEQ ID NO: 131. In one embodiment, the extracellular antigen-binding domain comprises an amino acid sequence of SEQ ID NO: 132. In one embodiment, the extracellular antigen-binding domain comprises an amino acid sequence of SEQ ID NO: 133. In one embodiment, the extracellular antigen-binding domain comprises an amino acid sequence of SEQ ID NO: 134. In one embodiment, the extracellular antigen-binding domain comprises an amino acid sequence of SEQ ID NO: 135. In one embodiment, the extracellular antigen-binding domain comprises an amino acid sequence of SEQ ID NO: 136. In one embodiment, the extracellular antigen-binding domain comprises an amino acid sequence of SEQ ID NO: 137. In one embodiment, the extracellular antigen-binding domain comprises an amino acid sequence of SEQ ID NO: 138. In one embodiment, the extracellular antigen-binding domain comprises an amino acid sequence of SEQ ID NO: 139. In one embodiment, the extracellular antigen-binding domain comprises an amino acid sequence of SEQ ID NO: 140. In one embodiment, the extracellular antigen-binding domain comprises an amino acid sequence of SEQ ID NO: 141. In one embodiment, the extracellular antigen-binding domain comprises an amino acid sequence of SEQ ID NO: 142. In one embodiment, the extracellular antigen-binding domain comprises an amino acid sequence of SEQ ID NO: 143. In one embodiment, the extracellular antigen-binding domain comprises an amino acid sequence of SEQ ID NO: 144. In one embodiment, the extracellular antigen-binding domain comprises an amino acid sequence of SEQ ID NO: 145. In one embodiment, the extracellular antigen-binding domain comprises an amino acid sequence of SEQ ID NO: 146. In one embodiment, the extracellular antigen-binding domain comprises an amino acid sequence of SEQ ID NO: 147. In one embodiment, the extracellular antigen-binding domain comprises an amino acid sequence of SEQ ID NO: 148. In one embodiment, the extracellular antigen-binding domain comprises an amino acid sequence of SEQ ID NO: 149. In one embodiment, the extracellular antigen-binding domain comprises an amino acid sequence of SEQ ID NO: 150. In one embodiment, the extracellular antigen-binding domain comprises an amino acid sequence of SEQ ID NO: 151. In one embodiment, the extracellular antigen-binding domain comprises an amino acid sequence of SEQ ID NO: 152. In one embodiment, the extracellular antigen-binding domain comprises an amino acid sequence of SEQ ID NO: 153. In one embodiment, the extracellular antigen-binding domain comprises an amino acid sequence of SEQ ID NO: 154. In one embodiment, the extracellular antigen-binding domain comprises an amino acid sequence of SEQ ID NO: 155. In one embodiment, the extracellular antigen-binding domain comprises an amino acid sequence of SEQ ID NO: 156. In one embodiment, the extracellular antigen-binding domain comprises an amino acid sequence of SEQ ID NO: 157. In one embodiment, the extracellular antigen-binding domain comprises an amino acid sequence of SEQ ID NO: 158. In one embodiment, the extracellular antigen-binding domain comprises an amino acid sequence of SEQ ID NO: 159. In one embodiment, the extracellular antigen-binding domain comprises an amino acid sequence of SEQ ID NO: 160. In one embodiment, the extracellular antigen-binding domain comprises an amino acid sequence of SEQ ID NO: 161. In one embodiment, the extracellular antigen-binding domain comprises an amino acid sequence of SEQ ID NO: 162.

In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with a sequence selected from the group consisting of SEQ ID NOS: 119-162. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 119. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 120. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 121. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 122. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 123. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 124. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 125. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 126. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 127. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 128. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 129. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 130. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 131. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 132. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 133. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 134. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 135. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 136. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 137. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 138. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 139. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 140. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 141. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 142. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 143. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 144. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 145. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 146. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 147. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 148. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 149. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 150. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 151. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 152. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 153. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 154. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 155. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 156. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 157. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 158. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 159. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 160. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 161. In one embodiment, the extracellular antigen-binding domain comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 162.

In one embodiment, the extracellular antigen-binding domain comprises an amino acid sequence of SEQ ID NO: 157, or an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 157.

CAR Constructs and Immunoresponsive Cells Expressing CARs

In one embodiment, the present disclosure provides a cell expressing the nucleic acid molecule encoding for a CAR. In one embodiment, the CAR of the present disclosure comprises an amino acid sequence selected from the group consisting of SEQ ID NOS: 164-207. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 164, or the sequence of SEQ ID NO: 164. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 165, or the sequence of SEQ ID NO: 165. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 166, or the sequence of SEQ ID NO: 166. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 167, or the sequence of SEQ ID NO: 167. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 168, or the sequence of SEQ ID NO: 168. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 169, or the sequence of SEQ ID NO: 169. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 170, or the sequence of SEQ ID NO: 170. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 171, or the sequence of SEQ ID NO: 171. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 172, or the sequence of SEQ ID NO: 172. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 173, or the sequence of SEQ ID NO: 173. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 174, or the sequence of SEQ ID NO: 174. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 175, or the sequence of SEQ ID NO: 175. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 176, or the sequence of SEQ ID NO: 176. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 177, or the sequence of SEQ ID NO: 177. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 178, or the sequence of SEQ ID NO: 178. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 179, or the sequence of SEQ ID NO: 179. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 180, or the sequence of SEQ ID NO: 180. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 181, or the sequence of SEQ ID NO: 181. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 182, or the sequence of SEQ ID NO: 182. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 183, or the sequence of SEQ ID NO: 183. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 184, or the sequence of SEQ ID NO: 184. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 185, or the sequence of SEQ ID NO: 185. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 186, or the sequence of SEQ ID NO: 186. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 187, or the sequence of SEQ ID NO: 187. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 188, or the sequence of SEQ ID NO: 188. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 189, or the sequence of SEQ ID NO: 189. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 190, or the sequence of SEQ ID NO: 190. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 191, or the sequence of SEQ ID NO: 191. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 192, or the sequence of SEQ ID NO: 192. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 193, or the sequence of SEQ ID NO: 193. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 194, or the sequence of SEQ ID NO: 194. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 195, or the sequence of SEQ ID NO: 195. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 196, or the sequence of SEQ ID NO: 196. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 197, or the sequence of SEQ ID NO: 197. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 198, or the sequence of SEQ ID NO: 198. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 199, or the sequence of SEQ ID NO: 199. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 200, or the sequence of SEQ ID NO: 200. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 201, or the sequence of SEQ ID NO: 201. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 202, or the sequence of SEQ ID NO: 202. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 203, or the sequence of SEQ ID NO: 203. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 204, or the sequence of SEQ ID NO: 204. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 205, or the sequence of SEQ ID NO: 205. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 206, or the sequence of SEQ ID NO: 206. In some embodiments, the CAR of the present disclosure comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 207, or the sequence of SEQ ID NO: 207.

In some embodiments, the CAR of the present disclosure comprises an amino acid sequence of SEQ ID NO: 202.

In one aspect, the present disclosure provides isolated immunoresponsive cells comprising the CARs described herein. In some embodiments, the isolated immunoresponsive cell is transduced with the CAR, for example, the CAR is constitutively expressed on the surface of the immunoresponsive cell. In certain embodiments, the isolated immunoresponsive cell is further transduced with at least one co-stimulatory ligand such that the immunoresponsive cell expresses the at least one co-stimulatory ligand. In certain embodiments, the at least one co-stimulatory ligand is selected from the group consisting of 4-1BBL, CD48, CD70, CD80, CD86, OX40L, TNFRSF14, and combinations thereof. In certain embodiments, the isolated immunoresponsive cell is further transduced with at least one cytokine such that the immunoresponsive cell secretes the at least one cytokine. In certain embodiments, the at least cytokine is selected from the group consisting of IL-2, IL-3, IL-6, IL-7, IL-11, IL-12, IL-15, IL-17, IL-21, and combinations thereof. In some embodiments, the isolated immunoresponsive cell is selected from the group consisting of a T lymphocyte (T cell), a Natural Killer (NK) cell, a cytotoxic T lymphocyte (CTL), a regulatory T cell, a human embryonic stem cell, a lymphoid progenitor cell, a T cell-precursor cell, and a pluripotent stem cell from which lymphoid cells may be differentiated.

In one embodiment, the CAR T cells of the disclosure can be generated by introducing a lentiviral vector comprising a desired CAR, for example, a CAR comprising anti-CD79b domain, CD8a hinge and transmembrane domain, and human 4-1BB and CD3-zeta signaling domains, into the cells. The CAR T cells of the invention are able to replicate in vivo resulting in long-term persistence that can lead to sustained tumor control.

Embodiments of the invention further provide host cells comprising any of the recombinant expression vectors described herein. As used herein, the term "host cell" refers to any type of cell that can contain the recombinant expression vector. The host cell can be a eukaryotic cell, e.g., plant, animal, or algae, fungi, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, polypeptide, or protein, the host cell may be a mammalian cell. The host cell may be a human cell. While the host cell can be of any cell type, can originate from any type of tissue, and can be of any developmental stage, the host cell may be a peripheral blood lymphocyte (PBL). The host cell may be a T cell.

For purposes herein, the T cell can be any T cell, such as a cultured T cell, e.g., a primary T cell, or a T cell from a cultured T cell line, e.g., Jurkat, SupTI, etc., or a T cell obtained from a mammal. If obtained from a mammal, the T cell can be obtained from numerous sources, including but not limited to bone marrow, blood, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD8^+$ T cells (e.g., cytotoxic T cells), $CD4^+$ helper T cells, e.g., Th1 and Th2 cells, peripheral blood mononuclear cells (PBMCs), peripheral blood leukocytes (PBLs), tumor infiltrating cells, memory T cells, naïve T cells, and the like. The T cell may be a CD8+ T cell or a CD4+ T cell.

Also provided are a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, an erythrocyte, a neutrophil, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment, the population of cells is a clonal population comprising host cells comprising a recombinant expression vector as described herein.

Pharmaceutical Compositions/Administration

In embodiments of the present disclosure, the CAR-expressing cells may be provided in compositions, e.g., suitable pharmaceutical composition(s) comprising the CAR-expressing cells and a pharmaceutically acceptable carrier. In one aspect, the present disclosure provides pharmaceutical compositions comprising an effective amount of a lymphocyte expressing one or more of the CARs described and a pharmaceutically acceptable excipient. Pharmaceutical compositions of the present disclosure may comprise a CAR-expressing cell, e.g., a plurality of CAR-expressing cells, as described herein, in combination with one or more pharmaceutically or physiologically acceptable carriers, excipients or diluents. A pharmaceutically acceptable carrier can be an ingredient in a pharmaceutical composition, other than an active ingredient, which is nontoxic to the subject.

A pharmaceutically acceptable carrier can include, but is not limited to, a buffer, excipient, stabilizer, or preservative. Examples of pharmaceutically acceptable carriers are solvents, dispersion media, coatings, antibacterial and antifungal agents, isotonic and absorption delaying agents, and the like that are physiologically compatible, such as salts, buffers, antioxidants, saccharides, aqueous or non-aqueous carriers, preservatives, wetting agents, surfactants or emulsifying agents, or combinations thereof. The amounts of pharmaceutically acceptable carrier(s) in the pharmaceutical compositions may be determined experimentally based on the activities of the carrier(s) and the desired characteristics of the formulation, such as stability and/or minimal oxidation.

Such compositions may comprise buffers such as acetic acid, citric acid, formic acid, succinic acid, phosphoric acid, carbonic acid, malic acid, aspartic acid, histidine, boric acid, Tris buffers, HEPPSO, HEPES, neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); antibacterial and antifungal agents; and preservatives.

Compositions of the present disclosure can be formulated for a variety of means of parenteral or non-parenteral administration. In one embodiment, the compositions can be formulated for infusion or intravenous administration. Compositions disclosed herein can be provided, for example, as sterile liquid preparations, e.g., isotonic aqueous solutions, emulsions, suspensions, dispersions, or viscous compositions, which may be buffered to a desirable pH. Formulations suitable for oral administration can include liquid solutions, capsules, sachets, tablets, lozenges, and troches, powders liquid suspensions in an appropriate liquid and emulsions.

The term "pharmaceutically acceptable," as used herein with regard to pharmaceutical compositions, means approved by a regulatory agency of the Federal or a state government or listed in the U.S. Pharmacopeia or other generally recognized pharmacopeia for use in animals and/or in humans.

In one aspect, the disclosure relates to administering a genetically modified T cell expressing a CAR for the treatment of a subject having cancer or at risk of having cancer using lymphocyte infusion. In at least one embodiment, autologous lymphocyte infusion is used in the treatment. Autologous PBMCs are collected from a subject in need of treatment and T cells are activated and expanded using the methods described herein and known in the art and then infused back into the subject.

In one aspect, the disclosure relates generally to the treatment of a subject at risk of developing cancer. The invention also includes treating a malignancy or an autoimmune disease in which chemotherapy and/or immunotherapy in a subject result in significant immunosuppression, thereby increasing the risk of the subject developing cancer. In one aspect, the present disclosure provides methods of preventing cancer, the methods comprising administering an amount of a lymphocyte expressing one or more of the CARs described to a subject in need thereof.

In one aspect, the present disclosure provides methods of treating a subject having cancer, the methods comprising administering a therapeutically effective amount of a lymphocyte expressing one or more of the CARs described to a subject in need thereof, whereby the lymphocyte induces or modulates killing of cancer cells in the subject.

In another aspect, the present disclosure provides methods of reducing tumor burden in a subject having cancer, the methods comprising administering a therapeutically effective amount of a lymphocyte expressing one or more of the CARs described herein to a subject in need thereof, whereby the lymphocyte induces killing of cancer cells in the subject. In another aspect, the present disclosure provides methods of increasing survival of a subject having cancer, the methods comprising administering a therapeutically effective amount of a lymphocyte expressing one or more of the CARs described to a subject in need thereof, whereby the survival of the subject is lengthened. Generally, the lymphocytes expressing the CAR(s) induce killing of cancer cells in the subject and result in reduction or eradication of the tumors/cancer cells in the subject. A non-limiting list of cancers, inclusive of metastatic lesions, that can be targeted, includes B-cell lymphoma and B-cell-derived cancer. In one embodiment, the cancer being treated in a subject is B-cell lymphoma. In some embodiments, the cancer is a non-Hodgkin lymphoma. In some embodiments, the cancer is a cancer of hematopoietic origin such as diffuse large B-cell lymphoma (DLBCL), mantle cell lymphoma (MCL), follicular lymphoma (FL), marginal zone lymphoma (MZ), acute lymphoblastic leukemia (ALL), chronic lymphocytic leukemia (CLL), multiple myeloma (MM), mucosa-associated lymphoid tissue (MALT) lymphoma, Hodgkin's lymphoma, Burkitt's lymphoma, hairy-cell leukemia or Plasmacytoma.

In one aspect, methods of treating a subject having cancer are provided that comprise administering a therapeutically effective amount of a lymphocyte expressing a CAR, the CAR having an extracellular antigen-binding domain that binds the CD79b antigen, to a subject in need thereof, whereby the lymphocyte induces killing of cancer cells in the subject. In some embodiments, the at least one of the CARs comprises an amino acid sequence selected from the group consisting of SEQ ID NOS: 164-207. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 164, or the sequence of SEQ ID NO: 164. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 165, or the sequence of SEQ ID NO: 165. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 166, or the sequence of SEQ ID NO: 166. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 167, or the sequence of SEQ ID NO: 167. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 168, or the sequence of SEQ ID NO: 168. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 169, or the sequence of SEQ ID NO: 169. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 170, or the sequence of SEQ ID NO: 170. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 171, or the sequence of SEQ ID NO: 171. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 172, or the sequence of SEQ ID NO: 172. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 173, or the sequence of SEQ ID NO: 173. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 174, or the sequence of SEQ ID NO: 174. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 175, or the sequence of SEQ ID NO: 175. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 176, or the sequence of SEQ ID NO: 176. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 177, or the sequence of SEQ ID NO: 177. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 178, or the sequence of SEQ ID NO: 178. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 179, or the sequence of SEQ ID NO: 179. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 180, or the sequence of SEQ ID NO: 180. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 181, or the sequence of SEQ ID NO: 181. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 182, or the sequence of SEQ ID NO: 182. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 183, or the sequence of SEQ ID NO: 183. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 184, or the sequence of SEQ ID NO: 184. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 185, or the sequence of SEQ ID NO: 185. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 186, or the sequence of SEQ ID NO: 186. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 187, or the sequence of SEQ ID NO: 187. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 188, or the sequence of SEQ ID NO: 188. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 189, or the sequence of SEQ ID NO: 189. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 190, or the sequence of SEQ ID NO: 190. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 191, or the sequence of SEQ ID NO: 191. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 192, or the sequence of SEQ ID NO: 192. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 193, or the sequence of SEQ ID NO: 193. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 194, or the sequence of SEQ ID NO: 194. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 195, or the sequence of SEQ ID NO: 195. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 196, or the sequence of SEQ ID NO: 196. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 197, or the sequence of SEQ ID NO: 197. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 198, or the sequence of SEQ ID NO: 198. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 199, or the sequence of SEQ ID NO: 199. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 200, or the sequence of SEQ ID NO: 200. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 201, or the sequence of SEQ ID NO: 201. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 202, or the sequence of SEQ ID NO: 202. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 203, or the sequence of SEQ ID NO: 203. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 204, or the sequence of SEQ ID NO: 204. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 205, or the sequence of SEQ ID NO: 205. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 206, or the sequence of SEQ ID NO: 206. In some embodiments, the CAR comprises an amino acid sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 207, or the sequence of SEQ ID NO: 207.

In one aspect, a method of targeted killing of a cancer cell is disclosed, the method comprising contacting the cancer cell with a lymphocyte expressing one or more of the CARs described, whereby the lymphocyte induces killing of the cancer cell. A non-limiting list of cancer cells, inclusive of metastatic cancer cells, that can be targeted include B-cell lymphoma, non-Hodgkin lymphoma, and combinations thereof. In one embodiment, the cancer cell is a malignant B cell.

Pharmaceutical compositions of the present disclosure may be administered in a manner appropriate to the disease to be treated (or prevented). The quantity and frequency of administration will be determined by such factors as the condition of the subject, and the type and severity of the subject's disease, although appropriate dosages may be determined by clinical trials.

When a therapeutically effective amount is indicated, the precise amount of the compositions of the present disclosure to be administered can be determined by a physician with consideration of individual differences in age, weight, tumor size, extent of infection or metastasis, and condition of the subject. It can generally be stated that a pharmaceutical composition comprising the T cells described herein may be administered at a dosage of about $10^4$ to about $10^{10}$ cells/kg body weight, in some instances about 10' to about $10^6$ cells/kg body weight, including all integer values within those ranges. In some embodiments, a pharmaceutical composition comprising the T cells described herein may be administered at a dosage of about $10^6$ cells/kg body weight. T cell compositions may also be administered multiple times at these dosages. The cells can be administered by using infusion techniques that are commonly known in immunotherapy (see, e.g., Rosenberg et al., *New Eng. J. of Med.* 319:1676, 1988).

Delivery systems useful in the context of embodiments of the invention may include time-released, delayed release, and sustained release delivery systems such that the delivery of the T cell compositions occurs prior to, and with sufficient time to cause, sensitization of the site to be treated. The composition can be used in conjunction with other therapeutic agents or therapies. Such systems can avoid repeated administrations of the composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polyesteramides, polyorthoesters, polycaprolactones, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; sylastic systems; peptide based systems; hydrogel release systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775; 4,667,014; 4,748,034; and 5,239,660 and (b) diffusional systems in which an active component permeates at a controlled rate from a polymer such as described in U.S. Pat. Nos. 3,854,480 and 3,832,253. In addition, pump-based hardware delivery systems can be used, some of which are adapted for implantation.

In certain aspects, it may be desirable to administer activated T cells to a subject and then subsequently redraw blood (or have an apheresis performed), activate the T cells according to the present disclosure, and reinfuse the subject with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

The administration of the CAR-T cells and compositions may be carried out in any manner, e.g., by parenteral or nonparenteral administration, including by aerosol inhalation, injection, infusions, ingestion, transfusion, implantation or transplantation. For example, the CAR-T cells and compositions described herein may be administered to a patient trans-arterially, intradermally, subcutaneously, intratumorally, intramedullary, intranodally, intramuscularly, by intravenous (i.v.) injection, or intraperitoneally. In one aspect, the compositions of the present disclosure are administered by i.v. injection. In one aspect, the compositions of the present disclosure are administered to a subject by intradermal or subcutaneous injection. The compositions of T cells may be injected, for instance, directly into a tumor, lymph node, tissue, organ, or site of infection.

Administration can be autologous or non-autologous. For example, immunoresponsive cells expressing a Cluster of Differentiation 79B protein (e.g., CD79b)-specific CAR can be obtained from one subject, and administered to the same subject or a different, compatible subject. Peripheral blood derived T cells of the present disclosure, or expanded T cells (e.g., in vivo, ex vivo or in vitro derived) can be administered via, e.g., intravenous injection, localized injection, systemic injection, catheter administration, or parenteral administration.

In particular embodiments, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the present disclosure may be introduced, thereby creating a CAR-T cell. Subjects in need thereof may subsequently undergo standard treatment with high dose chemotherapy followed by peripheral blood stem cell transplantation. In certain aspects, following or concurrent with the transplant, subjects receive an infusion of the expanded CAR-T cells. In one aspect, expanded cells are administered before or following surgery.

The dosage administered to a patient having a malignancy is sufficient to alleviate or at least partially arrest the disease being treated ("therapeutically effective amount"). The dosage of the above treatments to be administered to a subject will vary with the precise nature of the condition being treated and the recipient of the treatment. The scaling of dosages for human administration can be performed according to practices generally accepted in the art.

The CAR T cells of the invention can undergo in vivo T cell expansion and can establish CD79b-specific memory cells that persist at high levels for an extended amount of time in blood and bone marrow. In some instances, the CAR T cells of the invention infused into a subject can eliminate cancer cells, e.g., malignant B cells, in vivo in subjects with advanced chemotherapy-resistant cancer.

In one embodiment, a CAR of the present disclosure is introduced into T cells, e.g., using in vitro transcription, and the subject (e.g., human) receives an initial administration of CAR-T cells of the disclosure, and one or more subsequent administrations of the CAR-T cells, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR-T cells are administered to the subject (e.g., human) per week, e.g., 2, 3, or 4 administrations of the CAR-T cells are administered per week. In one embodiment, the subject receives more than one administration of the CAR-T cells per week (e.g., 2, 3 or 4 administrations per week) (also referred to herein as a cycle), followed by a week of no CAR-T cell administrations, and then one or more additional administration of the CAR-T cells (e.g., more than one administration of the CAR-T cells per week) is administered to the subject. In another embodiment, the subject receives more than one cycle of CAR-T cells, and the time between each cycle is less than 10, 9, 8, 7, 6, 5, 4, or 3 days. In one embodiment, the CAR-T cells are administered every other day for 3 administrations per week. In one embodiment, the CAR-T cells are administered for at least two, three, four, five, six, seven, eight or more weeks.

In one embodiment, administration may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

The CAR-T cells may be administered in the methods of the invention by maintenance therapy, such as, e.g., once a week for a period of 6 months or more.

In one embodiment, CAR-T cells are generated using lentiviral viral vectors, such as lentivirus. CAR-T cells generated with such viral vectors will generally have stable CAR expression.

In one embodiment, CAR-T cells transiently express CAR vectors for 4, 5, 6, 7, 8, 9, 10, 11, 12, 13, 14, 15 days after transduction. Transient expression of CARs can be affected by RNA CAR vector delivery. In one embodiment, the CAR RNA is transduced into the T cell by electroporation.

If a patient is at high risk of generating an anti-CAR antibody response during the course of transient CAR therapy (such as those generated by RNA transductions), CAR-T infusion breaks should not last more than ten to fourteen days.

A CAR-expressing cell described herein may be used in combination with other known agents and therapies. Administered "in combination", as used herein, means that two (or more) different treatments are delivered to the subject during the course of the subject's treatment e.g., the two or more treatments are delivered after the subject has been diagnosed with the cancer and before the cancer has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In one embodiment, other therapeutic agents such as factors may be administered before, after, or at the same time (simultaneous with) as the CAR-T cells, including, but not limited to, interleukins, as well as colony stimulating factors, such as G-, M- and GM-CSF, and interferons.

The CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

In further embodiments, the CAR-expressing cells described herein may be used in a treatment regimen in combination with surgery, radiation, chemotherapy, immunosuppressive agents, antibodies, or other immunoablative agents. In another embodiment, the CAR-expressing cell described herein can be used in combination with an anti-androgen treatment.

In one embodiment, the subject can be administered an agent which enhances the activity of a CAR-expressing cell. For example, in one embodiment, the agent can be an agent which inhibits an inhibitory molecule.

Kits

The invention also provides a kit comprising any of the chimeric antigen receptors (CARs) described herein, and/or nucleic acids encoding the CARs, vectors comprising the nucleic acids, and host cells comprising the vectors.

The kit may be used for therapeutic uses and as diagnostic kits.

The kit may be used to detect the presence of CD79b, or a cell expressing CD79b, in a sample.

The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

In some embodiments, the kit further comprises any of the above CARs, nucleic acids, vectors and/or host cells in a container and instructions for use of the kit.

In some embodiments, the CAR comprises the antigen binding domain that binds CD79b comprising the VH of SEQ ID NO: 1 and the VL of SEQ ID NO: 19;
the VH of SEQ ID NO: 1 and the VL of SEQ ID NO: 20;
the VH of SEQ ID NO: 2 and the VL of SEQ ID NO: 19;
the VH of SEQ ID NO: 2 and the VL of SEQ ID NO: 20;
the VH of SEQ ID NO: 3 and the VL of SEQ ID NO: 20;
the VH of SEQ ID NO: 4 and the VL of SEQ ID NO: 19;
the VH of SEQ ID NO: 5 and the VL of SEQ ID NO: 22;
the VH of SEQ ID NO: 5 and the VL of SEQ ID NO: 23;
the VH of SEQ ID NO: 6 and the VL of SEQ ID NO: 24;

the VH of SEQ ID NO: 7 and the VL of SEQ ID NO: 26;
the VH of SEQ ID NO: 8 and the VL of SEQ ID NO: 25;
the VH of SEQ ID NO: 9 and the VL of SEQ ID NO: 27;
the VH of SEQ ID NO: 10 and the VL of SEQ ID NO: 28;
the VH of SEQ ID NO: 11 and the VL of SEQ ID NO: 29;
the VH of SEQ ID NO: 12 and the VL of SEQ ID NO: 30;
the VH of SEQ ID NO: 13 and the VL of SEQ ID NO: 31;
the VH of SEQ ID NO: 14 and the VL of SEQ ID NO: 32;
the VH of SEQ ID NO: 15 and the VL of SEQ ID NO: 33;
the VH of SEQ ID NO: 16 and the VL of SEQ ID NO: 34;
the VH of SEQ ID NO: 16 and the VL of SEQ ID NO: 35;
the VH of SEQ ID NO: 17 and the VL of SEQ ID NO: 33;
or
the VH of SEQ ID NO: 18 and the VL of SEQ ID NO: 36.

In some embodiments, the kit comprises a CAR comprising SEQ ID NOs: 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 118.

Methods of Treatment and Uses

The disclosure also provides a method of treating a CD79b expressing cancer in a subject, comprising administering a therapeutically effective amount of any of the isolated lymphocytes expressing any of the CARs described herein that to the subject in need thereof for a time sufficient to treat the CD79b expressing cancer.

The disclosure also provides a method of treating a CD79b expressing cancer in a subject, comprising administering a therapeutically effective amount of a pharmaceutical composition comprising any of the isolated lymphocytes expressing any of the CARs described herein to the subject for a time sufficient to treat the CD79b expressing cancer.

In one aspect, the disclosure relates generally to the treatment of a subject at risk of developing cancer. The invention also includes treating a malignancy or an autoimmune disease in which chemotherapy and/or immunotherapy results in significant immunosuppression in a subject, thereby increasing the risk of the subject developing cancer.

The disclosure also provides a method of treating a noncancerous condition in a subject at risk of developing a cancerous condition, comprising administering any of the isolated lymphocytes expressing any of the CARs described herein to the subject to treat the noncancerous condition.

The disclosure also provides a method of treating a noncancerous condition in a subject at risk of developing a cancerous condition, comprising administering a pharmaceutical composition comprising a CAR described herein to the subject to treat the noncancerous condition.

The disclosure also provides a method of preventing CD79b expressing cancer in a subject, comprising administering a therapeutically effective amount of the antigen biding domain that binds CD79b of the disclosure to the subject for a time sufficient to prevent the CD79b expressing cancer. Examples of CD79b expressing cancers include, but are not limited to, B-cell lymphoma, non-Hodgkin lymphoma, diffuse large B-cell lymphoma (DLBCL), mantle cell lymphoma (MCL), follicular lymphoma (FL), marginal zone lymphoma (MZ), acute lymphoblastic leukemia (ALL), chronic lymphocytic leukemia (CLL), multiple myeloma (MM), mucosa-associated lymphoid tissue (MALT) lymphoma, Hodgkin's lymphoma, Burkitt's lymphoma, hairy-cell leukemia and Plasmacytoma.

The disclosure also provides a method of preventing a CD79b expressing cancer in a subject, comprising administering a therapeutically effective amount of the protein comprising the antigen biding domain that binds CD79b of the disclosure to the subject for a time sufficient to prevent the CD79b expressing cancer. Examples of CD79b expressing cancers include, but are not limited to, B-cell lymphoma, non-Hodgkin lymphoma, DLBCL, MCL, FL, MZ, ALL, CLL, MM, MALT lymphoma, Hodgkin's lymphoma, Burkitt's lymphoma, hairy-cell leukemia and Plasmacytoma.

The disclosure also provides a method of preventing a CD79b expressing cancer in a subject, comprising administering a therapeutically effective amount of the multispecific protein comprising the antigen biding domain that binds CD79b of the disclosure to the subject for a time sufficient to prevent the CD79b expressing cancer. Examples of CD79b expressing cancers include, but are not limited to, B-cell lymphoma, non-Hodgkin lymphoma, DLBCL, MCL, FL, MZ, ALL, CLL, MM, MALT lymphoma, Hodgkin's lymphoma, Burkitt's lymphoma, hairy-cell leukemia and Plasmacytoma.

The disclosure also provides a method of preventing a CD79b expressing cancer in a subject, comprising administering a therapeutically effective amount of any of the CAR-T cells described herein that bind CD79b of the disclosure to the subject for a time sufficient to prevent the CD79b expressing cancer. Examples of CD79b expressing cancers include, but are not limited to, B-cell lymphoma, non-Hodgkin lymphoma, DLBCL, MCL, FL, MZ, ALL, CLL, MM, MALT lymphoma, Hodgkin's lymphoma, Burkitt's lymphoma, hairy-cell leukemia and Plasmacytoma.

The disclosure also provides a method of preventing a CD79b expressing cancer in a subject, comprising administering a therapeutically effective amount of any of the isolated lymphocytes expressing any of the CARs described herein to the subject for a time sufficient to prevent the CD79b expressing cancer. Examples of CD79b expressing cancers include, but are not limited to, B-cell lymphoma, non-Hodgkin lymphoma, DLBCL, MCL, FL, MZ, ALL, CLL, MM, MALT lymphoma, Hodgkin's lymphoma, Burkitt's lymphoma, hairy-cell leukemia and Plasmacytoma.

In some embodiments, the CD79b expressing cancer is B-cell lymphoma.

In some embodiments, the CD79b expressing cancer is non-Hodgkin lymphoma.

In some embodiments, the CD79b expressing cancer has metastasized.

In some embodiments, the CD79b expressing cancer is diffuse large B-cell lymphoma (DLBCL), mantle cell lymphoma (MCL), follicular lymphoma (FL), marginal zone lymphoma (MZ), acute lymphoblastic leukemia (ALL), chronic lymphocytic leukemia (CLL), multiple myeloma (MM), mucosa-associated lymphoid tissue (MALT) lymphoma, Hodgkin's lymphoma, Burkitt's lymphoma, hairy-cell leukemia and Plasmacytoma.

In one aspect, the present disclosure provides methods of treating a subject having cancer, the methods comprising administering any of the isolated lymphocytes expressing any of the CARs described herein, whereby the lymphocyte induces or modulates killing of cancer cells in the subject.

The any of the isolated lymphocytes expressing any of the CARs described herein can be used in conjunction with other therapeutic agents or therapies. Such systems can avoid repeated administrations of the composition, thereby increasing convenience to the subject and the physician, and may be particularly suitable for certain composition embodiments of the invention.

The administration of the any of the isolated lymphocytes expressing any of the CARs described herein may be carried out in any manner, e.g., by parenteral or nonparenteral administration, including by aerosol inhalation, injection, infusions, ingestion, transfusion, implantation or transplantation. For example, the CD79-binding proteins and compositions described herein may be administered to a patient trans-arterially, intradermally, subcutaneously, intratumorally, intramedullary, intranodally, intramuscularly, by intravenous (i.v.) injection, or intraperitoneally. In one aspect, the compositions of the present disclosure are administered by i.v. injection. In one aspect, the compositions of the present disclosure are administered to a subject by intradermal or subcutaneous injection. The compositions of CD79-binding proteins may be injected, for instance, directly into a tumor, lymph node, tissue, organ, or site of infection.

In one embodiment, administration may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

Combination Therapies

The any of the isolated lymphocytes expressing any of the CARs described herein may be administered in combination with at least one additional therapeutics.

In some embodiments the at least one additional therapeutic is surgery, chemotherapy, androgen deprivation therapy or radiation, or any combination thereof.

In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In one embodiment, other therapeutic agents such as factors may be administered before, after, or at the same time (simultaneous with) as the any of the isolated lymphocytes expressing any of the CARs described herein, including, but not limited to, interleukins, as well as colony stimulating factors, such as G-, M- and GM-CSF, and interferons.

Any of the isolated lymphocytes expressing any of the CARs described herein described herein may comprise at least one additional therapeutic agent can be administered simultaneously, in the same or in separate compositions, or sequentially. For sequential administration, the lymphocytes described herein can be administered first, and the additional agent can be administered second, or the order of administration can be reversed.

In further embodiments, the lymphocytes described herein may be used in a treatment regimen in combination with surgery, radiation, chemotherapy, immunosuppressive agents, antibodies, or other immunoablative agents. In another embodiment, the lymphocytes described herein can be used in combination with an anti-androgen treatment. In one embodiment, the subject can be administered an agent which enhances the activity of a lymphocyte. For example, in one embodiment, the agent can be an agent which inhibits an inhibitory molecule.

The following examples are provided to further describe some of the embodiments disclosed herein. The examples are intended to illustrate, not to limit, the disclosed embodiments.

A description of example embodiments follows.

1. A chimeric antigen receptor (CAR) comprising:
   (a) an extracellular domain that specifically binds to the CD79b antigen,
   (b) a transmembrane domain, and
   (c) an intracellular signaling domain optionally comprising at least one co-stimulatory domain.
2. The CAR of embodiment 1, further comprising
   (d) a CD8a-hinge region,
   wherein the transmembrane domain comprises a CD8a transmembrane region (CD8a-TM) polypeptide; and
   wherein the intracellular signaling domain comprises a co-stimulatory domain comprising a TNF receptor superfamily member 9 (CD137) component and a primary signaling domain comprising a T-cell surface glycoprotein CD3 zeta chain (CD3z) component.
3. The CAR of embodiment 2, wherein
   the CD8a-hinge region comprises an amino acid sequence that is at least 90% identical to SEQ ID NO: 38;
   the transmembrane domain comprises an amino acid sequence that is at least 90% identical to SEQ ID NO: 39; and/or
   the intracellular signaling domain comprises a co-stimulatory domain having an amino acid sequence that is at least 90% identical to SEQ ID NO: 40, and a primary signaling domain having an amino acid sequence that is at least 90% identical to SEQ ID NO: 41.
4. A chimeric antigen receptor (CAR), comprising an extracellular antigen-binding domain, a transmembrane domain and an intracellular signaling domain, wherein the extracellular antigen-binding domain comprises:
   a heavy chain complementarity determining region 1 (CDR1) having the amino acid sequence of SEQ ID NO: 208, a heavy chain CDR2 having the amino acid sequence of SEQ ID NO: 209, and a heavy chain CDR3 having the amino acid sequence of SEQ ID NO: 210;
   a heavy chain CDR1 having the amino acid sequence of SEQ ID NO: 216, a heavy chain CDR2 having the amino acid sequence of SEQ ID NO: 217, and a heavy chain CDR3 having the amino acid sequence of SEQ ID NO: 218;
   a heavy chain CDR1 having the amino acid sequence of SEQ ID NO: 222, a heavy chain CDR2 having the amino acid sequence of SEQ ID NO: 223, and a heavy chain CDR3 having the amino acid sequence of SEQ ID NO: 224;
   a heavy chain CDR1 having the amino acid sequence of SEQ ID NO: 228, a heavy chain CDR2 having the amino acid sequence of SEQ ID NO: 217, and a heavy chain CDR3 having the amino acid sequence of SEQ ID NO: 229;
   a heavy chain CDR1 having the amino acid sequence of SEQ ID NO: 232, a heavy chain CDR2 having the amino acid sequence of SEQ ID NO: 233, and a heavy chain CDR3 having the amino acid sequence of SEQ ID NO: 234;

a heavy chain CDR1 having the amino acid sequence of SEQ ID NO: 238, a heavy chain CDR2 having the amino acid sequence of SEQ ID NO: 239, and a heavy chain CDR3 having the amino acid sequence of SEQ ID NO: 240;

a heavy chain CDR1 having the amino acid sequence of SEQ ID NO: 242, a heavy chain CDR2 having the amino acid sequence of SEQ ID NO: 243, and a heavy chain CDR3 having the amino acid sequence of SEQ ID NO: 244;

a heavy chain CDR1 having the amino acid sequence of SEQ ID NO: 248, a heavy chain CDR2 having the amino acid sequence of SEQ ID NO: 249, and a heavy chain CDR3 having the amino acid sequence of SEQ ID NO: 250;

a heavy chain CDR1 having the amino acid sequence of SEQ ID NO: 253, a heavy chain CDR2 having the amino acid sequence of SEQ ID NO: 254, and a heavy chain CDR3 having the amino acid sequence of SEQ ID NO: 255;

a heavy chain CDR1 having the amino acid sequence of SEQ ID NO: 257, a heavy chain CDR2 having the amino acid sequence of SEQ ID NO: 258, and a heavy chain CDR3 having the amino acid sequence of SEQ ID NO: 259;

a heavy chain CDR1 having the amino acid sequence of SEQ ID NO: 263, a heavy chain CDR2 having the amino acid sequence of SEQ ID NO: 243, and a heavy chain CDR3 having the amino acid sequence of SEQ ID NO: 264;

a heavy chain CDR1 having the amino acid sequence of SEQ ID NO: 268, a heavy chain CDR2 having the amino acid sequence of SEQ ID NO: 269, and a heavy chain CDR3 having the amino acid sequence of SEQ ID NO: 270; or a heavy chain CDR1 having the amino acid sequence of SEQ ID NO: 274, a heavy chain CDR2 having the amino acid sequence of SEQ ID NO: 275, and a heavy chain CDR3 having the amino acid sequence of SEQ ID NO: 276;

wherein the extracellular antigen-binding domain binds the CD79b antigen.

5. The CAR of embodiment 4, wherein the extracellular antigen-binding domain comprises the heavy chain CDR1 having the amino acid sequence of SEQ ID NO: 257, a heavy chain CDR2 having the amino acid sequence of SEQ ID NO: 258, and a heavy chain CDR3 having the amino acid sequence of SEQ ID NO: 259.

6. A chimeric antigen receptor (CAR), comprising an extracellular antigen-binding domain, a transmembrane domain and an intracellular signaling domain, wherein the extracellular antigen-binding domain comprises:

a light chain CDR1 having the amino acid sequence of SEQ ID NO: 211, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 214, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 215, a light chain CDR2 having the amino acid sequence of SEQ ID NO: 212, and a light chain CDR3 having the amino acid sequence of SEQ ID NO: 213;

a light chain CDR1 having the amino acid sequence of SEQ ID NO: 219, a light chain CDR2 having the amino acid sequence of SEQ ID NO: 220, and a light chain CDR3 having the amino acid sequence of SEQ ID NO: 221;

a light chain CDR1 having the amino acid sequence of SEQ ID NO: 225, a light chain CDR2 having the amino acid sequence of SEQ ID NO: 226, and a light chain CDR3 having the amino acid sequence of SEQ ID NO: 227;

a light chain CDR1 having the amino acid sequence of SEQ ID NO: 230, a light chain CDR2 having the amino acid sequence of SEQ ID NO: 231, and a light chain CDR3 having the amino acid sequence of SEQ ID NO: 221;

a light chain CDR1 having the amino acid sequence of SEQ ID NO: 235, a light chain CDR2 having the amino acid sequence of SEQ ID NO: 236, and a light chain CDR3 having the amino acid sequence of SEQ ID NO: 237;

a light chain CDR1 having the amino acid sequence of SEQ ID NO: 241, a light chain CDR2 having the amino acid sequence of SEQ ID NO: 226, and a light chain CDR3 having the amino acid sequence of SEQ ID NO: 227;

a light chain CDR1 having the amino acid sequence of SEQ ID NO: 245, a light chain CDR2 having the amino acid sequence of SEQ ID NO: 246, and a light chain CDR3 having the amino acid sequence of SEQ ID NO: 247;

a light chain CDR1 having the amino acid sequence of SEQ ID NO: 251, a light chain CDR2 having the amino acid sequence of SEQ ID NO: 236, and a light chain CDR3 having the amino acid sequence of SEQ ID NO: 252;

a light chain CDR1 having the amino acid sequence of SEQ ID NO: 251, a light chain CDR2 having the amino acid sequence of SEQ ID NO: 236, and a light chain CDR3 having the amino acid sequence of SEQ ID NO: 256;

a light chain CDR1 having the amino acid sequence of SEQ ID NO: 260, a light chain CDR2 having the amino acid sequence of SEQ ID NO: 261, and a light chain CDR3 having the amino acid sequence of SEQ ID NO: 262;

a light chain CDR1 having the amino acid sequence of SEQ ID NO: 265, a light chain CDR2 having the amino acid sequence of SEQ ID NO: 266, and a light chain CDR3 having the amino acid sequence of SEQ ID NO: 267;

a light chain CDR1 having the amino acid sequence of SEQ ID NO: 271, a light chain CDR2 having the amino acid sequence of SEQ ID NO: 272, and a light chain CDR3 having the amino acid sequence of SEQ ID NO: 273; or a light chain CDR1 having the amino acid sequence of SEQ ID NO: 277, a light chain CDR2 having the amino acid sequence of SEQ ID NO: 266, and a light chain CDR3 having the amino acid sequence of SEQ ID NO: 278;

wherein the extracellular antigen-binding domain binds the CD79b antigen.

7. The CAR of embodiment 6, wherein the extracellular antigen-binding domain comprises a light chain CDR1 having the amino acid sequence of SEQ ID NO: 260, a light chain CDR2 having the amino acid sequence of SEQ ID NO: 261, and a light chain CDR3 having the amino acid sequence of SEQ ID NO: 262.

8. The CAR according to embodiment 4 or embodiment 5, wherein the extracellular antigen-binding domain further comprises:
   - a light chain CDR1 having the amino acid sequence of SEQ ID NO: 211, a light chain CDR2 having the amino acid sequence of SEQ ID NO: 212, and a light chain CDR3 having the amino acid sequence of SEQ ID NO: 213;
   - a light chain CDR1 having the amino acid sequence of SEQ ID NO: 214, a light chain CDR2 having the amino acid sequence of SEQ ID NO: 212, and a light chain CDR3 having the amino acid sequence of SEQ ID NO: 213;
   - a light chain CDR1 having the amino acid sequence of SEQ ID NO: 215, a light chain CDR2 having the amino acid sequence of SEQ ID NO: 212, and a light chain CDR3 having the amino acid sequence of SEQ ID NO: 213;
   - a light chain CDR1 having the amino acid sequence of SEQ ID NO: 219, a light chain CDR2 having the amino acid sequence of SEQ ID NO: 220, and a light chain CDR3 having the amino acid sequence of SEQ ID NO: 221;
   - a light chain CDR1 having the amino acid sequence of SEQ ID NO: 225, a light chain CDR2 having the amino acid sequence of SEQ ID NO: 226, and a light chain CDR3 having the amino acid sequence of SEQ ID NO: 227;
   - a light chain CDR1 having the amino acid sequence of SEQ ID NO: 230, a light chain CDR2 having the amino acid sequence of SEQ ID NO: 231, and a light chain CDR3 having the amino acid sequence of SEQ ID NO: 221;
   - a light chain CDR1 having the amino acid sequence of SEQ ID NO: 235, a light chain CDR2 having the amino acid sequence of SEQ ID NO: 236, and a light chain CDR3 having the amino acid sequence of SEQ ID NO: 237;
   - a light chain CDR1 having the amino acid sequence of SEQ ID NO: 241, a light chain CDR2 having the amino acid sequence of SEQ ID NO: 226, and a light chain CDR3 having the amino acid sequence of SEQ ID NO: 227;
   - a light chain CDR1 having the amino acid sequence of SEQ ID NO: 245, a light chain CDR2 having the amino acid sequence of SEQ ID NO: 246, and a light chain CDR3 having the amino acid sequence of SEQ ID NO: 247;
   - a light chain CDR1 having the amino acid sequence of SEQ ID NO: 251, a light chain CDR2 having the amino acid sequence of SEQ ID NO: 236, and a light chain CDR3 having the amino acid sequence of SEQ ID NO: 252;
   - a light chain CDR1 having the amino acid sequence of SEQ ID NO: 251, a light chain CDR2 having the amino acid sequence of SEQ ID NO: 236, and a light chain CDR3 having the amino acid sequence of SEQ ID NO: 256;
   - a light chain CDR1 having the amino acid sequence of SEQ ID NO: 260, a light chain CDR2 having the amino acid sequence of SEQ ID NO: 261, and a light chain CDR3 having the amino acid sequence of SEQ ID NO: 262;
   - a light chain CDR1 having the amino acid sequence of SEQ ID NO: 265, a light chain CDR2 having the amino acid sequence of SEQ ID NO: 266, and a light chain CDR3 having the amino acid sequence of SEQ ID NO: 267;
   - a light chain CDR1 having the amino acid sequence of SEQ ID NO: 271, a light chain CDR2 having the amino acid sequence of SEQ ID NO: 272, and a light chain CDR3 having the amino acid sequence of SEQ ID NO: 273; or
   - a light chain CDR1 having the amino acid sequence of SEQ ID NO: 277, a light chain CDR2 having the amino acid sequence of SEQ ID NO: 266, and a light chain CDR3 having the amino acid sequence of SEQ ID NO: 278.

9. The CAR of embodiment 8, wherein the extracellular antigen-binding domain comprises a light chain CDR1 having the amino acid sequence of SEQ ID NO: 260, a light chain CDR2 having the amino acid sequence of SEQ ID NO: 261, and a light chain CDR3 having the amino acid sequence of SEQ ID NO: 262.

10. A chimeric antigen receptor (CAR), comprising an extracellular antigen-binding domain, a transmembrane domain and an intracellular signaling domain, wherein the extracellular antigen-binding domain comprises the heavy chain CDR1 having the amino acid sequence of SEQ ID NOs: 208, 216, 222, 228, 232, 238, 242, 248, 253, 257, 263, 268, or 274, the heavy chain CDR2 having the amino acid sequence of SEQ ID NOs: 209, 217, 223, 233, 239, 243, 249, 254, 258, 269, or 275, the heavy chain CDR3 having the amino acid sequence of SEQ ID NOs: 210, 218, 224, 229, 234, 240, 244, 250, 255, 259, 264, 270, or 276, the light chain CDR1 having the amino acid sequence of SEQ ID NOs: 211, 214, 215, 219, 225, 230, 235, 241, 245, 251, 260, 265, 271, or 277, the light chain CDR2 having the amino acid sequence of SEQ ID NOs: 212, 220, 226, 231, 236, 246, 261, 266, or 272, and the light chain CDR3 having the amino acid sequence of SEQ ID NOs: 213, 221, 227, 237, 247, 252, 256, 262, 267, 273, or 278.

11. The CAR of any one of embodiments 1-10, wherein the extracellular antigen-binding domain comprises the heavy chain CDR1, the heavy chain CDR2, the heavy chain CDR3, the light chain CDR1, the light chain CDR2 and the light chain CDR3 having the amino acid sequence of
   a) SEQ ID NOs: 208, 209, 210, 211, 212 and 213, respectively;
   b) SEQ ID NOs: 208, 209, 210, 214, 212 and 213, respectively;
   c) SEQ ID NOs: 208, 209, 210, 215, 212 and 213, respectively;
   d) SEQ ID NOs: 216, 217, 218, 219, 220 and 221, respectively;
   e) SEQ ID NOs: 222, 223, 224, 225, 226, and 227, respectively;
   f) SEQ ID NOs: 228, 217, 229, 230, 231, and 221, respectively;
   g) SEQ ID NOs: 232, 233, 234, 235, 236, and 237, respectively;
   h) SEQ ID NOs: 238, 239, 240, 241, 226, and 227, respectively;
   i) SEQ ID NOs: 242, 243, 244, 245, 246, and 247, respectively;
   j) SEQ ID NOs: 248, 249, 250, 251, 236, and 252, respectively;

k) SEQ ID NOs: 253, 254, 255, 251, 236, and 256, respectively;
l) SEQ ID NOs: 257, 258, 259, 260, 261, and 262, respectively;
m) SEQ ID NOs: 263, 243, 264, 265, 266, and 267, respectively;
n) SEQ ID NOs: 268, 269, 270, 271, 272, and 273, respectively; or
o) SEQ ID NOs: 274, 275, 276, 277, 266, and 278, respectively.

12. The CAR of any one of embodiments 1-11, wherein the extracellular antigen-binding domain comprises the heavy chain CDR1, the heavy chain CDR2, the heavy chain CDR3, the light chain CDR1, the light chain CDR2 and the light chain CDR3 having the amino acid sequence of SEQ ID NOs: 257, 258, 259, 260, 261, and 262, respectively.

13. A chimeric antigen receptor (CAR), comprising an extracellular antigen-binding domain, a transmembrane domain and an intracellular signaling domain, wherein the extracellular antigen-binding domain comprises:
a heavy chain variable domain (VH) comprising an amino acid sequence that is at least 90% identical to a sequence selected from SEQ ID NOS: 1-18; and/or
a light chain variable domain (VL) comprising an amino acid sequence that is at least 90% identical to a sequence selected from SEQ ID NOS: 19-36;
wherein the extracellular antigen-binding domain binds the CD79b antigen.

14. The CAR of embodiment 13, wherein the extracellular antigen-binding domain comprises:
a heavy chain variable domain (VH) comprising an amino acid sequence selected from SEQ ID NOS: 1-18; and/or
a light chain variable domain (VL) comprising an amino acid sequence selected from SEQ ID NOS: 19-36;
wherein the extracellular antigen-binding domain binds the CD79b antigen.

15. The CAR of embodiment 13, wherein the extracellular antigen-binding domain comprises:
a heavy chain variable region comprising an amino acid sequence that is at least 90% identical to SEQ ID NO: 1 and a light chain variable region comprising an amino acid sequence that is at least 90% identical to SEQ ID NO: 19;
a heavy chain variable region comprising an amino acid sequence that is at least 90% identical to SEQ ID NO: 1 and a light chain variable region comprising an amino acid sequence that is at least 90% identical to SEQ ID NO: 20;
a heavy chain variable region comprising an amino acid sequence that is at least 90% identical to SEQ ID NO: 2 and a light chain variable region comprising an amino acid sequence that is at least 90% identical to SEQ ID NO: 19;
a heavy chain variable region comprising an amino acid sequence that is at least 90% identical to SEQ ID NO: 2 and a light chain variable region comprising an amino acid sequence that is at least 90% identical to SEQ ID NO: 20;
a heavy chain variable region comprising an amino acid sequence that is at least 90% identical to SEQ ID NO: 3 and a light chain variable region comprising an amino acid sequence that is at least 90% identical to SEQ ID NO: 20;
a heavy chain variable region comprising an amino acid sequence that is at least 90% identical to SEQ ID NO: 4 and a light chain variable region comprising an amino acid sequence that is at least 90% identical to SEQ ID NO: 19;
a heavy chain variable region comprising an amino acid sequence that is at least 90% identical to SEQ ID NO: 5 and a light chain variable region comprising an amino acid sequence that is at least 90% identical to SEQ ID NO: 22;
a heavy chain variable region comprising an amino acid sequence that is at least 90% identical to SEQ ID NO: 5 and a light chain variable region comprising an amino acid sequence that is at least 90% identical to SEQ ID NO: 23;
a heavy chain variable region comprising an amino acid sequence that is at least 90% identical to SEQ ID NO: 6 and a light chain variable region comprising an amino acid sequence that is at least 90% identical to SEQ ID NO: 24;
a heavy chain variable region comprising an amino acid sequence that is at least 90% identical to SEQ ID NO: 7 and a light chain variable region comprising an amino acid sequence that is at least 90% identical to SEQ ID NO: 26;
a heavy chain variable region comprising an amino acid sequence that is at least 90% identical to SEQ ID NO: 8 and a light chain variable region comprising an amino acid sequence that is at least 90% identical to SEQ ID NO: 25;
a heavy chain variable region comprising an amino acid sequence that is at least 90% identical to SEQ ID NO: 9 and a light chain variable region comprising an amino acid sequence that is at least 90% identical to SEQ ID NO: 27;
a heavy chain variable region comprising an amino acid sequence that is at least 90% identical to SEQ ID NO: 10 and a light chain variable region comprising an amino acid sequence that is at least 90% identical to SEQ ID NO: 28;
a heavy chain variable region comprising an amino acid sequence that is at least 90% identical to SEQ ID NO: 11 and a light chain variable region comprising an amino acid sequence that is at least 90% identical to SEQ ID NO: 29;
a heavy chain variable region comprising an amino acid sequence that is at least 90% identical to SEQ ID NO: 12 and a light chain variable region comprising an amino acid sequence that is at least 90% identical to SEQ ID NO: 30;
a heavy chain variable region comprising an amino acid sequence that is at least 90% identical to SEQ ID NO: 13 and a light chain variable region comprising an amino acid sequence that is at least 90% identical to SEQ ID NO: 31;
a heavy chain variable region comprising an amino acid sequence that is at least 90% identical to SEQ ID NO: 14 and a light chain variable region comprising an amino acid sequence that is at least 90% identical to SEQ ID NO: 32;
a heavy chain variable region comprising an amino acid sequence that is at least 90% identical to SEQ ID NO: 15 and a light chain variable region comprising an amino acid sequence that is at least 90% identical to SEQ ID NO: 33;
a heavy chain variable region comprising an amino acid sequence that is at least 90% identical to SEQ ID NO: 16 and a light chain variable region comprising an amino acid sequence that is at least 90% identical to SEQ ID NO: 34;

a heavy chain variable region comprising an amino acid sequence that is at least 90% identical to SEQ ID NO: 16 and a light chain variable region comprising an amino acid sequence that is at least 90% identical to SEQ ID NO: 35;

a heavy chain variable region comprising an amino acid sequence that is at least 90% identical to SEQ ID NO: 17 and a light chain variable region comprising an amino acid sequence that is at least 90% identical to SEQ ID NO: 33; or a heavy chain variable region comprising an amino acid sequence that is at least 90% identical to SEQ ID NO: 18 and a light chain variable region comprising an amino acid sequence that is at least 90% identical to SEQ ID NO: 36.

16. The CAR of any of embodiments 13-15, wherein the extracellular antigen-binding domain comprises:

a heavy chain variable region comprising an amino acid sequence of SEQ ID NO: 1 and a light chain variable region comprising an amino acid sequence of SEQ ID NO: 19;

a heavy chain variable region comprising an amino acid sequence of SEQ ID NO: 1 and a light chain variable region comprising an amino acid sequence of SEQ ID NO: 20;

a heavy chain variable region comprising an amino acid sequence of SEQ ID NO: 2 and a light chain variable region comprising an amino acid of SEQ ID NO: 19;

a heavy chain variable region comprising an amino acid sequence of SEQ ID NO: 2 and a light chain variable region comprising an amino acid sequence of SEQ ID NO: 20;

a heavy chain variable region comprising an amino acid sequence of SEQ ID NO: 3 and a light chain variable region comprising an amino acid sequence of SEQ ID NO: 20;

a heavy chain variable region comprising an amino acid sequence of SEQ ID NO: 4 and a light chain variable region comprising an amino acid sequence of SEQ ID NO: 19;

a heavy chain variable region comprising an amino acid sequence of SEQ ID NO: 5 and a light chain variable region comprising an amino acid sequence of SEQ ID NO: 22;

a heavy chain variable region comprising an amino acid sequence of SEQ ID NO: 5 and a light chain variable region comprising an amino acid sequence of SEQ ID NO: 23;

a heavy chain variable region comprising an amino acid sequence of SEQ ID NO: 6 and a light chain variable region comprising an amino acid sequence of SEQ ID NO: 24;

a heavy chain variable region comprising an amino acid sequence of SEQ ID NO: 7 and a light chain variable region comprising an amino acid sequence of SEQ ID NO: 26;

a heavy chain variable region comprising an amino acid sequence of SEQ ID NO: 8 and a light chain variable region comprising an amino acid sequence of SEQ ID NO: 25;

a heavy chain variable region comprising an amino acid sequence of SEQ ID NO: 9 and a light chain variable region comprising an amino acid sequence of SEQ ID NO: 27;

a heavy chain variable region comprising an amino acid sequence of SEQ ID NO: 10 and a light chain variable region comprising an amino acid sequence of SEQ ID NO: 28;

a heavy chain variable region comprising an amino acid sequence of SEQ ID NO: 11 and a light chain variable region comprising an amino acid sequence of SEQ ID NO: 29;

a heavy chain variable region comprising an amino acid sequence of SEQ ID NO: 12 and a light chain variable region comprising an amino acid sequence of SEQ ID NO: 30;

a heavy chain variable region comprising an amino acid sequence of SEQ ID NO: 13 and a light chain variable region comprising an amino acid sequence of SEQ ID NO: 31;

a heavy chain variable region comprising an amino acid sequence of SEQ ID NO: 14 and a light chain variable region comprising an amino acid sequence of SEQ ID NO: 32;

a heavy chain variable region comprising an amino acid sequence of SEQ ID NO: 15 and a light chain variable region comprising an amino acid sequence of SEQ ID NO: 33;

a heavy chain variable region comprising an amino acid sequence of SEQ ID NO: 16 and a light chain variable region comprising an amino acid sequence of SEQ ID NO: 34;

a heavy chain variable region comprising an amino acid sequence of SEQ ID NO: 16 and a light chain variable region comprising an amino acid sequence of SEQ ID NO: 35;

a heavy chain variable region comprising an amino acid sequence of SEQ ID NO: 17 and a light chain variable region comprising an amino acid sequence of SEQ ID NO: 33; or a heavy chain variable region comprising an amino acid sequence of SEQ ID NO: 18 and a light chain variable region comprising an amino acid sequence of SEQ ID NO: 36.

17. The CAR of embodiment 13 or 15, wherein the extracellular antigen-binding domain comprises:

a heavy chain variable region comprising an amino acid sequence that is at least 90% identical to SEQ ID NO: 14 and a light chain variable region comprising an amino acid sequence that is at least 90% identical to SEQ ID NO: 32.

18. The CAR of any of embodiments 13-17, wherein the extracellular antigen-binding domain comprises:

a heavy chain variable region comprising an amino acid sequence of SEQ ID NO: 14 and a light chain variable region comprising an amino acid sequence of SEQ ID NO: 32.

19. The CAR of any of embodiments 1-18, wherein the extracellular antigen-binding domain comprises a single-chain variable fragment (scFv), the scFv comprising a heavy chain variable region (VH) and a light chain variable region (VL).

20. The CAR of embodiment 19, wherein the scFv comprises a linker polypeptide between the heavy chain variable region (VH) and the light chain variable region (VL).

21. The CAR of embodiment 20, wherein the linker polypeptide comprises an amino acid sequence that is at least 90% identical to SEQ ID NO: 42.

22. The CAR of embodiment 20 or 21, wherein the linker polypeptide comprises an amino acid sequence of SEQ ID NO: 42.
23. The CAR of any of embodiments 19-22, wherein the scFv comprises an amino acid sequence that is at least 90% identical to a sequence selected from the group consisting of SEQ ID NOS: 75-118.
24. The CAR of any of embodiments 19-23, wherein the scFv comprises an amino acid sequence that is selected from the group consisting of SEQ ID NOS: 75-118.
25. The CAR of any of embodiments 19-23, wherein the scFv comprises an amino acid sequence that is at least 90% identical to SEQ ID NO: 113.
26. The CAR of any of embodiments 19-25, wherein the scFv comprises an amino acid sequence of SEQ ID NO: 113.
27. The CAR of any of embodiments 1-26, wherein the extracellular antigen-binding domain comprises a signal polypeptide.
28. The CAR of embodiment 27, wherein the signal polypeptide comprises an amino acid sequence that is at least 90% identical to SEQ ID NO: 37.
29. The CAR of embodiment 27 or 28, wherein the signal polypeptide comprises an amino acid sequence of SEQ ID NO: 37.
30. The CAR of any of embodiments 4-29, wherein the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member component, and a combination thereof.
31. The CAR of embodiment 30, wherein the CD137 component comprises an amino acid sequence that is at least 90% identical to SEQ ID NO: 40.
32. The CAR of embodiment 30 or 31, wherein the CD137 component comprises an amino acid sequence of SEQ ID NO: 40.
33. The CAR of any one of embodiments 30-32, wherein the CD3z component comprises an amino acid sequence that is at least 90% identical to SEQ ID NO: 41.
34. The CAR of any one of embodiments 30-33, wherein the CD3z component comprises an amino acid sequence of SEQ ID NO: 41
35. The CAR of any one of embodiments 30-34, wherein the intracellular signaling domain comprises an amino acid sequence that is at least 90% identical to SEQ ID NO: 163.
36. The CAR of any one of embodiments 30-35, wherein the intracellular signaling domain comprises an amino acid sequence of SEQ ID NO: 163.
37. The CAR of any of embodiments 4-36, wherein the transmembrane domain comprises a CD8a transmembrane region (CD8a-TM) polypeptide.
38. The CAR of embodiment 37, wherein the CD8a-TM polypeptide comprises an amino acid sequence that is at least 90% identical to SEQ ID NO: 39.
39. The CAR of embodiment 37 or 38, wherein the CD8a-TM polypeptide comprises an amino acid sequence of SEQ ID NO: 39.
40. The CAR of any of embodiments 4-39, further comprising a hinge region linking the transmembrane domain to the extracellular antigen-binding domain.
41. The CAR of embodiment 40, wherein the hinge region is a CD8a-hinge region.
42. The CAR of embodiment 41, wherein the CD8a-hinge region comprises an amino acid sequence that is at least 90% identical to of SEQ ID NO: 38.
43. The CAR of embodiment 41 or 42, wherein the CD8a-hinge region comprises an amino acid sequence of SEQ ID NO: 38.
44. The CAR of any of embodiments 1-43, wherein the extracellular antigen-binding domain comprises an amino acid sequence selected from the group consisting of SEQ ID NOS: 119-162, or a sequence having 90% identity thereof.
45. The CAR of any of embodiments 1-44, wherein the extracellular antigen-binding domain comprises an amino acid sequence that is at least 90% identical to SEQ ID NO: 157.
46. The CAR of any of embodiments 1-45, wherein the extracellular antigen-binding domain comprises an amino acid sequence of SEQ ID NO: 157.
47. The CAR of any of embodiments 1-46, wherein the CAR comprises an amino acid sequence selected from the group consisting of SEQ ID NOS: 164-207, or a sequence having 90% identity thereof.
48. The CAR of any of embodiments 1-47, wherein the CAR comprises an amino acid sequence that is at least 90% identical to SEQ ID NO: 202.
49. The CAR of any of embodiments 1-48, wherein the CAR comprises an amino acid sequence of SEQ ID NO: 202.
50. An isolated lymphocyte expressing the CAR of any of embodiments 1-49.
51. The isolated lymphocyte of embodiment 50, wherein the lymphocyte is a T lymphocyte.
52. The isolated lymphocyte of embodiment 51, wherein the lymphocyte is a natural killer (NK) cell.
53. An isolated nucleic acid molecule encoding the CAR of any of embodiments 1-49.
54. A vector comprising the nucleic acid molecule of embodiment 53.
55. A cell expressing the nucleic acid molecule of embodiment 53.
56. A pharmaceutical composition, comprising an effective amount of the lymphocyte of any of embodiments 50-52 and a pharmaceutically acceptable excipient.
57. A method of treating a subject having cancer, the method comprising:

administering a therapeutically effective amount of the lymphocyte of any of embodiments 50-52 or the pharmaceutical composition of embodiment 56 to the subject, whereby the lymphocyte induces killing of cancer cells in the subject.

58. The method of embodiment 57, wherein the cancer is a B-cell lymphoma.
59. The method of embodiment 57 or embodiment 58, wherein the cancer is a non-Hodgkin lymphoma.
60. The method of any one of embodiments 57-59, wherein the cancer is a diffuse large B-cell lymphoma (DLBCL), mantle cell lymphoma (MCL), follicular lymphoma (FL), marginal zone lymphoma (MZ), acute lymphoblastic leukemia (ALL), chronic lymphocytic leukemia (CLL), multiple myeloma (MM), mucosa-associated lymphoid tissue (MALT) lymphoma, Hodgkin's lymphoma, Burkitt's lymphoma, hairy-cell leukemia, or Plasmacytoma.

61. A method of targeted killing of a cancer cell, the method comprising:
contacting the cancer cell with the lymphocyte of any of embodiments 50-52, whereby the lymphocyte induces killing of the cancer cell.
62. The method of embodiment 61, wherein the cancer cell is a malignant B cell.
63. The method of embodiment 61 or embodiment 62, wherein the cancer cell is a cell of a non-Hodgkin lymphoma.
64. The method of any of embodiments 61-63, wherein the cancer cell is a cell of diffuse large B-cell lymphoma (DLBCL), mantle cell lymphoma (MCL), follicular lymphoma (FL), marginal zone lymphoma (MZ), acute lymphoblastic leukemia (ALL), chronic lymphocytic leukemia (CLL), multiple myeloma (MM), mucosa-associated lymphoid tissue (MALT) lymphoma, Hodgkin's lymphoma, Burkitt's lymphoma, hairy-cell leukemia or Plasmacytoma.
65. A method of detecting the presence of cancer in a subject, comprising:
contacting a cell sample obtained from the subject with the CAR of any one of embodiments 1-49, thereby forming a CAR-cell complex, and
detecting the complex, wherein detection of the complex is indicative of the presence of cancer in the subject.

EXAMPLES

The following examples are provided to further describe some of the embodiments disclosed herein. The examples are intended to illustrate, not to limit, the disclosed embodiments.

Example 1: Construction and Lentiviral Transduction of CD79b CARs

Figure 1:
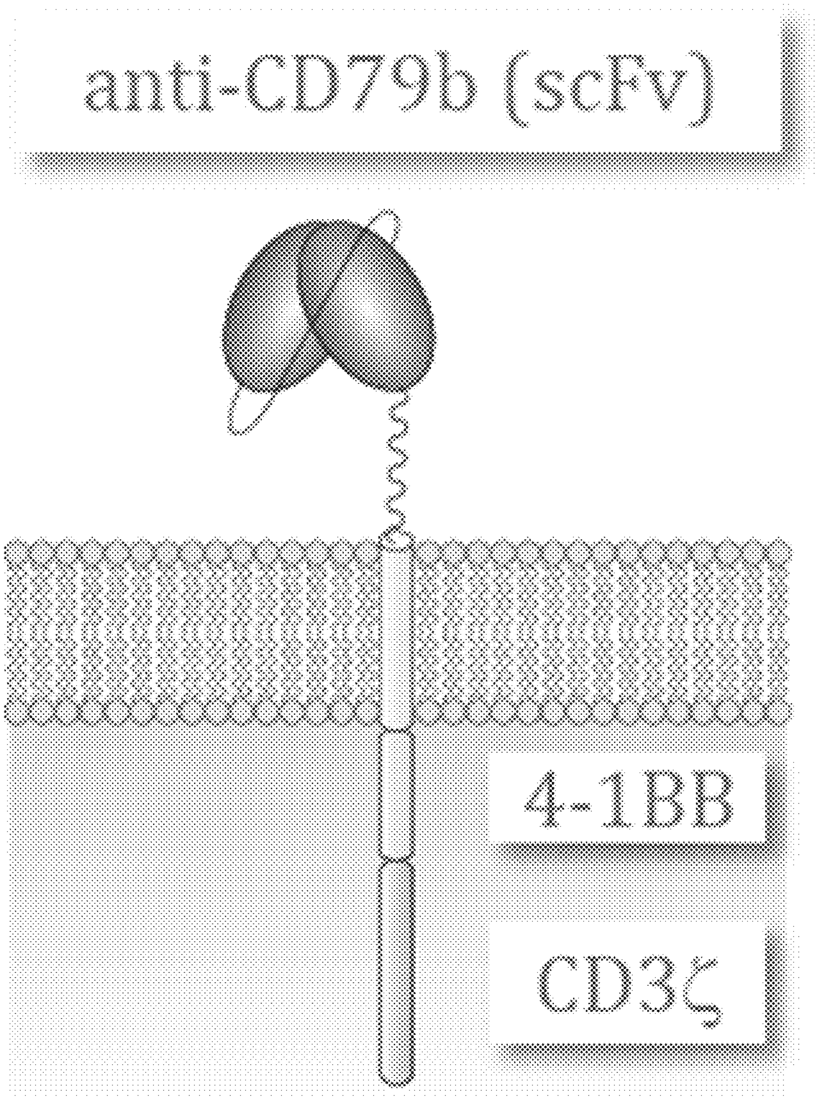
FIG. 1 is a diagram of an exemplary aCD79b CAR molecular structure. aCD79b scFvs were cloned in sequence with a CD8a hinge/transmembrane domain, a CD137 intracellular domain, and a CD3zeta intracellular domain.
Figure 2A:
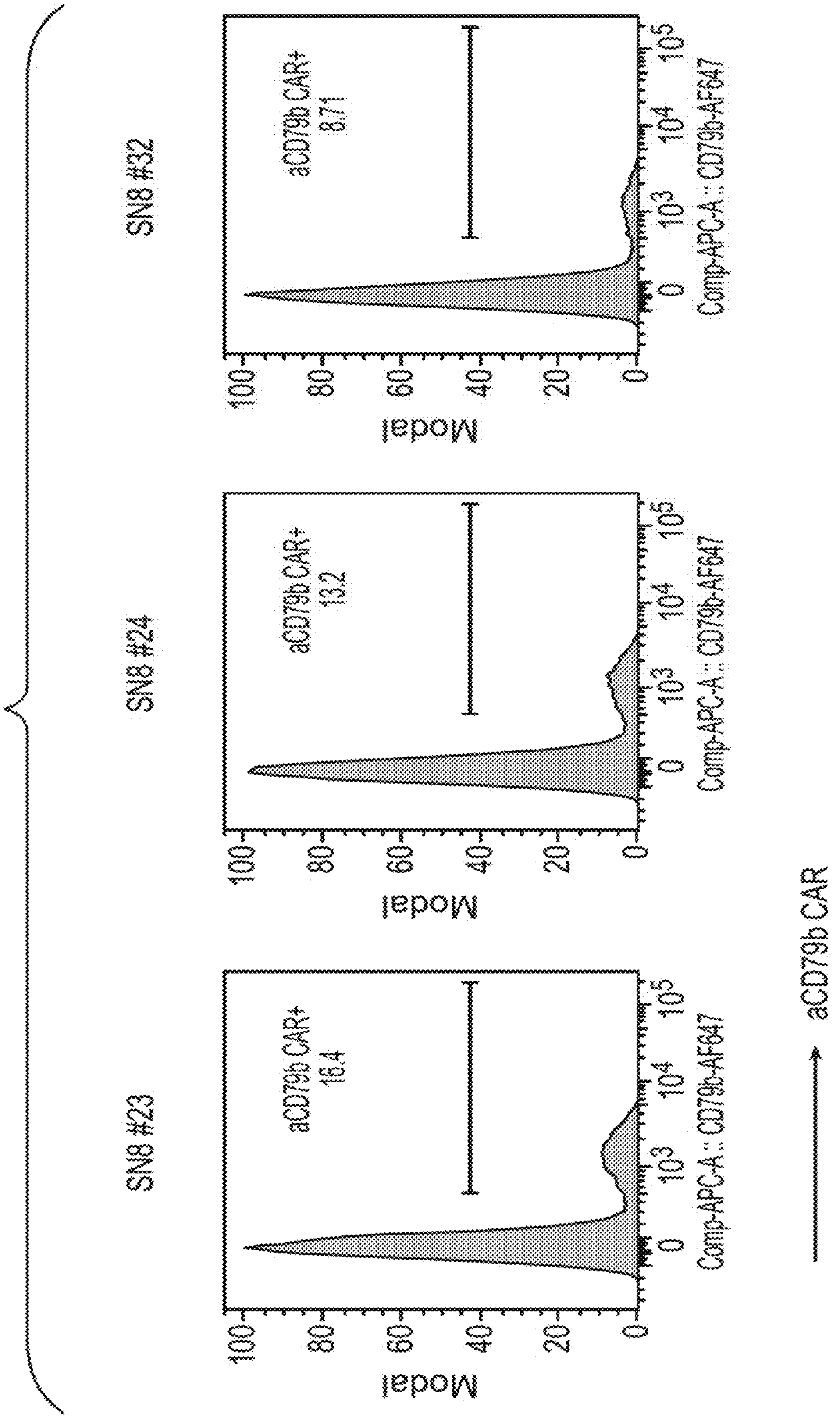
FIGS. 2A-2I show the generation of primary human CAR-T cells expressing aCD79b CARs. Primary human T cells were isolated via negative selection and stimulated with either TransAct™ (Miltenyi) (T-cell activation reagent) in TexMACS™ media (T-cell media) (FIGS. 2A-2C, FIGS. 2G-2I), or using anti-CD3/anti-CD28 beads (Dynabeads™, Invitrogen) in Optimizer media (FIGS. 2D-2F). In both cases media was supplemented with 100 U/mL IL-2 (Miltenyi). Cells were transduced with lentiviral vectors encoding the CAR construct 24 hours post-stimulation and cultured for 12-14 days. Media and cytokines were refreshed every 2-4 days. CD79b CAR expression was quantified via flow cytometry using recombinant human CD79b extracellular domain fused to AF647 protein. Frequency of CAR+ cells is shown.
Figure 2B:
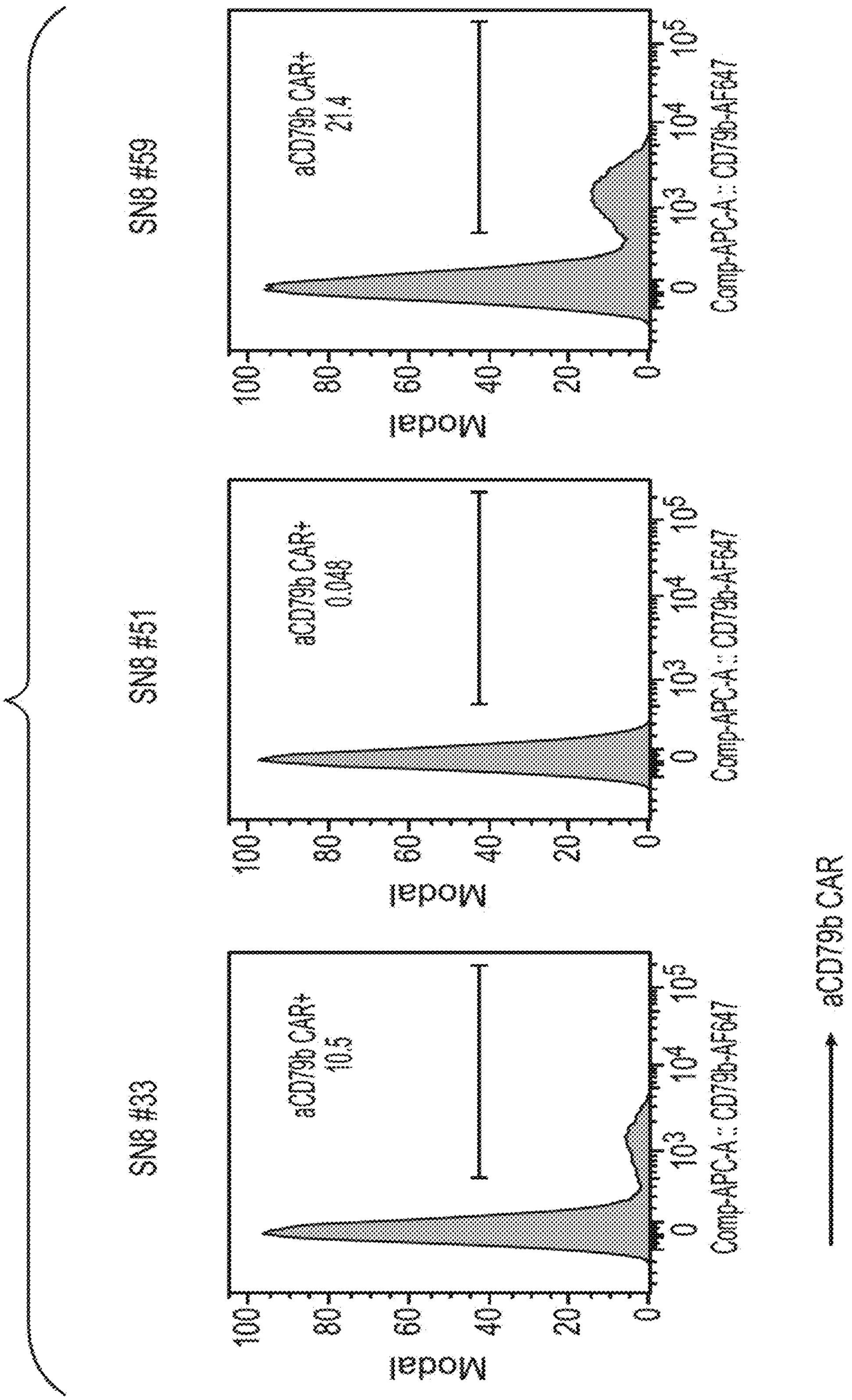
Figure 2C:
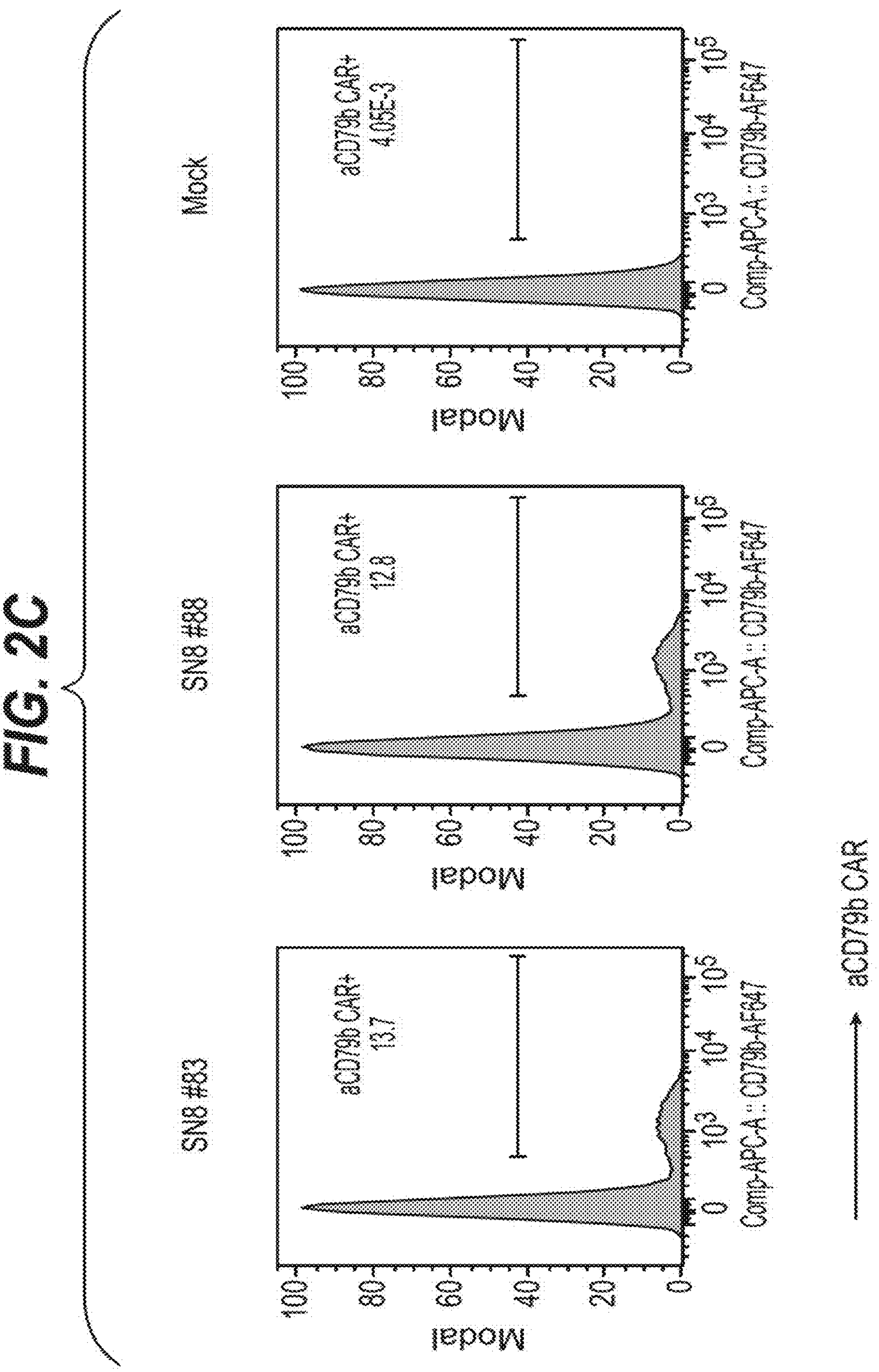
Figure 2D:
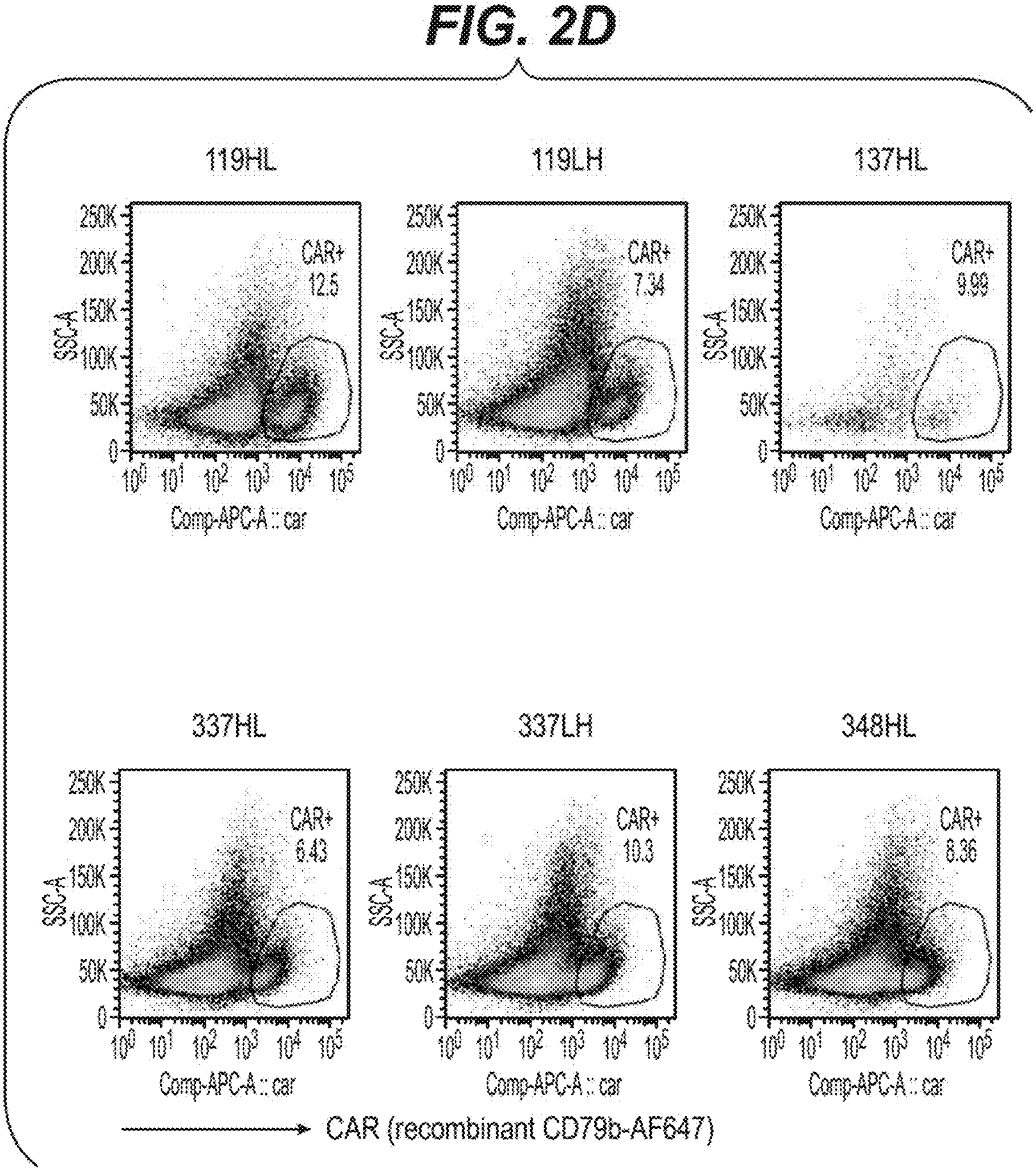
Figure 2E:
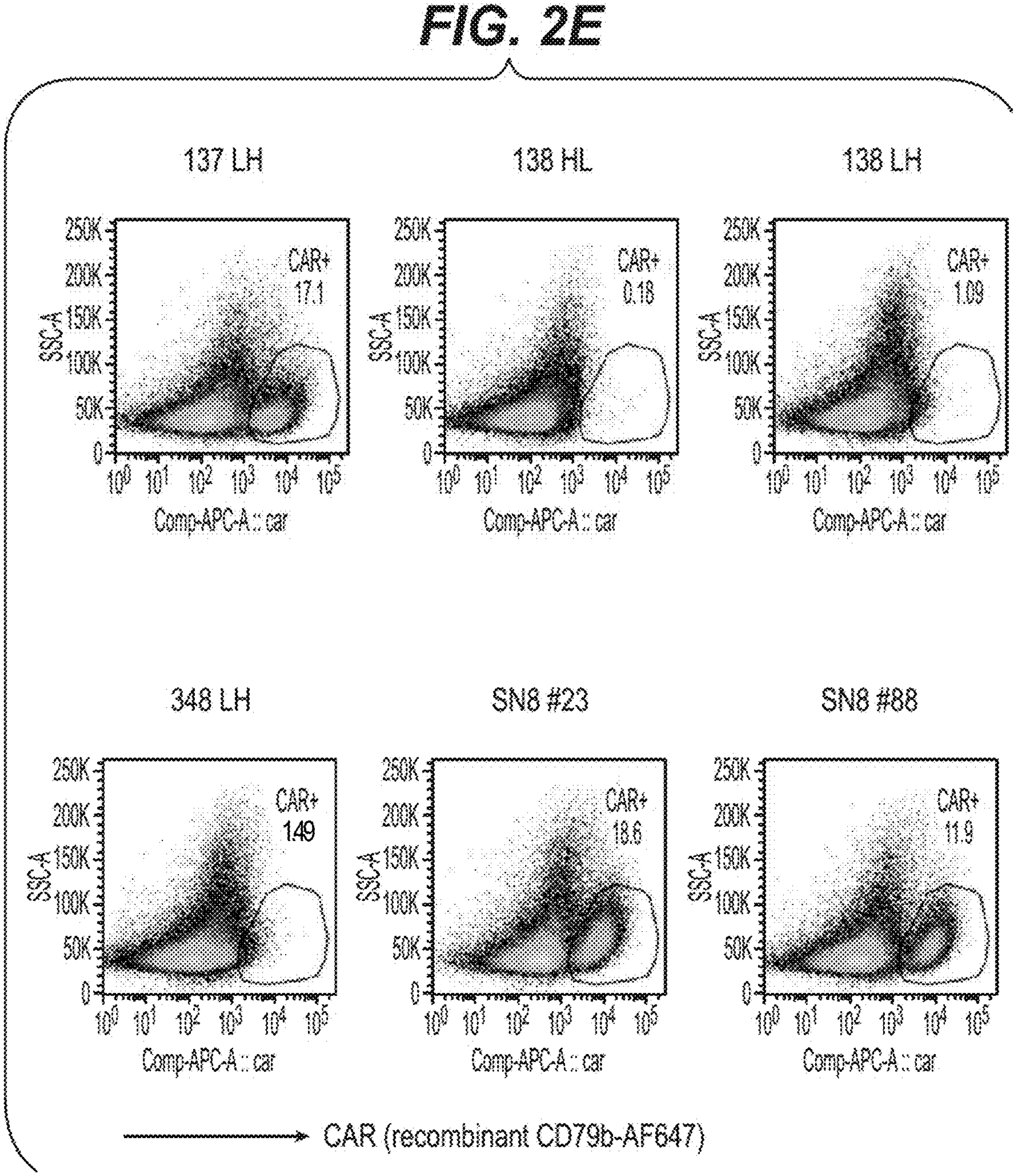
Figure 2F:
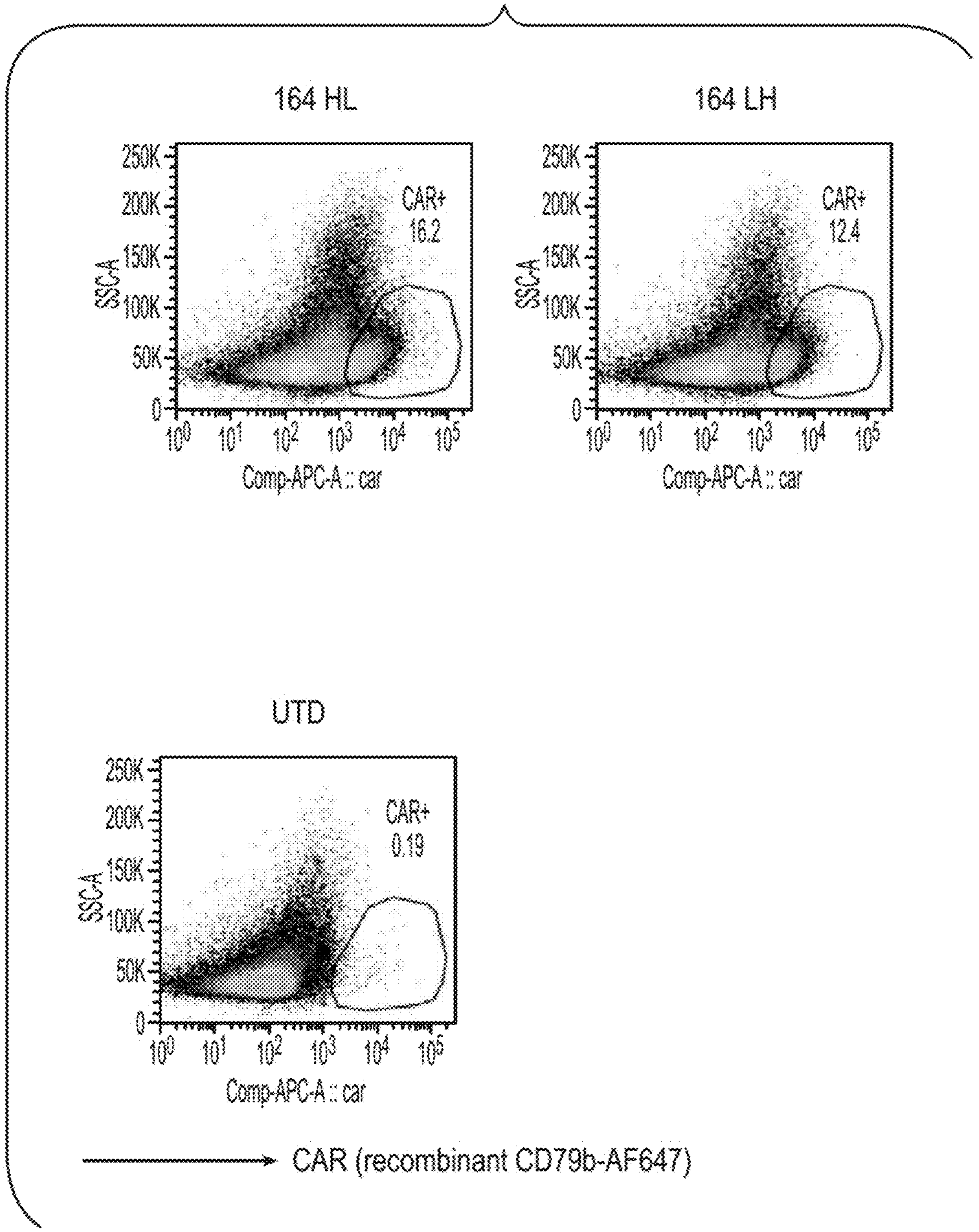
Figure 2G:
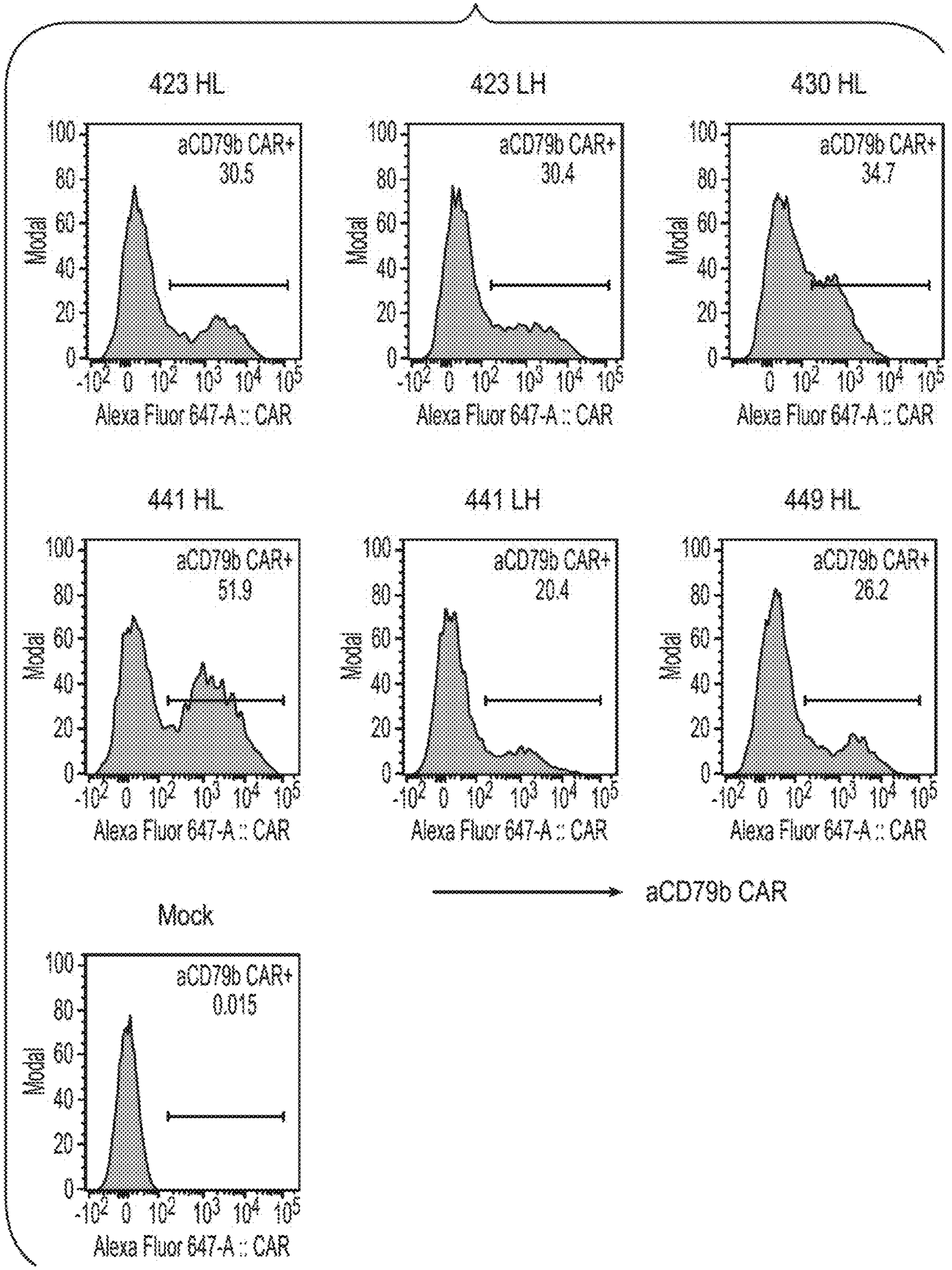
Figure 2H:
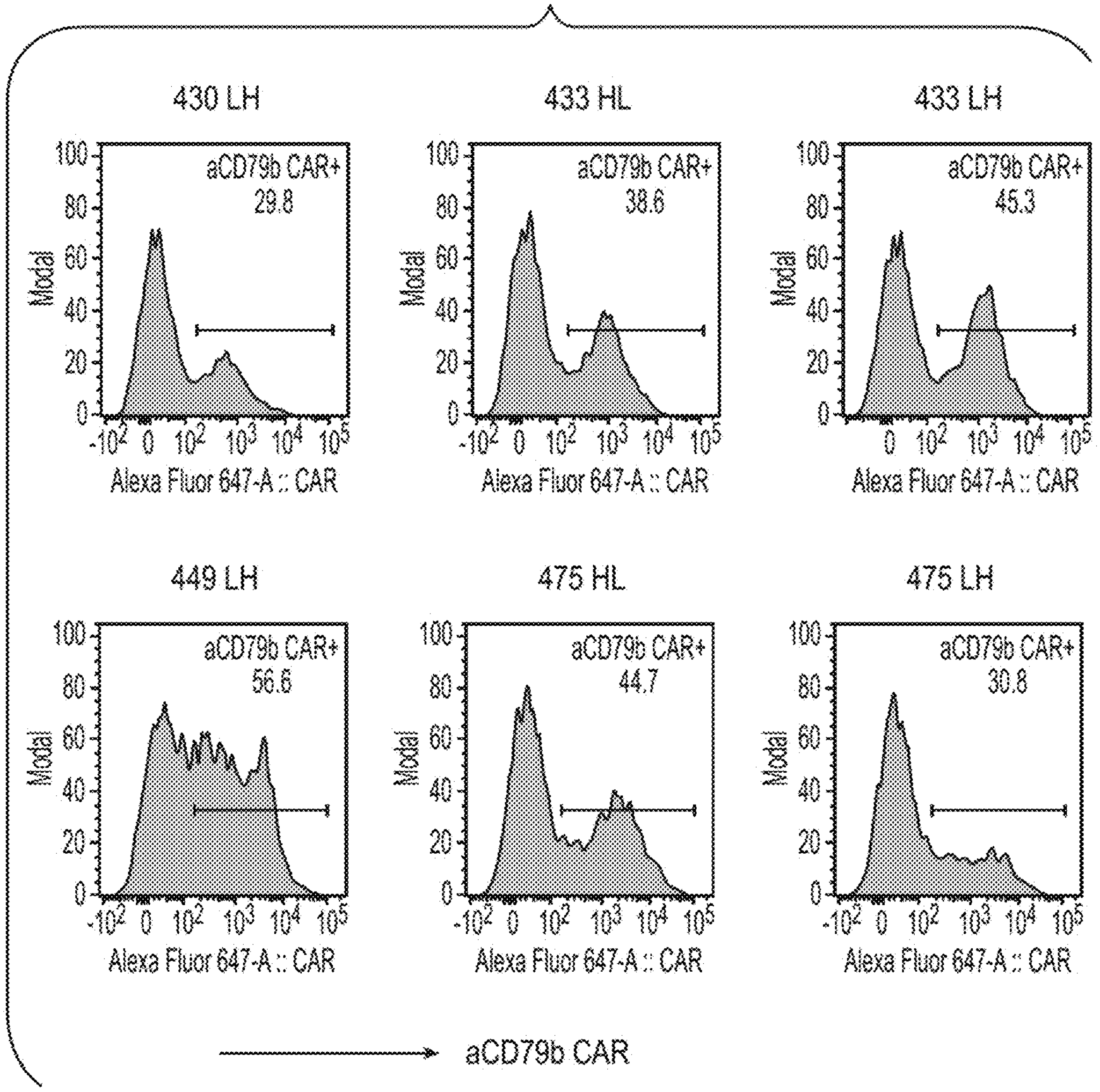
Figure 2I:
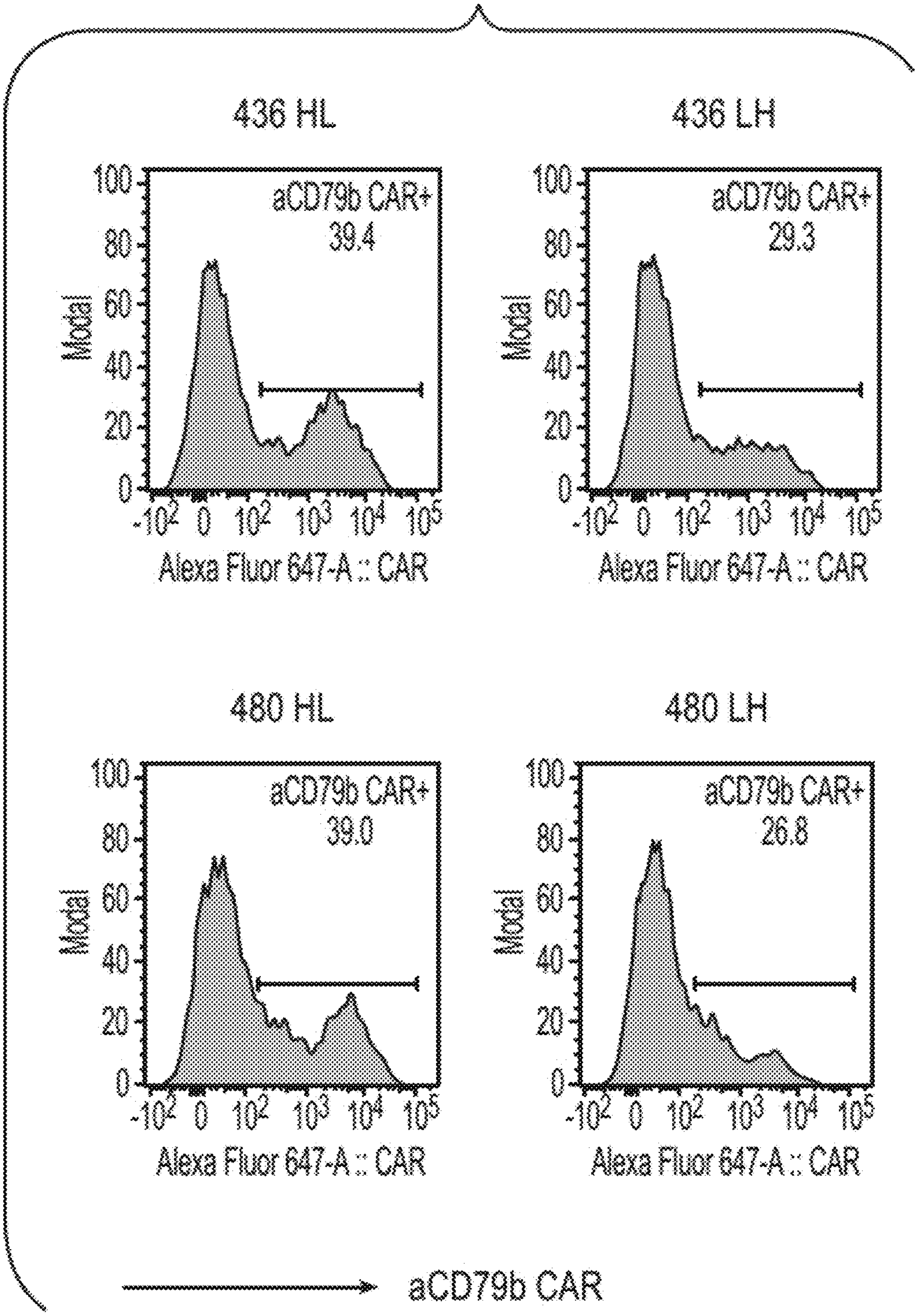

CD79b specific CARs were constructed as illustrated in FIG. 1. gBlocks (IDT) encoding the scFv sequence were cloned via In-Fusion© (Clontech) (a cloning kit) into a third generation self-inactivating lentiviral vector backbone with an EF1a promoter and a CD8a hinge/transmembrane domain followed by a 4-1BB (CD137) and CD3z intracellular domain in series. CAR-T cells were generated as follows: Primary human T cells were isolated via negative selection using the Pan-T cell isolation kit (StemCell Technologies Inc.) $1\times10^6$ cells were stimulated according to manufacturer's instructions with either TransAct™ (Miltenyi) in TexMACS™ media supplemented with 100 U/mL recombinant human IL-2 (FIGS. 2A-2C, 2G-2I), or with anti-CD3/anti-CD28 beads (Dynabeads™, Invitrogen) in Optimizer media supplemented with 100 U/mL IL-2 (Miltenyi) (FIGS. 2D-2F). Cells were transduced with lentiviral vectors encoding the CAR construct 24 hours post-stimulation. Cells were de-beaded and transferred to G-Rex® (Wilson Wolf) (Gas Permeable Cell Culture Device) at day 5 of culture. T cells were cultured for 12-14 days total prior to harvest and freezing in CryoStor® CS10 media. During culture, media and cytokine were refreshed every 2-4 days. CD79b CAR expression was quantified via flow cytometry using recombinant human CD79b extracellular domain fused to AF647 protein. The frequency of CAR+ cells is shown FIGS. 2A-2I.

Example 2: Tumor Lysis Mediated by CD79b CAR-T Cells

Figure 3A:
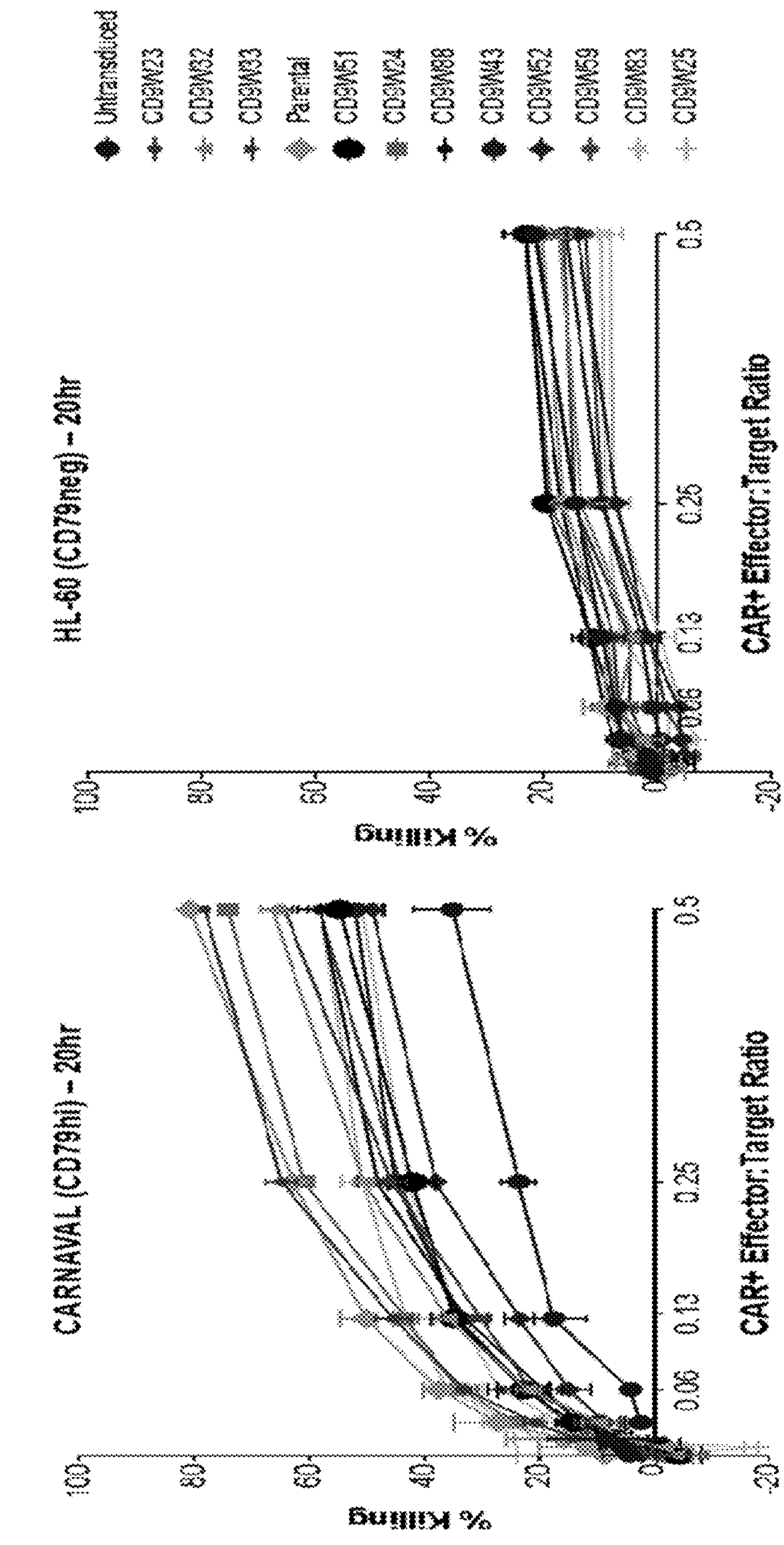
FIGS. 3A-3F demonstrate that aCD79b CARs exhibit cytotoxicity against CD79b+ tumor cell lines. aCD79B CARs were co-cultured with the indicated target cell lines and at the indicated effector:target (E:T) ratio (based upon CAR+ frequency) for 16-20 hours. Tumor lysis was evaluated via flow cytometry following live/dead staining (FIG. 3A) or via loss of tumor cell luciferase signal (FIGS. 3B-3F) using the Promega Bright-Glo™ kit (Luciferase Assay System), per manufacturer's instructions. In each case % lysis was calculated relative to tumor alone condition. CAR dose-dependent anti-tumor activity of CD79b+ target cells was observed, with no lysis above background against CD79b$^{neg}$ targets.
Figure 3B:
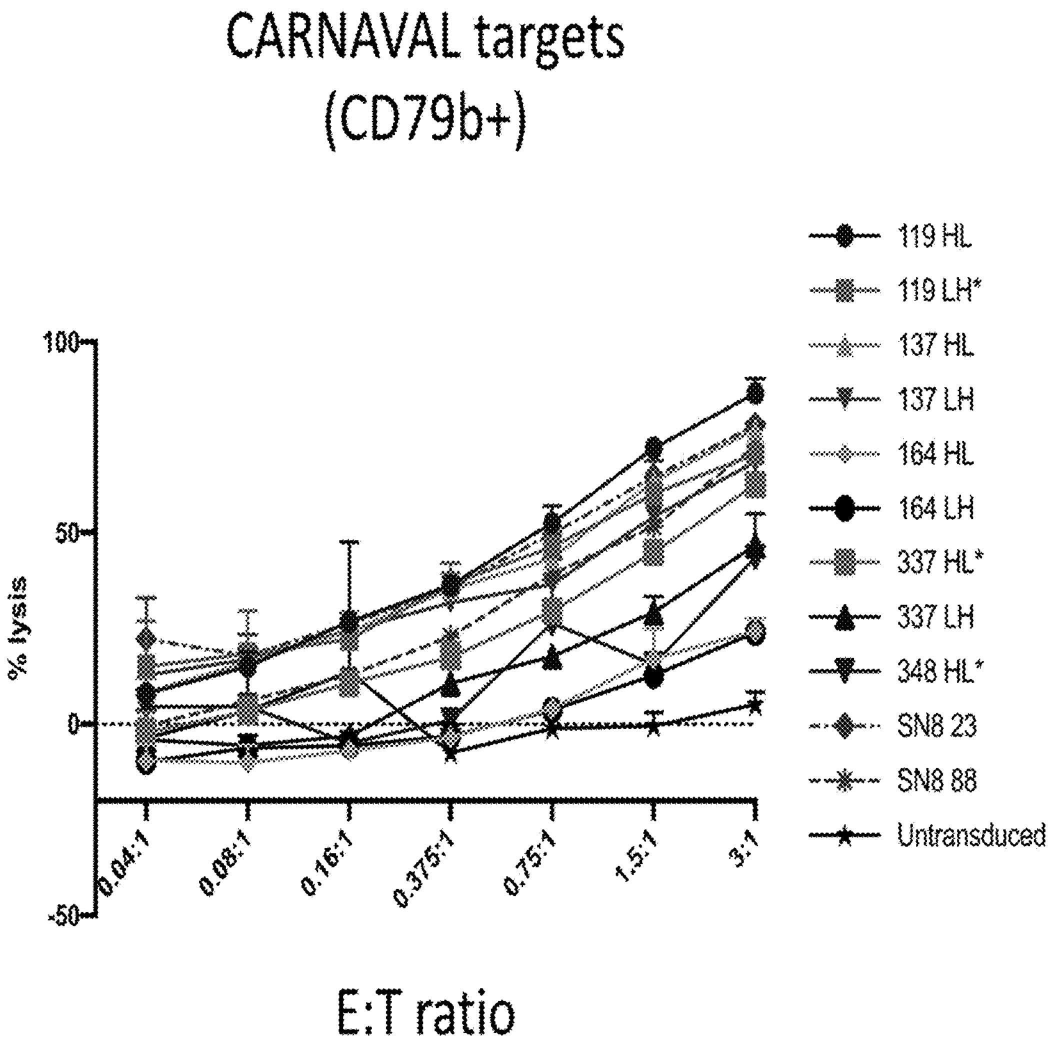
Figure 3C:
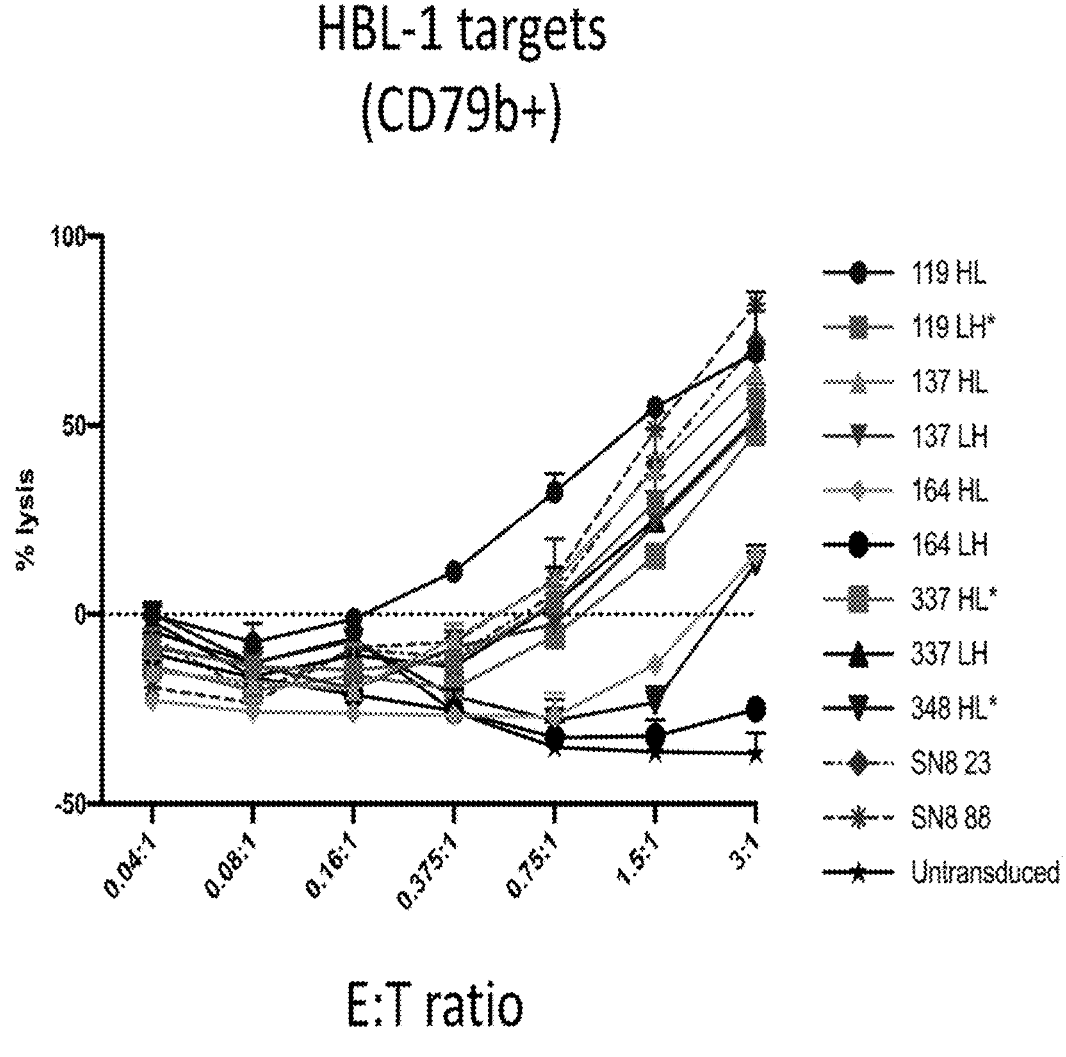
Figure 3D:
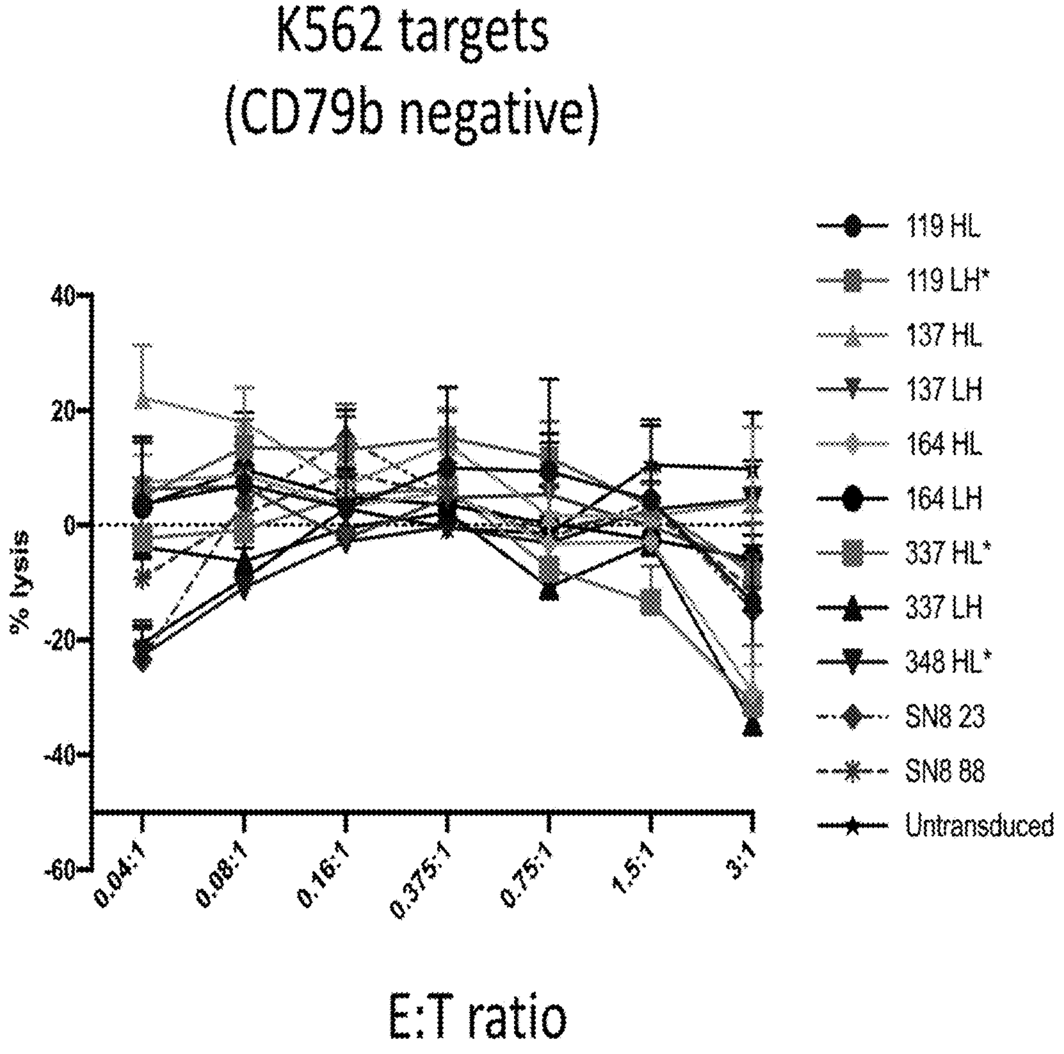
Figure 3E:
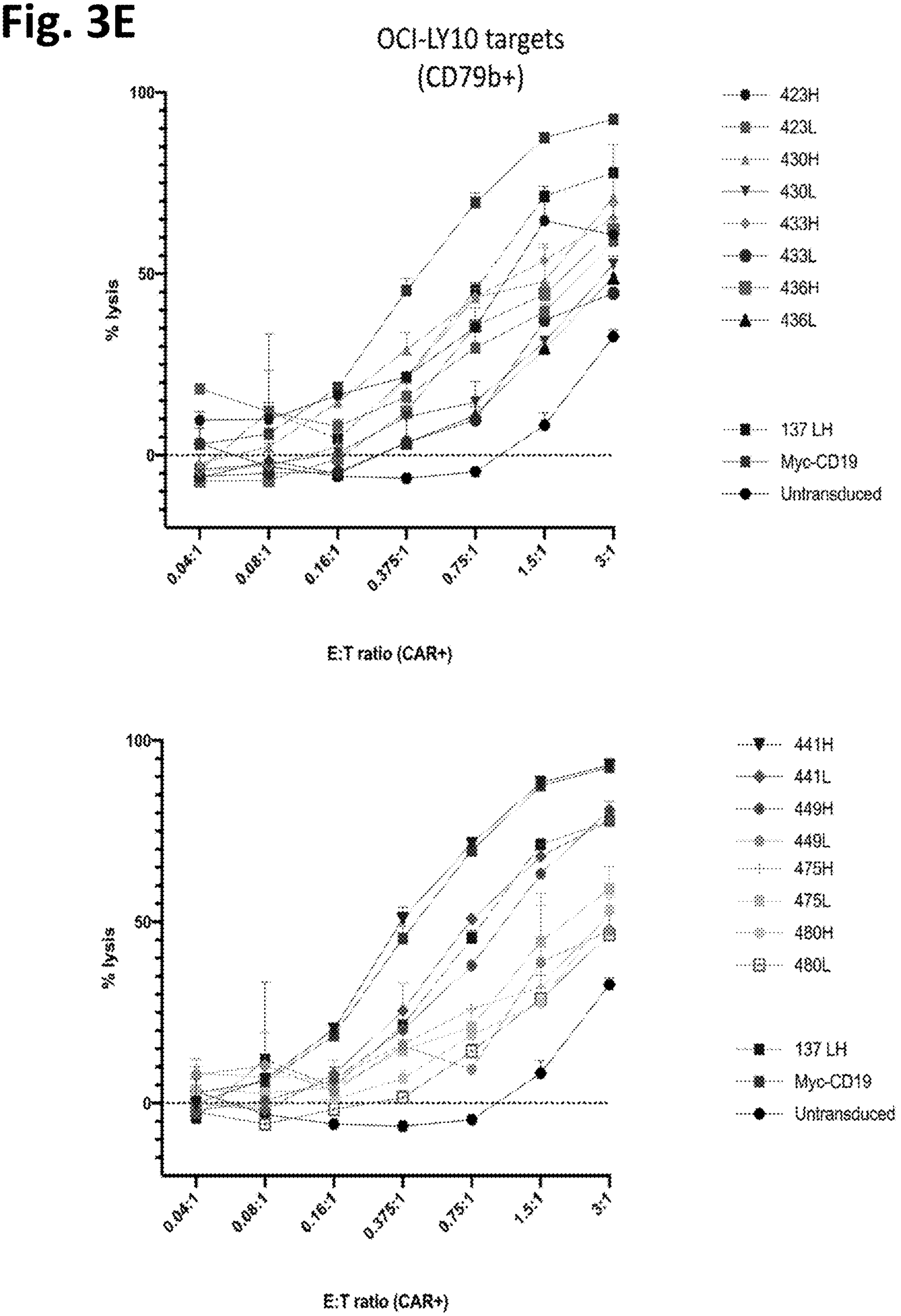
Figure 3F:
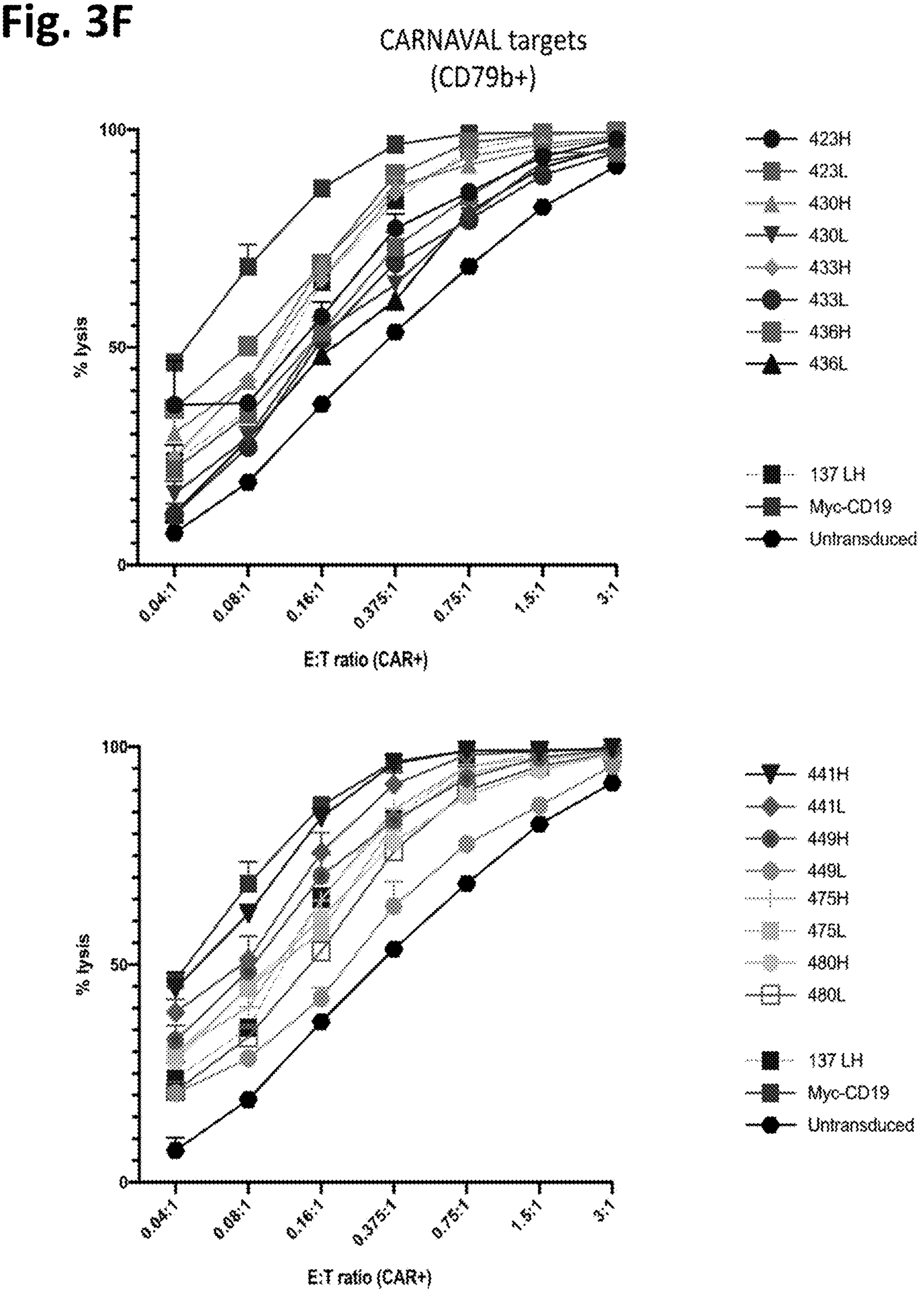
Figure 4A:
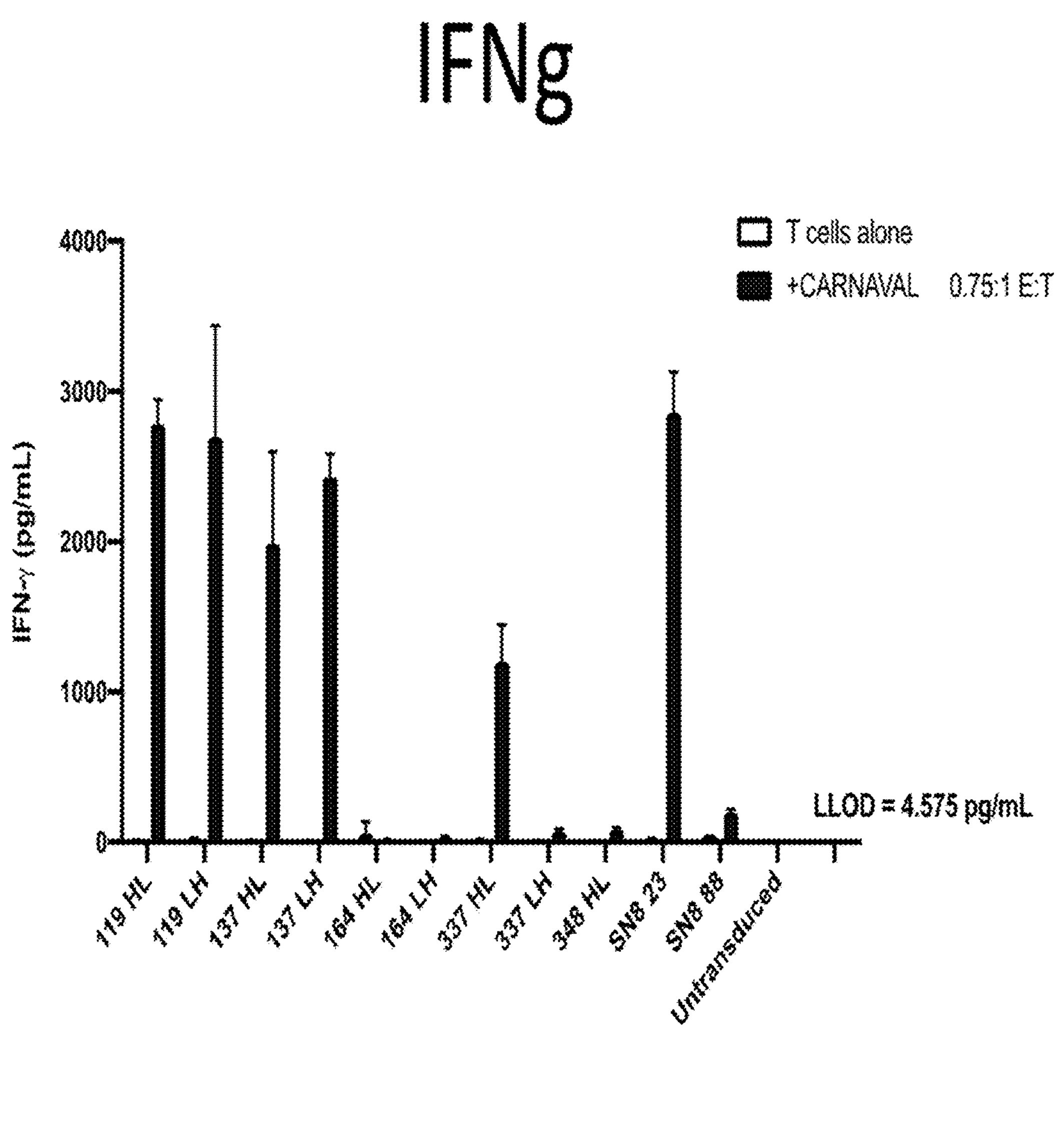
FIGS. 4A-4D show aCD79b CARs secrete cytokine in response to stimulation with antigen positive tumor cells. Supernatants from co-cultures setup as described in FIG. 3 were harvested 16-20 hours after setup, and cytokine quantified via MSD kit (Meso Scale Diagnostics) per manufacturer's protocol. aCD79b CARs demonstrated antigen dependent cytokine production.
Figure 4B:
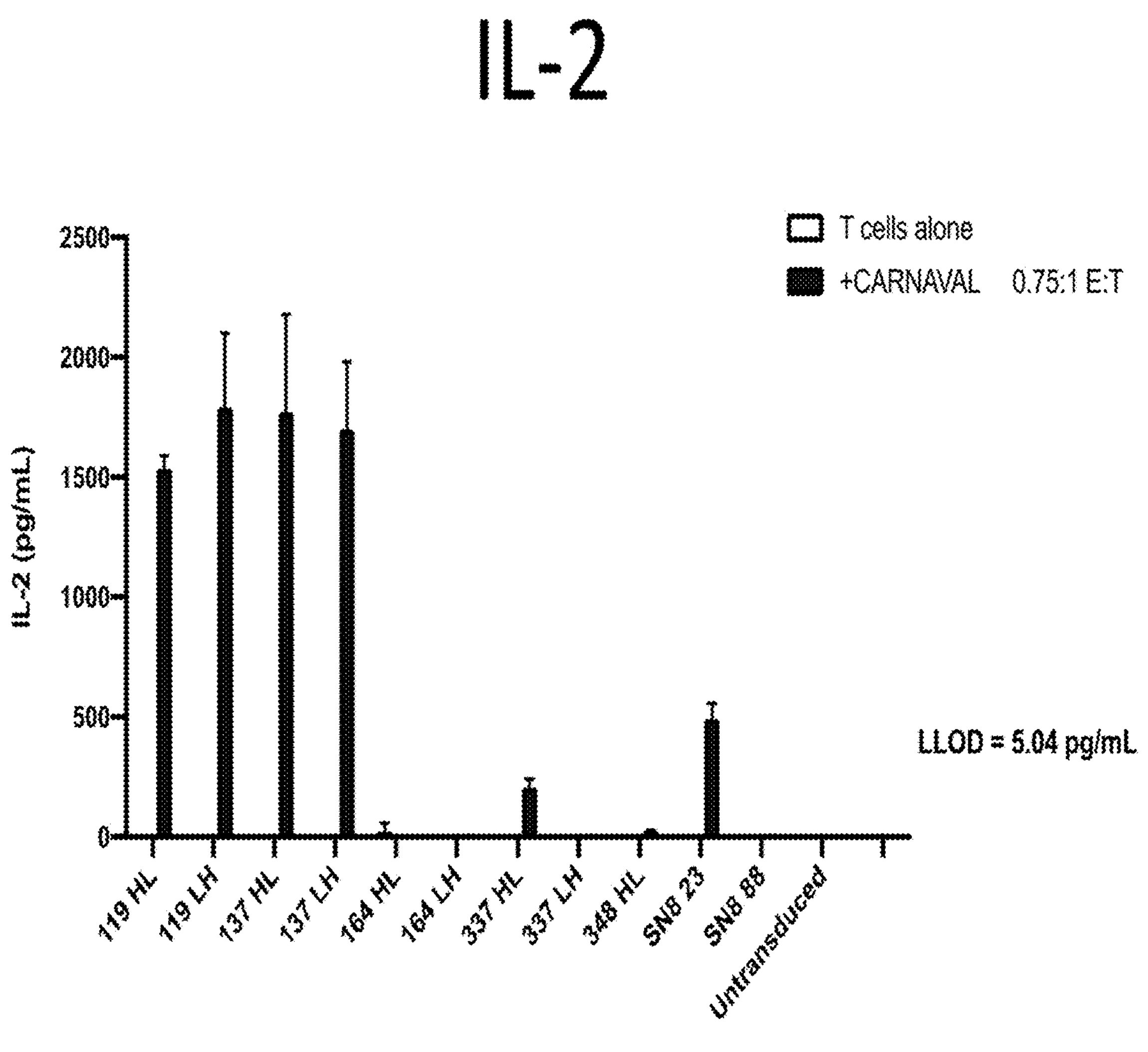
Figure 4C:
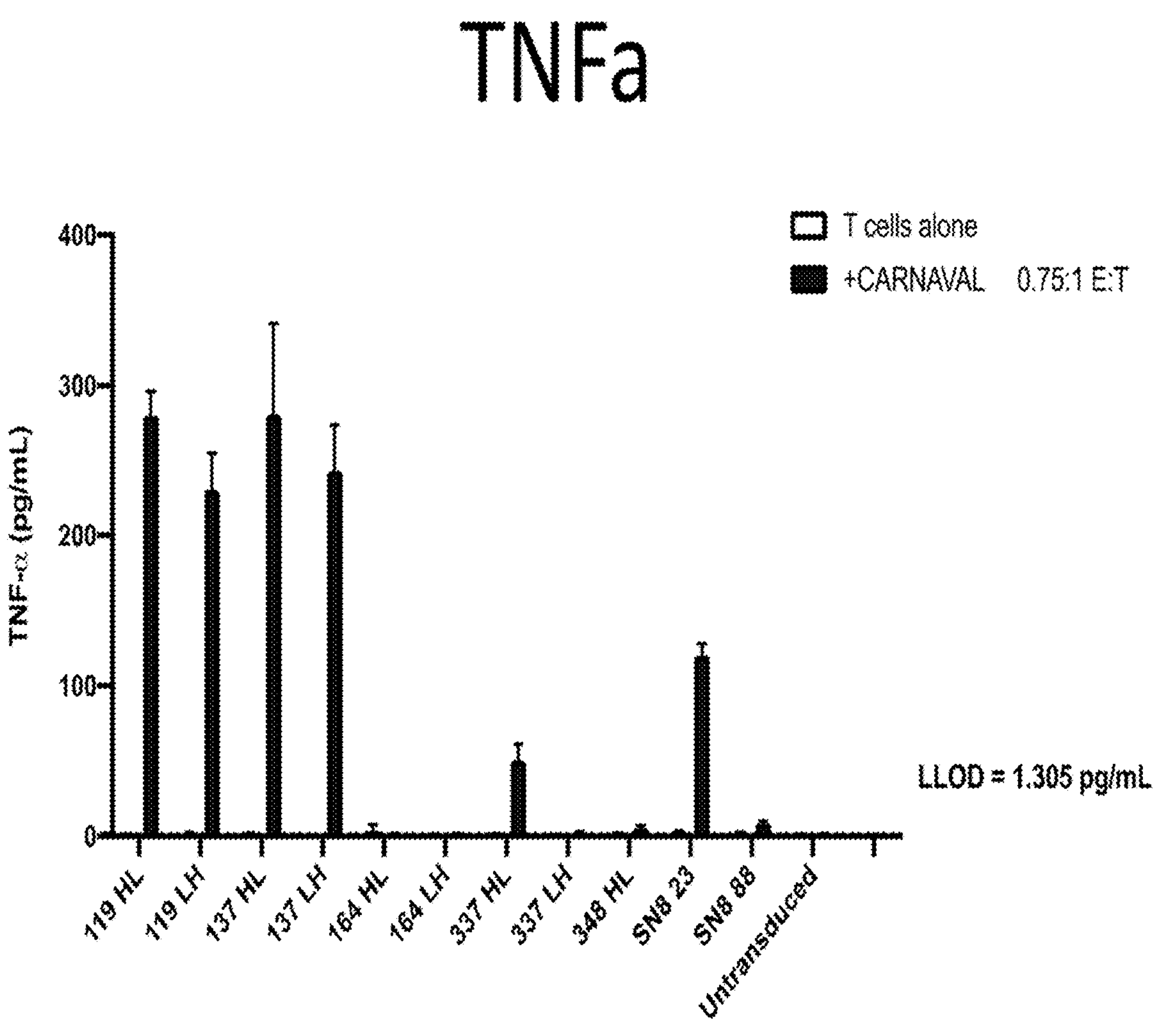
Figure 4D:
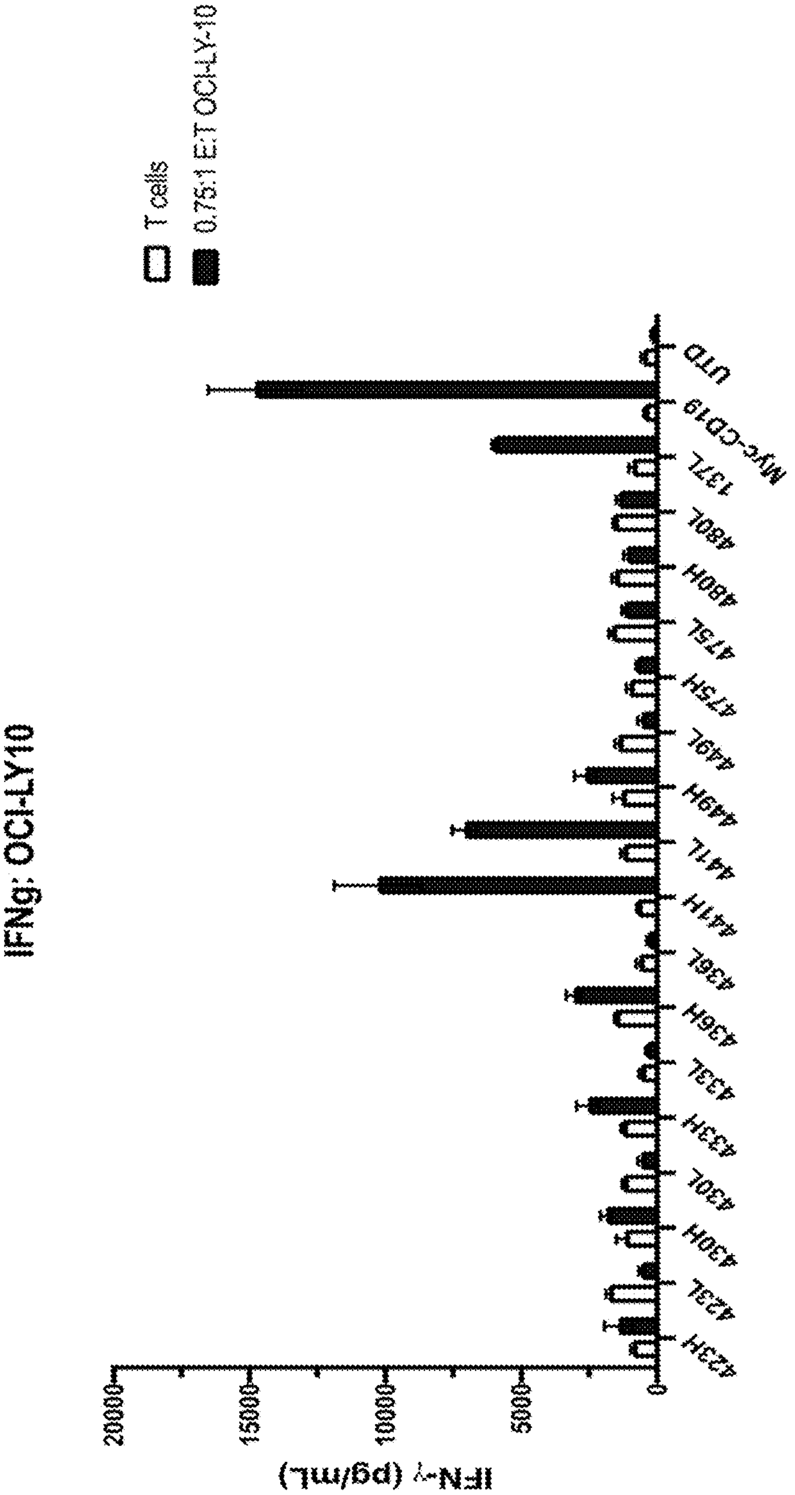

Frozen CAR-T cells were thawed into either TexMACS™ or OpTmizer™ media and rested overnight with 100 U/mL recombinant human IL-2 (Miltenyi). Co-cultures were performed by incubating aCD79B CAR-T cells with the indicated target cell lines at the indicated effector:target (E:T) ratio (based upon CAR+ frequency) for 16-20 hours. Co-cultures were set up in triplicate. For FIG. 3A, tumor cells were labeled with 10 μM CellTrace™ Violet (CTV) prior to co-culture. Tumor cells were stained with LIVE/DEAD™ fixable near-IR (Thermo) viability dye for 30 minutes at 4° C., and total viable tumor cells were quantified via flow cytometry. For FIGS. 3B-3F, plates were centrifuged at 400 g for 4 min 16-20 hours post-setup, and ½ culture volume was harvested for supernatant. One volume of Promega Bright-Glo™ luciferase substrate was added per manufacturer's instructions, and luminescence was quantified via Perkin Elmer EnVision® Multilabel Plate Reader. In each case % lysis (or % killing) was calculated as follows:

% lysis=[1−(Signal in test well/Tumor alone well signal)]*100

The results are shown in FIGS. 3A-3F. Mean % lysis±SD is shown.

Example 3: Antigen Induced Cytokine Production by CD79b CAR-T Cells

CAR driven cytokine production, in particular IL-2, can promote CAR-T cell persistence and ultimately anti-tumor function. To quantify cytokine production by CD79b CAR-T cells, supernatants harvested as per FIGS. 3B-3F were assayed using V-Plex MSD 4-plex (IFNg, IL-2, TNFa, IL-10) (Meso Scale Diagnostics) per manufacturer's protocol. aCD79b CAR-T cells demonstrated antigen dependent cytokine production. Results are shown in FIGS. 4A-4D. Mean cytokine concentration±SD (pg/ml) is shown.

Example 4: Generation and Characterization of Thermally Stabilized scFvs CAR Constructs The anti-CD79b antibody clone SN8 was identified by Astsaturov et al [9]. Humanization of the murine-derived clone SN8 was performed by the method described in Singh et al., MAbs. 2015; 7(4):778-91. Humanization was performed in the form of scFvs and the *E. coli*—expressed supernatants from the humanized variants were incubated at 60° C. for 15 minutes, followed by screening for binding to recombinant CD79b using ELISA.

Description and SEQ ID NOs of exemplary CAR constructs containing thermally stabilized SN8 scFvs are provided in Table 2.

TABLE 2

CAR constructs with SN8 thermally stabilized scFvs

| # of construct | Description | SEQ ID NO |
|---|---|---|
| 1 | CD9W23-LH | 75 |
| 2 | CD9W24-LH | 76 |
| 3 | CD9W32-LH | 77 |
| 4 | CD9W33-LH | 78 |
| 5 | CD9W51-LH | 79 |
| 6 | CD9W59-LH | 80 |
| 7 | CD9W83-LH | 81 |
| 8 | CD9W88-LH | 82 |
| 9 | CD9W23-HL | 97 |
| 10 | CD9W24-HL | 98 |
| 11 | CD9W32-HL | 99 |
| 12 | CD9W33-HL | 100 |
| 13 | CD9W51-HL | 101 |
| 14 | CD9W59-HL | 102 |

TABLE 2-continued

| CAR constructs with SN8 thermally stabilized scFvs | | |
|---|---|---|
| # of construct | Description | SEQ ID NO |
| 15 | CD9W83-HL | 103 |
| 16 | CD9W88-HL | 104 |

Figure 5A:
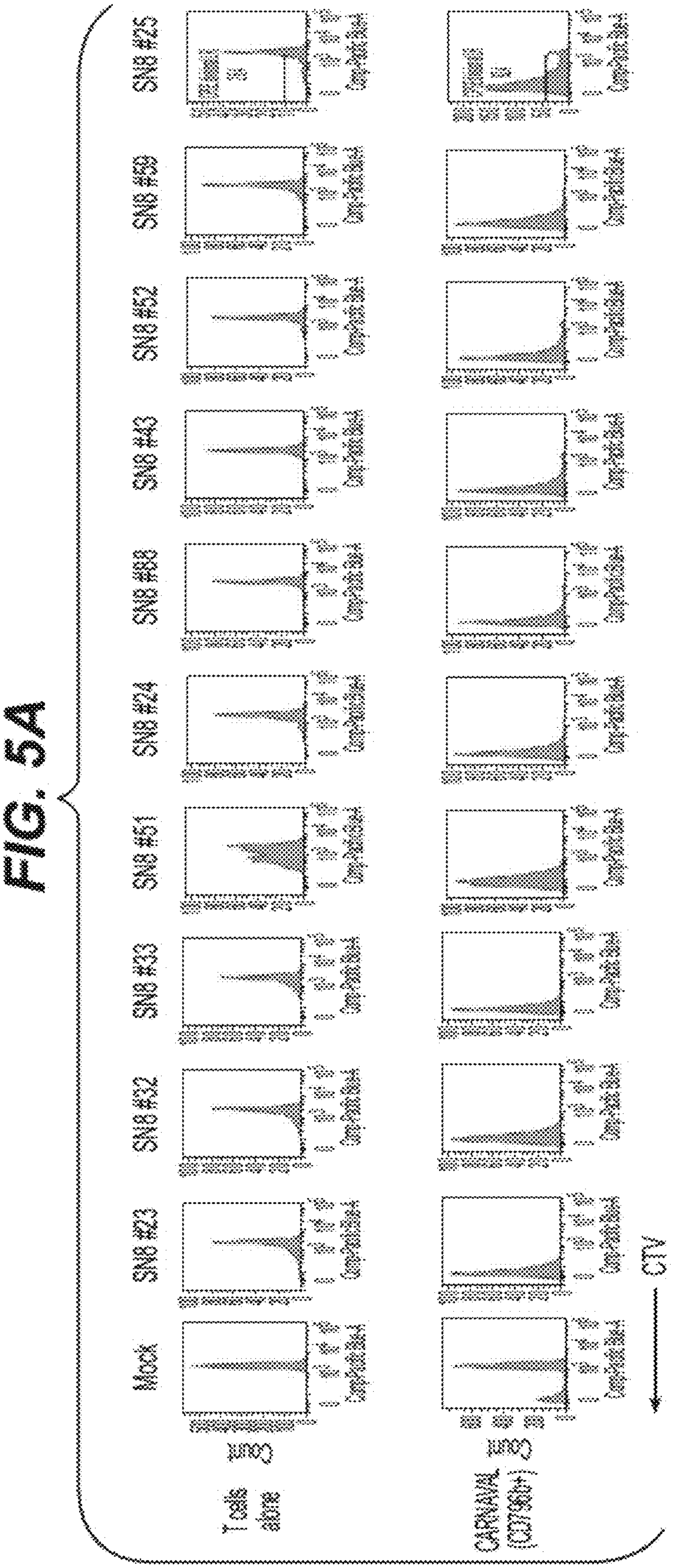
FIGS. 5A-5C show that aCD79b CARS proliferate specifically in the presence of antigen. aCD79b CARs were labeled with CellTrace™ Violet (CTV) (fluorescent dye) per manufacturer's instructions (Invitrogen). Labeled CAR-T cells were co-cultured with indicated targets at 1:2 E:T ratio for 4-5 days and then stained with CAR detection reagent (recombinant CD79b-AF647). Proliferation of CAR+ cells was then analyzed via flow cytometry. Plots show CTV dilution of CAR+ cells. aCD79b CARs exhibited CTV dilution (proliferation) specifically upon stimulation with CD79b+ tumor lines, and not against antigen negative target lines.
Figure 5B:
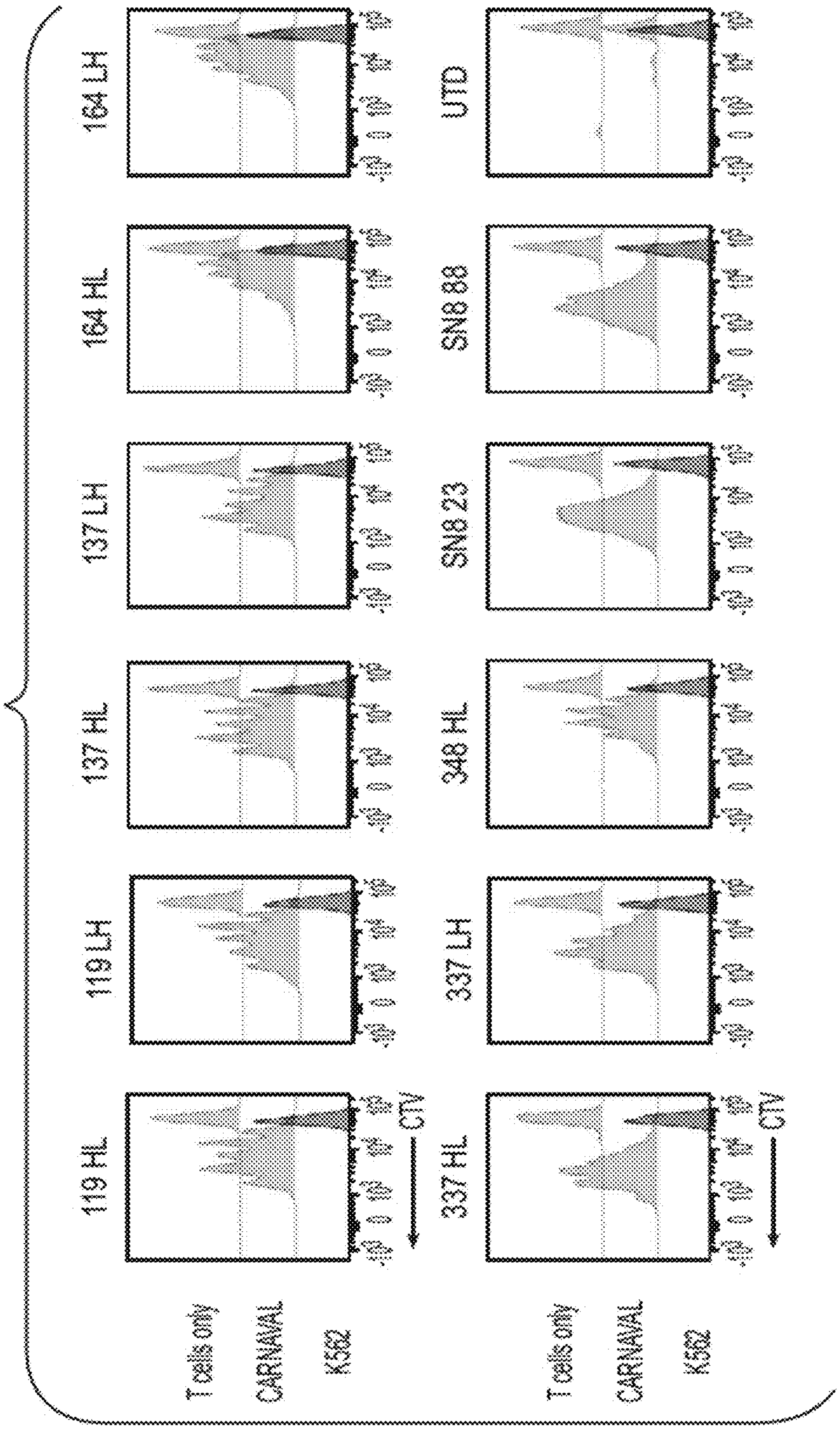
Figure 5C:
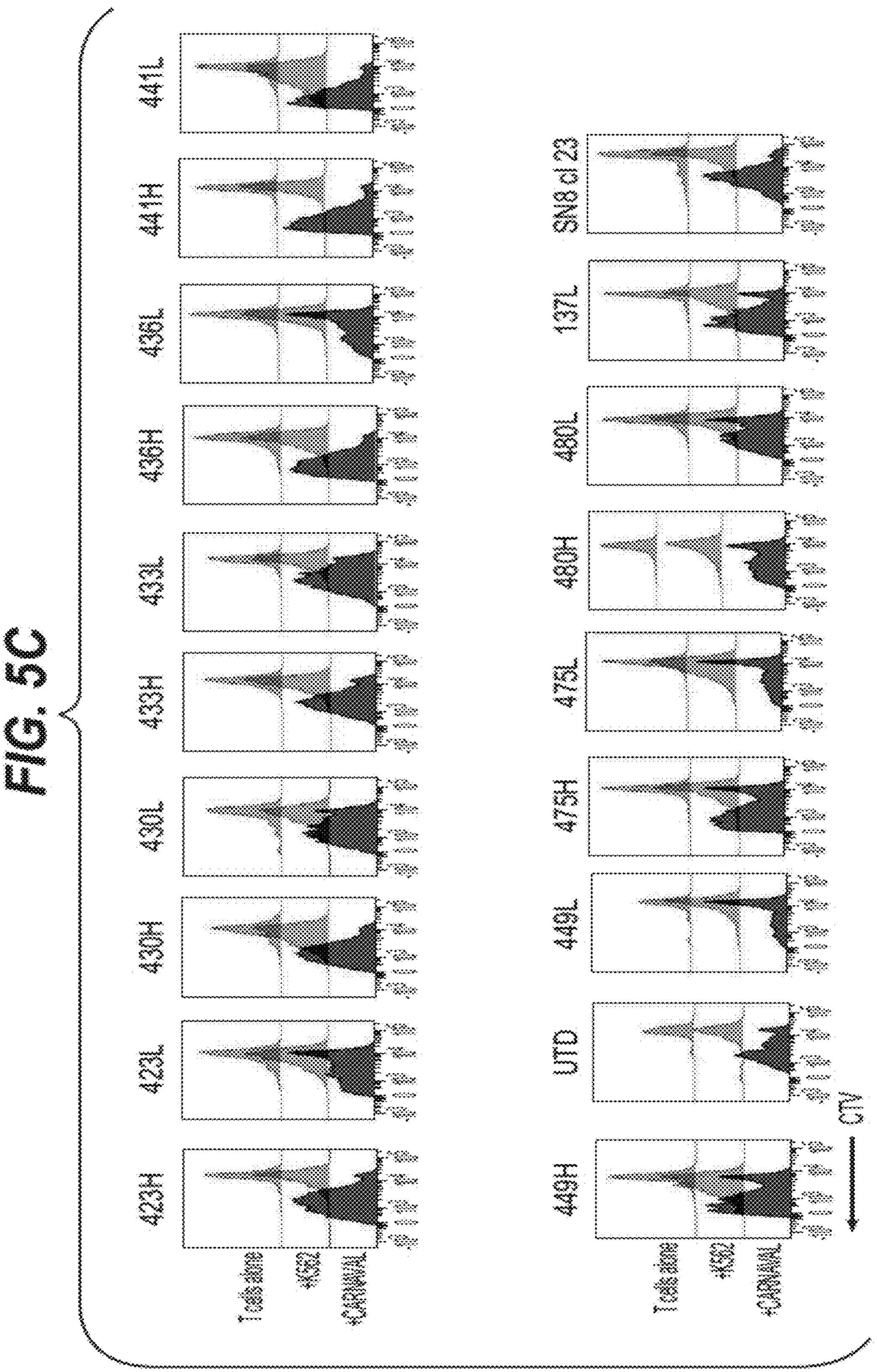

Example 5: Antigen Dependent Proliferation of CD79b CARs aCD79b CAR-T cells were labeled with 1 μM CellTrace™ Violet (CTV) at $1\times10^6$ cells/mL per manufacturer's instructions (Invitrogen). Labeled CAR-T cells were co-cultured with indicated targets at 1:2 E:T ratio for 4-5 days. E:T ratio was calculated based on CAR+, and total T cells were normalized across constructs by addition of untransduced T cells. On day 4-5, cells were harvested and stained with CAR detection reagent (recombinant CD79b-AF647) and fixable LIVE/DEADh (Invitrogen). Proliferation of CAR+ cells was then analyzed via flow cytometry. In FIGS. 5A-5C, plots show CTV dilution of CAR+ cells. aCD79b CAR-T cells exhibited CTV dilution specifically upon stimulation with CD79b+ tumor lines, and not against antigen negative target lines, suggesting antigen dependent proliferation.

Figure 6:
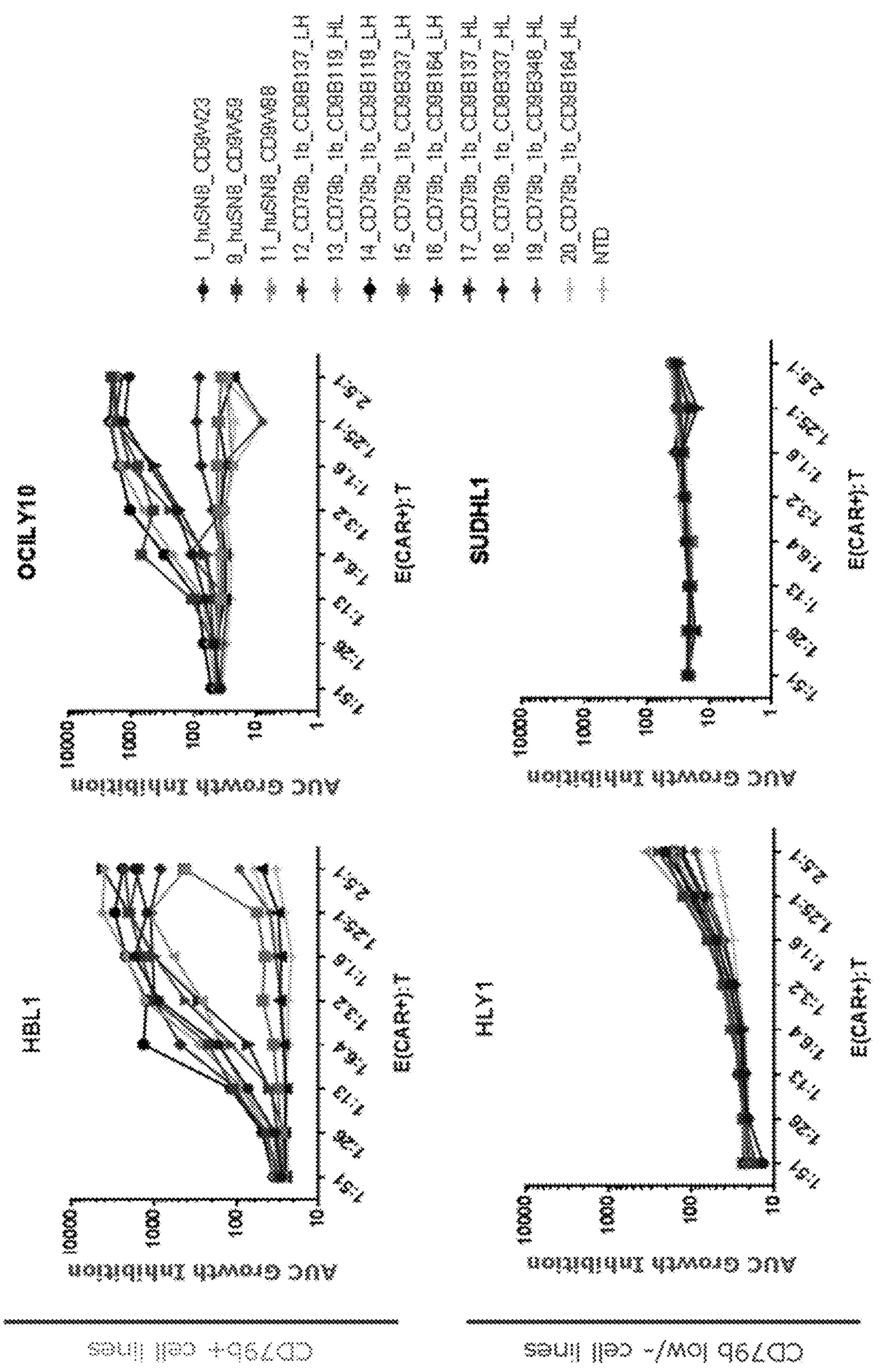
FIG. 6 shows that aCD79b CARs exhibit long-term cytotoxicity against CD79b+ tumor cell lines. aCD79B CARs were co-cultured for 4-7 days with the indicated RFP-expressing target cell lines and at the indicated effector:target (E:T) ratio (based upon CAR+ frequency). Cell proliferation was followed over time by imaging each well every 4 hours and calculating total RFP+ area/well using IncuCyte® technology (live cell imaging and analysis system). Growth inhibition was calculated for each of the constructs tested.

Example 6: CD79b Specific Lysis of Tumors in Extended Cytotoxicity Assay aCD79B CAR-T cells were co-cultured for 4-7 days with the indicated red fluorescent protein (RFP)-expressing target cell lines and at the indicated effector:target (E:T) ratio (based upon CAR+ frequency). Cell proliferation was followed over time by imaging each well every 4 hours and calculating total RFP+ area per well using IncuCyte® technology. Growth inhibition was calculated for each of the constructs tested (FIG. 6)

Example 7: Antitumor Activity of CD79b CAR in CARNAVAL Xenograft Model

CARNAVAL cells were maintained in RPMI 1640 supplemented with 10% fetal bovine serum (FBS). $5\times10^5$ CARNAVAL cells in logarithmic growth phase were implanted subcutaneously in NOD/scid/IL-2Rg$^{-/-}$ (NSG) mice on day 0. CAR-T cells (huSN8 clone 23 or CD19 4-1BBz reference CAR) were generated as described previously (Example 1).

Figure 7A:
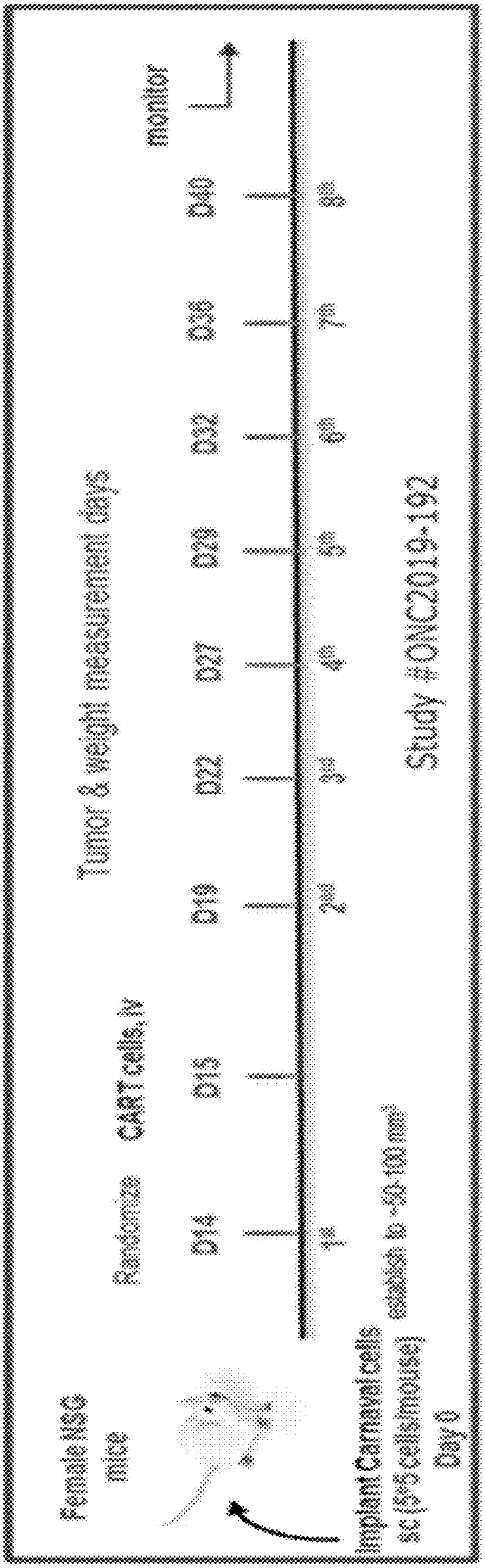
FIGS. 7A-7C show that aCD79b CAR-T cells eradicate CD79b+ tumors in vivo. $5\times10^5$ CARNAVAL cells were implanted subcutaneously in NOD/scid/IL-2Rg$^{-/-}$ (NSG) mice. When mean group tumor volume reached about 50-100 mm$^3$/mouse, CAR-T cells were injected intravenously (FIG. 7A). Tumors (FIG. 7B) and body weights (FIG. 7C) were monitored twice a week.
Figure 7B:
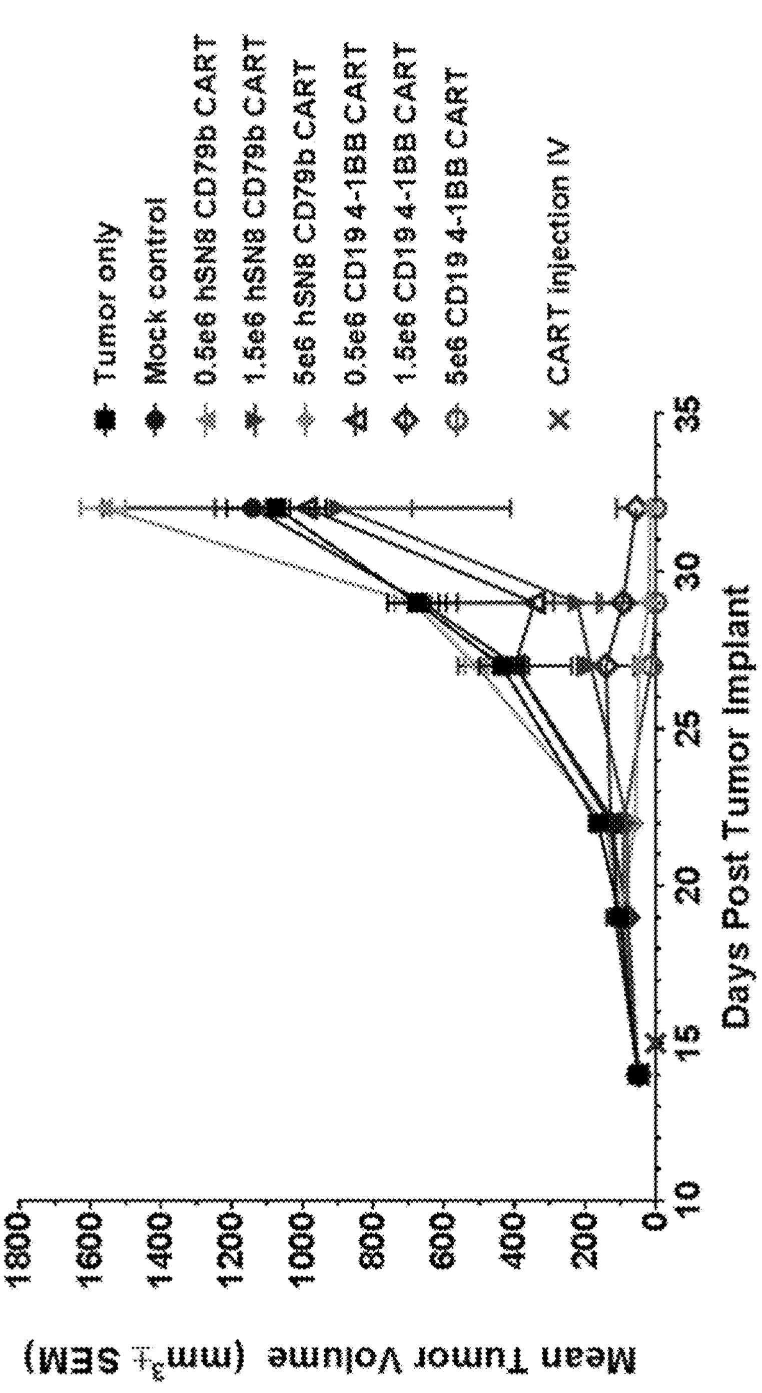
Figure 7C:
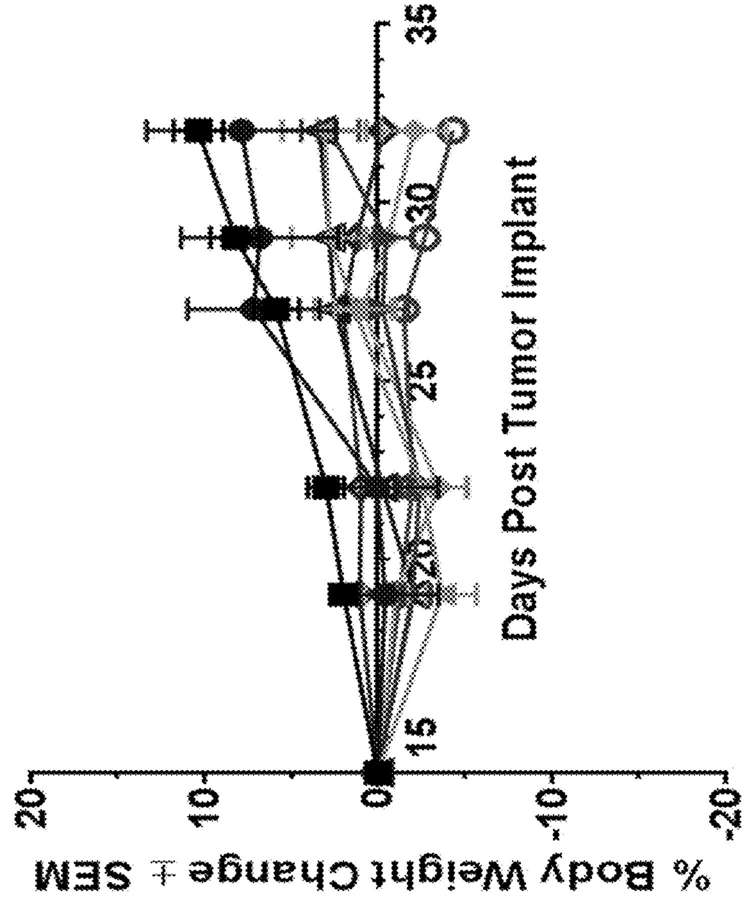

When mean group tumor volume reached about 50-100 $mm^3$/mouse about 14 days post-implant, indicated doses of CAR+ T cells were injected intravenously (FIG. 7A); untransduced CAR-T cells were added to normalize the number of both CAR+ and total T cells administered for each CAR. Tumor volume was measured twice weekly via caliper (FIG. 7B), along with body weight (FIG. 7C). huSN8 clone 23 (CD9W23-LH) CARs mediated complete tumor regression at a dose of $5\times10^6$ CAR+ cells, with no concomitant body weight loss observed.

Example 8: Biophysical Characterization of Recombinant scFv-Fc Protein

Various generated scFvs were fused with an Fc to generate recombinant scFv-Fc proteins. Biophysical characterization of the recombinant scFv-Fc proteins was performed, and the results are presented in Table 3 below. The purity of recombinant scFv-Fc proteins was measured by analytical size exclusion chromatography technique.

Binding Studies of scFv-Fc Fusion Proteins to Human CD79b by Surface Plasmon Resonance The binding affinity of scFv-Fc fusion proteins to recombinant human CD79b isoform-1 (long) and isoform-2 (short) was determined by Surface Plasmon Resonance (SPR) using a Biacore™ 8k instrument. scFv-Fc molecules were captured on the surface of a C1 sensor chip using a goat anti-human Fc IgG antibody at a density of 30-60 response units (RUs). The recombinant human CD79b antigen was then injected over the surface of the chip at concentrations from 3.70-300 nM at 3-fold dilutions, with an association time of 3 minutes and a dissociation time of 30 minutes. The raw binding sensorgrams were referenced by subtracting the analyte binding signals from blank surface, and the processed sensorgrams were analyzed using a 1:1 Langmuir binding model using Biacore™ Insight evaluation software to obtain binding kinetics and affinity.

Differential Scanning Fluorimetry (DSF)

Thermal stability of recombinant scFv-Fc fusion protein samples was determined by Nano Differential Scanning Fluorimetry (NanoDSF) method using an automated Prometheus instrument. Measurements were made by loading samples into 24-well capillary from a 384-well sample plate. Duplicate runs were performed for each sample. Prometheus NanoDSF user interface (Melting Scan tab) was used to establish the experimental parameters for the run. The thermal scans for a typical IgG sample span from 20° C. to 95° C. at a rate of 1° C./minute. Dual-UV technology monitors intrinsic tryptophan and tyrosine fluorescence at emission wavelengths of 330 nm and 350 nm, and this ratio (F350 nm/F330 nm) was plotted against temperature to generate an unfolding curve. Using back reflection technology, the instrument measured the on-set temperature of aggregation, which was plotted as mAU (milli Attenuation Units) against temperature. NanoDSF was used for measuring thermal unfolding parameters ($T_m$ and $T_{agg}$) of scFv-Fc samples at 0.5 mg/mL concentration in Phosphate Buffered Saline (PBS), pH 7.4.

Self-Association of scFv-Fc Fusion Proteins by Self Interaction Nanoparticle Spectroscopy Affinity Capture Self Interaction Nanoparticle Spectroscopy (AC-SINS) was used to measure the propensity of scFv-Fc candidates to self-interact. Propensity for self-interaction is potentially a predictive marker for CAR-T expression and stability on the cell surface. In this assay, gold nanoparticles (AuNPs) were coated with goat anti-human IgG (H+L) capture antibody and later incubated with candidate scFv-Fc in the presence of polyclonal goat IgG. Any candidate scFv-Fc that self-associated in turn brought the AuNPs into proximity, resulting in a shift of the nanoparticles' plasmon wavelength ($\lambda_p$), also referred to as the wavelength at maximum absorbance ($\lambda_{max}$). The magnitude of the shift ($\Delta\lambda_{max}$) for each candidate scFv-Fc is indicative of the strength of its self-association.

Non-Specific Binding Assessment by Surface Plasmon Resonance

Non-specific binding of antibodies to unrelated charged proteins and polyclonal IgG were determined by biosensor technology. scFv-Fc was passed over Surface Plasmon Resonance (SPR) surfaces coated with unrelated proteins (such as Soybean Trypsin Inhibitor, Lysozyme, Beta Defensin, pooled human IgG, Integrin a4b7, PLBL2). If the antibody displays significant non-specific binding to these surfaces, it is likely that this binding translates to poor pharmacokinetics (PK) and bio-distribution, and suboptimal expression of the scFv on the CAR-T cell surface. A description of biophysical characteristics of recombinant scFv-Fc fusion proteins are provided in Table 3.

TABLE 3

Biophysical characterization of recombinant scFv-Fc protein

| Name | Purity (% Monomer) | Binding Affinity to CD79b ($K_D$) | $T_m$ (Thermal Stability) (° C.) | Self-Association (AC-SINS) | Non-Specific Binding (SPR) |
|---|---|---|---|---|---|
| CD9B137 LH | 93.7 | Long: 0.6 nM<br>Short: 2.1 nM | 59.3 | None | <25 RU |
| CD9B137 HL | 95.8 | Long: 0.6 nM<br>Short: 2.4 nM | 61.7 | None | <25 RU |
| CD9B119 LH | 93.8 | Long: 1.6 nM<br>Short: 9.7 nM | 54.1 | None | <25 RU |
| CD9B119 HL | 93.7 | Long: 2.2 nM<br>Short: 9.4 nM | 55.7 | None | <25 RU |
| CD9B337 LH | 95.7 | Long: Biphasic<br>Short: 27 nM | 62.4 | None | <25 RU |
| CD9B337 HL | 94.4 | Long: Biphasic<br>Short: 22 nM | 60.0 | None | <25 RU |
| CD9W23 LH | 96.6 | Long: Biphasic<br>Short: 11.5 nM | 61.1 | None | <25 RU |
| CD9W59 LH | 96.4 | Long: Biphasic<br>Short: 6.9 nM | 59.6 | None | <25 RU |
| CD9B423 HL | >90 | Long: 0.53 nM<br>Short: Weak/No | 62.1 | None | <25 RU |
| CD9B430 HL | 89.41 | Long: Biphasic<br>Short: Weak/No | 70.9 | None | <25 RU |
| CD9B433 HL | 93.41 | Long: Biphasic<br>Short: Weak/No | 71.1 | None | <25 RU |
| CD9B436 HL | >90 | Long: 0.54 nM<br>Short: Weak/No | 60.9 | None | <25 RU |
| CD9B441 HL | 94.99 | Long: 3.9 nM<br>Short: 18.2 nM | 55.4 | None | <25 RU |
| CD9B449 HL | 94.04 | Long: 1.52 nM<br>Short: Weak/No | 57.8 | None | <25 RU |
| CD9B475 HL | 92.60 | Long: 0.04 nM<br>Short: Weak/No | 56.1 | None | <25 RU |
| CD9B480 HL | 89.13 | Long 0.28 nM<br>Short: Weak/No | 51.3 | None | <25 RU |

Example 9: Basal Cytokine Production in Absence of Antigen

Figure 8A:
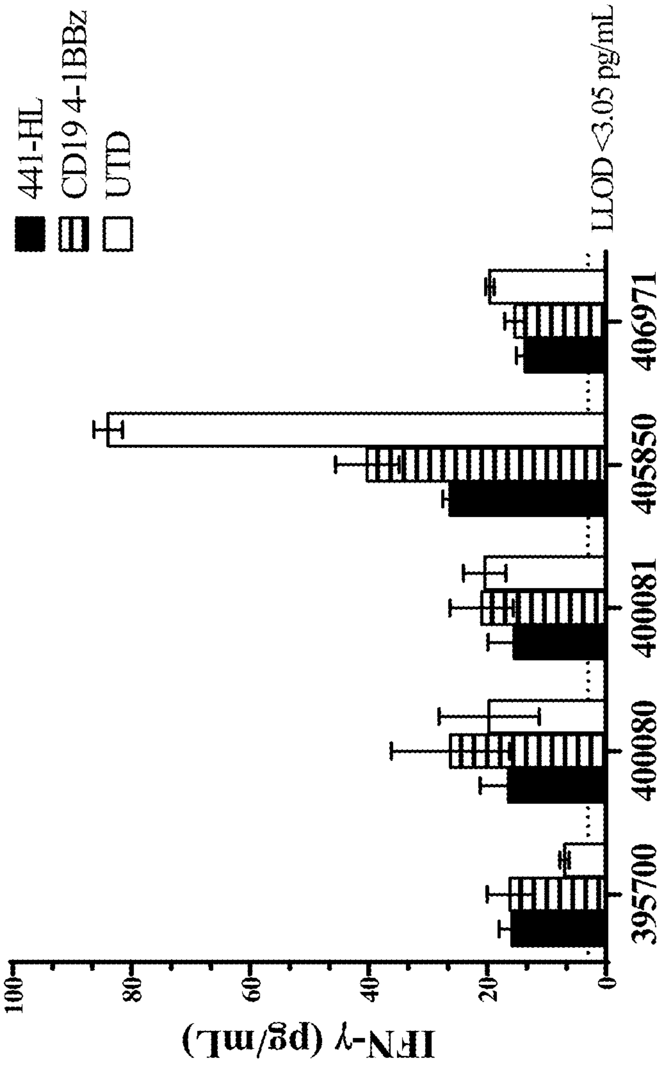
FIGS. 8A-8C demonstrates that basal cytokine levels in aCD79b CAR-T-transduced cells are not elevated in the absence of antigen or cytokine stimulation. Previously generated aCD79b CAR-T cells were plated in triplicate at 50,000 CAR+ cells per well. The total number of T cells per well was normalized across conditions via addition of untransduced (UTD) cells. Culture supernatants were collected following overnight culture and cytokine levels quantified using MSD (V Plex Proinflammation Panel 1 [human] kit). INFγ, IL-2, and TNFα levels detected in supernatants of 441-HL CAR-T, CD19 CAR-T and UTD cells are plotted as mean (pg per mL)±SEM for each donor.
Figure 8B:
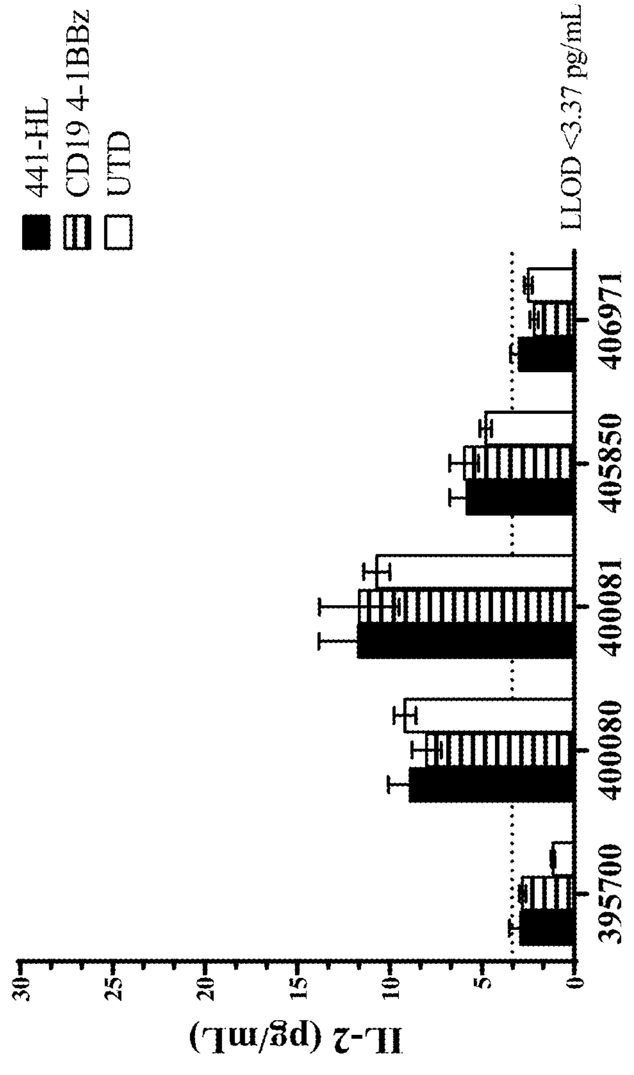
Figure 8C:
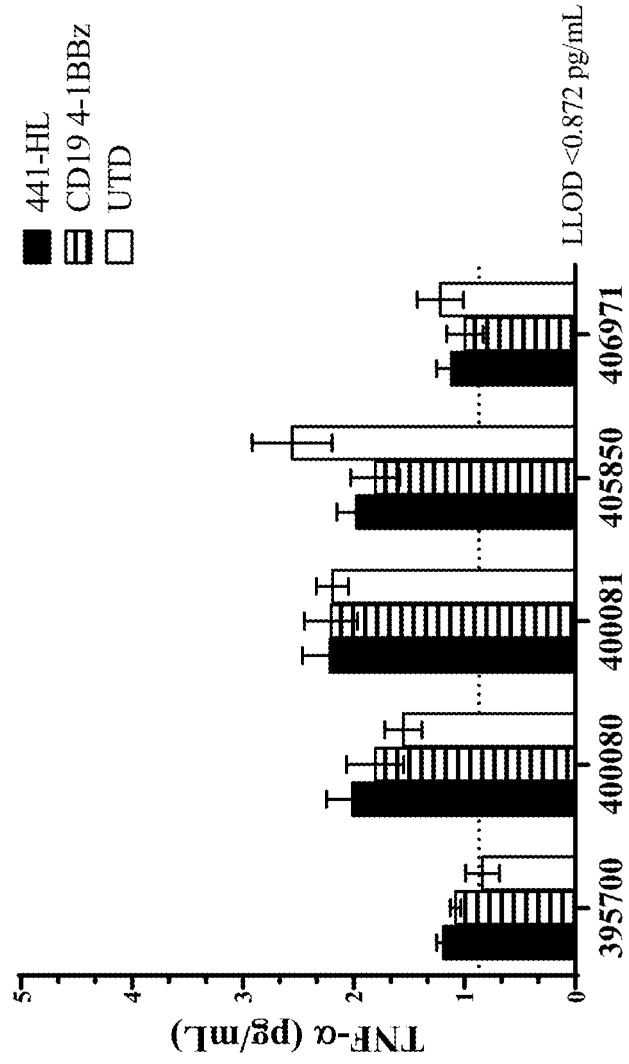

Basal cytokine secretion in the absence of antigen can indicate potential tonic signaling by CARs. To screen for this property, CAR-T cells generated as previously described were thawed and rested overnight in complete media (37° C., 5% $CO_2$). The day after, cells were counted, plated in triplicate at a density of 50,000 CAR+ cells per well and incubated overnight in the absence of antigen. The total T cell number per well was normalized across conditions via addition of untransduced cells. Culture supernatants were collected following overnight culture, and cytokines quantified via Meso Scale Discovery (MSD; V Plex Proinflammation Panel 1 [human] kit) according to manufacturer's instructions. Data analysis was performed using the MSD Workbench program, and results for each donor were plotted as mean SEM (two independent experiments, technical triplicates) using GraphPad® Prism. Results are shown in FIGS. 8A-8C. No evidence of elevated basal cytokine expression in CAR-transduced cultures was detected in absence of antigen or cytokine stimulation, consistent with a lack of tonic signaling.

Example 10: Proliferation in the Absence of Antigen

Figure 9A:
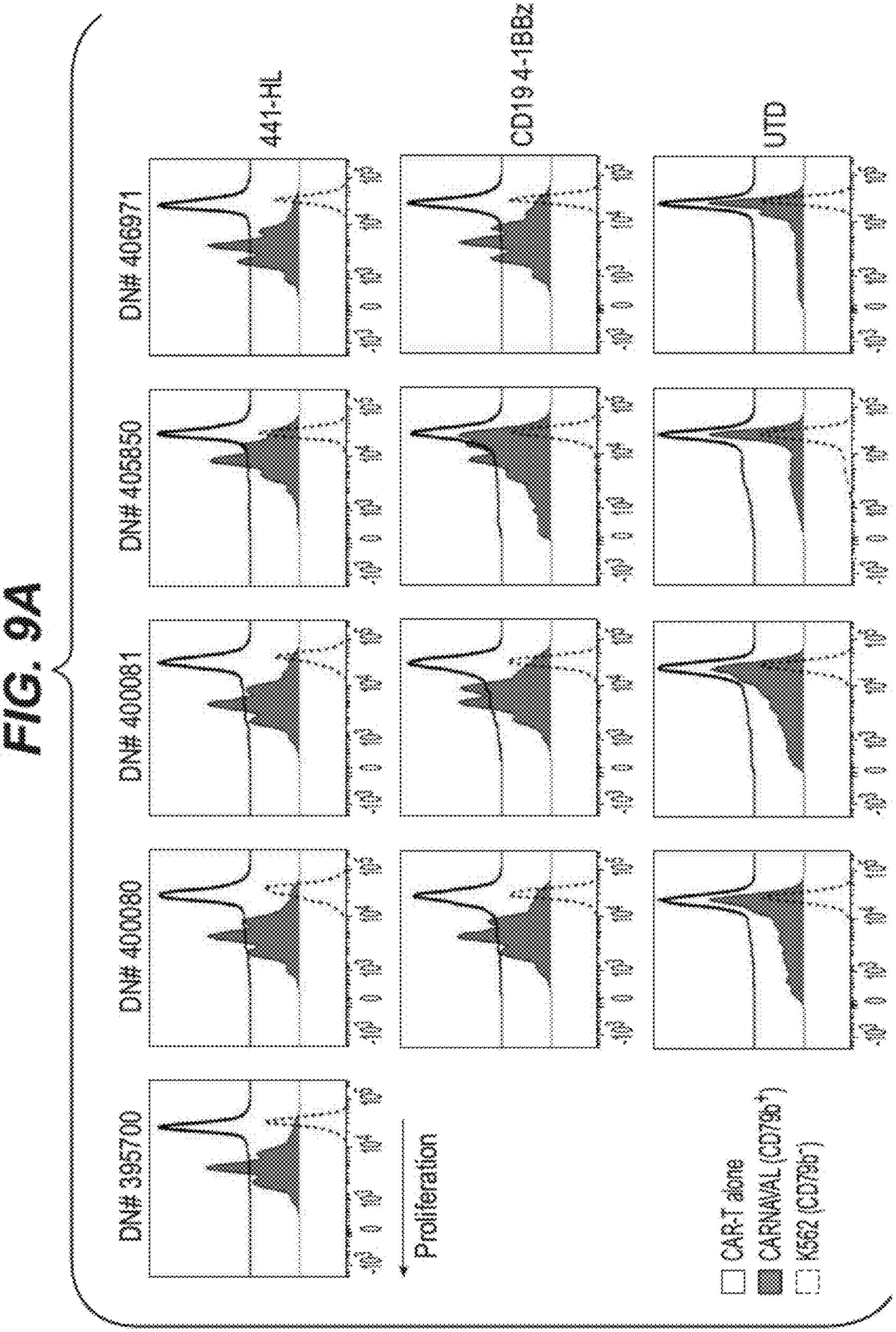
FIGS. 9A-9B demonstrate the absence of aberrant basal proliferation or activation by 441-HL CAR-T cells in the absence of antigen or cytokine stimulation. A five-day proliferation assay was performed in 441-HL CAR-T cells to screen for aberrant basal proliferation or activation. After labeling with Cell Trace™ Violet (CTV) dye (5 mM) CAR-T cells were diluted to $5\times10^5$ viable CAR+ T cells per mL. Cells (100 μL) were then added to a 96-well round bottom plate, where they were grown in the absence of target cells or cytokine stimulation for five days. Target positive cells (CARNAVAL) and target negative cells (K562) were similarly plated to yield at a CAR+ effector:target (E:T) ratio of 1:1 and cultured under the same conditions. On day five, cells were analyzed via flow cytometry gating on CD3 followed by CAR. CTV dye dilution (Pacific Blue channel) and CD71 marker expression were used to determine the percent of proliferating (FIG. 9A) and activated (FIG. 9B) CAR-T cells, respectively, across the five donors.
Figure 9B:
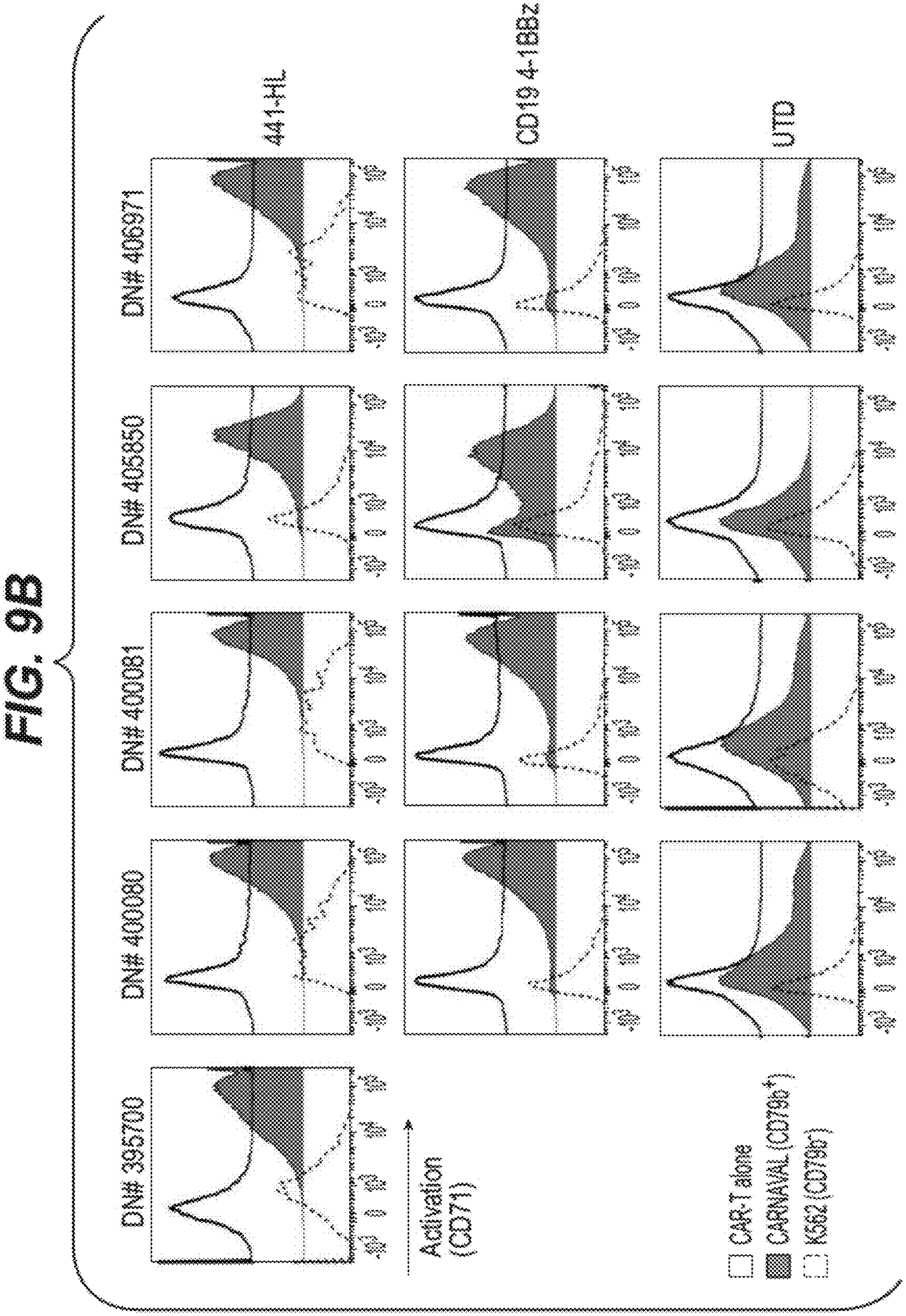

Tonic signaling from CARs can drive basal proliferation in the absence of antigen. To this end, 441-HL CAR-T cells were screened for basal proliferation by performing five-day proliferation assay. CAR-T cells were thawed and rested overnight in complete media (37° C., 5% $CO_2$). The day after, cells were counted and CAR+ percentages were normalized for each donor via addition of untransduced cells. Cells were labeled with Cell Trace™ Violet (CTV) dye at 5 mM according to manufacturer's instructions. After labeling, CAR-T cells were diluted to $5\times10^5$ viable CAR+ T cells per mL. Cells were added to a 96-well round bottom plate (100 μL per well) and grown in the absence of target cells and cytokine stimulation. As a control, target positive cells (CARNAVAL) and target negative cells (K562) were harvested, counted, and diluted to $5\times10^5$ viable cells per mL in complete medium, and were added to the respective wells (100 μL per well) to yield a CAR+ effector:target (E:T) of 1:1. The plates were incubated at 37° C., 5% $CO_2$ for five days. On day five, cells were analyzed by flow cytometry, gating on CD3+ followed by CAR. CTV dye dilution (Pacific Blue channel) and CD71 marker expression were used to determine the percent of proliferating (FIG. 9A) and activated (FIG. 9B) CAR-T cells, respectively. Across five donors, there was no evidence of aberrant proliferation or activation by 441-HL CAR-T in the absence of antigen or cytokine stimulation.

Example 11: Flow-Cytometry-Based Cytotoxicity

The effects of 441-HL CAR-T cells were tested in a panel of five CD79b/CD19+ cell lines (HBL-1, OCI-LY-10, CARNAVAL, WILL-2 and JEKO-1) and five CD79b/CD19−cell lines (K562, HLY-1, SU-DHL-1, HL-60 and JURKAT E6.1) using a flow cytometry-based assay. K562 cells engineered to express CD79b were included in the panel as an additional control for antigen-specific killing.

441-HL CAR-T, CD19 CAR-T, or UTD cells were thawed and rested overnight in complete media (37° C., 5% $CO_2$). The day after, cells were counted and the percentage of CAR+ cells was normalized per donor via addition of untransduced cells. CAR-T cells were resuspended at a concentration of $5\times10^5$ CAR+ cells per mL for a starting CAR+ effector:target (E:T) ratio of 2.5:1 ($2.5\times10^4$ CAR+ cells at the highest dilution). A total of eight two-fold dilutions (ratio of 2.5:1, $2.5\times10^4$ CAR+ cells; ratio of 1.25:1, $1.25\times10^4$ CAR+ cells; ratio of 1:1.6, $6.25\times10^3$ CAR+ cells; ratio of 1:3.2, $3.13\times10^3$ CAR+ cells; ratio of 1:6.4, $1.56\times10^3$ CAR+ cells; ratio of 1:13, $7.81\times10^2$ CAR+ cells; ratio of 1:26, $3.91\times10^2$ CAR+ cells; and, ratio of 1:51, $1.95\times10^2$ CAR+ cells), were made and 100 μL of effector cells were seeded in 96-well round bottom plates according to plate layout.

Next, the target cell lines were harvested, counted and resuspended at 4 million cells/mL in Dulbecco's phosphate-buffered saline (DPBS). Tumor targets were labeled with Cell Trace™ Violet (CTV) at 1 mM per manufacturer's instructions. Labeled target cells were diluted to $2\times10^5$ viable cells per mL in complete medium and 100 μL of labeled cells were added to 96-well plates ($2\times10^4$ viable cells per well) containing the CAR-T cells. Plates were incubated (37° C., 5% $CO_2$) for approximately 24 hours.

After 24 hours, cells were stained with Fixable Viability Dye eFluor™ 660 (Thermo Fisher Scientific, 65-0864-14) per manufacturer's instructions. Tumor cell death was assessed via flow cytometry by gating on forward-scatter and side-scatter to identify cell populations; then on LIVE/DEAD™ to identify the viable cell; and, finally on CTV+ tumor events to assess the number of viable cancer cells in each well. The percentage of cancer cell killing was calculated using the formula below (based on absolute counts):

$$\left(\frac{\text{Absolute \# of viable cancer cells at each } E:T \text{ ratio}}{\text{Average absolute \# of viable cancer cells in the } 0:1\ E:T \text{ ratio wells}}\right)\times 100$$

Figure 10A:
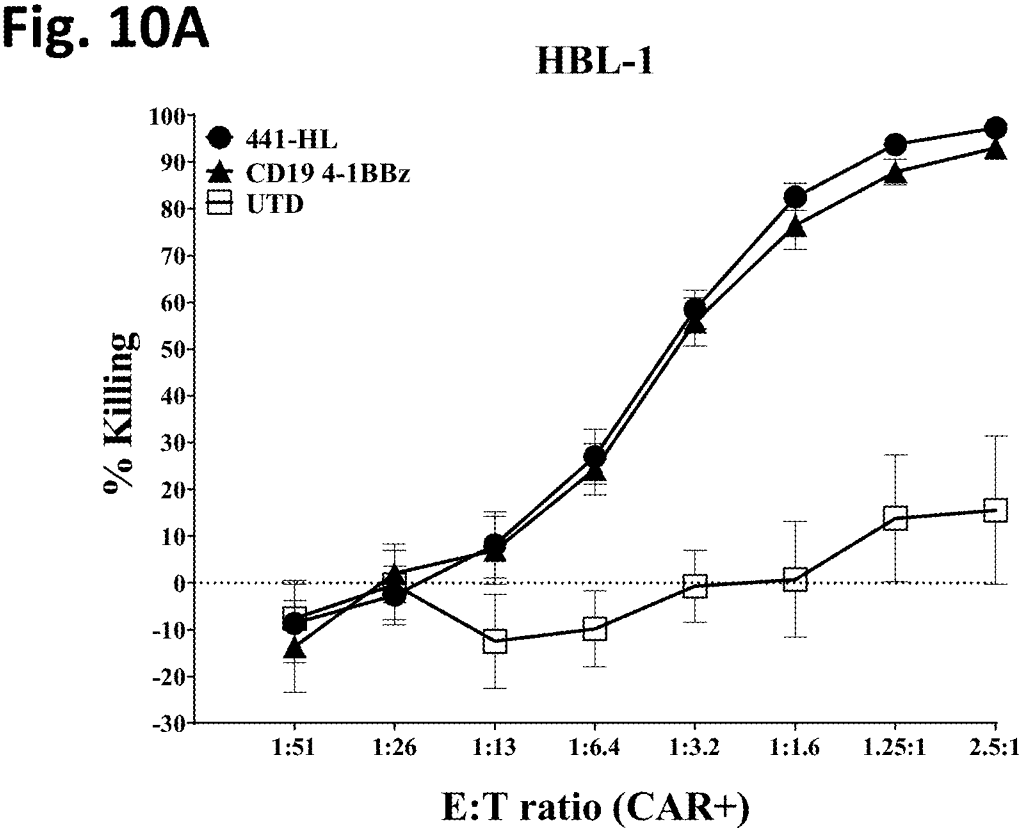
FIGS. 10A-10R demonstrate antigen-specific cancer cell killing by 441-HL CAR-T cells in the presence of CD79b/CD19+ cells, across all donors tested. Flow cytometry was used to test the effects of 441-HL CAR-T cells in a panel of five CD79b/CD19+ cell lines (HBL-1, OCI-LY-10, CARNAVAL, WILL-2 and JEKO-1), and five CD79b/CD19−cell lines (K562, HLY-1, SU-DHL-1, HL-60 and JURKAT E6.1). K562 engineered to express CD79b were included as an additional control. Following thawing and overnight rest, cells were counted and the percentage CAR+ cells normalized per donor via addition of untransduced cells. Normalized CAR-T cells were then counted and resuspended the at a concentration of $5\times10^5$ CAR+ cells per mL for a starting CAR+E:T ratio of 2.5:1. A total of eight 2-fold dilutions were made, and effector cells were seeded in a 96-well plate (100 μL per well). Target cell lines were harvested, counted and resuspended at 4 million cells per mL. They were then labeled with Cell Trace™ Violet (CTV), diluted to $2\times10^5$ viable cells per mL, and 100 μL of the labeled cells were added to 96-well plates containing the CAR-T cells. Following a 24-hour incubation period, cells were stained with Fixable Viability Dye eFluor™ 660 (viability dye). Tumor cell death was assessed via flow cytometry by gating on forward-scatter and side-scatter to identify cell populations; then on LIVE/DEAD to identify the viable cell; and, finally on CTV+ tumor events to assess the number of viable cancer cells in each well. The percentage (%) of cancer cell killing was calculated as the absolute number of viable cancer cells at each E:T ratio divided by the average absolute number of viable cancer cells in the 0:1 E:T ratio wells, and then multiplied by 100. Data were plotted as mean+/−SEM (3 individual experiments). Merged graphs for the five donors are shown in FIGS. 10A-10C and FIGS. 10D-10F for CD79b/CD19+ cells and CD79b/CD19− cells, respectively. Plots showing the individual kill curve for each of the five donors are shown in FIGS. 10G-10L and FIGS. 10M-10R for CD79b/CD19+ cells and CD79b/CD19− cells, respectively.
Figure 10A:
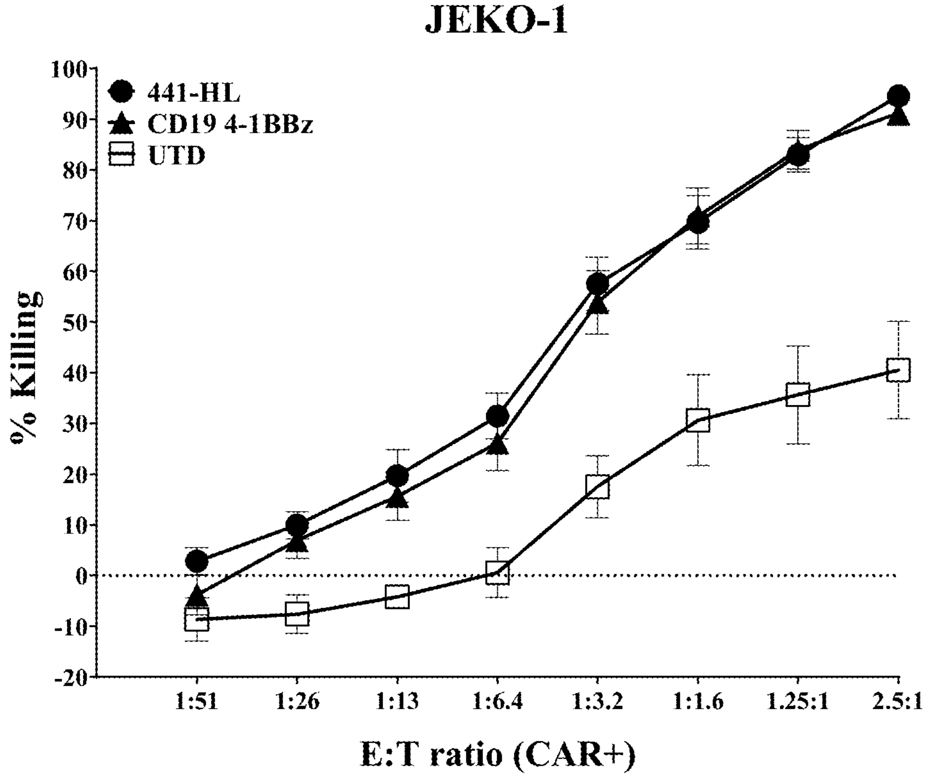
Figure 10B:
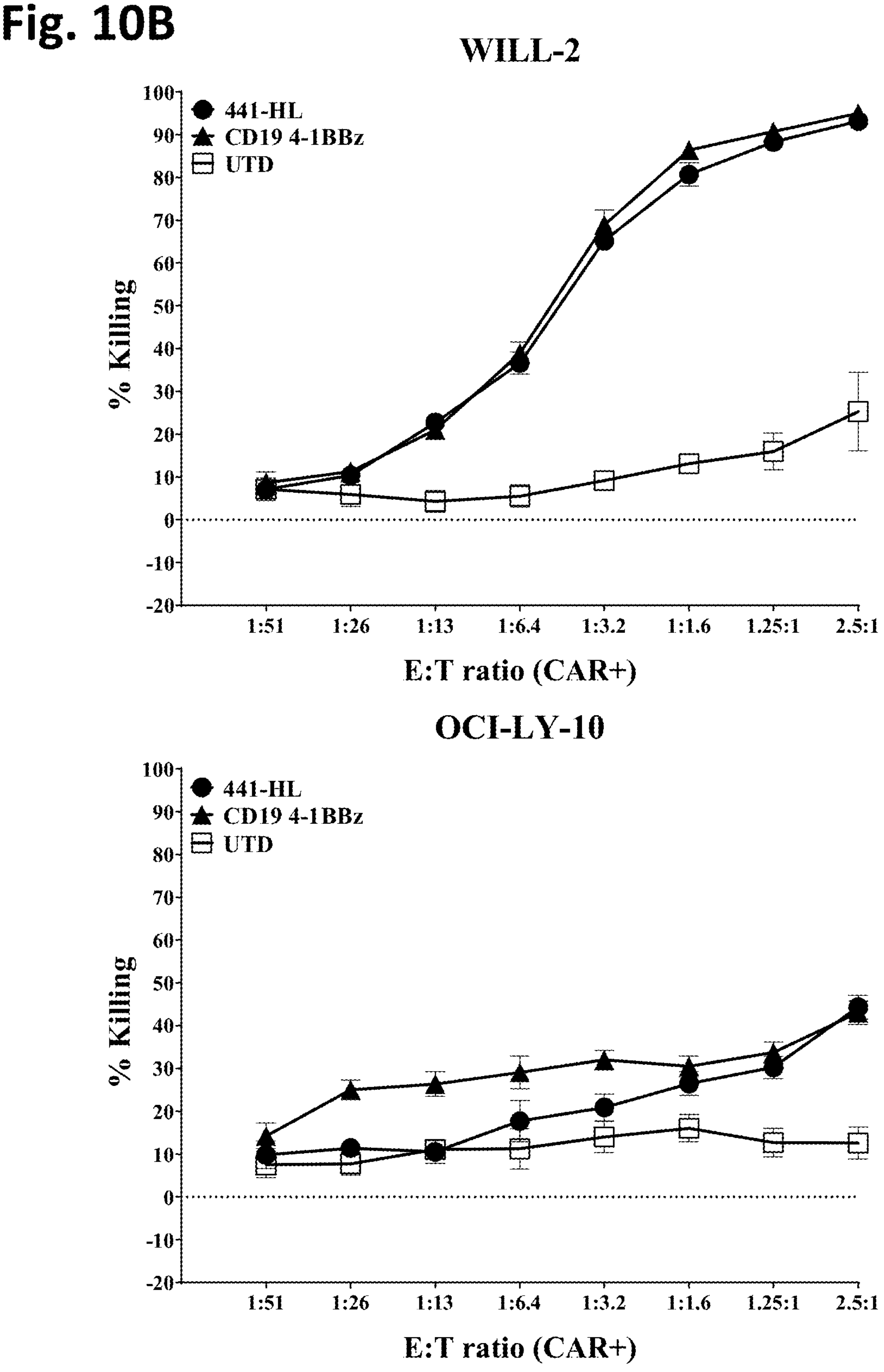
Figure 10C:
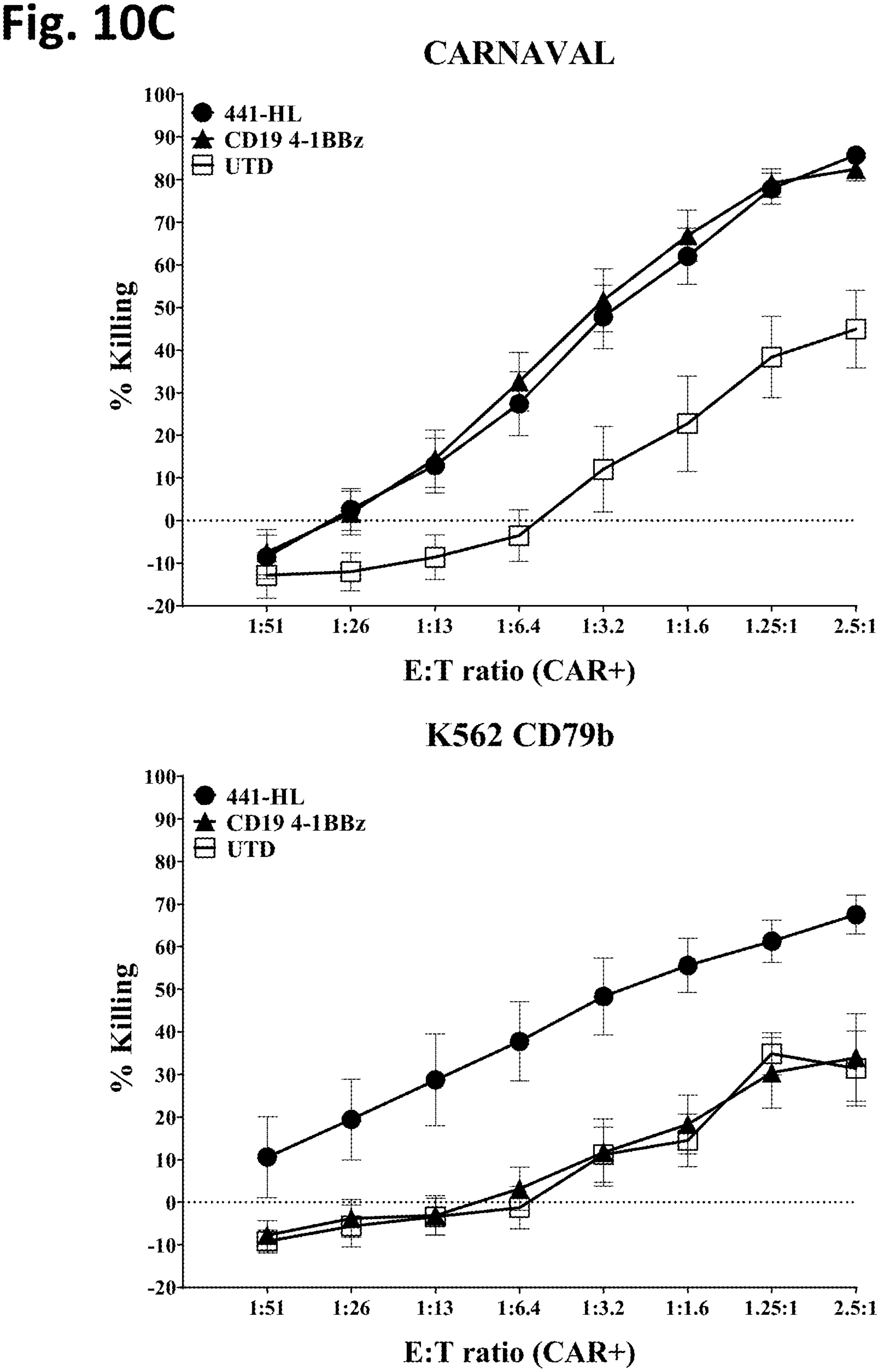
Figure 10D:
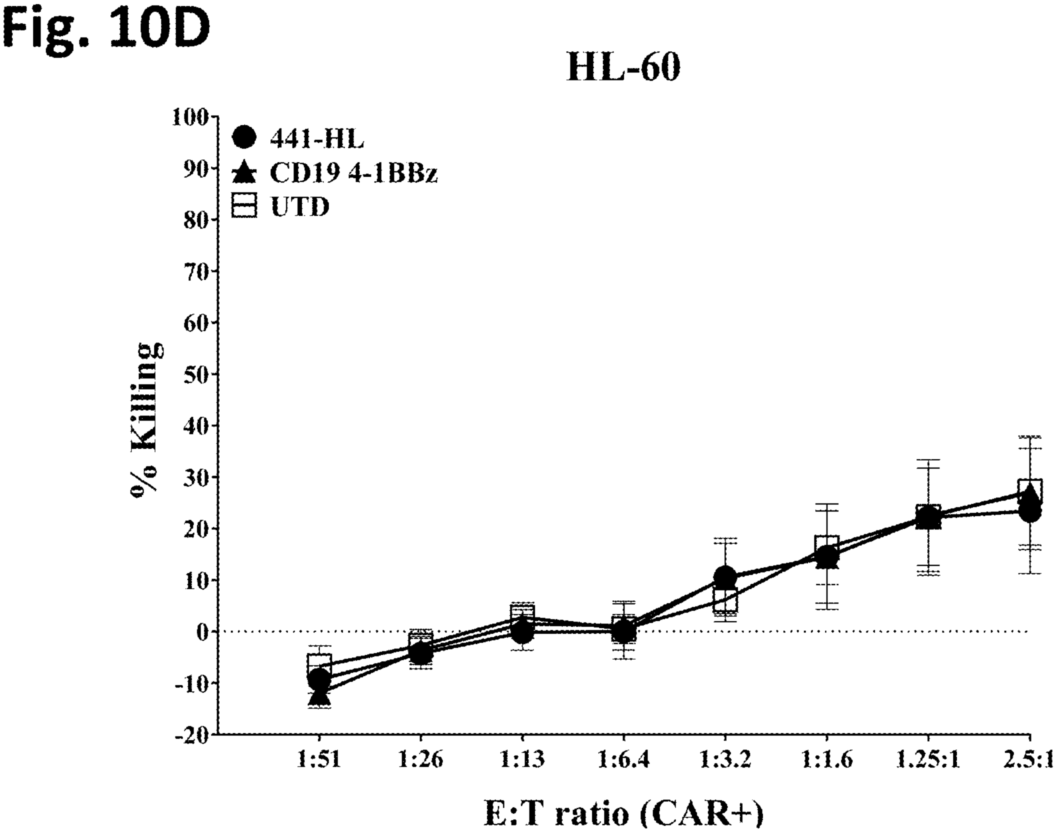
Figure 10D:
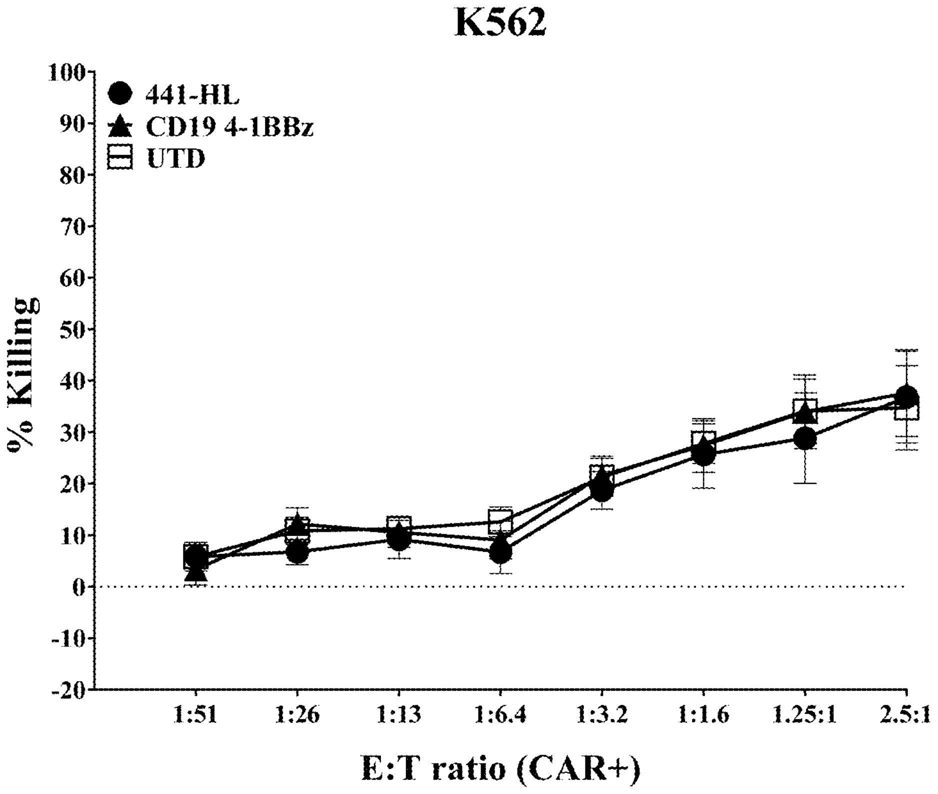
Figure 10E:
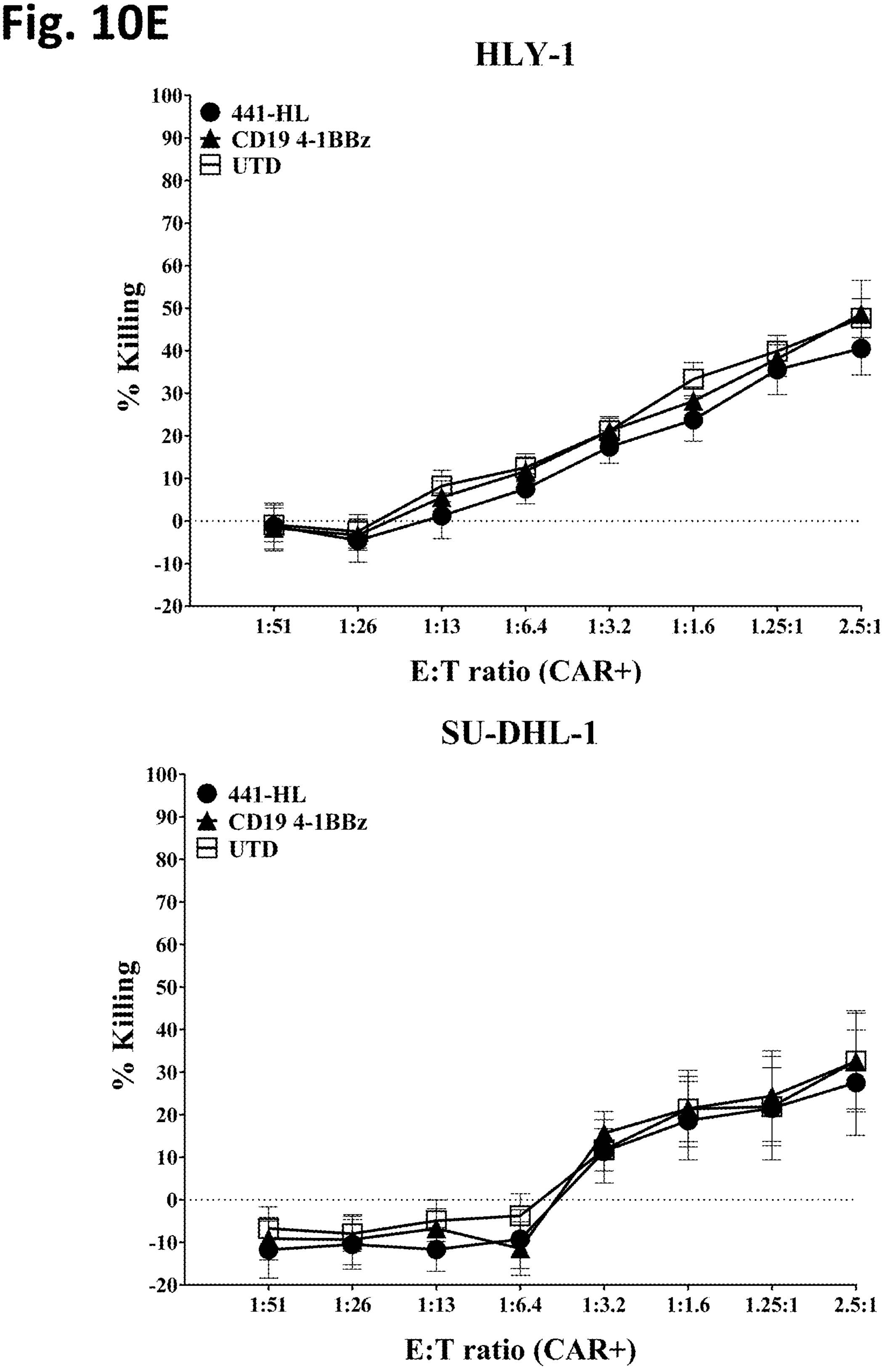
Figure 10F:
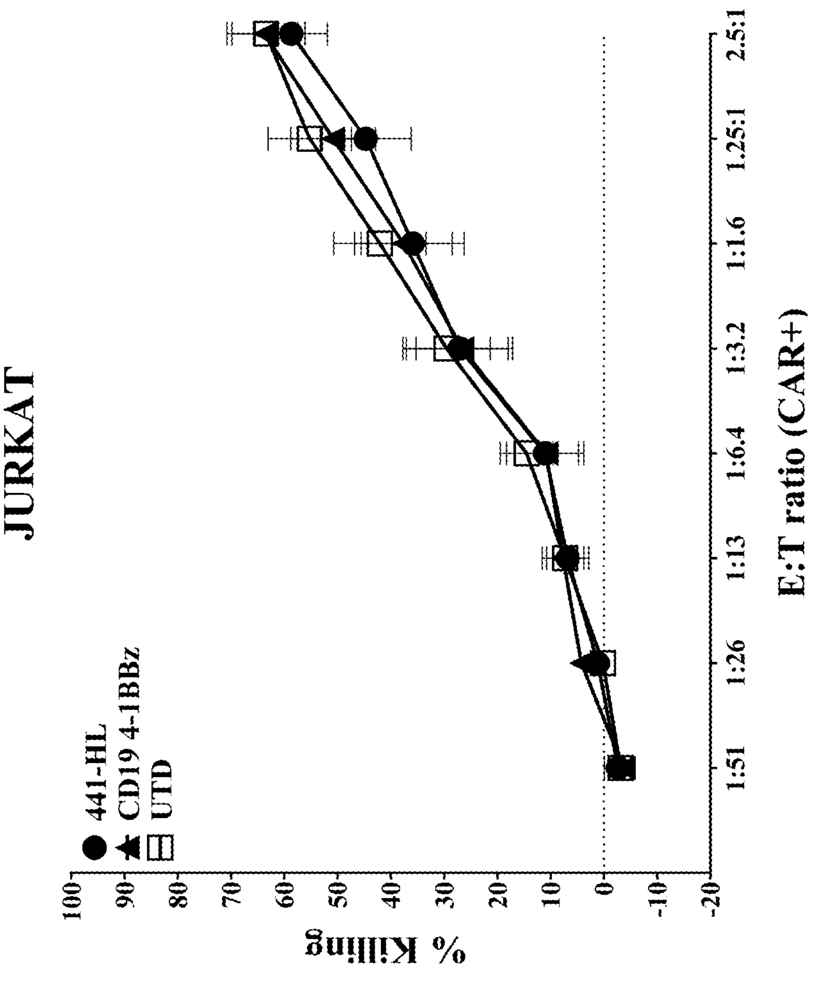
Figure 10G:
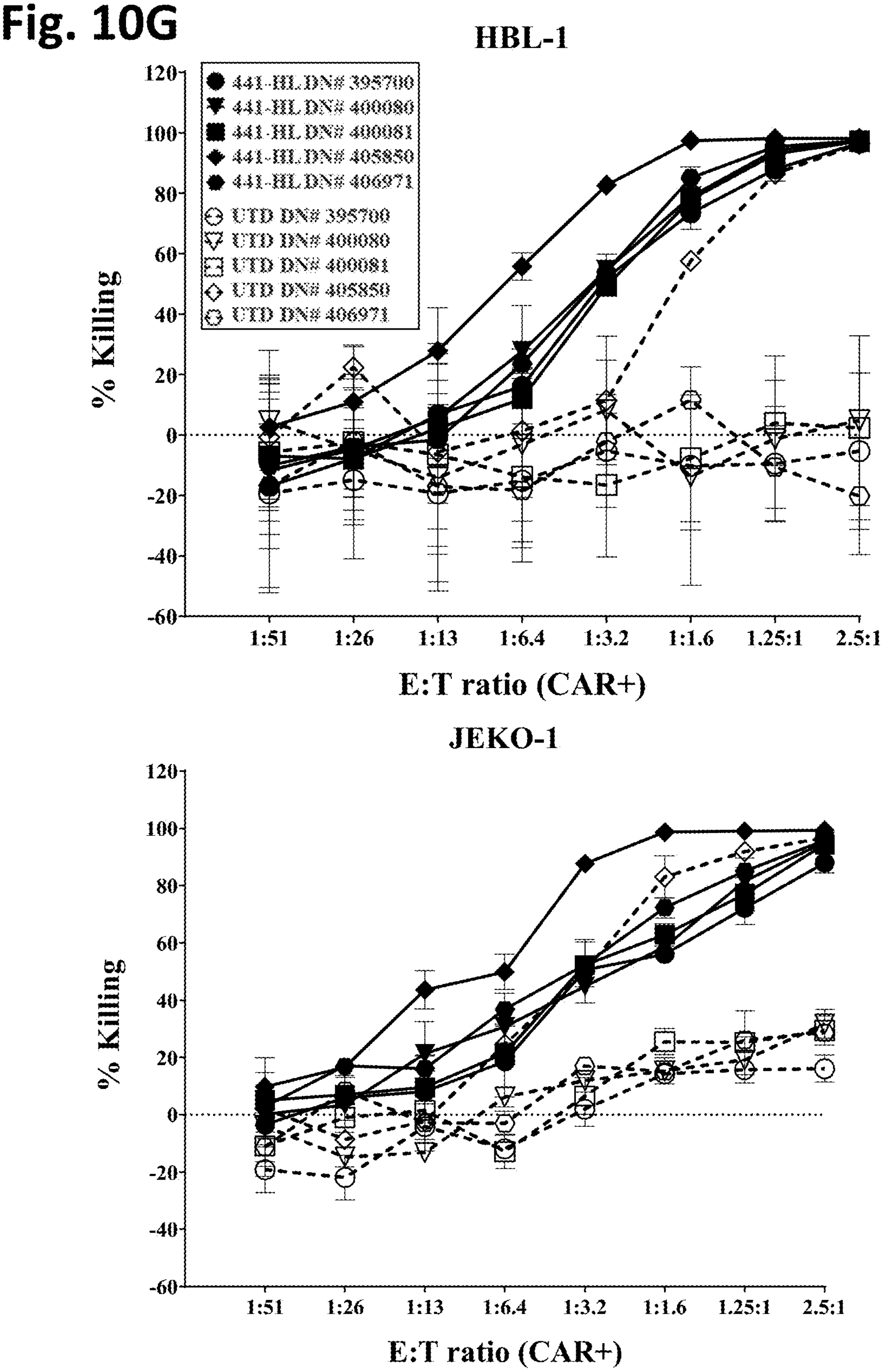
Figure 10H:
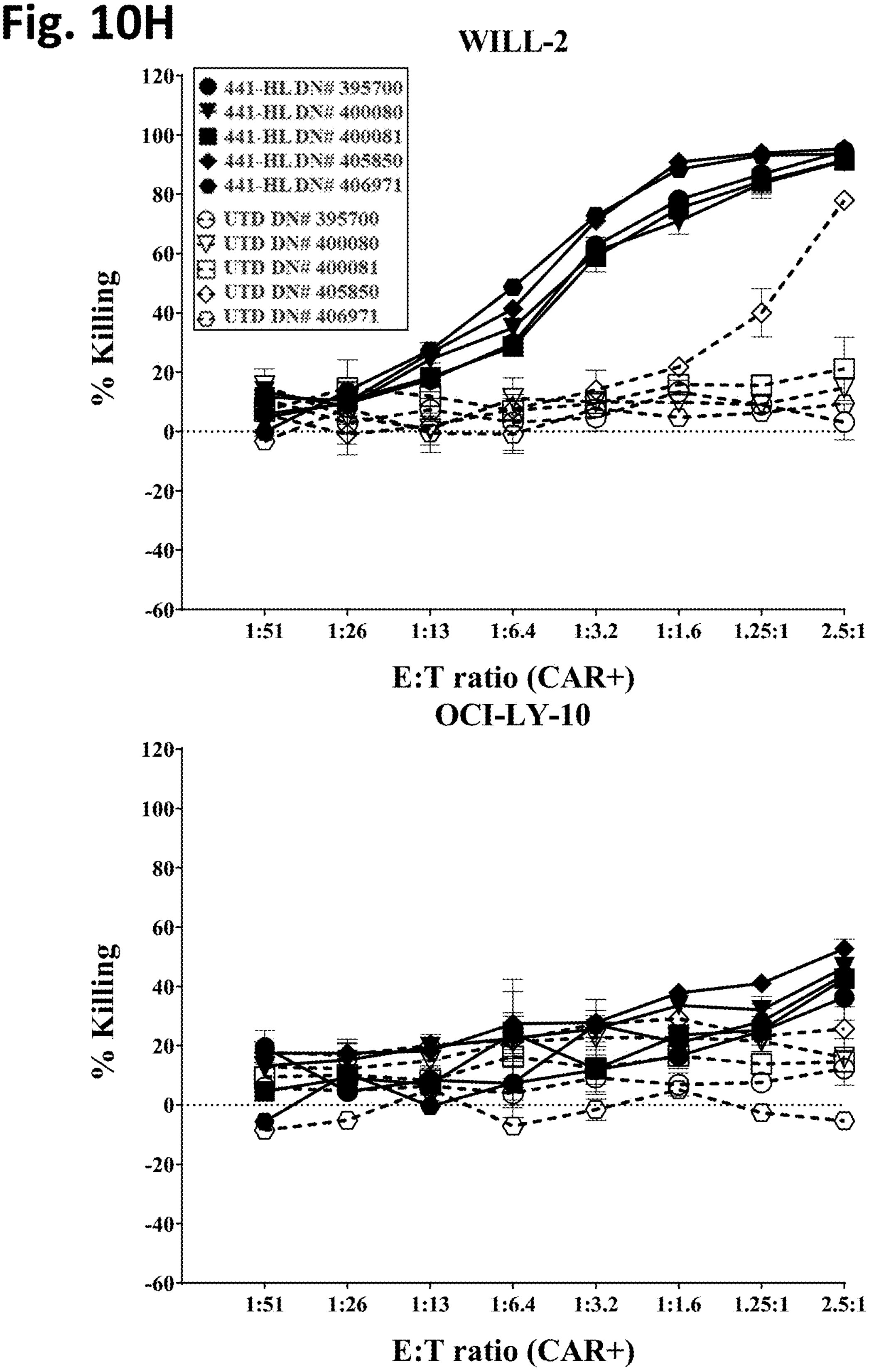
Figure 10I:
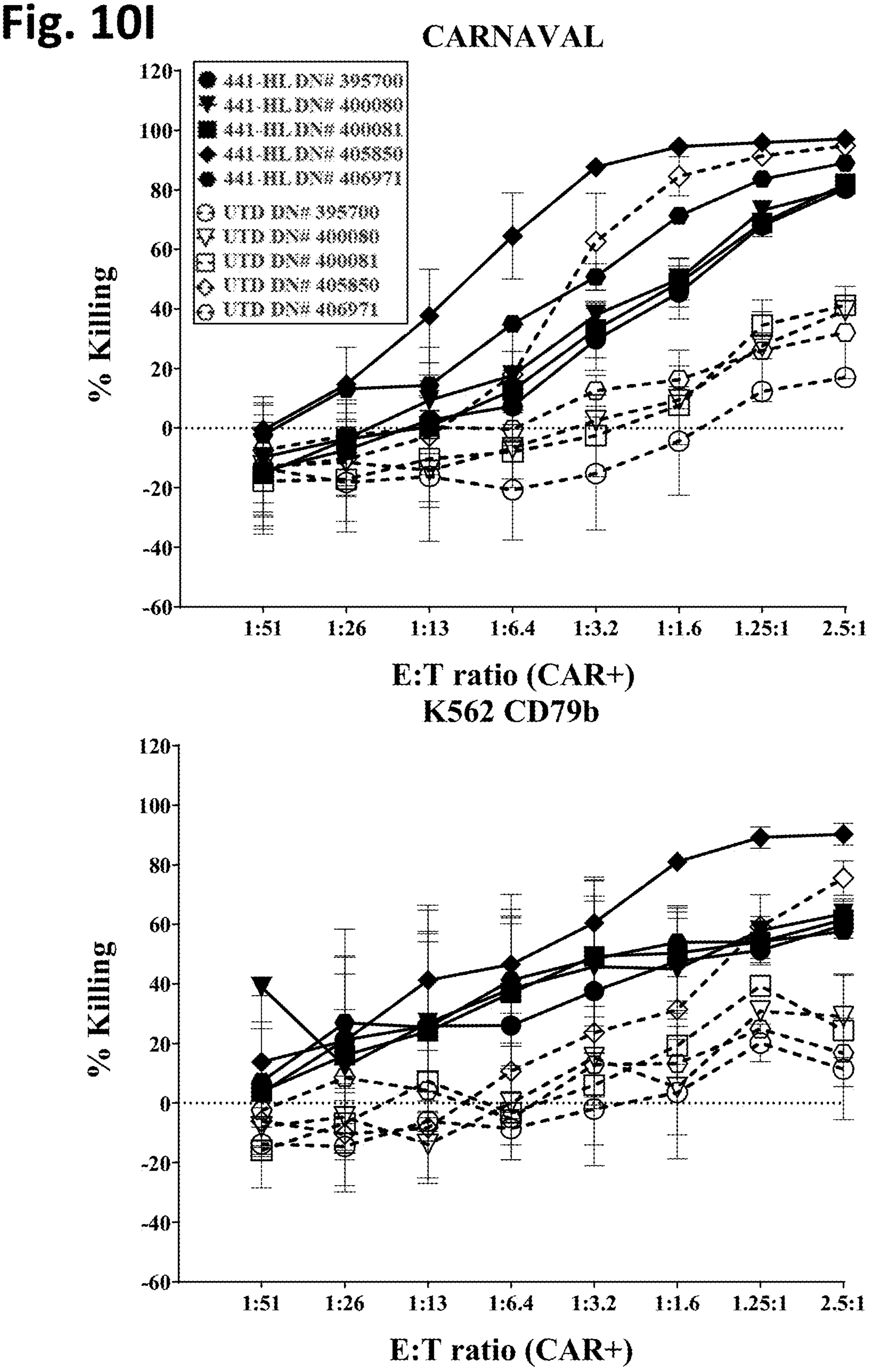
Figure 10J:
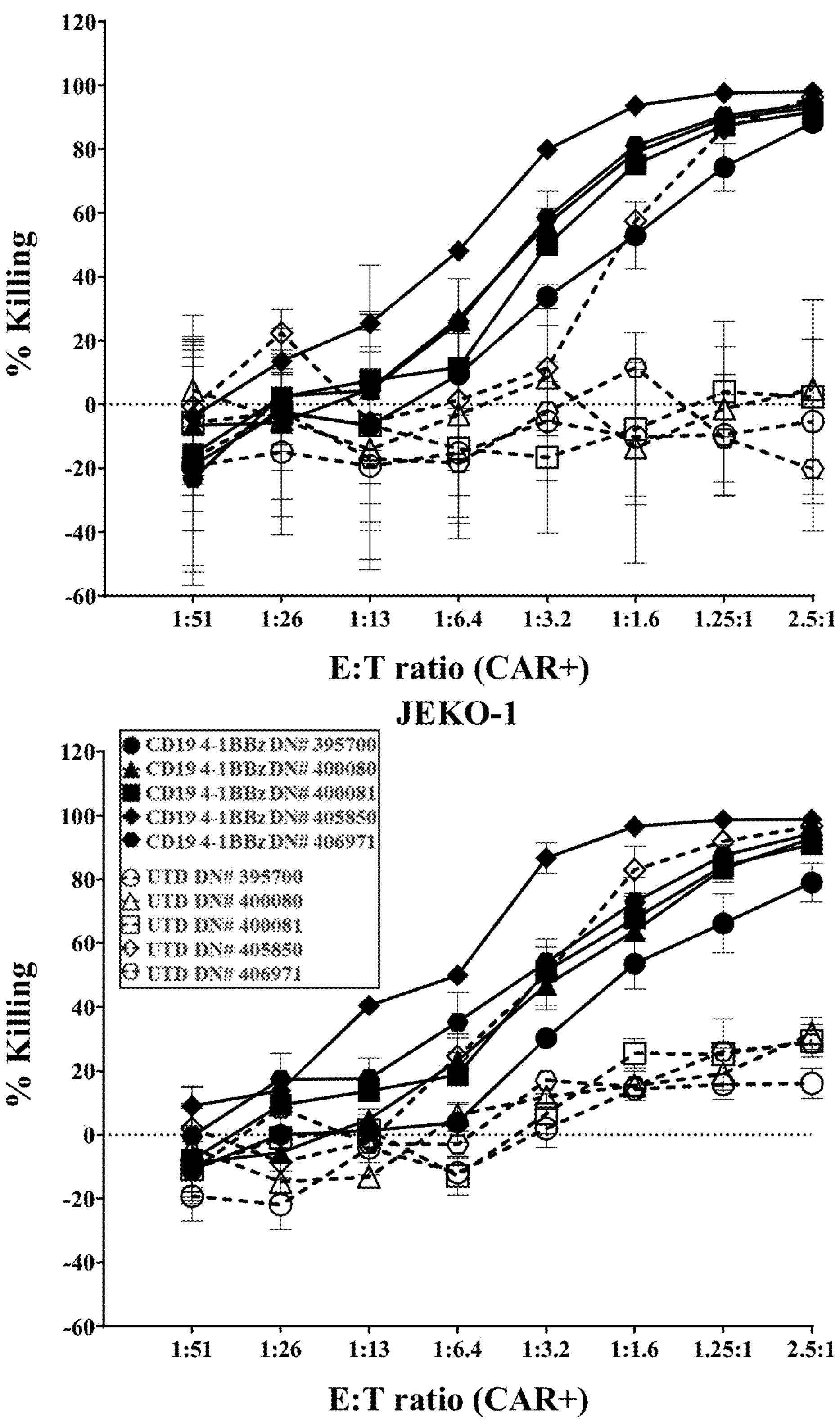
Figure 10K:
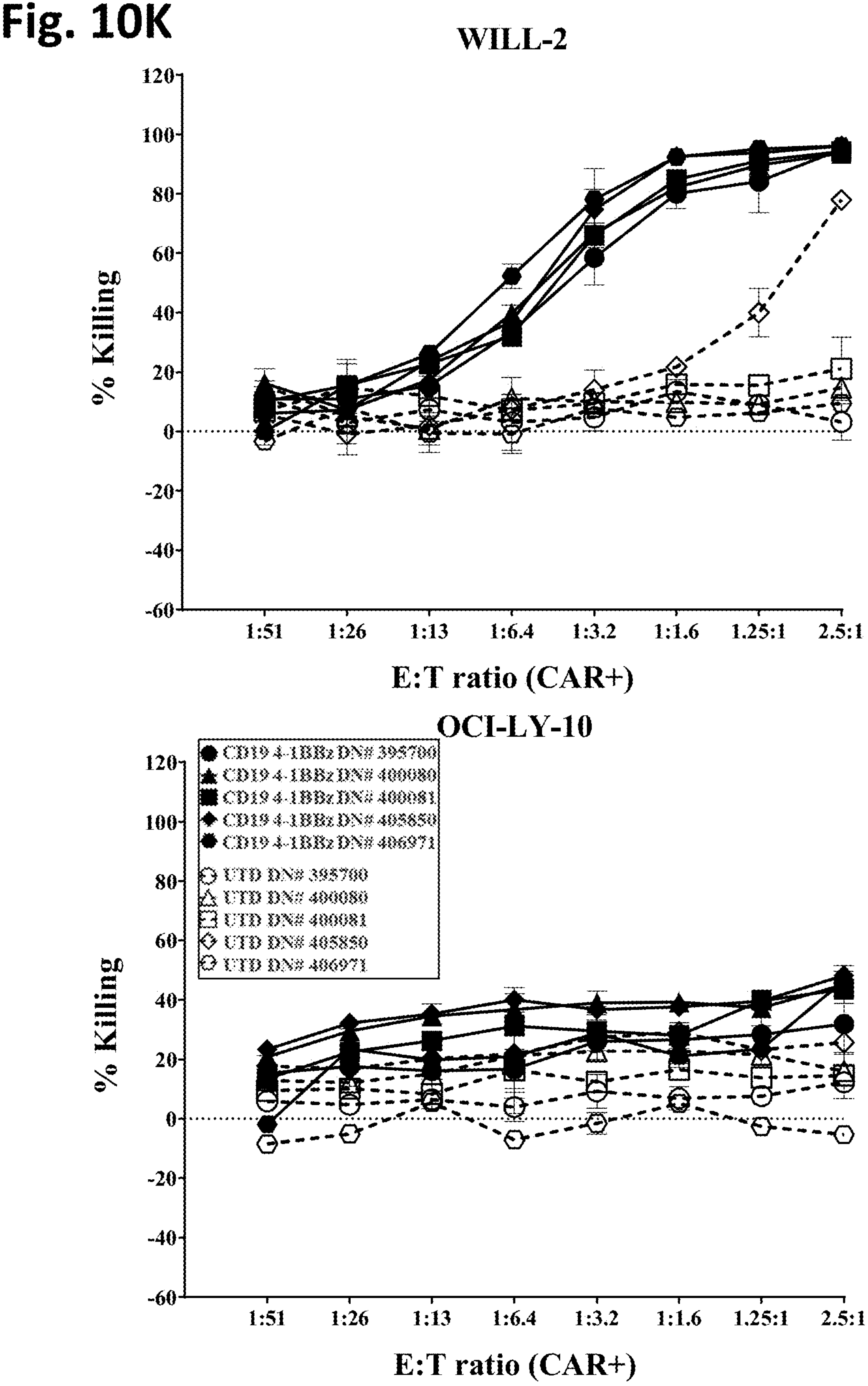
Figure 10L:
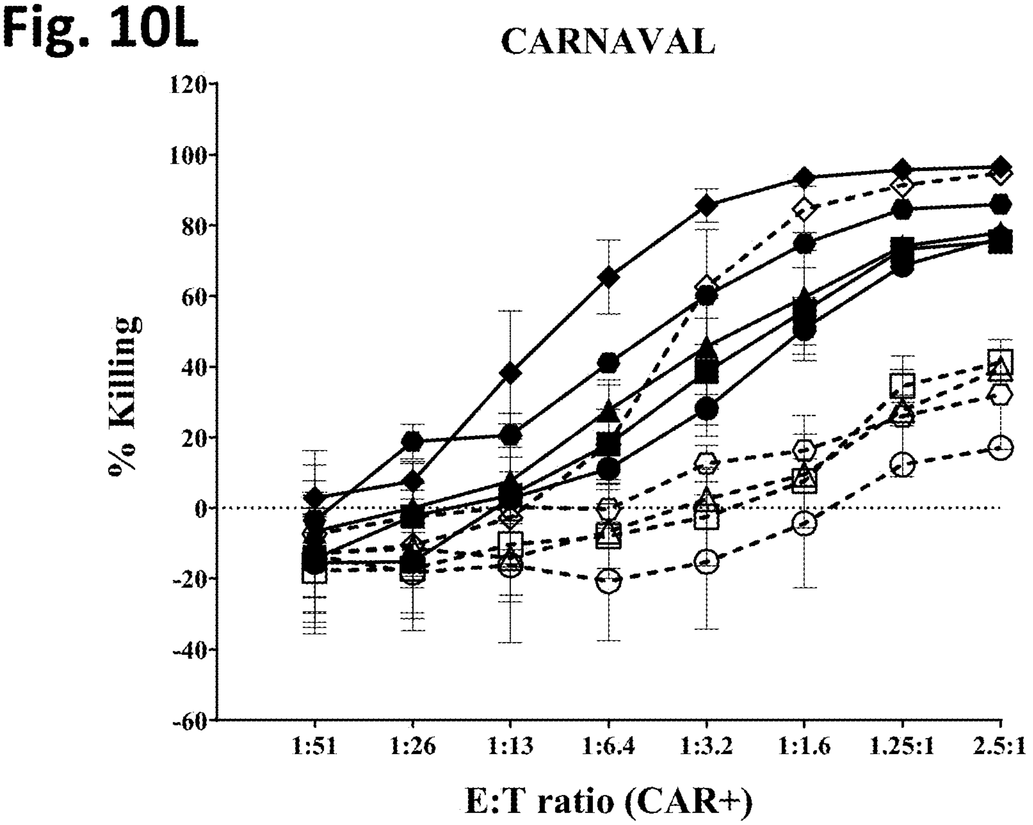
Figure 10L:
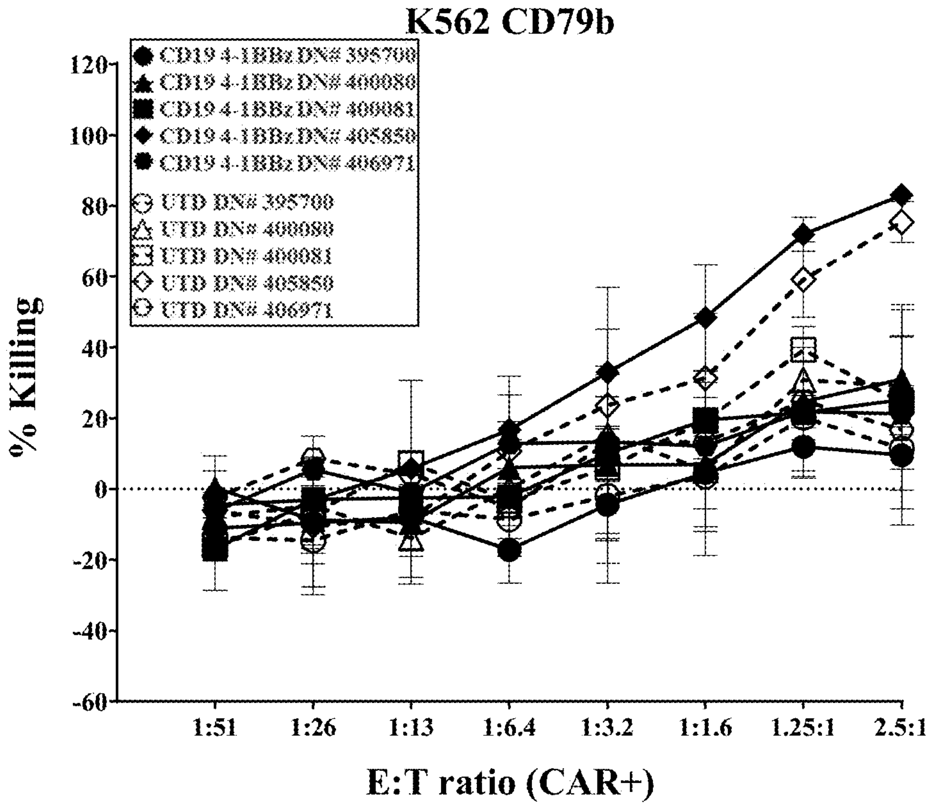
Figure 10M:
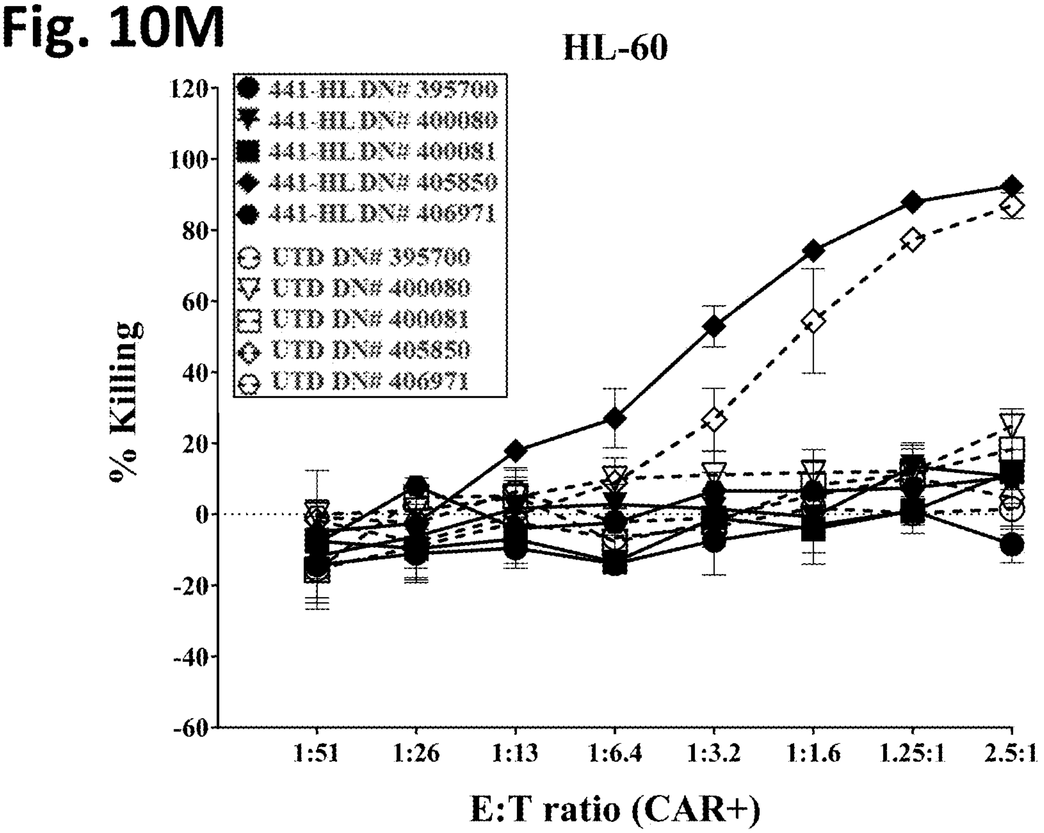
Figure 10M:
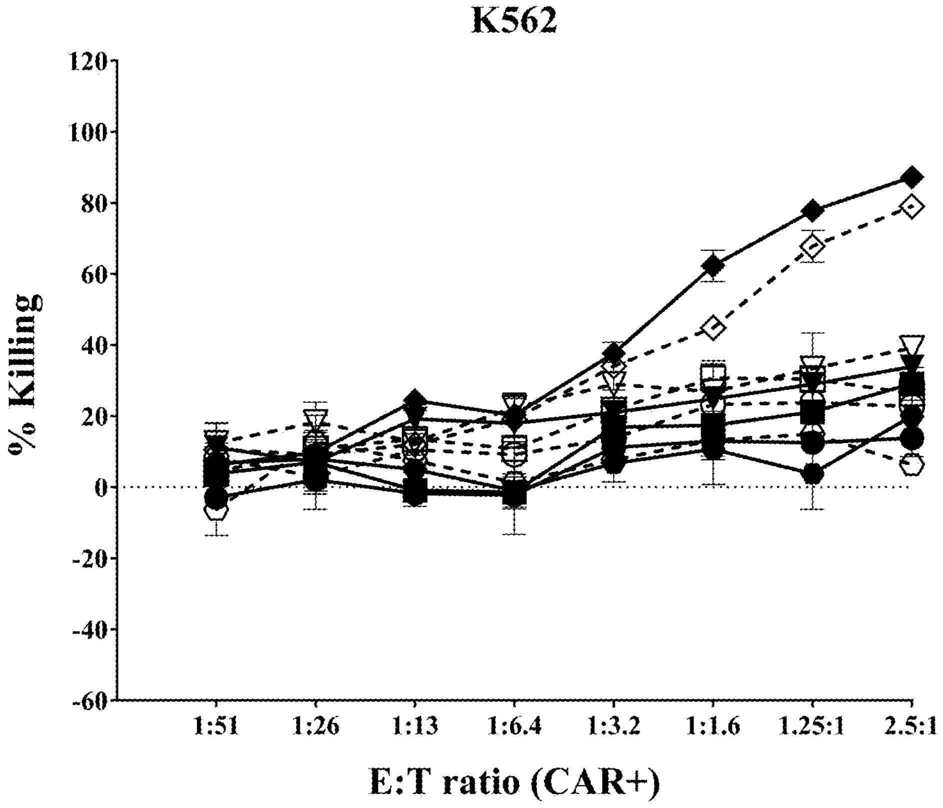
Figure 10N:
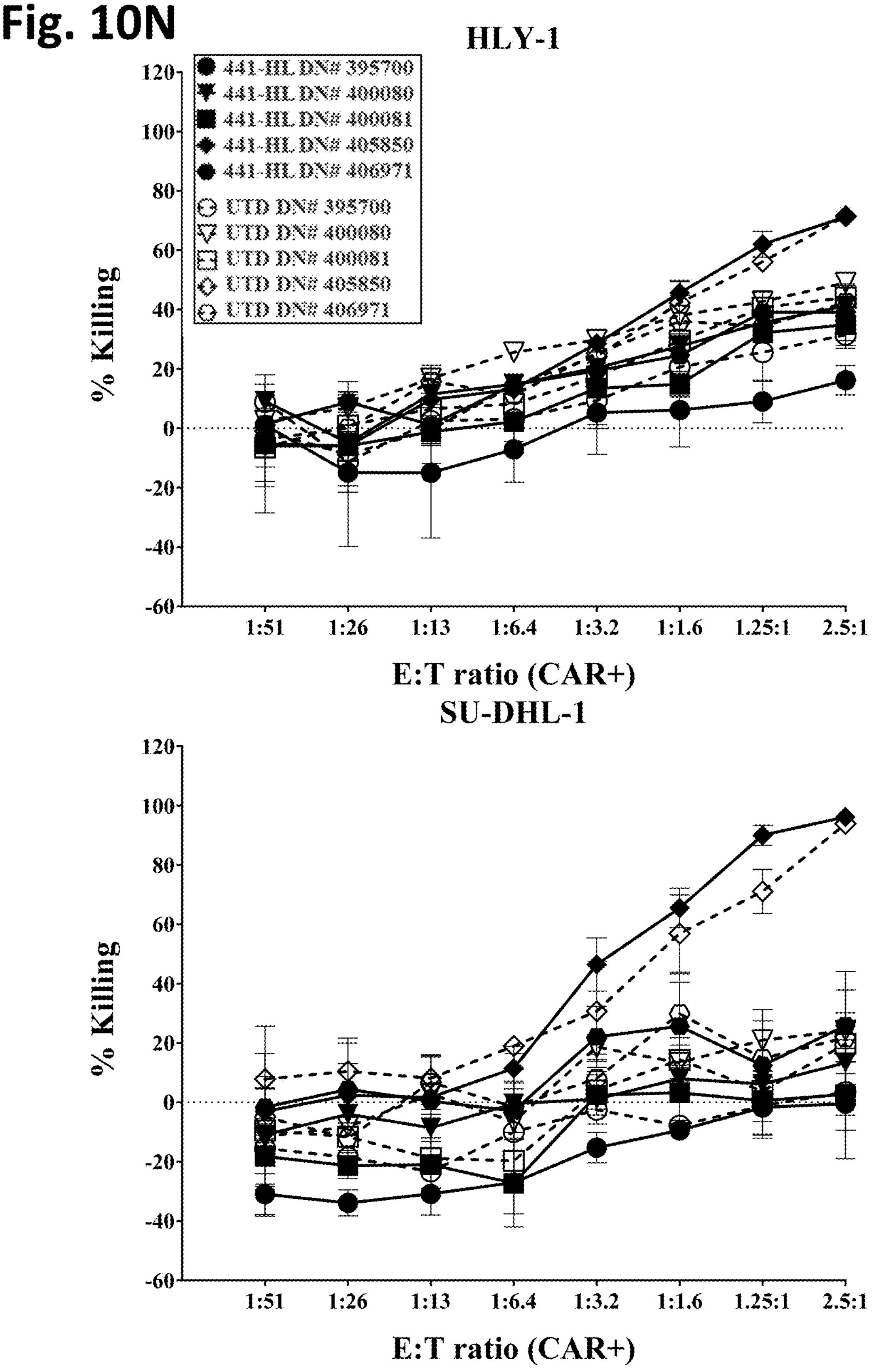
Figure 10O:
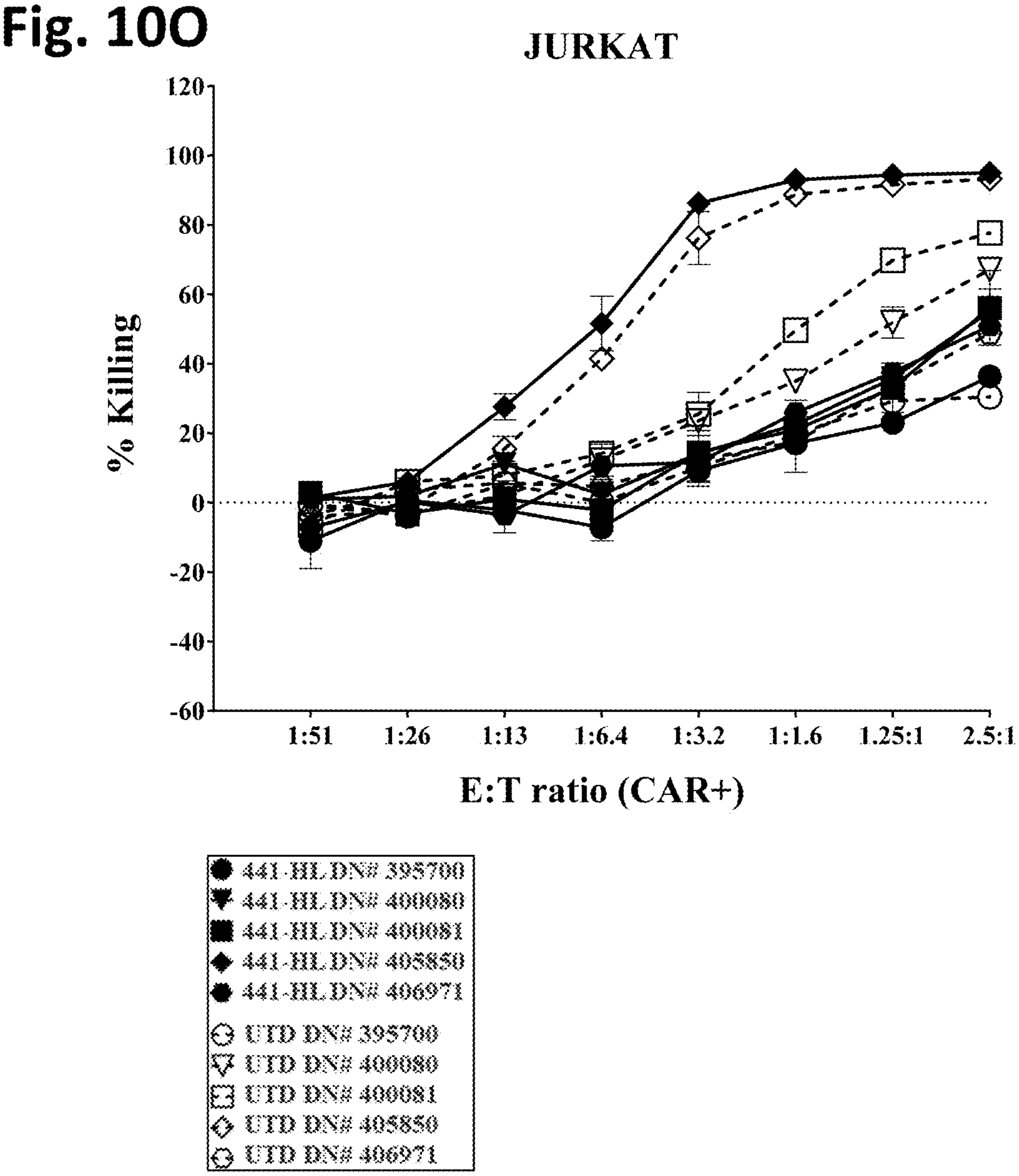
Figure 10P:
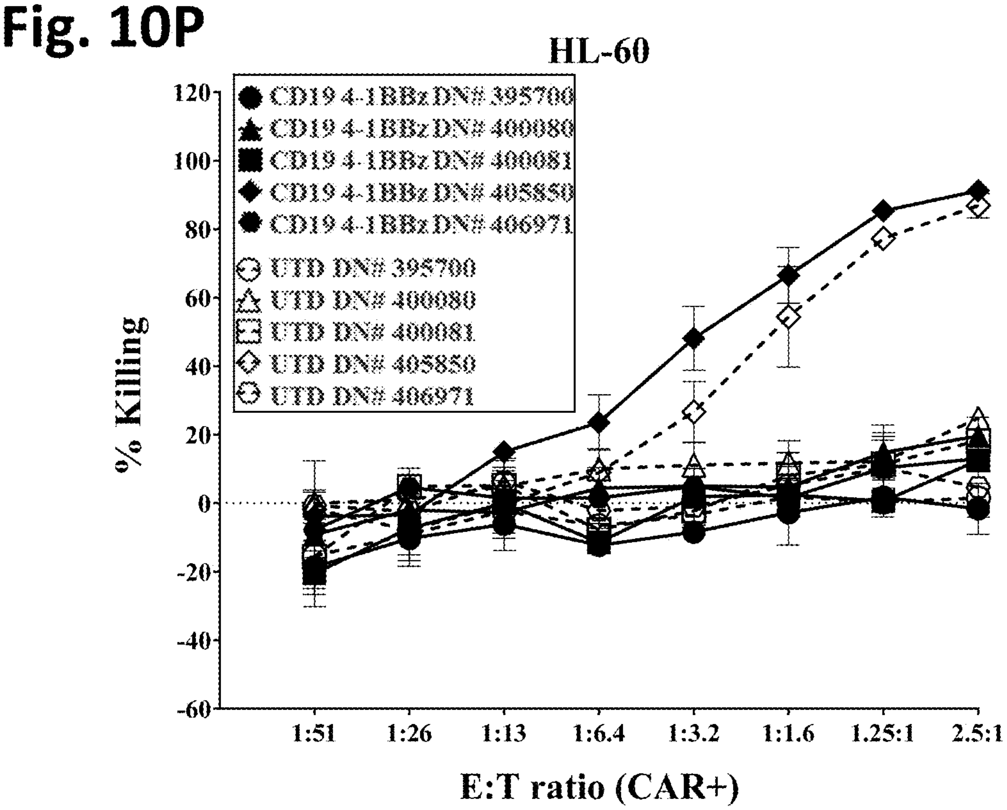
Figure 10P:
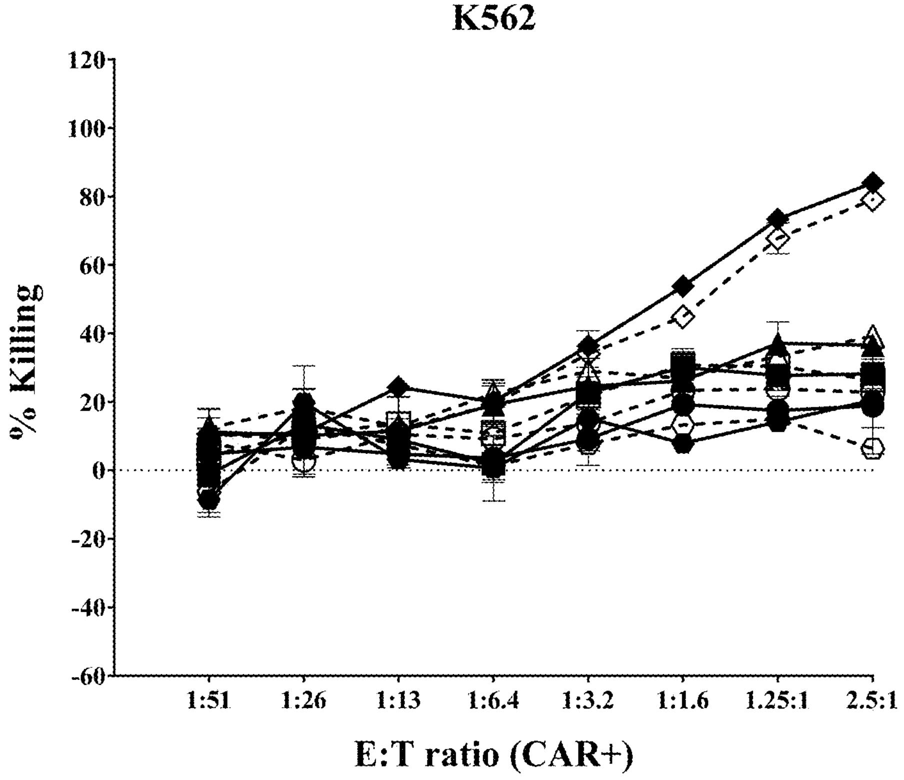
Figure 10Q:
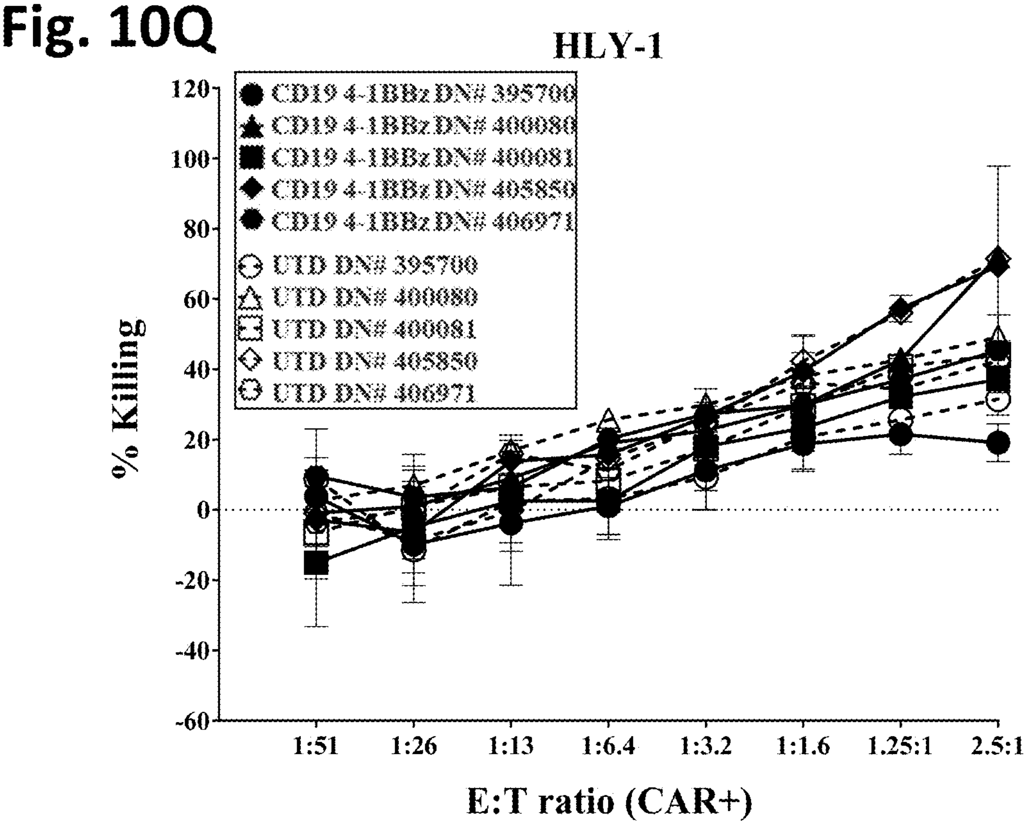
Figure 10Q:
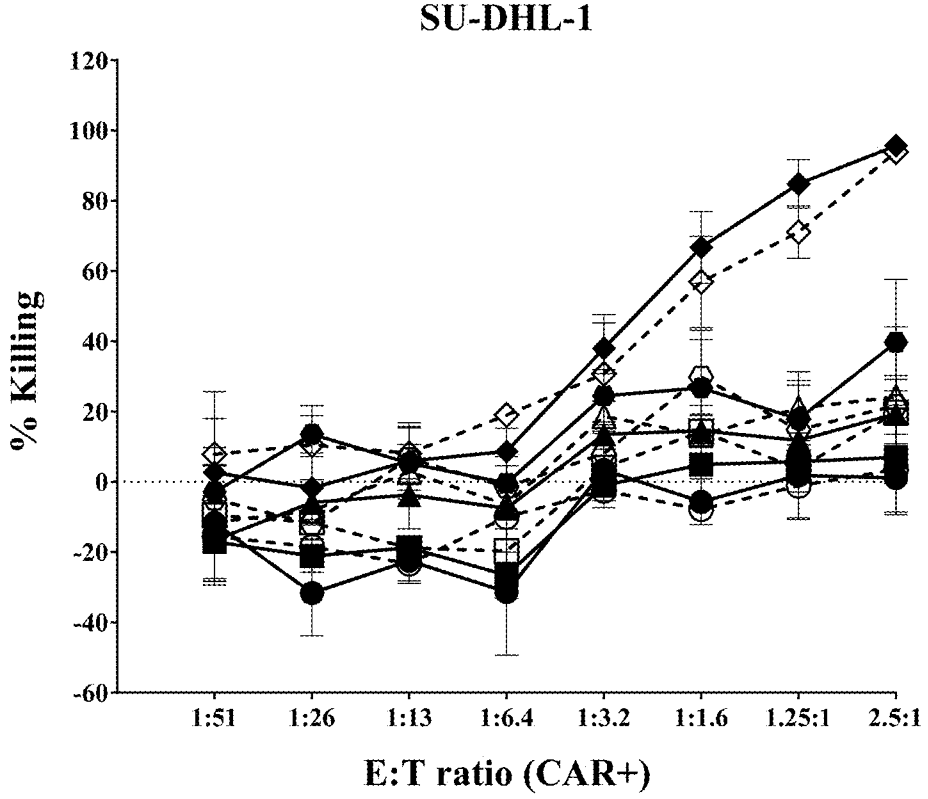
Figure 10R:
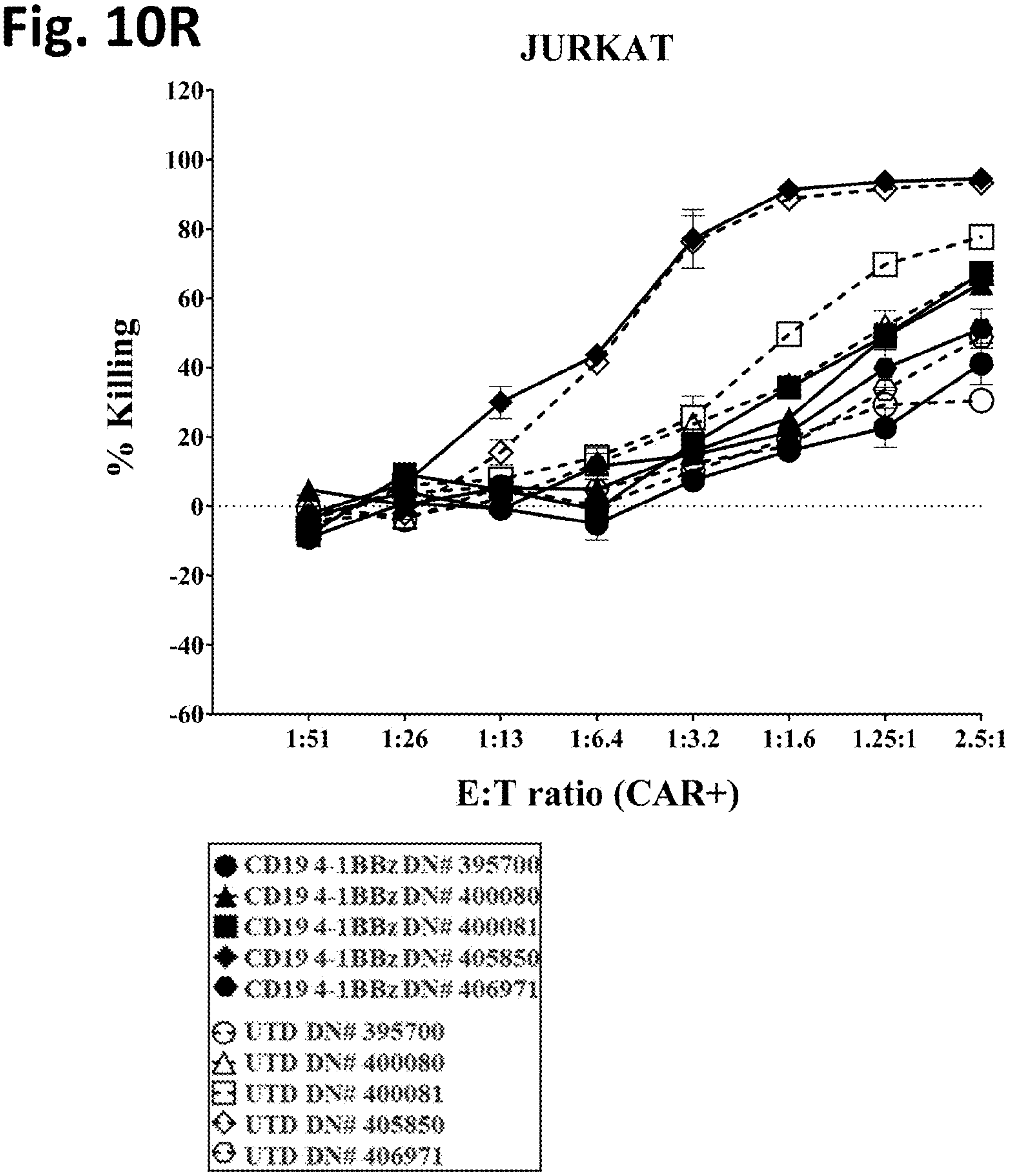

Data were plotted as mean % killing+/−SEM (3 individual experiments) for each CAR+E:T ratio. Merged graphs for the five donors (FIG. 10A-10C for CD79b/CD19+ cells and FIG. 10D-10F for CD79b/CD19−cells) as well as plots showing the individual kill curve for each donor (FIGS. 10G-10L for CD79b/CD19+ cells and FIGS. 10M-10R for CD79b/CD19−cells) were generated. In the presence of CD79b/CD19+ target cell lines, antigen-specific cancer cell killing can be achieved in all the donors tested. No specific killing could be observed in presence of any of the target negative cell lines.

Example 12: IncuCyte®-Based Cytotoxicity

The killing kinetics of 441-HL CAR-T were assessed in a panel of two CD79b/CD19+(HBL-1, OCI-LY-10) and two CD79b/CD19−(HLY-1, SU-DHL-1) mKATE2-expressing cell lines taking advantage of the IncuCyte® technology.

441-HL CAR-T, CD19 CAR-T or UTD cells were thawed and rested overnight in complete media (37° C., 5% $CO_2$). The day after, cells were counted and the percentage of CAR+ cells was normalized per donor via addition of untransduced cells. Normalized CAR-T cells were resuspended at a concentration of $2.5\times10^5$ CAR+ cells per mL in phenol red-free media for a starting CAR+E:T ratio of 2.5:1. A total of eight 2-fold dilutions (ratio of 2.5:1, $2.5\times10^5$ CAR+ cells; ratio of 1.25:1, $1.25\times10^5$ CAR+ cells; ratio of 1:1.6, $6.25\times10^4$ CAR+ cells; ratio of 1:3.2, $3.13\times10^4$ CAR+ cells; ratio of 1:6.4, $1.56\times10^4$ CAR+ cells; ratio of 1:13, $7.81\times10^3$ CAR+ cells; ratio of 1:26, $3.91\times10^3$ CAR+ cells; and, ratio of 1:51, $1.95\times10^3$ CAR+ cells) were made, and of effector cells were seeded in a 96-well plate according to plate layout (100 μL per well).

Next, the target cell lines were harvested, counted, resuspended at $1\times10^5$ cells per mL in phenol red-free media, and seeded according to plate layout (100 μL per well).

Figure 11A:
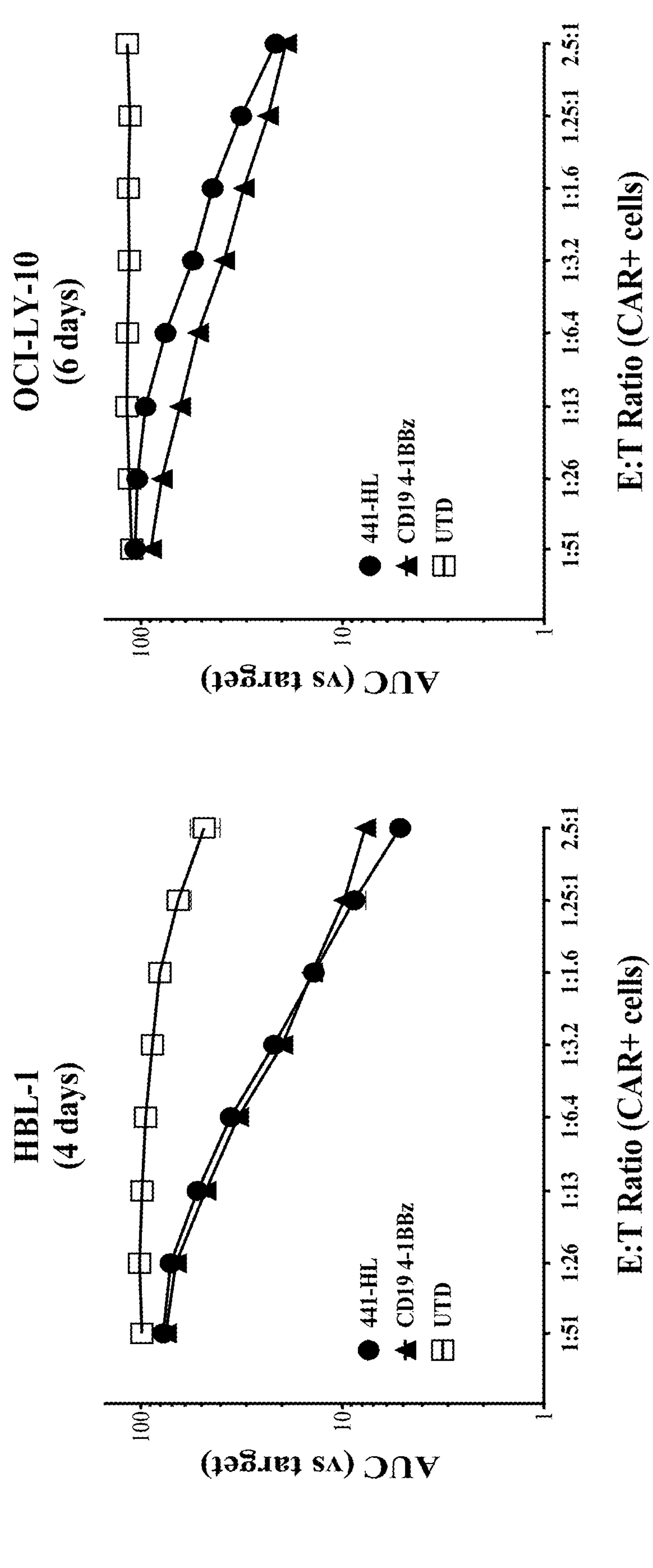
FIGS. 11A-11F show specific killing of antigen-positive cell lines by 441-HL CAR-T cells using IncuCyte® technology. Taking advantage of the IncuCyte® technology, killing kinetics of 441-HL CAR-T were assessed in a panel of two CD79b/CD19+(HBL-1, OCI-LY-10) and two CD79b/CD19−(HLY-1, SU-DHL-1) mKATE2-expressing cell lines. Following thawing and overnight rest, cells were counted and the percentage CAR+ cells normalized per donor via addition of untransduced cells. Normalized CAR-T cells were then counted and resuspended at a concentration of $5\times10^5$ CAR+ cells per mL for a starting CAR+E:T ratio of 2.5:1. A total of eight 2-fold dilutions were made, and effector cells were seeded in a 96-well plate (100 μL per well). Target cell lines were harvested, counted, resuspended at $1\times10^5$ cells per mL, and seeded according to plate layout (96-well plate; 100 μL per well). Following mixing of CAR-T cells and target cells, 80 μL from each well was dispensed in duplicate in a 384-well plate. The co-cultures were then placed in an IncuCyte® ZOOM live-content imaging system, and images were automatically acquired in both phase and fluorescence channels every 4 hours for 4 to 6 days with a 4× objective lens (single image). The level of target cells was quantified based on mKATE2 red fluorescent protein expression. To quantify cancer cell killing over time, the average area for each replicate was exported to GraphPad® Prism and area under the curve (AUC) values derived for each condition. After normalizing to the untreated control, E:T ratios were plotted against the AUC values as a dose-response. Dose-response graphs for both merged (mean±SEM) or individual values for the five donors (two independent experiments) were generated. Merged graphs are shown in FIG. 11A and FIG. 11B for CD79b/CD19+ cells and CD79b/CD19−cells, respectively. Plots showing the individual kill curve for each donor are shown in FIGS. 11C-11D and FIGS. 11E-11F for CD79b/CD19+ cells and CD79b/CD19−cells, respectively.
Figure 11B:
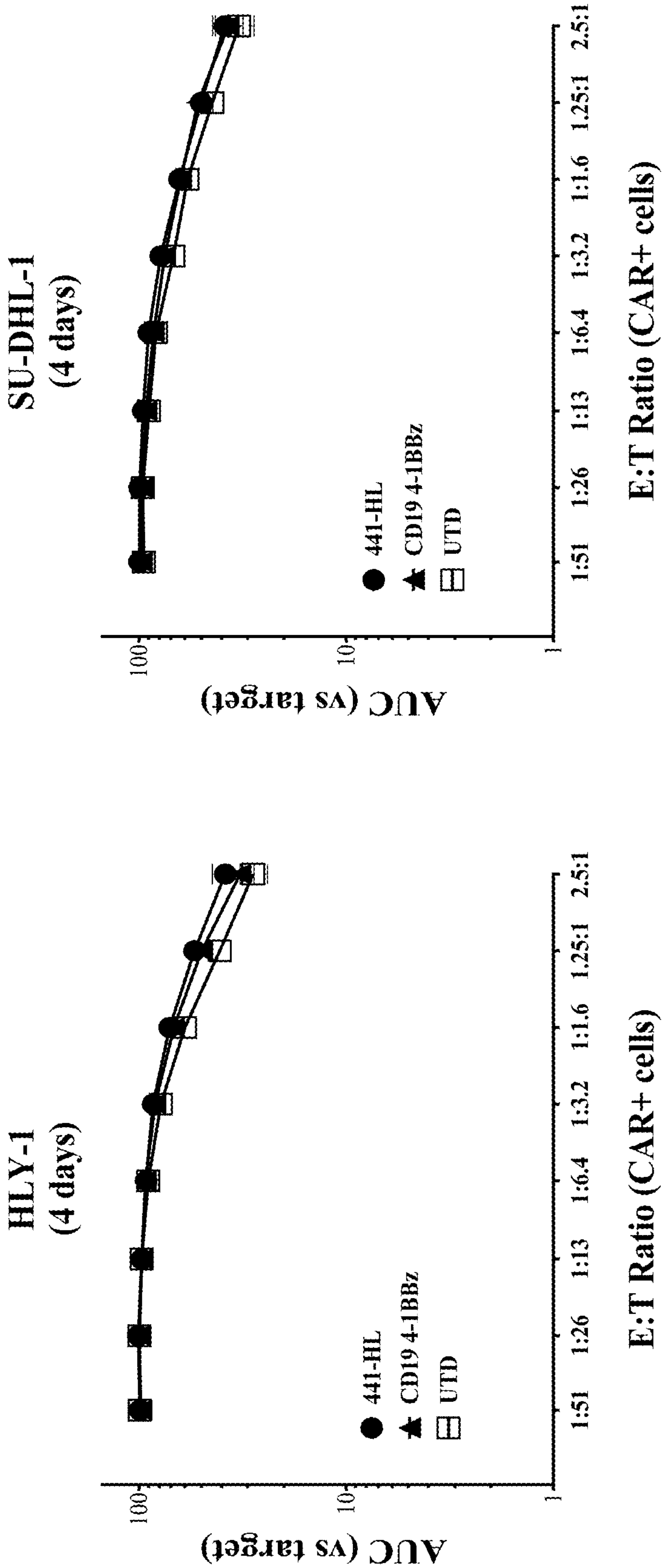
Figure 11C:
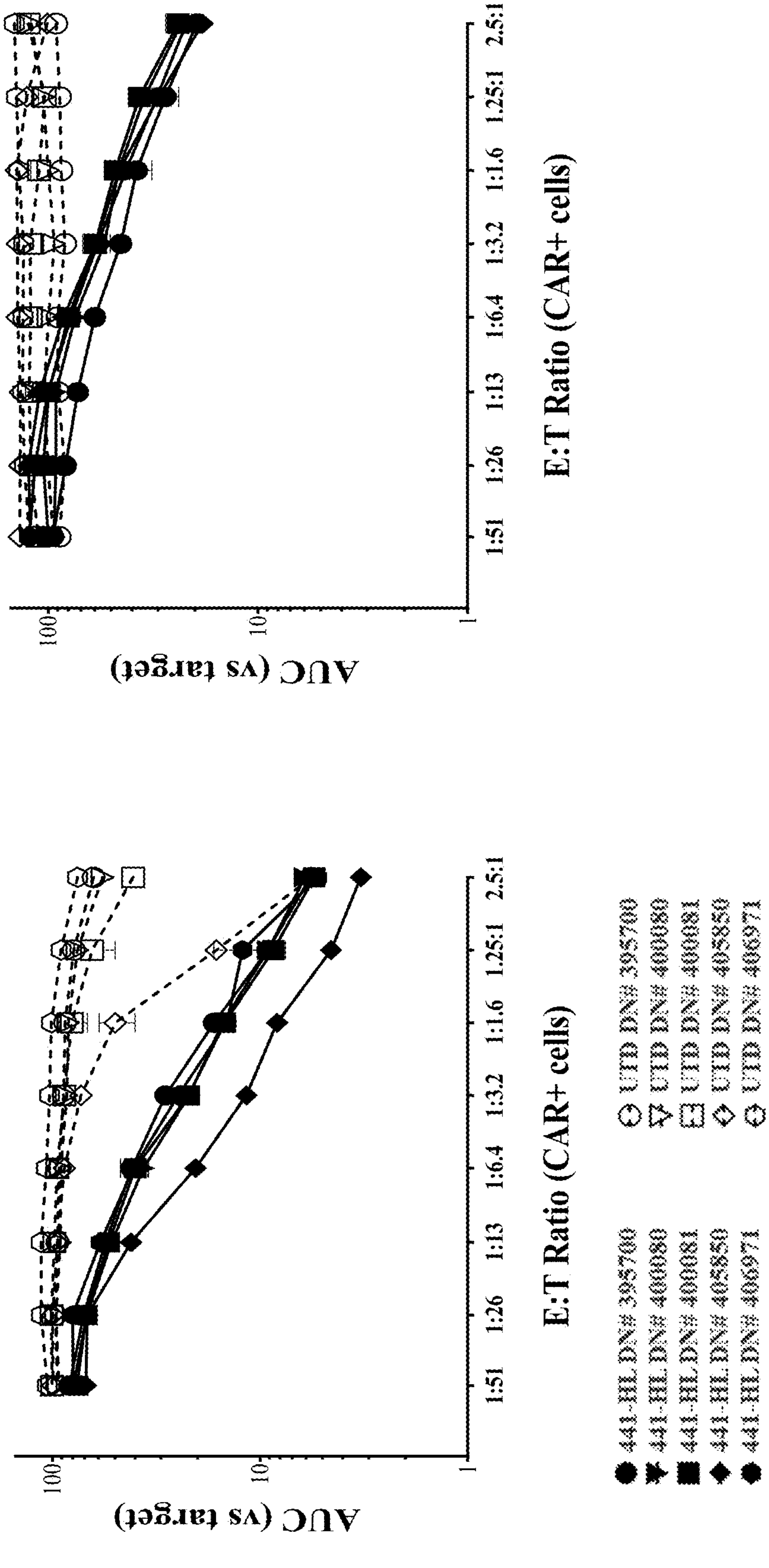
Figure 11D:
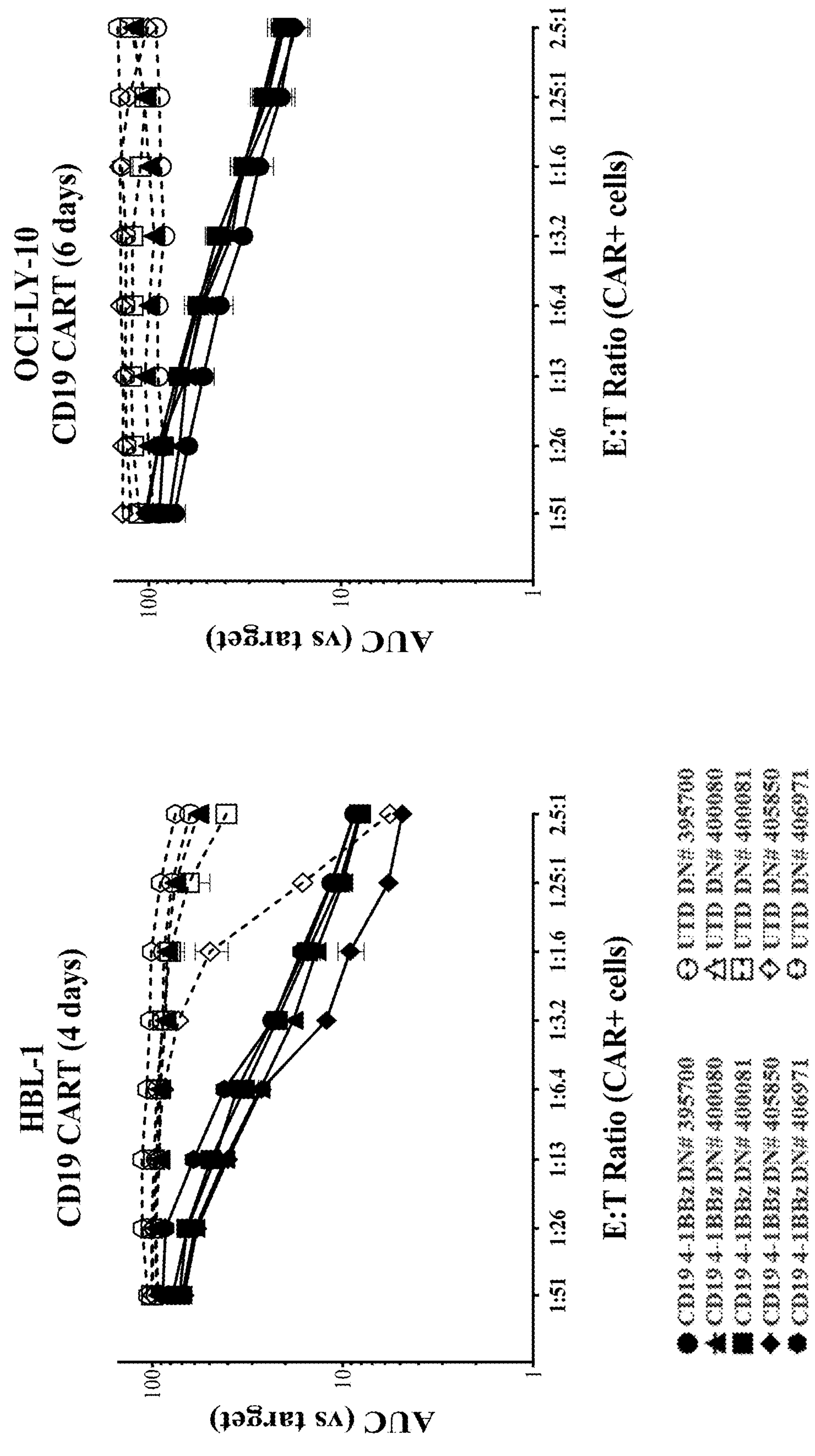
Figure 11E:
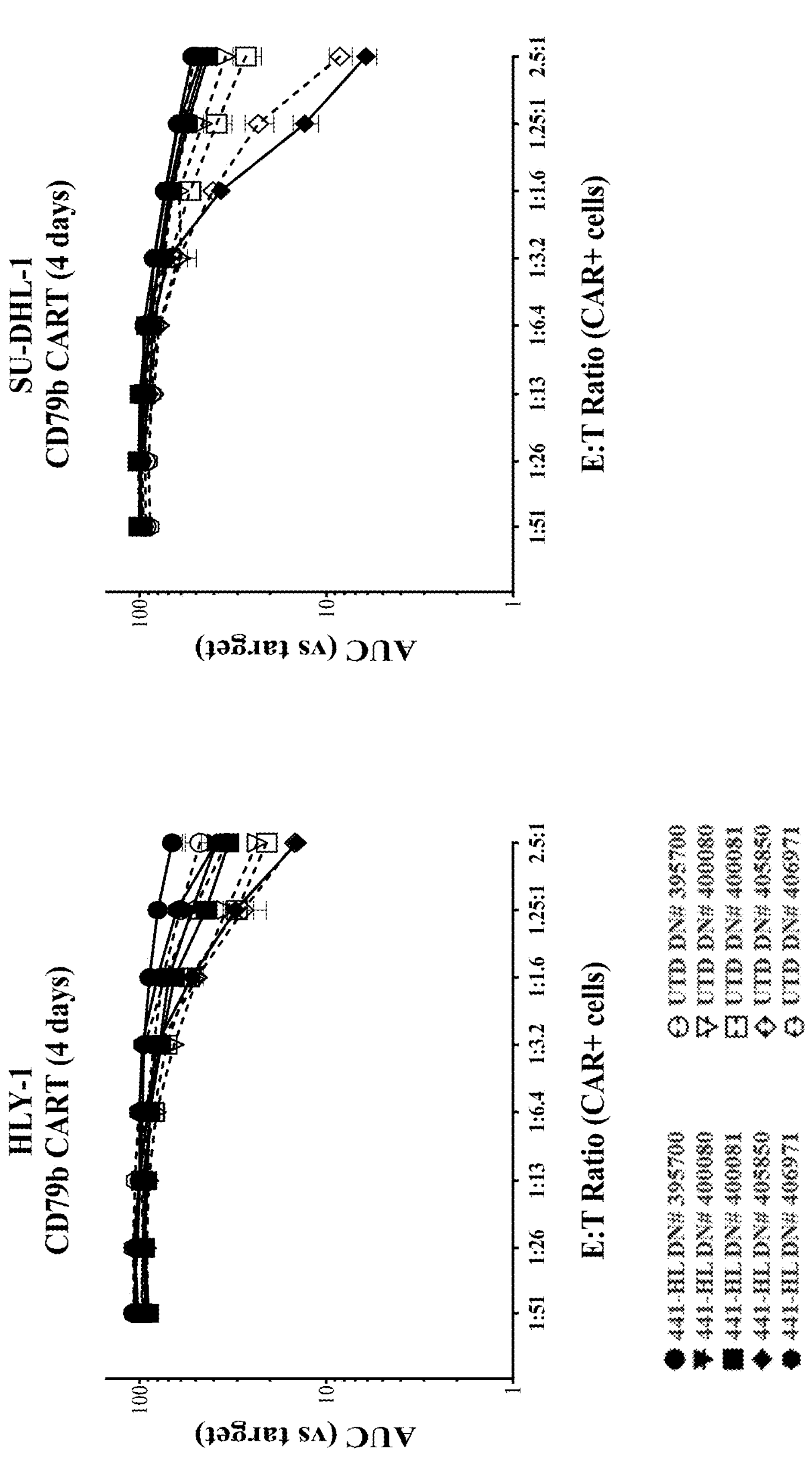
Figure 11F:
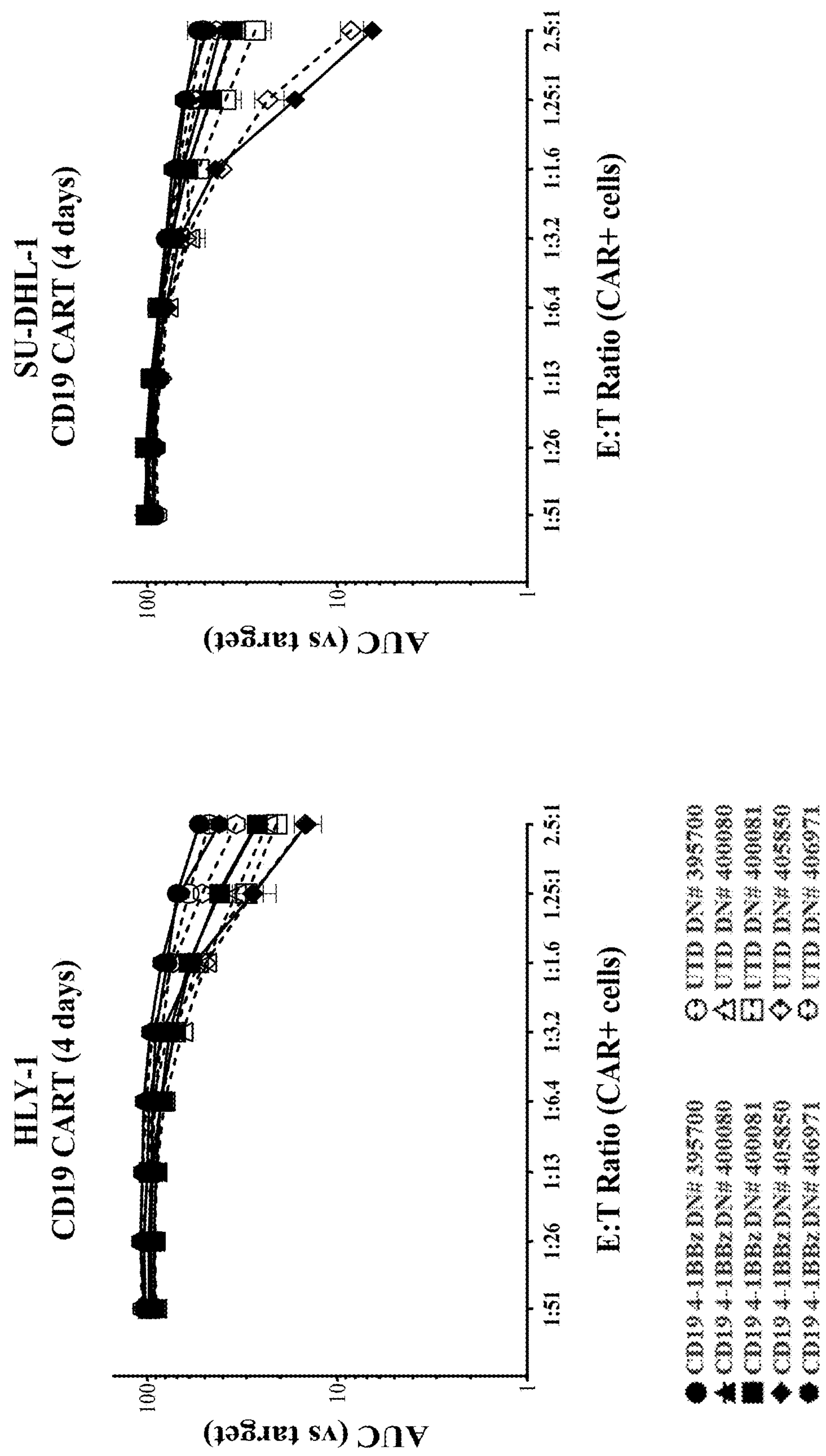

After mixing target and CAR-T cells, 80 μL from each well was dispensed in a 384-well plate, in duplicate. Following seeding, co-cultures were placed in an IncuCyte® ZOOM live-content imaging system, and images were automatically acquired in both phase and fluorescence channels every four hours for four to six days with a 4× objective lens (single image). IncuCyte® ZOOM software was used to detect target cells based on mKATE2 red fluorescent protein expression using optimized process definition parameters. To measure the level of target cells per well, the total red area was quantified, and raw values were exported to Excel. To quantify cancer cell killing over time, the average values for each replicate were exported to GraphPad® Prism, and area under the curve (AUC) values derived for each condition. After normalizing the data to the untreated control (target alone), E:T ratios were plotted against the AUC values as a dose response. Graphs for both merged (mean±SEM) or individual values for the five donors (two independent experiments) were generated. Merged results are shown in FIG. 11A for CD79b/CD19+ cells and FIG. 11B for CD79b/CD19−cells. Plots showing the individual kill curve for each donor are shown in FIGS. 11C-11D for CD79b/CD19+ cells and FIGS. 11E-11F for CD79b/CD19− cells.

Specific killing was detected in presence of the antigen-positive cell lines while no killing was observed in the antigen-negative models.

Example 13: Cytokine Release Assay

To assess the levels of cytokine release upon CAR-T cells killing, supernatants from four CD79b/CD19+(HBL-1, OCI-LY-10, CARNAVAL, WILL-2) and two CD79b/CD19−(HLY-1 and SU-DHL-1) cell lines were collected during the flow cytometry-based killing assay described above and tested by Meso Scale Discovery (MSD). Supernatants were thawed and analyzed via manufacturer's instructions using MSD plate (V Plex Proinflammation Panel 1 [human] kit). Data analysis was performed using the MSD Discovery Workbench program and results for each cytokine were plotted as individual values for the five donors (two independent experiments; N=10 total values per treatment group) using GraphPad® Prism. Mean±SEM values calculated and plotted for each of the treatment groups. Results are shown in FIGS. 12A-12J.

MSD analysis revealed antigen-specific production of pro-inflammatory cytokines by 441-HL CAR-T. No induction of cytokine release, compared to the UTDs, was observed in presence of the antigen-negative cell lines tested.

Example 14: In Vivo Efficacy of CD79b CAR-T Cells in CARNAVAL Xenograft Model

CARNAVAL cells were maintained in RPMI 1640 media supplemented with 10% fetal bovine serum (FBS). CAR- NAVAL cells ($5\times10^5$ cells) in logarithmic growth phase were implanted subcutaneously in NOD/scid/IL-2Rg−/− (NSG) mice on Day 0. CAR-T cells (441 HL or CD19 4-1BBz reference CAR) were generated as follows: Primary human T cells were thawed and rested overnight in TexMACS™ media supplemented with 300 IU/ml IL-2. The day after thaw, T cells were stimulated with TransAct™ beads per the manufacturer's instructions; 24 hours after stimulation cells were transduced with lentiviral vectors encoding the CAR constructs at a multiplicity of infection (MOI) of 5. T cells were cultured for 14 days total prior to harvest and freezing in CryoStar™ CS10 media. During culture, media and cytokine were refreshed every 2-4 days. CD79b CAR expression was quantified via flow cytometry using recombinant human CD79b extracellular domain fused to AF647 protein. When mean group tumor volume reached approximately 50-100 $mm^3$/mouse at about 14 days postimplant, indicated doses of CAR+ T cells (doses of $1\times10^6$ cells, $2\times10^6$ cells, and $4\times10^6$ cells for 441 HL and CD19 4-1BBz conditions; dose of $1\times10^6$ cells for UTD condition) were injected intravenously (FIG. 13A). Untransduced CAR-T cells were added to normalize the number of both CAR+ and total T cells administered for each CAR. Tumor volume was measured twice weekly via caliper (FIG. 13B), along with body weight (FIG. 13C). 441-HL CARs mediated tumor growth inhibition in a dose-dependent way, with no concomitant body weight loss observed. By Day 47, mice achieved cytokine release syndrome (CRS) in the $4\times10^6$ 441-HL CAR-T cells dose group.

REFERENCE

1. Kochenderfer, J. N. et al. Chemotherapy-refractory diffuse large B-cell lymphoma and indolent B-cell malignancies can be effectively treated with autologous T cells expressing an anti-CD19 chimeric antigen receptor. *J Clin Oncol* 33, 540-549 (2015).
2. Schuster, S. J. et al. Chimeric Antigen Receptor T Cells in Refractory B-Cell Lymphomas. *N Engl J Med* 377, 2545-2554 (2017).
3. Shalabi, H. et al. Sequential loss of tumor surface antigens following chimeric antigen receptor T-cell therapies in diffuse large B-cell lymphoma. *Haematologica* 103, e215-e218 (2018).
4. Sotillo, E. et al. Convergence of Acquired Mutations and Alternative Splicing of CD19 Enables Resistance to CART-19 Immunotherapy. *Cancer Discov* 5, 1282-1295 (2015).
5. Packard, T. A. & Cambier, J. C. B lymphocyte antigen receptor signaling: initiation, amplification, and regulation. *F1000Prime Rep* 5, 40 (2013).
6. Puri, K. D., Di Paolo, J. A. & Gold, M. R. B-cell receptor signaling inhibitors for treatment of autoimmune inflammatory diseases and B-cell malignancies. *Int Rev Immunol* 32, 397-427 (2013).
7. Polson, A. G. et al. Antibody-drug conjugates targeted to CD79 for the treatment of non-Hodgkin lymphoma. *Blood* 110, 616-623 (2007).
8. Palanca-Wessels, M. C. A. et al. Safety and activity of the anti-CD79B antibody-drug conjugate polatuzumab vedotin in relapsed or refractory B-cell non-Hodgkin lymphoma and chronic lymphocytic leukaemia: a phase 1 study. *The Lancet Oncology* 16, 704-715 (2015).
9. Astsaturov, I. A. et al. Differential expression of B29 (CD79b) and mb-1 (CD79a) proteins in acute lymphoblastic leukaemia. Leukemia 10, 769-773 (1996).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A chimeric antigen receptor (CAR) comprising:

(A) an extracellular antigen-binding domain that specifically binds to a CD79b antigen comprising SEQ ID NO: 282, wherein the extracellular antigen-binding domain comprises a signal polypeptide comprising SEQ ID NO: 37 and an scFv, comprising a heavy chain complementarity determining region 1 (CDR1), a heavy chain CDR2, a heavy chain CDR3, a light chain CDR1, a light chain CDR2 and a light chain CDR3 having the amino acid sequence of a) SEQ ID NOs: 208, 209, 210, 211, 212, and 213, respectively;

b) SEQ ID NOs: 208, 209, 210, 214, 212, and 213, respectively;

c) SEQ ID NOs: 208, 209, 210, 215, 212, and 213, respectively;

d) SEQ ID NOs: 216, 217, 218, 219, 220, and 221, respectively;

e) SEQ ID NOs: 222, 223, 224, 225, 226, and 227, respectively;

f) SEQ ID NOs: 228, 217, 229, 230, 231, and 221, respectively;

g) SEQ ID NOs: 232, 233, 234, 235, 236, and 237, respectively;

h) SEQ ID NOs: 238, 239, 240, 241, 226, and 227, respectively;

i) SEQ ID NOs: 242, 243, 244, 245, 246, and 247, respectively;

j) SEQ ID NOs: 248, 249, 250, 251, 236, and 252, respectively;

k) SEQ ID NOs: 253, 254, 255, 251, 236, and 256, respectively;

l) SEQ ID NOs: 257, 258, 259, 260, 261, and 262, respectively;

m) SEQ ID NOs: 263, 243, 264, 265, 266, and 267, respectively;

n) SEQ ID NOs: 268, 269, 270, 271, 272, and 273, respectively; or o) SEQ ID NOs: 274, 275, 276, 277, 266, and 278, respectively; and wherein the scFv further comprises a linker polypeptide comprising SEQ ID NO: 42;

(B) a transmembrane domain, comprising a CD8a transmembrane region (CD8a-TM) polypeptide, comprising SEQ ID NO: 39;

(C) an intracellular signaling domain comprising a co-stimulatory domain comprising a TNF receptor superfamily member 9 (CD137) component comprising SEQ ID NO: 40, and a primary signaling domain comprising a T-cell surface glycoprotein CD3 zeta chain (CD3z) component comprising SEQ ID NO: 41; and (D) a CD8a-hinge region linking the transmembrane domain to the extracellular antigen-binding domain comprising SEQ ID NO: 38.

2. The CAR of claim 1, wherein the extracellular antigen-binding domain comprises the heavy chain CDR1, the heavy chain CDR2, the heavy chain CDR3, the light chain CDR1, the light chain CDR2 and the light chain CDR3 having the amino acid sequence of SEQ ID NOs: 257, 258, 259, 260, 261, and 262, respectively.

3. The CAR of claim 1, wherein the extracellular antigen-binding domain comprises:

a heavy chain variable region comprising an amino acid sequence of SEQ ID NO: 1 and a light chain variable region comprising an amino acid sequence of SEQ ID NO: 19;

a heavy chain variable region comprising an amino acid sequence of SEQ ID NO: 1 and a light chain variable region comprising an amino acid sequence of SEQ ID NO: 20;

a heavy chain variable region comprising an amino acid sequence of SEQ ID NO: 2 and a light chain variable region comprising an amino acid of SEQ ID NO: 19;

a heavy chain variable region comprising an amino acid sequence of SEQ ID NO: 2 and a light chain variable region comprising an amino acid sequence of SEQ ID NO: 20;

a heavy chain variable region comprising an amino acid sequence of SEQ ID NO: 3 and a light chain variable region comprising an amino acid sequence of SEQ ID NO: 20;

a heavy chain variable region comprising an amino acid sequence of SEQ ID NO: 4 and a light chain variable region comprising an amino acid sequence of SEQ ID NO: 19;

a heavy chain variable region comprising an amino acid sequence of SEQ ID NO: 5 and a light chain variable region comprising an amino acid sequence of SEQ ID NO: 22;

a heavy chain variable region comprising an amino acid sequence of SEQ ID NO: 5 and a light chain variable region comprising an amino acid sequence of SEQ ID NO: 23;

a heavy chain variable region comprising an amino acid sequence of SEQ ID NO: 6 and a light chain variable region comprising an amino acid sequence of SEQ ID NO: 24;

a heavy chain variable region comprising an amino acid sequence of SEQ ID NO: 7 and a light chain variable region comprising an amino acid sequence of SEQ ID NO: 26;

a heavy chain variable region comprising an amino acid sequence of SEQ ID NO: 8 and a light chain variable region comprising an amino acid sequence of SEQ ID NO: 25;

a heavy chain variable region comprising an amino acid sequence of SEQ ID NO: 9 and a light chain variable region comprising an amino acid sequence of SEQ ID NO: 27;

a heavy chain variable region comprising an amino acid sequence of SEQ ID NO: 10 and a light chain variable region comprising an amino acid sequence of SEQ ID NO: 28;

a heavy chain variable region comprising an amino acid sequence of SEQ ID NO: 11 and a light chain variable region comprising an amino acid sequence of SEQ ID NO: 29;

a heavy chain variable region comprising an amino acid sequence of SEQ ID NO: 12 and a light chain variable region comprising an amino acid sequence of SEQ ID NO: 30;

a heavy chain variable region comprising an amino acid sequence of SEQ ID NO: 13 and a light chain variable region comprising an amino acid sequence of SEQ ID NO: 31;

a heavy chain variable region comprising an amino acid sequence of SEQ ID NO: 14 and a light chain variable region comprising an amino acid sequence of SEQ ID NO: 32;

a heavy chain variable region comprising an amino acid sequence of SEQ ID NO: 15 and a light chain variable region comprising an amino acid sequence of SEQ ID NO: 33;

a heavy chain variable region comprising an amino acid sequence of SEQ ID NO: 16 and a light chain variable region comprising an amino acid sequence of SEQ ID NO: 34;

a heavy chain variable region comprising an amino acid sequence of SEQ ID NO: 16 and a light chain variable region comprising an amino acid sequence of SEQ ID NO: 35;

a heavy chain variable region comprising an amino acid sequence of SEQ ID NO: 17 and a light chain variable region comprising an amino acid sequence of SEQ ID NO: 33; or a heavy chain variable region comprising an amino acid sequence of SEQ ID NO: 18 and a light chain variable region comprising an amino acid sequence of SEQ ID NO: 36.

4. A chimeric antigen receptor (CAR) comprising:

(a) an extracellular antigen-binding domain that specifically binds to a CD79b antigen comprising SEQ ID NO: 282, wherein the extracellular antigen-binding domain comprises a signal polypeptide comprising SEQ ID NO: 37 and an scFv, wherein the scFv comprises an amino acid sequence that is selected from the group consisting of SEQ ID NOS: 75-118, (b) a transmembrane domain, comprising a CD8a transmembrane region (CD8a-TM) polypeptide, comprising SEQ ID NO: 39;

(c) an intracellular signaling domain comprising a co-stimulatory domain comprising a TNF receptor superfamily member 9 (CD137) component comprising SEQ ID NO: 40, and a primary signaling domain comprising a T-cell surface glycoprotein CD3 zeta chain (CD3z) component comprising SEQ ID NO: 41; and (d) a CD8a-hinge region linking the transmembrane domain to the extracellular antigen-binding domain comprising SEQ ID NO: 38.

5. The CAR of claim 1, wherein the intracellular signaling domain comprises SEQ ID NO: 163.

6. A chimeric antigen receptor (CAR) comprising:

(a) an extracellular antigen-binding domain that specifically binds to a CD79b antigen comprising SEQ ID NO: 282, wherein the extracellular antigen-binding domain comprises an amino acid sequence selected from the group consisting of SEQ ID NOS: 119-162;

(b) a transmembrane domain, comprising a CD8a transmembrane region (CD8a-TM) polypeptide, comprising SEQ ID NO: 39;

(c) an intracellular signaling domain comprising a co-stimulatory domain comprising a TNF receptor superfamily member 9 (CD137) component comprising SEQ ID NO: 40, and a primary signaling domain comprising a T-cell surface glycoprotein CD3 zeta chain (CD3z) component comprising SEQ ID NO: 41; and (d) a CD8a-hinge region linking the transmembrane domain to the extracellular antigen-binding domain comprising SEQ ID NO: 38.

7. A chimeric antigen receptor (CAR) that specifically binds to a CD79b antigen comprising SEQ ID NO: 282, wherein the CAR comprises an amino acid sequence selected from the group consisting of SEQ ID NOS: 164-207.

8. An isolated T lymphocyte expressing the CAR of claim 1.

9. An isolated nucleic acid molecule encoding the CAR of claim 1.

10. A vector comprising the nucleic acid molecule of claim 9.

11. An isolated cell expressing the nucleic acid molecule of claim 9.

12. A pharmaceutical composition, comprising the lymphocyte of claim 8 and a pharmaceutically acceptable excipient.

* * * * *

SEQUENCE LISTING

```
<160> NUMBER OF SEQ ID NOS: 288

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Arg Pro Gly Gln Gly Leu Glu Trp Met
        35                  40                  45

Gly Glu Ile Leu Pro Gly Gly Gly Asp Thr Asn Tyr Asn Gln Lys Phe
    50                  55                  60

Gln Gly Lys Val Thr Phe Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Val Pro Val Tyr Phe Asp Tyr Trp Gly Gln Gly Thr Leu
```

```
            100                 105                 110

Val Thr Val Ser Ser
        115


<210> SEQ ID NO 2
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Arg Pro Gly Gln Gly Leu Glu Trp Met
        35                  40                  45

Gly Glu Ile Leu Pro Gly Gly Gly Asp Thr Asn Tyr Asn Gln Lys Phe
    50                  55                  60

Gln Gly Lys Val Thr Phe Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Val Pro Val Tyr Phe Asp Tyr Trp Gly Gln Gly Thr Leu
            100                 105                 110

Val Thr Val Ser Ser
        115


<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Ala Pro Gly Gln Gly Leu Glu Trp Met
        35                  40                  45

Gly Glu Ile Leu Pro Gly Gly Gly Asp Thr Asn Tyr Asn Gln Lys Phe
    50                  55                  60

Gln Gly Lys Val Thr Phe Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Val Pro Val Tyr Phe Asp Tyr Trp Gly Gln Gly Thr Leu
            100                 105                 110

Val Thr Val Ser Ser
        115


<210> SEQ ID NO 4
<211> LENGTH: 117
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 4

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Ala Pro Gly Gln Gly Leu Glu Trp Met
        35                  40                  45

Gly Glu Ile Leu Pro Gly Gly Gly Asp Thr Asn Tyr Asn Gln Lys Phe
    50                  55                  60

Gln Gly Lys Val Thr Phe Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Val Pro Val Tyr Phe Asp Tyr Trp Gly Gln Gly Thr Leu
            100                 105                 110

Val Thr Val Ser Ser
        115
```

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Gln Val Gln Leu Val Gln Ser Gly Ala Glu Val Met Lys Pro Gly Ala
1               5                   10                  15

Ser Val Lys Ile Ser Cys Lys Ala Ser Gly Tyr Thr Phe Thr Gly Tyr
            20                  25                  30

Trp Ile Glu Trp Val Arg Gln Arg Pro Gly Gln Gly Leu Glu Trp Met
        35                  40                  45

Gly Glu Ile Leu Pro Gly Gly Gly Asp Thr Asn Tyr Asn Gln Lys Phe
    50                  55                  60

Gln Gly Lys Val Thr Phe Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Val Pro Val Tyr Phe Asp Tyr Trp Gly Gln Gly Thr Leu
            100                 105                 110

Val Thr Val Ser Ser
        115
```

<210> SEQ ID NO 6
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Glu Val Gln Leu Gln Glu Ser Gly Pro Gly Leu Val Lys Pro Ser Glu
1               5                   10                  15
```

```
Thr Leu Ser Leu Thr Cys Ser Val Ser Gly Gly Ser Ile Ser Gly Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Lys Leu Arg Ser Val Thr Ala Ala Asp Thr Ala Val Tyr Tyr
                85                  90                  95

Cys Ala Arg Glu Glu Asp Ser Gly Ser Tyr Tyr Val Gly Ala Phe Asp
            100                 105                 110

Ile Trp Gly Gln Gly Thr Met Val Thr Val Ser Ser
        115                 120


<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Asn Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Lys Lys Ser Leu Trp
65                  70                  75                  80

Leu Gln Met Ser Ser Leu Arg Val Glu Asp Thr Ala Val Tyr Tyr Cys
                85                  90                  95

Ala Arg Asp Pro Ile Glu Ser Arg Phe Asp Tyr Trp Gly Gln Gly Thr
            100                 105                 110

Leu Val Thr Val Ser Ser
        115


<210> SEQ ID NO 8
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Arg Ser Ser
            20                  25                  30

Thr Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Ser Asn Pro Ser
    50                  55                  60
```

```
Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Ile Tyr Tyr
                85                  90                  95

Cys Ala Arg Glu Glu Asp Ser Gly Ser Tyr Tyr Val Gly Thr Phe Asp
            100                 105                 110

Ile Trp Gly Gln Gly Thr Met Val Thr Val Ser Ser
        115                 120


<210> SEQ ID NO 9
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ile Tyr
            20                  25                  30

Ala Met Thr Trp Val Arg Gln Ala Pro Gly Lys Gly Leu Glu Trp Val
        35                  40                  45

Ser Gly Ile Ser Val Ser Gly Ile Arg Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Ser Ala Glu Asp Thr Ala Val Tyr Tyr Cys
                85                  90                  95

Ala Lys Gly Leu Ser Ser Gly Asp Arg Asp Ala Ser Asp Ile Trp Gly
            100                 105                 110

Gln Gly Thr Met Val Thr Val Ser Ser
        115                 120


<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Thr Tyr
            20                  25                  30

Trp Met Ser Trp Val Arg Gln Ala Pro Gly Lys Gly Leu Glu Trp Val
        35                  40                  45

Ala Asn Ile Asn Pro Asp Gly Asn Glu Lys Tyr Tyr Val Asp Ser Val
    50                  55                  60

Glu Gly Arg Phe Thr Ile Ser Arg Asp Asn Ala Gln Asp Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ile Ser Ala Arg Phe Asp Phe Trp Gly Gln Gly Thr
            100                 105                 110
```

Leu Val Thr Val Ser Ser
        115

<210> SEQ ID NO 11
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Gly Ser Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Pro Ser Gly Thr Phe Trp Asn Asp Ala Phe Asp Ile Trp Gly
            100                 105                 110

Gln Gly Thr Met Val Thr Val Ser Ser
        115                 120

<210> SEQ ID NO 12
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Glu Trp Val
        35                  40                  45

Ser Val Ile Ser Gly Asn Gly Gly Ser Ile His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Arg Gly Tyr Thr Gly Tyr Asp Gly Asp Ala Phe Asp Phe
            100                 105                 110

Trp Gly Gln Gly Thr Met Val Thr Val Ser Ser
        115                 120

<210> SEQ ID NO 13
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Glu Val Gln Leu Val Glu Ser Gly Gly Asp Leu Val Gln Pro Gly Gly
1               5                   10                  15

Ser Leu Arg Leu Ser Cys Glu Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ser Gly Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Leu Leu Leu Trp Leu Gly Tyr His Gly Asp Gly Phe Asp Leu
            100                 105                 110

Trp Gly Gln Gly Thr Met Val Thr Val Ser Ser
        115                 120
```

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Gly Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Glu Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Thr Arg Val Asp Thr Asp Phe Asp Tyr Trp Gly Gln Gly
            100                 105                 110

Thr Leu Val Thr Val Ser Ser
        115
```

<210> SEQ ID NO 15
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Arg His
20 25 30

Thr Met Asn Trp Val Arg Gln Ala Pro Gly Lys Gly Leu Glu Trp Val
35 40 45

Ser Ser Ile Ser Gly Ser Gly Gly Ser Thr Tyr Tyr Ala Asp Ser Val
50 55 60

Lys Gly Arg Phe Thr Val Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Glu Ser Tyr Asp Ser Ser Gly Val Trp Tyr Phe Asp Leu Trp
100 105 110

Gly Arg Gly Thr Leu Val Thr Val Ser Ser
115 120

<210> SEQ ID NO 16
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Gln Val Gln Leu Gln Glu Ser Gly Pro Gly Leu Val Lys Pro Ser Glu
1 5 10 15

Thr Leu Ser Leu Thr Cys Thr Val Ser Ser Gly Ser Ile Ser Ser Tyr
20 25 30

Tyr Trp Asn Trp Ile Arg Gln Pro Ala Gly Lys Gly Leu Glu Trp Ile
35 40 45

Gly Arg Ile Tyr Thr Ser Gly Thr Thr His Tyr Asn Pro Ser Leu Lys
50 55 60

Ser Arg Val Thr Met Ser Ile Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Glu Ile Arg Glu Leu Arg Gly Phe Asp Tyr Trp Gly Gln Gly Thr
100 105 110

Leu Val Thr Val Ser Ser
115

<210> SEQ ID NO 17
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg His
20 25 30

Thr Met Asn Trp Val Arg Gln Ala Pro Gly Lys Gly Leu Glu Trp Val
35 40 45

Ser Ser Ile Ser Gly Ser Gly Gly Ser Thr Tyr Tyr Ala Asp Ser Val
50 55 60

```
Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ser Tyr Asp Ser Ser Gly Val Trp Tyr Phe Asp Leu Trp
            100                 105                 110

Gly Lys Gly Thr Thr Val Thr Val Ser Ser
        115                 120


<210> SEQ ID NO 18
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Asn Met Asn Trp Val Arg Gln Ala Pro Gly Lys Gly Leu Glu Trp Val
        35                  40                  45

Ser Tyr Ile Ser Ser Ser Gly Tyr Thr Ile Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asp Ser Leu Arg Asp Glu Asp Thr Ala Ile Tyr Tyr Cys
                85                  90                  95

Ala Arg Asp Arg Tyr Asn Tyr Asp Asn Gly Gly Tyr His Tyr Tyr Thr
            100                 105                 110

Gly Met Asp Val Trp Gly Gln Gly Thr Met Val Thr Val Ser Ser
        115                 120                 125


<210> SEQ ID NO 19
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Phe Leu Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Leu Thr Phe Gly Gly Gly Thr Lys Val Glu Ile Lys
            100                 105                 110
```

<210> SEQ ID NO 20
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 20

Asp Ile Val Leu Thr Gln Ser Pro Asp Ser Leu Ala Val Ser Leu Gly
1 5 10 15

Glu Arg Ala Thr Ile Asn Cys Lys Ala Ser Gln Ser Val Asp Tyr Glu
20 25 30

Gly Asp Ser Phe Leu Asn Trp Tyr Gln Gln Lys Pro Gly Gln Pro Pro
35 40 45

Lys Leu Leu Ile Tyr Ala Ala Ser Asn Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Ser Asn
85 90 95

Glu Asp Pro Leu Thr Phe Gly Gly Gly Thr Lys Val Glu Ile Lys
100 105 110

<210> SEQ ID NO 21
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 21

Asp Ile Val Leu Thr Gln Ser Pro Asp Ser Leu Ala Val Ser Leu Gly
1 5 10 15

Glu Arg Ala Thr Ile Asn Cys Lys Ala Ser Gln Ser Val Asp Tyr Glu
20 25 30

Gly Asp Ser Phe Leu Asn Trp Tyr Gln Gln Lys Pro Gly Gln Pro Pro
35 40 45

Lys Leu Leu Ile Tyr Ala Ala Ser Asn Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Ser Asn
85 90 95

Glu Asp Pro Leu Thr Phe Gly Gly Gly Thr Lys Val Glu Ile Lys
100 105 110

<210> SEQ ID NO 22
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

Asp Ile Val Met Thr Gln Ser Pro Asp Ser Leu Ala Val Ser Leu Gly
1 5 10 15

Glu Arg Ala Thr Ile Asn Cys Lys Ala Ser Gln Ser Val Asp Tyr Asp

```
            20                  25                  30

Gly Asp Ser Phe Leu Asn Trp Tyr Gln Gln Lys Pro Gly Gln Pro Pro
        35                  40                  45

Lys Leu Phe Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Ala Ala Val Tyr Tyr Cys Gln Gln Ser Asn
                85                  90                  95

Glu Asp Pro Leu Thr Phe Gly Gly Gly Thr Lys Val Glu Ile Lys
            100                 105                 110


<210> SEQ ID NO 23
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Lys
            20                  25                  30

Gly Asp Ser Phe Leu Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Leu Thr Phe Gly Gly Gly Thr Lys Val Glu Ile Lys
            100                 105                 110


<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser Ser Glu Leu Thr Gln Asp Pro Ala Val Ser Val Ala Leu Gly Gln
1               5                   10                  15

Thr Val Arg Ile Arg Cys Gln Gly Asp Ser Leu Arg Lys Tyr Tyr Gly
            20                  25                  30

Ser Trp Tyr Gln Gln Lys Pro Gly Gln Ala Pro Val Leu Val Ile Tyr
        35                  40                  45

Gly Glu Thr Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys His
                85                  90                  95

Val Val Phe Gly Gly Gly Thr Lys Leu Thr Val Leu
```

100 105

<210> SEQ ID NO 25
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Asn Tyr Tyr Gly
20 25 30

Ser Trp Tyr Gln Gln Lys Pro Gly Gln Ala Pro Val Leu Val Ile Tyr
35 40 45

Gly Glu Lys Asn Arg Pro Ser Gly Ile Pro Asp Arg Phe Ser Gly Ser
50 55 60

Ser Ser Gly Asn Thr Val Ser Leu Thr Ile Thr Gly Thr Gln Ala Glu
65 70 75 80

Asp Glu Ala Asp Tyr Tyr Cys Asn Ser Arg Asp Ser Ser Gly Lys His
85 90 95

Val Val Phe Gly Gly Gly Thr Lys Leu Thr Val Leu
100 105

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Ser Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Pro Thr Phe Gly Gly Gly Thr Lys Val Glu Ile Lys
100 105 110

<210> SEQ ID NO 27
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

Ser Ser Glu Leu Thr Gln Pro Pro Ser Val Ser Val Ser Pro Gly Gln
1 5 10 15

```
Thr Ala Arg Ile Thr Cys Ser Gly Asp Ala Leu Pro Arg Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Thr Met Ala Thr Leu Thr Ile Ser Gly Ala Gln Val Glu
65                  70                  75                  80

Asp Glu Ala Ala Tyr Tyr Cys Tyr Ser Thr Asp Ser Ser Ala Asn His
                85                  90                  95

Arg Val Phe Gly Gly Gly Thr Lys Leu Thr Val Leu
            100                 105


<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Ile Val Met Thr Gln Ser Pro Leu Ser Leu Pro Val Thr Pro Gly
1               5                   10                  15

Lys Pro Ala Ser Ile Ser Cys Arg Ser Ser Gln Ser Leu Glu Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gly Gly Thr Lys Val Asp Ile Lys
            100                 105                 110


<210> SEQ ID NO 29
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Glu Phe Ala
            20                  25                  30

Ser Trp Tyr Gln Gln Lys Pro Gly Gln Ser Pro Val Val Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Thr Ala Val
                85                  90                  95
```

Phe Gly Gly Gly Thr Lys Leu Thr Val Leu
100 105

<210> SEQ ID NO 30
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Ser Tyr Glu Leu Thr Gln Pro Pro Ser Val Ser Val Ser Pro Gly Gln
1 5 10 15

Thr Ala Arg Ile Thr Cys Ser Gly Asp Ala Leu Pro Lys Lys Tyr Ala
20 25 30

Tyr Trp Tyr Gln Gln Lys Ser Gly Gln Ala Pro Val Leu Val Ile Tyr
35 40 45

Glu Asp Ser Lys Arg Pro Ser Gly Ile Pro Glu Arg Phe Ser Ala Ser
50 55 60

Ser Ser Gly Thr Met Ala Thr Leu Thr Ile Ser Gly Ala Gln Val Glu
65 70 75 80

Asp Glu Ala Asp Tyr Tyr Cys Tyr Ser Ala Asp Ser Ser Gly Ser His
85 90 95

Trp Val Phe Gly Gly Gly Thr Lys Leu Thr Val Leu
100 105

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Ser Tyr Glu Leu Thr Gln Pro Pro Ser Val Ser Val Ser Pro Gly Gln
1 5 10 15

Thr Ala Arg Ile Thr Cys Ser Gly Asp Ala Leu Pro Lys Lys Tyr Ala
20 25 30

Tyr Trp Tyr Gln Lys Lys Ser Gly Gln Ala Pro Val Leu Val Ile His
35 40 45

Glu Asp Ser Lys Arg Pro Ser Gly Ile Pro Glu Arg Phe Ser Gly Ser
50 55 60

Ser Ser Gly Thr Met Ala Thr Leu Thr Ile Ser Gly Ala Gln Val Glu
65 70 75 80

Asp Glu Ala Asp Tyr Tyr Cys Phe Ser Thr Asp Arg Ser Gly Asn His
85 90 95

Val Val Phe Gly Gly Gly Thr Lys Leu Thr Val Leu
100 105

<210> SEQ ID NO 32
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Gln Ser Ala Leu Thr Gln Pro Pro Ser Val Ser Glu Ala Pro Arg Gln
1 5 10 15

Arg Val Thr Ile Ser Cys Ser Gly Ser Ala Ser Asn Ile Gly Asn Asn
20 25 30

Gly Val Asn Trp Tyr Gln Gln Leu Pro Gly Lys Thr Pro Lys Leu Leu
35 40 45

Ile Tyr Asn Asp Asp Leu Leu Pro Ser Gly Val Ser Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Phe Cys Ala Ala Trp Asp Asp Ser Leu
85 90 95

Asn Gly Leu Val Phe Gly Gly Gly Thr Lys Leu Thr Val Leu
100 105 110

<210> SEQ ID NO 33
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Ser Tyr Glu Leu Thr Gln Pro Pro Ser Val Ser Val Ser Pro Gly Gln
1 5 10 15

Thr Ala Ser Ile Thr Cys Ser Gly His Lys Leu Gly Asp Lys Tyr Ala
20 25 30

Ser Trp Tyr Gln Gln Lys Pro Gly Gln Ser Pro Val Leu Val Ile Tyr
35 40 45

Gln Asp Ser Lys Arg Pro Ser Gly Ile Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Gln Ala Trp Asp Ser Ile Thr Ala Trp
85 90 95

Val Phe Gly Gly Gly Thr Lys Leu Thr Val Leu
100 105

<210> SEQ ID NO 34
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Ser Tyr Glu Leu Met Gln Pro Pro Ser Val Ser Val Ser Pro Gly Gln
1 5 10 15

Thr Ala Arg Ile Thr Cys Ser Gly Asp Ala Leu Pro Arg Gln Tyr Ala
20 25 30

Tyr Trp Tyr Gln Gln Lys Pro Gly Gln Ala Pro Val Leu Val Ile Tyr
35 40 45

Lys Asp Ser Glu Arg Pro Ser Gly Ile Pro Glu Arg Phe Ser Gly Ser
50 55 60

Ser Ser Gly Thr Thr Val Thr Leu Thr Ile Ser Gly Val Gln Ala Glu
65 70 75 80

```
Asp Glu Ala Asp Tyr Tyr Cys Gln Ser Ala Asp Arg Thr Gly Ile Tyr
                85                  90                  95

Val Leu Phe Gly Gly Gly Thr Lys Leu Thr Val Leu
            100                 105


<210> SEQ ID NO 35
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Arg Thr Gly Ile Tyr
                85                  90                  95

Val Leu Phe Gly Gly Gly Thr Lys Leu Thr Val Leu
            100                 105


<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Phe Ala
            20                  25                  30

Ser Trp Tyr Gln Gln Lys Pro Gly Gln Ser Pro Val Leu Val Ile Phe
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Ala Trp Asp Ser Thr Thr Ala Trp
                85                  90                  95

Val Phe Gly Gly Gly Thr Lys Leu Thr Val Leu
            100                 105


<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 37

Met Ala Trp Val Trp Thr Leu Leu Phe Leu Met Ala Ala Ala Gln Ser
1               5                   10                  15

Ile Gln Ala

<210> SEQ ID NO 38
<211> LENGTH: 45
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 38

Thr Ser Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 39
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 40
<211> LENGTH: 42
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 41
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 41

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr

```
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Ser Glu Gly Lys Ser Ser Gly Ser Gly Ser Glu Ser Lys Ser
1               5                   10                  15

Thr Gly Gly Ser
            20


<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Gly Ser Gly Gly Gly Ser
1               5


<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Gly Ser Gly Gly Gly Ser Gly Gly Gly Ser
1               5                   10


<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Gly Ser Gly Gly Gly Ser Gly Gly Gly Ser Gly Gly Gly Ser
1               5                   10                  15


<210> SEQ ID NO 46
<211> LENGTH: 20
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Gly Ser Gly Gly Gly Ser Gly Gly Gly Ser Gly Gly Gly Ser
1               5                   10                  15

Gly Gly Gly Ser
            20

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Gly Gly Ser Gly Gly Gly Gly Ser Gly Gly Gly Gly Ser
1               5                   10                  15

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Gly Gly Ser Gly Gly Gly Gly Ser Gly Gly Gly Gly Ser Gly
1               5                   10                  15

Gly Gly Gly Ser
            20

<210> SEQ ID NO 49
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Ser Thr Ser Gly Ser Gly Lys Pro Gly Ser Gly Glu Gly Ser Thr
1               5                   10                  15

Lys Gly

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Arg Pro Arg Ala Ile Gly Gly Ser Lys Pro Arg Val Ala
1               5                   10

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Lys Gly Gly Ser Gly Lys Gly Gly Ser Gly Lys Gly Gly Ser
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gly Lys Gly Ser Gly Gly Lys Gly Ser Gly Gly Lys Gly Ser
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Gly Lys Ser Gly Gly Gly Lys Ser Gly Gly Gly Lys Ser
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Lys Gly Lys Ser Gly Lys Gly Lys Ser Gly Lys Gly Lys Ser
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly Gly Lys Ser Gly Gly Lys Gly Ser Gly Lys Gly Gly Ser
1 5 10 15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Gly Lys Pro Gly Ser Gly Lys Pro Gly Ser Gly Lys Pro Gly Ser
1 5 10 15

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Gly Lys Pro Gly Ser Gly Lys Pro Gly Ser Gly Lys Pro Gly Ser Gly
1 5 10 15

Lys Pro Gly Ser
20

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Gly Lys Gly Lys Ser Gly Lys Gly Lys Ser Gly Lys Gly Lys Ser Gly
1 5 10 15

Lys Gly Lys Ser
20

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Ser Thr Ala Gly Asp Thr His Leu Gly Gly Glu Asp Phe Asp
1 5 10

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Gly Glu Gly Gly Ser Gly Glu Gly Gly Ser Gly Glu Gly Gly Ser
1 5 10 15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Gly Gly Glu Gly Ser Gly Gly Glu Gly Ser Gly Gly Glu Gly Ser
1 5 10 15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Gly Glu Gly Glu Ser Gly Glu Gly Glu Ser Gly Glu Gly Glu Ser
1 5 10 15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Gly Gly Gly Glu Ser Gly Gly Glu Gly Ser Gly Glu Gly Gly Ser
1 5 10 15

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Gly Glu Gly Glu Ser Gly Glu Gly Glu Ser Gly Glu Gly Glu Ser Gly
1 5 10 15

Glu Gly Glu Ser
20

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Gly Ser Thr Ser Gly Ser Gly Lys Pro Gly Ser Gly Glu Gly Ser Thr
1 5 10 15

Lys Gly

<210> SEQ ID NO 67
<211> LENGTH: 19

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Pro Arg Gly Ala Ser Lys Ser Gly Ser Ala Ser Gln Thr Gly Ser Ala
1 5 10 15

Pro Gly Ser

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Gly Thr Ala Ala Ala Gly Ala Gly Ala Ala Gly Gly Ala Ala Ala Gly
1 5 10 15

Ala Ala Gly

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Gly Thr Ser Gly Ser Ser Gly Ser Gly Ser Gly Gly Ser Gly Ser Gly
1 5 10 15

Gly Gly Gly

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Gly Lys Pro Gly Ser Gly Lys Pro Gly Ser Gly Lys Pro Gly Ser Gly
1 5 10 15

Lys Pro Gly Ser
20

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Gly Ser Gly Ser
1

<210> SEQ ID NO 72
<211> LENGTH: 10

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Ala Pro Ala Pro Ala Pro Ala Pro Ala Pro
1 5 10

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Ala Pro Ala Pro Ala Pro Ala Pro Ala Pro Ala Pro Ala Pro Ala Pro
1 5 10 15

Ala Pro Ala Pro
20

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 74

Ala Glu Ala Ala Ala Lys Glu Ala Ala Ala Lys Glu Ala Ala Ala Ala
1 5 10 15

Lys Glu Ala Ala Ala Ala Lys Glu Ala Ala Ala Ala Lys Ala Ala Ala
20 25 30

<210> SEQ ID NO 75
<211> LENGTH: 248
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 75

Asp Ile Val Leu Thr Gln Ser Pro Asp Ser Leu Ala Val Ser Leu Gly
1 5 10 15

Glu Arg Ala Thr Ile Asn Cys Lys Ala Ser Gln Ser Val Asp Tyr Asp
20 25 30

Gly Asp Ser Phe Leu Asn Trp Tyr Gln Gln Lys Pro Gly Gln Pro Pro
35 40 45

Lys Leu Leu Ile Tyr Ala Ala Ser Asn Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Ser Asn
85 90 95

Glu Asp Pro Leu Thr Phe Gly Gly Gly Thr Lys Val Glu Ile Lys Gly
100 105 110

Gly Ser Glu Gly Lys Ser Ser Gly Ser Gly Ser Glu Ser Lys Ser Thr
115 120 125

```
Gly Gly Ser Gln Val Gln Leu Val Gln Ser Gly Ala Glu Val Lys Lys
    130                 135                 140

Pro Gly Ala Ser Val Lys Val Ser Cys Lys Ala Ser Gly Tyr Thr Phe
145                 150                 155                 160

Thr Gly Tyr Trp Ile Glu Trp Val Arg Gln Arg Pro Gly Gln Gly Leu
                165                 170                 175

Glu Trp Met Gly Glu Ile Leu Pro Gly Gly Gly Asp Thr Asn Tyr Asn
            180                 185                 190

Gln Lys Phe Gln Gly Lys Val Thr Phe Thr Arg Asp Thr Ser Thr Ser
        195                 200                 205

Thr Ala Tyr Met Glu Leu Ser Ser Leu Arg Ser Glu Asp Thr Ala Val
    210                 215                 220

Tyr Tyr Cys Ala Arg Arg Val Pro Val Tyr Phe Asp Tyr Trp Gly Gln
225                 230                 235                 240

Gly Thr Leu Val Thr Val Ser Ser
                245


<210> SEQ ID NO 76
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Glu
            20                  25                  30

Gly Asp Ser Phe Leu Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Leu Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Val Gln Ser Gly Ala Glu Val Lys Lys
    130                 135                 140

Pro Gly Ala Ser Val Lys Val Ser Cys Lys Ala Ser Gly Tyr Thr Phe
145                 150                 155                 160

Thr Gly Tyr Trp Ile Glu Trp Val Arg Gln Arg Pro Gly Gln Gly Leu
                165                 170                 175

Glu Trp Met Gly Glu Ile Leu Pro Gly Gly Gly Asp Thr Asn Tyr Asn
            180                 185                 190

Gln Lys Phe Gln Gly Lys Val Thr Phe Thr Arg Asp Thr Ser Thr Ser
        195                 200                 205

Thr Ala Tyr Met Glu Leu Ser Ser Leu Arg Ser Glu Asp Thr Ala Val
    210                 215                 220

Tyr Tyr Cys Ala Arg Arg Val Pro Val Tyr Phe Asp Tyr Trp Gly Gln
```

225 230 235 240

Gly Thr Leu Val Thr Val Ser Ser
245

<210> SEQ ID NO 77
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

Asp Ile Val Leu Thr Gln Ser Pro Asp Ser Leu Ala Val Ser Leu Gly
1 5 10 15

Glu Arg Ala Thr Ile Asn Cys Lys Ala Ser Gln Ser Val Asp Tyr Asp
20 25 30

Gly Asp Ser Phe Leu Asn Trp Tyr Gln Gln Lys Pro Gly Gln Pro Pro
35 40 45

Lys Leu Leu Ile Tyr Ala Ala Ser Asn Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Ser Asn
85 90 95

Glu Asp Pro Leu Thr Phe Gly Gly Gly Thr Lys Val Glu Ile Lys Gly
100 105 110

Gly Ser Glu Gly Lys Ser Ser Gly Ser Gly Ser Glu Ser Lys Ser Thr
115 120 125

Gly Gly Ser Gln Val Gln Leu Val Gln Ser Gly Ala Glu Val Lys Lys
130 135 140

Pro Gly Ala Ser Val Lys Val Ser Cys Lys Ala Ser Gly Tyr Thr Phe
145 150 155 160

Thr Gly Tyr Trp Ile Glu Trp Val Arg Gln Arg Pro Gly Gln Gly Leu
165 170 175

Glu Trp Met Gly Glu Ile Leu Pro Gly Gly Gly Asp Thr Asn Tyr Asn
180 185 190

Gln Lys Phe Gln Gly Lys Val Thr Phe Thr Arg Asp Thr Ser Thr Ser
195 200 205

Thr Val Tyr Met Glu Leu Ser Ser Leu Arg Ser Glu Asp Thr Ala Val
210 215 220

Tyr Tyr Cys Ala Arg Arg Val Pro Val Tyr Phe Asp Tyr Trp Gly Gln
225 230 235 240

Gly Thr Leu Val Thr Val Ser Ser
245

<210> SEQ ID NO 78
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

Asp Ile Val Leu Thr Gln Ser Pro Asp Ser Leu Ala Val Ser Leu Gly
1 5 10 15

Glu Arg Ala Thr Ile Asn Cys Lys Ala Ser Gln Ser Val Asp Tyr Glu

```
                20                  25                  30

Gly Asp Ser Phe Leu Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Leu Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Val Gln Ser Gly Ala Glu Val Lys Lys
    130                 135                 140

Pro Gly Ala Ser Val Lys Val Ser Cys Lys Ala Ser Gly Tyr Thr Phe
145                 150                 155                 160

Thr Gly Tyr Trp Ile Glu Trp Val Arg Gln Arg Pro Gly Gln Gly Leu
                165                 170                 175

Glu Trp Met Gly Glu Ile Leu Pro Gly Gly Gly Asp Thr Asn Tyr Asn
            180                 185                 190

Gln Lys Phe Gln Gly Lys Val Thr Phe Thr Arg Asp Thr Ser Thr Ser
        195                 200                 205

Thr Val Tyr Met Glu Leu Ser Ser Leu Arg Ser Glu Asp Thr Ala Val
    210                 215                 220

Tyr Tyr Cys Ala Arg Arg Val Pro Val Tyr Phe Asp Tyr Trp Gly Gln
225                 230                 235                 240

Gly Thr Leu Val Thr Val Ser Ser
                245


<210> SEQ ID NO 79
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Glu
            20                  25                  30

Gly Asp Ser Phe Leu Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Leu Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125
```

```
Gly Gly Ser Gln Val Gln Leu Val Gln Ser Gly Ala Glu Val Lys Lys
    130                 135                 140

Pro Gly Ala Ser Val Lys Val Ser Cys Lys Ala Ser Gly Tyr Thr Phe
145                 150                 155                 160

Thr Gly Tyr Trp Ile Glu Trp Val Arg Gln Ala Pro Gly Gln Gly Leu
                165                 170                 175

Glu Trp Met Gly Glu Ile Leu Pro Gly Gly Gly Asp Thr Asn Tyr Asn
            180                 185                 190

Gln Lys Phe Gln Gly Lys Val Thr Phe Thr Arg Asp Thr Ser Thr Ser
        195                 200                 205

Thr Ala Tyr Met Glu Leu Ser Ser Leu Arg Ser Glu Asp Thr Ala Val
    210                 215                 220

Tyr Tyr Cys Ala Arg Arg Val Pro Val Tyr Phe Asp Tyr Trp Gly Gln
225                 230                 235                 240

Gly Thr Leu Val Thr Val Ser Ser
                245


<210> SEQ ID NO 80
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Phe Leu Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Leu Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Val Gln Ser Gly Ala Glu Val Lys Lys
    130                 135                 140

Pro Gly Ala Ser Val Lys Val Ser Cys Lys Ala Ser Gly Tyr Thr Phe
145                 150                 155                 160

Thr Gly Tyr Trp Ile Glu Trp Val Arg Gln Ala Pro Gly Gln Gly Leu
                165                 170                 175

Glu Trp Met Gly Glu Ile Leu Pro Gly Gly Gly Asp Thr Asn Tyr Asn
            180                 185                 190

Gln Lys Phe Gln Gly Lys Val Thr Phe Thr Arg Asp Thr Ser Thr Ser
        195                 200                 205

Thr Val Tyr Met Glu Leu Ser Ser Leu Arg Ser Glu Asp Thr Ala Val
    210                 215                 220

Tyr Tyr Cys Ala Arg Arg Val Pro Val Tyr Phe Asp Tyr Trp Gly Gln
225                 230                 235                 240
```

Gly Thr Leu Val Thr Val Ser Ser
245

<210> SEQ ID NO 81
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

Asp Ile Val Met Thr Gln Ser Pro Asp Ser Leu Ala Val Ser Leu Gly
1 5 10 15

Glu Arg Ala Thr Ile Asn Cys Lys Ala Ser Gln Ser Val Asp Tyr Asp
20 25 30

Gly Asp Ser Phe Leu Asn Trp Tyr Gln Gln Lys Pro Gly Gln Pro Pro
35 40 45

Lys Leu Phe Ile Tyr Ala Ala Ser Asn Leu Glu Ser Gly Val Pro Asp
50 55 60

Arg Phe Ser Gly Ser Gly Ser Gly Thr Asp Phe Thr Leu Thr Ile Ser
65 70 75 80

Ser Val Gln Ala Glu Asp Ala Ala Val Tyr Tyr Cys Gln Gln Ser Asn
85 90 95

Glu Asp Pro Leu Thr Phe Gly Gly Gly Thr Lys Val Glu Ile Lys Gly
100 105 110

Gly Ser Glu Gly Lys Ser Ser Gly Ser Gly Ser Glu Ser Lys Ser Thr
115 120 125

Gly Gly Ser Gln Val Gln Leu Val Gln Ser Gly Ala Glu Val Met Lys
130 135 140

Pro Gly Ala Ser Val Lys Ile Ser Cys Lys Ala Ser Gly Tyr Thr Phe
145 150 155 160

Thr Gly Tyr Trp Ile Glu Trp Val Arg Gln Arg Pro Gly Gln Gly Leu
165 170 175

Glu Trp Met Gly Glu Ile Leu Pro Gly Gly Gly Asp Thr Asn Tyr Asn
180 185 190

Gln Lys Phe Gln Gly Lys Val Thr Phe Thr Arg Asp Thr Ser Thr Ser
195 200 205

Thr Val Tyr Met Glu Leu Ser Ser Leu Arg Ser Glu Asp Thr Ala Val
210 215 220

Tyr Tyr Cys Ala Arg Arg Val Pro Val Tyr Phe Asp Tyr Trp Gly Gln
225 230 235 240

Gly Thr Leu Val Thr Val Ser Ser
245

<210> SEQ ID NO 82
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

Asp Ile Val Leu Thr Gln Ser Pro Asp Ser Leu Ala Val Ser Leu Gly
1 5 10 15

Glu Arg Ala Thr Ile Asn Cys Lys Ala Ser Gln Ser Val Asp Tyr Lys
20 25 30

```
Gly Asp Ser Phe Leu Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Leu Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Val Gln Ser Gly Ala Glu Val Met Lys
    130                 135                 140

Pro Gly Ala Ser Val Lys Ile Ser Cys Lys Ala Ser Gly Tyr Thr Phe
145                 150                 155                 160

Thr Gly Tyr Trp Ile Glu Trp Val Arg Gln Arg Pro Gly Gln Gly Leu
                165                 170                 175

Glu Trp Met Gly Glu Ile Leu Pro Gly Gly Gly Asp Thr Asn Tyr Asn
            180                 185                 190

Gln Lys Phe Gln Gly Lys Val Thr Phe Thr Arg Asp Thr Ser Thr Ser
        195                 200                 205

Thr Val Tyr Met Glu Leu Ser Ser Leu Arg Ser Glu Asp Thr Ala Val
    210                 215                 220

Tyr Tyr Cys Ala Arg Arg Val Pro Val Tyr Phe Asp Tyr Trp Gly Gln
225                 230                 235                 240

Gly Thr Leu Val Thr Val Ser Ser
                245
```

<210> SEQ ID NO 83
<211> LENGTH: 252
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

```
Ser Ser Glu Leu Thr Gln Asp Pro Ala Val Ser Val Ala Leu Gly Gln
1               5                   10                  15

Thr Val Arg Ile Arg Cys Gln Gly Asp Ser Leu Arg Lys Tyr Tyr Gly
            20                  25                  30

Ser Trp Tyr Gln Gln Lys Pro Gly Gln Ala Pro Val Leu Val Ile Tyr
        35                  40                  45

Gly Glu Thr Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys His
                85                  90                  95

Val Val Phe Gly Gly Gly Thr Lys Leu Thr Val Leu Gly Gly Ser Glu
            100                 105                 110

Gly Lys Ser Ser Gly Ser Gly Ser Glu Ser Lys Ser Thr Gly Gly Ser
        115                 120                 125

Glu Val Gln Leu Gln Glu Ser Gly Pro Gly Leu Val Lys Pro Ser Glu
```

```
    130                 135                 140

Thr Leu Ser Leu Thr Cys Ser Val Ser Gly Gly Ser Ile Ser Gly Ser
145                 150                 155                 160

Ser Tyr Tyr Trp Gly Trp Ile Arg Gln Pro Pro Gly Lys Gly Leu Glu
                165                 170                 175

Trp Ile Gly Ser Ile Tyr Tyr Ser Gly Ser Thr Tyr Tyr Asn Pro Ser
            180                 185                 190

Leu Lys Ser Arg Val Thr Ile Ser Val Asp Thr Ser Lys Lys Gln Phe
        195                 200                 205

Ser Leu Lys Leu Arg Ser Val Thr Ala Ala Asp Thr Ala Val Tyr Tyr
    210                 215                 220

Cys Ala Arg Glu Glu Asp Ser Gly Ser Tyr Tyr Val Gly Ala Phe Asp
225                 230                 235                 240

Ile Trp Gly Gln Gly Thr Met Val Thr Val Ser Ser
                245                 250


<210> SEQ ID NO 84
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Tyr Gly
            20                  25                  30

Ser Trp Tyr Gln Gln Lys Pro Gly Gln Ala Pro Val Leu Val Ile Tyr
        35                  40                  45

Gly Glu Lys Asn Arg Pro Ser Gly Ile Pro Asp Arg Phe Ser Gly Ser
    50                  55                  60

Ser Ser Gly Asn Thr Val Ser Leu Thr Ile Thr Gly Thr Gln Ala Glu
65                  70                  75                  80

Asp Glu Ala Asp Tyr Tyr Cys Asn Ser Arg Asp Ser Ser Gly Lys His
                85                  90                  95

Val Val Phe Gly Gly Gly Thr Lys Leu Thr Val Leu Gly Gly Ser Glu
            100                 105                 110

Gly Lys Ser Ser Gly Ser Gly Ser Glu Ser Lys Ser Thr Gly Gly Ser
        115                 120                 125

Gln Val Gln Leu Gln Glu Ser Gly Pro Gly Leu Val Lys Pro Ser Glu
    130                 135                 140

Thr Leu Ser Leu Thr Cys Ser Val Ser Gly Gly Ser Ile Arg Ser Ser
145                 150                 155                 160

Thr Tyr Tyr Trp Gly Trp Ile Arg Gln Pro Pro Gly Lys Gly Leu Glu
                165                 170                 175

Trp Ile Gly Ser Ile Tyr Tyr Ser Gly Ser Thr Tyr Ser Asn Pro Ser
            180                 185                 190

Leu Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Ile Tyr Tyr
    210                 215                 220

Cys Ala Arg Glu Glu Asp Ser Gly Ser Tyr Tyr Val Gly Thr Phe Asp
225                 230                 235                 240
```

```
Ile Trp Gly Gln Gly Thr Met Val Thr Val Ser Ser
                245                 250


<210> SEQ ID NO 85
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gly Gly Thr Lys Val Glu Ile Lys
            100                 105                 110

Gly Gly Ser Glu Gly Lys Ser Ser Gly Ser Gly Ser Glu Ser Lys Ser
        115                 120                 125

Thr Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Leu Arg Asn Tyr Trp Met Ser Trp Val Arg Gln Ala Pro Gly Lys Gly
                165                 170                 175

Leu Glu Trp Val Ala Asn Ile Asn Gln Asp Gly Ser Glu Lys Tyr Tyr
            180                 185                 190

Val Asp Ser Val Glu Gly Arg Phe Thr Ile Ser Arg Asp Asn Ala Lys
        195                 200                 205

Lys Ser Leu Trp Leu Gln Met Ser Ser Leu Arg Val Glu Asp Thr Ala
    210                 215                 220

Val Tyr Tyr Cys Ala Arg Asp Pro Ile Glu Ser Arg Phe Asp Tyr Trp
225                 230                 235                 240

Gly Gln Gly Thr Leu Val Thr Val Ser Ser
                245                 250


<210> SEQ ID NO 86
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ser Ser Glu Leu Thr Gln Pro Pro Ser Val Ser Val Ser Pro Gly Gln
1               5                   10                  15

Thr Ala Arg Ile Thr Cys Ser Gly Asp Ala Leu Pro Arg Lys Tyr Ala
            20                  25                  30
```

```
Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Thr Met Ala Thr Leu Thr Ile Ser Gly Ala Gln Val Glu
65                  70                  75                  80

Asp Glu Ala Ala Tyr Tyr Cys Tyr Ser Thr Asp Ser Ser Ala Asn His
                85                  90                  95

Arg Val Phe Gly Gly Gly Thr Lys Leu Thr Val Leu Gly Gly Ser Glu
            100                 105                 110

Gly Lys Ser Ser Gly Ser Gly Ser Glu Ser Lys Ser Thr Gly Gly Ser
        115                 120                 125

Glu Val Gln Leu Leu Glu Ser Gly Gly Gly Leu Val Gln Pro Gly Gly
    130                 135                 140

Ser Leu Arg Leu Ser Cys Ala Ala Ser Gly Phe Thr Phe Thr Ile Tyr
145                 150                 155                 160

Ala Met Thr Trp Val Arg Gln Ala Pro Gly Lys Gly Leu Glu Trp Val
                165                 170                 175

Ser Gly Ile Ser Val Ser Gly Ile Arg Thr Tyr Tyr Ala Asp Ser Val
            180                 185                 190

Lys Gly Arg Phe Thr Ile Ser Arg Asp Asn Ser Lys Asn Thr Leu Phe
        195                 200                 205

Leu Gln Met Asn Ser Leu Ser Ala Glu Asp Thr Ala Val Tyr Tyr Cys
    210                 215                 220

Ala Lys Gly Leu Ser Ser Gly Asp Arg Asp Ala Ser Asp Ile Trp Gly
225                 230                 235                 240

Gln Gly Thr Met Val Thr Val Ser Ser
                245


<210> SEQ ID NO 87
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Ile Val Met Thr Gln Ser Pro Leu Ser Leu Pro Val Thr Pro Gly
1               5                   10                  15

Lys Pro Ala Ser Ile Ser Cys Arg Ser Ser Gln Ser Leu Glu Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gly Gly Thr Lys Val Asp Ile Lys
            100                 105                 110

Gly Gly Ser Glu Gly Lys Ser Ser Gly Ser Gly Ser Glu Ser Lys Ser
        115                 120                 125

Thr Gly Gly Ser Glu Val Gln Leu Val Glu Ser Gly Gly Gly Leu Val
    130                 135                 140
```

```
Gln Pro Gly Gly Ser Leu Arg Leu Ser Cys Ala Ala Ser Gly Phe Ile
145                 150                 155                 160

Phe Ser Thr Tyr Trp Met Ser Trp Val Arg Gln Ala Pro Gly Lys Gly
                165                 170                 175

Leu Glu Trp Val Ala Asn Ile Asn Pro Asp Gly Asn Glu Lys Tyr Tyr
            180                 185                 190

Val Asp Ser Val Glu Gly Arg Phe Thr Ile Ser Arg Asp Asn Ala Gln
        195                 200                 205

Asp Ser Leu Tyr Leu Gln Met Asn Ser Leu Arg Ala Glu Asp Thr Ala
    210                 215                 220

Val Tyr Tyr Cys Ala Arg Asp Pro Ile Ser Ala Arg Phe Asp Phe Trp
225                 230                 235                 240

Gly Gln Gly Thr Leu Val Thr Val Ser Ser
                245                 250


<210> SEQ ID NO 88
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Glu Phe Ala
            20                  25                  30

Ser Trp Tyr Gln Gln Lys Pro Gly Gln Ser Pro Val Val Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Thr Ala Val
                85                  90                  95

Phe Gly Gly Gly Thr Lys Leu Thr Val Leu Gly Gly Ser Glu Gly Lys
            100                 105                 110

Ser Ser Gly Ser Gly Ser Glu Ser Lys Ser Thr Gly Gly Ser Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Phe Ser Ser Tyr Ala Met
145                 150                 155                 160

Asn Trp Val Arg Gln Ala Pro Gly Lys Gly Leu Glu Trp Val Ser Thr
                165                 170                 175

Ile Ser Gly Ser Gly Gly Ser Ser Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Ala Asn
    210                 215                 220

Pro Ser Gly Thr Phe Trp Asn Asp Ala Phe Asp Ile Trp Gly Gln Gly
225                 230                 235                 240

Thr Met Val Thr Val Ser Ser
```

245

<210> SEQ ID NO 89
<211> LENGTH: 251
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 89

Ser Tyr Glu Leu Thr Gln Pro Pro Ser Val Ser Val Ser Pro Gly Gln
1 5 10 15

Thr Ala Arg Ile Thr Cys Ser Gly Asp Ala Leu Pro Lys Lys Tyr Ala
20 25 30

Tyr Trp Tyr Gln Gln Lys Ser Gly Gln Ala Pro Val Leu Val Ile Tyr
35 40 45

Glu Asp Ser Lys Arg Pro Ser Gly Ile Pro Glu Arg Phe Ser Ala Ser
50 55 60

Ser Ser Gly Thr Met Ala Thr Leu Thr Ile Ser Gly Ala Gln Val Glu
65 70 75 80

Asp Glu Ala Asp Tyr Tyr Cys Tyr Ser Ala Asp Ser Ser Gly Ser His
85 90 95

Trp Val Phe Gly Gly Gly Thr Lys Leu Thr Val Leu Gly Gly Ser Glu
100 105 110

Gly Lys Ser Ser Gly Ser Gly Ser Glu Ser Lys Ser Thr Gly Gly Ser
115 120 125

Glu Val Gln Leu Val Glu Ser Gly Gly Gly Leu Val Gln Pro Gly Gly
130 135 140

Ser Leu Arg Leu Ser Cys Ala Ala Ser Gly Phe Thr Phe Asn Asn Tyr
145 150 155 160

Ala Met Asn Trp Val Arg Gln Ala Pro Gly Lys Gly Leu Glu Trp Val
165 170 175

Ser Val Ile Ser Gly Asn Gly Gly Ser Ile His Tyr Ala Asp Ser Val
180 185 190

Lys Gly Arg Phe Thr Ile Ser Arg Asp Asn Ser Lys Asn Thr Leu Tyr
195 200 205

Leu Gln Met Asn Ser Leu Arg Ala Glu Asp Thr Ala Val Tyr Tyr Cys
210 215 220

Ala Thr Pro Arg Gly Tyr Thr Gly Tyr Asp Gly Asp Ala Phe Asp Phe
225 230 235 240

Trp Gly Gln Gly Thr Met Val Thr Val Ser Ser
245 250

<210> SEQ ID NO 90
<211> LENGTH: 251
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 90

Ser Tyr Glu Leu Thr Gln Pro Pro Ser Val Ser Val Ser Pro Gly Gln
1 5 10 15

Thr Ala Arg Ile Thr Cys Ser Gly Asp Ala Leu Pro Lys Lys Tyr Ala
20 25 30

Tyr Trp Tyr Gln Lys Lys Ser Gly Gln Ala Pro Val Leu Val Ile His

```
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Phe Ser Thr Asp Arg Ser Gly Asn His
                85                  90                  95

Val Val Phe Gly Gly Gly Thr Lys Leu Thr Val Leu Gly Gly Ser Glu
            100                 105                 110

Gly Lys Ser Ser Gly Ser Gly Ser Glu Ser Lys Ser Thr Gly Gly Ser
        115                 120                 125

Glu Val Gln Leu Val Glu Ser Gly Gly Asp Leu Val Gln Pro Gly Gly
    130                 135                 140

Ser Leu Arg Leu Ser Cys Glu Ala Ser Gly Phe Thr Phe Ser Asn Tyr
145                 150                 155                 160

Gly Met Asn Trp Val Arg Gln Ala Pro Gly Lys Gly Leu Glu Trp Val
                165                 170                 175

Ser Gly Ile Ser Gly Ser Gly Gly Thr Thr Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Asn Leu Leu Leu Trp Leu Gly Tyr His Gly Asp Gly Phe Asp Leu
225                 230                 235                 240

Trp Gly Gln Gly Thr Met Val Thr Val Ser Ser
                245                 250
```

<210> SEQ ID NO 91
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Gln Ser Ala Leu Thr Gln Pro Pro Ser Val Ser Glu Ala Pro Arg Gln
1               5                   10                  15

Arg Val Thr Ile Ser Cys Ser Gly Ser Ala Ser Asn Ile Gly Asn Asn
            20                  25                  30

Gly Val Asn Trp Tyr Gln Gln Leu Pro Gly Lys Thr Pro Lys Leu Leu
        35                  40                  45

Ile Tyr Asn Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ala Trp Asp Asp Ser Leu
                85                  90                  95

Asn Gly Leu Val Phe Gly Gly Gly Thr Lys Leu Thr Val Leu Gly Gly
            100                 105                 110

Ser Glu Gly Lys Ser Ser Gly Ser Gly Ser Glu Ser Lys Ser Thr Gly
        115                 120                 125

Gly Ser Gln Val Gln Leu Gln Gln Ser Gly Pro Gly Leu Val Lys Pro
    130                 135                 140
```

```
Ser Gln Thr Leu Ser Leu Thr Cys Ala Ile Ser Gly Asp Ser Val Ser
145                 150                 155                 160

Ser Lys Ser Gly Ala Trp Asn Trp Ile Arg Gln Ser Pro Ser Arg Gly
                165                 170                 175

Leu Glu Trp Leu Gly Arg Thr Tyr Tyr Arg Ser Lys Trp Tyr Asn Glu
            180                 185                 190

Tyr Ala Val Ser Val Lys Ser Arg Ile Thr Ile Asn Pro Asp Thr Ser
        195                 200                 205

Lys Asn Gln Phe Ser Leu Gln Leu Asn Ser Val Thr Pro Glu Asp Thr
    210                 215                 220

Ala Val Tyr Tyr Cys Thr Arg Val Asp Thr Asp Phe Asp Tyr Trp Gly
225                 230                 235                 240

Gln Gly Thr Leu Val Thr Val Ser Ser
                245


<210> SEQ ID NO 92
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Ser Tyr Glu Leu Thr Gln Pro Pro Ser Val Ser Val Ser Pro Gly Gln
1               5                   10                  15

Thr Ala Ser Ile Thr Cys Ser Gly His Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ile Thr Ala Trp
                85                  90                  95

Val Phe Gly Gly Gly Thr Lys Leu Thr Val Leu Gly Gly Ser Glu Gly
            100                 105                 110

Lys Ser Ser Gly Ser Gly Ser Glu Ser Lys Ser Thr Gly Gly Ser Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Thr Phe Ser Arg His Thr
145                 150                 155                 160

Met Asn Trp Val Arg Gln Ala Pro Gly Lys Gly Leu Glu Trp Val Ser
                165                 170                 175

Ser Ile Ser Gly Ser Gly Gly Ser Thr Tyr Tyr Ala Asp Ser Val Lys
            180                 185                 190

Gly Arg Phe Thr Val Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
    210                 215                 220

Lys Glu Ser Tyr Asp Ser Ser Gly Val Trp Tyr Phe Asp Leu Trp Gly
225                 230                 235                 240

Arg Gly Thr Leu Val Thr Val Ser Ser
                245
```

<210> SEQ ID NO 93
<211> LENGTH: 246
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 93

```
Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Arg Thr Gly Ile Tyr
                85                  90                  95

Val Leu Phe Gly Gly Gly Thr Lys Leu Thr Val Leu Gly Gly Ser Glu
            100                 105                 110

Gly Lys Ser Ser Gly Ser Gly Ser Glu Ser Lys Ser Thr Gly Gly Ser
        115                 120                 125

Gln Val Gln Leu Gln Glu Ser Gly Pro Gly Leu Val Lys Pro Ser Glu
    130                 135                 140

Thr Leu Ser Leu Thr Cys Thr Val Ser Ser Gly Ser Ile Ser Ser Tyr
145                 150                 155                 160

Tyr Trp Asn Trp Ile Arg Gln Pro Ala Gly Lys Gly Leu Glu Trp Ile
                165                 170                 175

Gly Arg Ile Tyr Thr Ser Gly Thr Thr His Tyr Asn Pro Ser Leu Lys
            180                 185                 190

Ser Arg Val Thr Met Ser Ile Asp Thr Ser Lys Asn Gln Phe Ser Leu
        195                 200                 205

Lys Leu Ser Ser Val Thr Ala Ala Asp Thr Ala Val Tyr Tyr Cys Ala
    210                 215                 220

Arg Glu Ile Arg Glu Leu Arg Gly Phe Asp Tyr Trp Gly Gln Gly Thr
225                 230                 235                 240

Leu Val Thr Val Ser Ser
                245
```

<210> SEQ ID NO 94
<211> LENGTH: 246
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 94

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Val Leu Val Ile Tyr
        35                  40                  45
```

```
Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Arg Thr Gly Ile Tyr
                85                  90                  95

Val Leu Phe Gly Gly Gly Thr Lys Leu Thr Val Leu Gly Gly Ser Glu
            100                 105                 110

Gly Lys Ser Ser Gly Ser Gly Ser Glu Ser Lys Ser Thr Gly Gly Ser
        115                 120                 125

Gln Val Gln Leu Gln Glu Ser Gly Pro Gly Leu Val Lys Pro Ser Glu
    130                 135                 140

Thr Leu Ser Leu Thr Cys Thr Val Ser Ser Gly Ser Ile Ser Ser Tyr
145                 150                 155                 160

Tyr Trp Asn Trp Ile Arg Gln Pro Ala Gly Lys Gly Leu Glu Trp Ile
                165                 170                 175

Gly Arg Ile Tyr Thr Ser Gly Thr Thr His Tyr Asn Pro Ser Leu Lys
            180                 185                 190

Ser Arg Val Thr Met Ser Ile Asp Thr Ser Lys Asn Gln Phe Ser Leu
        195                 200                 205

Lys Leu Ser Ser Val Thr Ala Ala Asp Thr Ala Val Tyr Tyr Cys Ala
    210                 215                 220

Arg Glu Ile Arg Glu Leu Arg Gly Phe Asp Tyr Trp Gly Gln Gly Thr
225                 230                 235                 240

Leu Val Thr Val Ser Ser
                245


<210> SEQ ID NO 95
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ser Tyr Glu Leu Thr Gln Pro Pro Ser Val Ser Val Ser Pro Gly Gln
1               5                   10                  15

Thr Ala Ser Ile Thr Cys Ser Gly His Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ile Thr Ala Trp
                85                  90                  95

Val Phe Gly Gly Gly Thr Lys Leu Thr Val Leu Gly Gly Ser Glu Gly
            100                 105                 110

Lys Ser Ser Gly Ser Gly Ser Glu Ser Lys Ser Thr Gly Gly Ser Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Thr Phe Ser Arg His Thr
```

145 150 155 160

Met Asn Trp Val Arg Gln Ala Pro Gly Lys Gly Leu Glu Trp Val Ser
165 170 175

Ser Ile Ser Gly Ser Gly Gly Ser Thr Tyr Tyr Ala Asp Ser Val Lys
180 185 190

Gly Arg Phe Thr Val Ser Arg Asp Asn Ser Lys Asn Thr Leu Tyr Leu
195 200 205

Gln Met Asn Ser Leu Arg Ala Glu Asp Thr Ala Val Tyr Tyr Cys Ala
210 215 220

Lys Glu Ser Tyr Asp Ser Ser Gly Val Trp Tyr Phe Asp Leu Trp Gly
225 230 235 240

Lys Gly Thr Thr Val Thr Val Ser Ser
245

<210> SEQ ID NO 96
<211> LENGTH: 254
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Ser Tyr Glu Leu Thr Gln Pro Pro Ser Val Ser Val Ser Pro Gly Gln
1 5 10 15

Thr Ala Ser Ile Thr Cys Ser Gly Asp Lys Leu Gly Asp Lys Phe Ala
20 25 30

Ser Trp Tyr Gln Gln Lys Pro Gly Gln Ser Pro Val Leu Val Ile Phe
35 40 45

Gln Asp Ser Lys Arg Pro Ser Gly Ile Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Phe Cys Gln Ala Trp Asp Ser Thr Thr Ala Trp
85 90 95

Val Phe Gly Gly Gly Thr Lys Leu Thr Val Leu Gly Gly Ser Glu Gly
100 105 110

Lys Ser Ser Gly Ser Gly Ser Glu Ser Lys Ser Thr Gly Gly Ser Glu
115 120 125

Val Gln Leu Val Glu Ser Gly Gly Gly Leu Val Gln Pro Gly Gly Ser
130 135 140

Leu Arg Leu Ser Cys Ala Ala Ser Gly Phe Thr Phe Asn Ser Tyr Asn
145 150 155 160

Met Asn Trp Val Arg Gln Ala Pro Gly Lys Gly Leu Glu Trp Val Ser
165 170 175

Tyr Ile Ser Ser Ser Gly Tyr Thr Ile Tyr Tyr Ala Asp Ser Val Glu
180 185 190

Gly Arg Phe Thr Ile Ser Arg Asp Asn Ala Lys Asn Ser Leu Tyr Leu
195 200 205

Gln Met Asp Ser Leu Arg Asp Glu Asp Thr Ala Ile Tyr Tyr Cys Ala
210 215 220

Arg Asp Arg Tyr Asn Tyr Asp Asn Gly Gly Tyr His Tyr Tyr Thr Gly
225 230 235 240

Met Asp Val Trp Gly Gln Gly Thr Met Val Thr Val Ser Ser
245 250

<210> SEQ ID NO 97
<211> LENGTH: 248
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 97

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Arg Pro Gly Gln Gly Leu Glu Trp Met
        35                  40                  45

Gly Glu Ile Leu Pro Gly Gly Gly Asp Thr Asn Tyr Asn Gln Lys Phe
    50                  55                  60

Gln Gly Lys Val Thr Phe Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Val Pro Val Tyr Phe Asp Tyr Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Gln Ser Val Asp Tyr Asp Gly Asp Ser Phe Leu Asn Trp
                165                 170                 175

Tyr Gln Gln Lys Pro Gly Gln Pro Pro Lys Leu Leu Ile Tyr Ala Ala
            180                 185                 190

Ser Asn Leu Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln Gln Ser Asn Glu Asp Pro Leu Thr Phe Gly
225                 230                 235                 240

Gly Gly Thr Lys Val Glu Ile Lys
                245
```

<210> SEQ ID NO 98
<211> LENGTH: 248
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 98

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Arg Pro Gly Gln Gly Leu Glu Trp Met
        35                  40                  45
```

```
Gly Glu Ile Leu Pro Gly Gly Gly Asp Thr Asn Tyr Asn Gln Lys Phe
    50                  55                  60

Gln Gly Lys Val Thr Phe Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Val Pro Val Tyr Phe Asp Tyr Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Gln Ser Val Asp Tyr Glu Gly Asp Ser Phe Leu Asn Trp
                165                 170                 175

Tyr Gln Gln Lys Pro Gly Gln Pro Pro Lys Leu Leu Ile Tyr Ala Ala
            180                 185                 190

Ser Asn Leu Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln Gln Ser Asn Glu Asp Pro Leu Thr Phe Gly
225                 230                 235                 240

Gly Gly Thr Lys Val Glu Ile Lys
                245


<210> SEQ ID NO 99
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Arg Pro Gly Gln Gly Leu Glu Trp Met
        35                  40                  45

Gly Glu Ile Leu Pro Gly Gly Gly Asp Thr Asn Tyr Asn Gln Lys Phe
    50                  55                  60

Gln Gly Lys Val Thr Phe Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Val Pro Val Tyr Phe Asp Tyr Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160
```

Lys Ala Ser Gln Ser Val Asp Tyr Asp Gly Asp Ser Phe Leu Asn Trp
165 170 175

Tyr Gln Gln Lys Pro Gly Gln Pro Pro Lys Leu Leu Ile Tyr Ala Ala
180 185 190

Ser Asn Leu Glu Ser Gly Val Pro Asp Arg Phe Ser Gly Ser Gly Ser
195 200 205

Gly Thr Asp Phe Thr Leu Thr Ile Ser Ser Leu Gln Ala Glu Asp Val
210 215 220

Ala Val Tyr Tyr Cys Gln Gln Ser Asn Glu Asp Pro Leu Thr Phe Gly
225 230 235 240

Gly Gly Thr Lys Val Glu Ile Lys
245

<210> SEQ ID NO 100
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Trp Ile Glu Trp Val Arg Gln Arg Pro Gly Gln Gly Leu Glu Trp Met
35 40 45

Gly Glu Ile Leu Pro Gly Gly Gly Asp Thr Asn Tyr Asn Gln Lys Phe
50 55 60

Gln Gly Lys Val Thr Phe Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Arg Val Pro Val Tyr Phe Asp Tyr Trp Gly Gln Gly Thr Leu
100 105 110

Val Thr Val Ser Ser Gly Gly Ser Glu Gly Lys Ser Ser Gly Ser Gly
115 120 125

Ser Glu Ser Lys Ser Thr Gly Gly Ser Asp Ile Val Leu Thr Gln Ser
130 135 140

Pro Asp Ser Leu Ala Val Ser Leu Gly Glu Arg Ala Thr Ile Asn Cys
145 150 155 160

Lys Ala Ser Gln Ser Val Asp Tyr Glu Gly Asp Ser Phe Leu Asn Trp
165 170 175

Tyr Gln Gln Lys Pro Gly Gln Pro Pro Lys Leu Leu Ile Tyr Ala Ala
180 185 190

Ser Asn Leu Glu Ser Gly Val Pro Asp Arg Phe Ser Gly Ser Gly Ser
195 200 205

Gly Thr Asp Phe Thr Leu Thr Ile Ser Ser Leu Gln Ala Glu Asp Val
210 215 220

Ala Val Tyr Tyr Cys Gln Gln Ser Asn Glu Asp Pro Leu Thr Phe Gly
225 230 235 240

Gly Gly Thr Lys Val Glu Ile Lys
245

<210> SEQ ID NO 101
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Ala Pro Gly Gln Gly Leu Glu Trp Met
        35                  40                  45

Gly Glu Ile Leu Pro Gly Gly Gly Asp Thr Asn Tyr Asn Gln Lys Phe
    50                  55                  60

Gln Gly Lys Val Thr Phe Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Val Pro Val Tyr Phe Asp Tyr Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Gln Ser Val Asp Tyr Glu Gly Asp Ser Phe Leu Asn Trp
                165                 170                 175

Tyr Gln Gln Lys Pro Gly Gln Pro Pro Lys Leu Leu Ile Tyr Ala Ala
            180                 185                 190

Ser Asn Leu Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln Gln Ser Asn Glu Asp Pro Leu Thr Phe Gly
225                 230                 235                 240

Gly Gly Thr Lys Val Glu Ile Lys
                245
```

<210> SEQ ID NO 102
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Ala Pro Gly Gln Gly Leu Glu Trp Met
        35                  40                  45

Gly Glu Ile Leu Pro Gly Gly Gly Asp Thr Asn Tyr Asn Gln Lys Phe
```

```
    50                  55                  60

Gln Gly Lys Val Thr Phe Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Val Pro Val Tyr Phe Asp Tyr Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Gln Ser Val Asp Tyr Asp Gly Asp Ser Phe Leu Asn Trp
                165                 170                 175

Tyr Gln Gln Lys Pro Gly Gln Pro Pro Lys Leu Leu Ile Tyr Ala Ala
            180                 185                 190

Ser Asn Leu Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln Gln Ser Asn Glu Asp Pro Leu Thr Phe Gly
225                 230                 235                 240

Gly Gly Thr Lys Val Glu Ile Lys
                245


<210> SEQ ID NO 103
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Val Gln Ser Gly Ala Glu Val Met Lys Pro Gly Ala
1               5                   10                  15

Ser Val Lys Ile Ser Cys Lys Ala Ser Gly Tyr Thr Phe Thr Gly Tyr
            20                  25                  30

Trp Ile Glu Trp Val Arg Gln Arg Pro Gly Gln Gly Leu Glu Trp Met
        35                  40                  45

Gly Glu Ile Leu Pro Gly Gly Gly Asp Thr Asn Tyr Asn Gln Lys Phe
    50                  55                  60

Gln Gly Lys Val Thr Phe Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Val Pro Val Tyr Phe Asp Tyr Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Met Thr Gln Ser
    130                 135                 140

Pro Asp Ser Leu Ala Val Ser Leu Gly Glu Arg Ala Thr Ile Asn Cys
145                 150                 155                 160
```

Lys Ala Ser Gln Ser Val Asp Tyr Asp Gly Asp Ser Phe Leu Asn Trp
165 170 175

Tyr Gln Gln Lys Pro Gly Gln Pro Pro Lys Leu Phe Ile Tyr Ala Ala
180 185 190

Ser Asn Leu Glu Ser Gly Val Pro Asp Arg Phe Ser Gly Ser Gly Ser
195 200 205

Gly Thr Asp Phe Thr Leu Thr Ile Ser Ser Val Gln Ala Glu Asp Ala
210 215 220

Ala Val Tyr Tyr Cys Gln Gln Ser Asn Glu Asp Pro Leu Thr Phe Gly
225 230 235 240

Gly Gly Thr Lys Val Glu Ile Lys
245

<210> SEQ ID NO 104
<211> LENGTH: 248
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 104

Gln Val Gln Leu Val Gln Ser Gly Ala Glu Val Met Lys Pro Gly Ala
1 5 10 15

Ser Val Lys Ile Ser Cys Lys Ala Ser Gly Tyr Thr Phe Thr Gly Tyr
20 25 30

Trp Ile Glu Trp Val Arg Gln Arg Pro Gly Gln Gly Leu Glu Trp Met
35 40 45

Gly Glu Ile Leu Pro Gly Gly Gly Asp Thr Asn Tyr Asn Gln Lys Phe
50 55 60

Gln Gly Lys Val Thr Phe Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Arg Val Pro Val Tyr Phe Asp Tyr Trp Gly Gln Gly Thr Leu
100 105 110

Val Thr Val Ser Ser Gly Gly Ser Glu Gly Lys Ser Ser Gly Ser Gly
115 120 125

Ser Glu Ser Lys Ser Thr Gly Gly Ser Asp Ile Val Leu Thr Gln Ser
130 135 140

Pro Asp Ser Leu Ala Val Ser Leu Gly Glu Arg Ala Thr Ile Asn Cys
145 150 155 160

Lys Ala Ser Gln Ser Val Asp Tyr Lys Gly Asp Ser Phe Leu Asn Trp
165 170 175

Tyr Gln Gln Lys Pro Gly Gln Pro Pro Lys Leu Leu Ile Tyr Ala Ala
180 185 190

Ser Asn Leu Glu Ser Gly Val Pro Asp Arg Phe Ser Gly Ser Gly Ser
195 200 205

Gly Thr Asp Phe Thr Leu Thr Ile Ser Ser Leu Gln Ala Glu Asp Val
210 215 220

Ala Val Tyr Tyr Cys Gln Gln Ser Asn Glu Asp Pro Leu Thr Phe Gly
225 230 235 240

Gly Gly Thr Lys Val Glu Ile Lys
245

<210> SEQ ID NO 105

<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ser Gly Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Lys Leu Arg Ser Val Thr Ala Ala Asp Thr Ala Val Tyr Tyr
                85                  90                  95

Cys Ala Arg Glu Glu Asp Ser Gly Ser Tyr Tyr Val Gly Ala Phe Asp
            100                 105                 110

Ile Trp Gly Gln Gly Thr Met Val Thr Val Ser Ser Gly Gly Ser Glu
        115                 120                 125

Gly Lys Ser Ser Gly Ser Gly Ser Glu Ser Lys Ser Thr Gly Gly Ser
    130                 135                 140

Ser Ser Glu Leu Thr Gln Asp Pro Ala Val Ser Val Ala Leu Gly Gln
145                 150                 155                 160

Thr Val Arg Ile Arg Cys Gln Gly Asp Ser Leu Arg Lys Tyr Tyr Gly
                165                 170                 175

Ser Trp Tyr Gln Gln Lys Pro Gly Gln Ala Pro Val Leu Val Ile Tyr
            180                 185                 190

Gly Glu Thr Asn Arg Pro Ser Gly Ile Pro Asp Arg Phe Ser Gly Ser
        195                 200                 205

Ser Ser Gly Asn Thr Ala Ser Leu Thr Ile Thr Gly Ala Gln Ala Glu
    210                 215                 220

Asp Glu Ala Asp Tyr Tyr Cys Asn Ser Arg Asp Ser Ser Gly Lys His
225                 230                 235                 240

Val Val Phe Gly Gly Gly Thr Lys Leu Thr Val Leu
                245                 250

<210> SEQ ID NO 106
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Arg Ser Ser
            20                  25                  30

Thr Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Ser Asn Pro Ser
    50                  55                  60

```
Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Ile Tyr Tyr
                85                  90                  95

Cys Ala Arg Glu Glu Asp Ser Gly Ser Tyr Tyr Val Gly Thr Phe Asp
            100                 105                 110

Ile Trp Gly Gln Gly Thr Met Val Thr Val Ser Ser Gly Gly Ser Glu
        115                 120                 125

Gly Lys Ser Ser Gly Ser Gly Ser Glu Ser Lys Ser Thr Gly Gly Ser
    130                 135                 140

Ser Ser Glu Leu Thr Gln Asp Pro Ala Val Ser Val Ala Leu Gly Gln
145                 150                 155                 160

Thr Val Arg Ile Thr Cys Gln Gly Asp Ser Leu Arg Asn Tyr Tyr Gly
                165                 170                 175

Ser Trp Tyr Gln Gln Lys Pro Gly Gln Ala Pro Val Leu Val Ile Tyr
            180                 185                 190

Gly Glu Lys Asn Arg Pro Ser Gly Ile Pro Asp Arg Phe Ser Gly Ser
        195                 200                 205

Ser Ser Gly Asn Thr Val Ser Leu Thr Ile Thr Gly Thr Gln Ala Glu
    210                 215                 220

Asp Glu Ala Asp Tyr Tyr Cys Asn Ser Arg Asp Ser Ser Gly Lys His
225                 230                 235                 240

Val Val Phe Gly Gly Gly Thr Lys Leu Thr Val Leu
                245                 250


<210> SEQ ID NO 107
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Asn Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Lys Lys Ser Leu Trp
65                  70                  75                  80

Leu Gln Met Ser Ser Leu Arg Val Glu Asp Thr Ala Val Tyr Tyr Cys
                85                  90                  95

Ala Arg Asp Pro Ile Glu Ser Arg Phe Asp Tyr Trp Gly Gln Gly Thr
            100                 105                 110

Leu Val Thr Val Ser Ser Gly Gly Ser Glu Gly Lys Ser Ser Gly Ser
        115                 120                 125

Gly Ser Glu Ser Lys Ser Thr Gly Gly Ser Asp Val Val Met Thr Gln
    130                 135                 140

Ser Pro Leu Ser Leu Pro Val Thr Leu Gly Gln Pro Ala Ser Ile Ser
145                 150                 155                 160

Cys Arg Ser Ser Gln Ser Leu Val Tyr Ser Asp Gly Asn Thr Tyr Leu
```

```
                165                 170                 175

Ser Trp Phe Gln Gln Arg Pro Gly Gln Ser Pro Arg Arg Leu Ile Tyr
            180                 185                 190

Lys Val Ser Asn Arg Asp Ser Gly Val Pro Asp Arg Phe Ser Gly Ser
        195                 200                 205

Gly Ser Gly Thr Asp Phe Thr Leu Lys Ile Ser Arg Val Glu Ala Glu
    210                 215                 220

Asp Val Gly Val Tyr Tyr Cys Met Gln Gly Thr His Trp Pro Pro Thr
225                 230                 235                 240

Phe Gly Gly Gly Thr Lys Val Glu Ile Lys
                245                 250


<210> SEQ ID NO 108
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ile Tyr
            20                  25                  30

Ala Met Thr Trp Val Arg Gln Ala Pro Gly Lys Gly Leu Glu Trp Val
        35                  40                  45

Ser Gly Ile Ser Val Ser Gly Ile Arg Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Ser Ala Glu Asp Thr Ala Val Tyr Tyr Cys
                85                  90                  95

Ala Lys Gly Leu Ser Ser Gly Asp Arg Asp Ala Ser Asp Ile Trp Gly
            100                 105                 110

Gln Gly Thr Met Val Thr Val Ser Ser Gly Gly Ser Glu Gly Lys Ser
        115                 120                 125

Ser Gly Ser Gly Ser Glu Ser Lys Ser Thr Gly Gly Ser Ser Ser Glu
    130                 135                 140

Leu Thr Gln Pro Pro Ser Val Ser Val Ser Pro Gly Gln Thr Ala Arg
145                 150                 155                 160

Ile Thr Cys Ser Gly Asp Ala Leu Pro Arg Lys Tyr Ala Tyr Trp Tyr
                165                 170                 175

Gln Gln Lys Ser Gly Gln Ala Pro Val Leu Val Ile Tyr Glu Asp Ser
            180                 185                 190

Lys Arg Pro Ser Gly Ile Pro Glu Arg Phe Ser Gly Ser Asn Ser Gly
        195                 200                 205

Thr Met Ala Thr Leu Thr Ile Ser Gly Ala Gln Val Glu Asp Glu Ala
    210                 215                 220

Ala Tyr Tyr Cys Tyr Ser Thr Asp Ser Ser Ala Asn His Arg Val Phe
225                 230                 235                 240

Gly Gly Gly Thr Lys Leu Thr Val Leu
                245


<210> SEQ ID NO 109
<211> LENGTH: 250
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 109

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ile Phe Ser Thr Tyr
20 25 30

Trp Met Ser Trp Val Arg Gln Ala Pro Gly Lys Gly Leu Glu Trp Val
35 40 45

Ala Asn Ile Asn Pro Asp Gly Asn Glu Lys Tyr Tyr Val Asp Ser Val
50 55 60

Glu Gly Arg Phe Thr Ile Ser Arg Asp Asn Ala Gln Asp Ser Leu Tyr
65 70 75 80

Leu Gln Met Asn Ser Leu Arg Ala Glu Asp Thr Ala Val Tyr Tyr Cys
85 90 95

Ala Arg Asp Pro Ile Ser Ala Arg Phe Asp Phe Trp Gly Gln Gly Thr
100 105 110

Leu Val Thr Val Ser Ser Gly Gly Ser Glu Gly Lys Ser Ser Gly Ser
115 120 125

Gly Ser Glu Ser Lys Ser Thr Gly Gly Ser Glu Ile Val Met Thr Gln
130 135 140

Ser Pro Leu Ser Leu Pro Val Thr Pro Gly Lys Pro Ala Ser Ile Ser
145 150 155 160

Cys Arg Ser Ser Gln Ser Leu Glu Tyr Ser Asp Gly Asn Thr Tyr Leu
165 170 175

Asn Trp Phe Gln Gln Arg Pro Gly Gln Ser Pro Arg Arg Leu Ile Tyr
180 185 190

Lys Val Ser Asn Arg Asp Ser Gly Val Pro Asp Arg Phe Ser Gly Ser
195 200 205

Gly Ser Gly Thr Asp Phe Thr Leu Lys Ile Ser Arg Val Glu Ala Glu
210 215 220

Asp Val Gly Val Tyr Tyr Cys Met Gln Gly Thr His Trp Pro Pro Thr
225 230 235 240

Phe Gly Gly Gly Thr Lys Val Asp Ile Lys
245 250

<210> SEQ ID NO 110
<211> LENGTH: 247
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 110

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Asn Trp Val Arg Gln Ala Pro Gly Lys Gly Leu Glu Trp Val
35 40 45

Ser Thr Ile Ser Gly Ser Gly Gly Ser Ser Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Asn Pro Ser Gly Thr Phe Trp Asn Asp Ala Phe Asp Ile Trp Gly
100 105 110

Gln Gly Thr Met Val Thr Val Ser Ser Gly Gly Ser Glu Gly Lys Ser
115 120 125

Ser Gly Ser Gly Ser Glu Ser Lys Ser Thr Gly Gly Ser Ser Tyr Glu
130 135 140

Leu Thr Gln Pro Pro Ser Val Ser Val Ser Pro Gly Gln Thr Ala Ser
145 150 155 160

Ile Thr Cys Ser Gly Asp Lys Leu Gly Asp Glu Phe Ala Ser Trp Tyr
165 170 175

Gln Gln Lys Pro Gly Gln Ser Pro Val Val Val Ile Tyr Gln Asp Thr
180 185 190

Lys Arg Pro Ser Gly Ile Pro Glu Arg Phe Ser Gly Ser Asn Ser Gly
195 200 205

Asn Thr Ala Thr Leu Thr Ile Ser Gly Thr Gln Ala Met Asp Glu Ala
210 215 220

Asp Tyr Tyr Cys Gln Ala Trp Asp Ser Asn Thr Ala Val Phe Gly Gly
225 230 235 240

Gly Thr Lys Leu Thr Val Leu
245

<210> SEQ ID NO 111
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Asn Tyr
20 25 30

Ala Met Asn Trp Val Arg Gln Ala Pro Gly Lys Gly Leu Glu Trp Val
35 40 45

Ser Val Ile Ser Gly Asn Gly Gly Ser Ile His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Thr Pro Arg Gly Tyr Thr Gly Tyr Asp Gly Asp Ala Phe Asp Phe
100 105 110

Trp Gly Gln Gly Thr Met Val Thr Val Ser Ser Gly Gly Ser Glu Gly
115 120 125

Lys Ser Ser Gly Ser Gly Ser Glu Ser Lys Ser Thr Gly Gly Ser Ser
130 135 140

Tyr Glu Leu Thr Gln Pro Pro Ser Val Ser Val Ser Pro Gly Gln Thr
145 150 155 160

Ala Arg Ile Thr Cys Ser Gly Asp Ala Leu Pro Lys Lys Tyr Ala Tyr
165 170 175

```
Trp Tyr Gln Gln Lys Ser Gly Gln Ala Pro Val Leu Val Ile Tyr Glu
            180                 185                 190

Asp Ser Lys Arg Pro Ser Gly Ile Pro Glu Arg Phe Ser Ala Ser Ser
        195                 200                 205

Ser Gly Thr Met Ala Thr Leu Thr Ile Ser Gly Ala Gln Val Glu Asp
    210                 215                 220

Glu Ala Asp Tyr Tyr Cys Tyr Ser Ala Asp Ser Ser Gly Ser His Trp
225                 230                 235                 240

Val Phe Gly Gly Gly Thr Lys Leu Thr Val Leu
                245                 250


<210> SEQ ID NO 112
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Val Gln Leu Val Glu Ser Gly Gly Asp Leu Val Gln Pro Gly Gly
1               5                   10                  15

Ser Leu Arg Leu Ser Cys Glu Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ser Gly Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Leu Leu Leu Trp Leu Gly Tyr His Gly Asp Gly Phe Asp Leu
            100                 105                 110

Trp Gly Gln Gly Thr Met Val Thr Val Ser Ser Gly Gly Ser Glu Gly
        115                 120                 125

Lys Ser Ser Gly Ser Gly Ser Glu Ser Lys Ser Thr Gly Gly Ser Ser
    130                 135                 140

Tyr Glu Leu Thr Gln Pro Pro Ser Val Ser Val Ser Pro Gly Gln Thr
145                 150                 155                 160

Ala Arg Ile Thr Cys Ser Gly Asp Ala Leu Pro Lys Lys Tyr Ala Tyr
                165                 170                 175

Trp Tyr Gln Lys Lys Ser Gly Gln Ala Pro Val Leu Val Ile His Glu
            180                 185                 190

Asp Ser Lys Arg Pro Ser Gly Ile Pro Glu Arg Phe Ser Gly Ser Ser
        195                 200                 205

Ser Gly Thr Met Ala Thr Leu Thr Ile Ser Gly Ala Gln Val Glu Asp
    210                 215                 220

Glu Ala Asp Tyr Tyr Cys Phe Ser Thr Asp Arg Ser Gly Asn His Val
225                 230                 235                 240

Val Phe Gly Gly Gly Thr Lys Leu Thr Val Leu
                245                 250


<210> SEQ ID NO 113
<211> LENGTH: 249
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 113

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Gly Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Glu Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Thr Arg Val Asp Thr Asp Phe Asp Tyr Trp Gly Gln Gly
            100                 105                 110

Thr Leu Val Thr Val Ser Ser Gly Gly Ser Glu Gly Lys Ser Ser Gly
        115                 120                 125

Ser Gly Ser Glu Ser Lys Ser Thr Gly Gly Ser Gln Ser Ala Leu Thr
    130                 135                 140

Gln Pro Pro Ser Val Ser Glu Ala Pro Arg Gln Arg Val Thr Ile Ser
145                 150                 155                 160

Cys Ser Gly Ser Ala Ser Asn Ile Gly Asn Asn Gly Val Asn Trp Tyr
                165                 170                 175

Gln Gln Leu Pro Gly Lys Thr Pro Lys Leu Leu Ile Tyr Asn Asp Asp
            180                 185                 190

Leu Leu Pro Ser Gly Val Ser Asp Arg Phe Ser Gly Ser Lys Ser Gly
        195                 200                 205

Thr Ser Ala Ser Leu Ala Ile Ser Gly Leu Gln Ser Glu Asp Glu Ala
    210                 215                 220

Asp Tyr Phe Cys Ala Ala Trp Asp Asp Ser Leu Asn Gly Leu Val Phe
225                 230                 235                 240

Gly Gly Gly Thr Lys Leu Thr Val Leu
                245
```

<210> SEQ ID NO 114
<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 114

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Thr Met Asn Trp Val Arg Gln Ala Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Arg Phe Thr Val Ser Arg Asp Asn Ser Lys Asn Thr Leu Tyr
```

```
65                  70                  75                  80

Leu Gln Met Asn Ser Leu Arg Ala Glu Asp Thr Ala Val Tyr Tyr Cys
                85                  90                  95

Ala Lys Glu Ser Tyr Asp Ser Ser Gly Val Trp Tyr Phe Asp Leu Trp
            100                 105                 110

Gly Arg Gly Thr Leu Val Thr Val Ser Ser Gly Gly Ser Glu Gly Lys
        115                 120                 125

Ser Ser Gly Ser Gly Ser Glu Ser Lys Ser Thr Gly Gly Ser Ser Tyr
    130                 135                 140

Glu Leu Thr Gln Pro Pro Ser Val Ser Val Ser Pro Gly Gln Thr Ala
145                 150                 155                 160

Ser Ile Thr Cys Ser Gly His Lys Leu Gly Asp Lys Tyr Ala Ser Trp
                165                 170                 175

Tyr Gln Gln Lys Pro Gly Gln Ser Pro Val Leu Val Ile Tyr Gln Asp
            180                 185                 190

Ser Lys Arg Pro Ser Gly Ile Pro Glu Arg Phe Ser Gly Ser Asn Ser
        195                 200                 205

Gly Asn Thr Ala Thr Leu Thr Ile Ser Gly Thr Gln Ala Met Asp Glu
    210                 215                 220

Ala Asp Tyr Tyr Cys Gln Ala Trp Asp Ser Ile Thr Ala Trp Val Phe
225                 230                 235                 240

Gly Gly Gly Thr Lys Leu Thr Val Leu
                245


<210> SEQ ID NO 115
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Leu Gln Glu Ser Gly Pro Gly Leu Val Lys Pro Ser Glu
1               5                   10                  15

Thr Leu Ser Leu Thr Cys Thr Val Ser Ser Gly Ser Ile Ser Ser Tyr
            20                  25                  30

Tyr Trp Asn Trp Ile Arg Gln Pro Ala Gly Lys Gly Leu Glu Trp Ile
        35                  40                  45

Gly Arg Ile Tyr Thr Ser Gly Thr Thr His Tyr Asn Pro Ser Leu Lys
    50                  55                  60

Ser Arg Val Thr Met Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ile Arg Glu Leu Arg Gly Phe Asp Tyr Trp Gly Gln Gly Thr
            100                 105                 110

Leu Val Thr Val Ser Ser Gly Gly Ser Glu Gly Lys Ser Ser Gly Ser
        115                 120                 125

Gly Ser Glu Ser Lys Ser Thr Gly Gly Ser Ser Tyr Glu Leu Met Gln
    130                 135                 140

Pro Pro Ser Val Ser Val Ser Pro Gly Gln Thr Ala Arg Ile Thr Cys
145                 150                 155                 160

Ser Gly Asp Ala Leu Pro Arg Gln Tyr Ala Tyr Trp Tyr Gln Gln Lys
                165                 170                 175
```

```
Pro Gly Gln Ala Pro Val Leu Val Ile Tyr Lys Asp Ser Glu Arg Pro
            180                 185                 190

Ser Gly Ile Pro Glu Arg Phe Ser Gly Ser Ser Ser Gly Thr Thr Val
        195                 200                 205

Thr Leu Thr Ile Ser Gly Val Gln Ala Glu Asp Glu Ala Asp Tyr Tyr
    210                 215                 220

Cys Gln Ser Ala Asp Arg Thr Gly Ile Tyr Val Leu Phe Gly Gly Gly
225                 230                 235                 240

Thr Lys Leu Thr Val Leu
                245


<210> SEQ ID NO 116
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Gln Glu Ser Gly Pro Gly Leu Val Lys Pro Ser Glu
1               5                   10                  15

Thr Leu Ser Leu Thr Cys Thr Val Ser Ser Gly Ser Ile Ser Ser Tyr
            20                  25                  30

Tyr Trp Asn Trp Ile Arg Gln Pro Ala Gly Lys Gly Leu Glu Trp Ile
        35                  40                  45

Gly Arg Ile Tyr Thr Ser Gly Thr Thr His Tyr Asn Pro Ser Leu Lys
    50                  55                  60

Ser Arg Val Thr Met Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ile Arg Glu Leu Arg Gly Phe Asp Tyr Trp Gly Gln Gly Thr
            100                 105                 110

Leu Val Thr Val Ser Ser Gly Gly Ser Glu Gly Lys Ser Ser Gly Ser
        115                 120                 125

Gly Ser Glu Ser Lys Ser Thr Gly Gly Ser Ser Tyr Glu Leu Thr Gln
    130                 135                 140

Pro Pro Ser Val Ser Val Ser Pro Gly Gln Thr Ala Arg Ile Thr Cys
145                 150                 155                 160

Ser Gly Asp Ala Leu Pro Arg Gln Tyr Ala Tyr Trp Tyr Gln Gln Lys
                165                 170                 175

Pro Gly Gln Ala Pro Val Leu Val Ile Tyr Lys Asp Ser Glu Arg Pro
            180                 185                 190

Ser Gly Ile Pro Glu Arg Phe Ser Gly Ser Ser Ser Gly Thr Thr Val
        195                 200                 205

Thr Leu Thr Ile Ser Gly Val Gln Ala Glu Asp Glu Ala Asp Tyr Tyr
    210                 215                 220

Cys Gln Ser Ala Asp Arg Thr Gly Ile Tyr Val Leu Phe Gly Gly Gly
225                 230                 235                 240

Thr Lys Leu Thr Val Leu
                245


<210> SEQ ID NO 117
<211> LENGTH: 249
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 117

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Thr Met Asn Trp Val Arg Gln Ala Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ser Tyr Asp Ser Ser Gly Val Trp Tyr Phe Asp Leu Trp
            100                 105                 110

Gly Lys Gly Thr Thr Val Thr Val Ser Ser Gly Gly Ser Glu Gly Lys
        115                 120                 125

Ser Ser Gly Ser Gly Ser Glu Ser Lys Ser Thr Gly Gly Ser Ser Tyr
    130                 135                 140

Glu Leu Thr Gln Pro Pro Ser Val Ser Val Ser Pro Gly Gln Thr Ala
145                 150                 155                 160

Ser Ile Thr Cys Ser Gly His Lys Leu Gly Asp Lys Tyr Ala Ser Trp
                165                 170                 175

Tyr Gln Gln Lys Pro Gly Gln Ser Pro Val Leu Val Ile Tyr Gln Asp
            180                 185                 190

Ser Lys Arg Pro Ser Gly Ile Pro Glu Arg Phe Ser Gly Ser Asn Ser
        195                 200                 205

Gly Asn Thr Ala Thr Leu Thr Ile Ser Gly Thr Gln Ala Met Asp Glu
    210                 215                 220

Ala Asp Tyr Tyr Cys Gln Ala Trp Asp Ser Ile Thr Ala Trp Val Phe
225                 230                 235                 240

Gly Gly Gly Thr Lys Leu Thr Val Leu
                245
```

<210> SEQ ID NO 118
<211> LENGTH: 254
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 118

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Asn Met Asn Trp Val Arg Gln Ala Pro Gly Lys Gly Leu Glu Trp Val
        35                  40                  45

Ser Tyr Ile Ser Ser Ser Gly Tyr Thr Ile Tyr Tyr Ala Asp Ser Val
    50                  55                  60

Glu Gly Arg Phe Thr Ile Ser Arg Asp Asn Ala Lys Asn Ser Leu Tyr
65                  70                  75                  80
```

```
Leu Gln Met Asp Ser Leu Arg Asp Glu Asp Thr Ala Ile Tyr Tyr Cys
                85                  90                  95

Ala Arg Asp Arg Tyr Asn Tyr Asp Asn Gly Gly Tyr His Tyr Tyr Thr
            100                 105                 110

Gly Met Asp Val Trp Gly Gln Gly Thr Met Val Thr Val Ser Ser Gly
        115                 120                 125

Gly Ser Glu Gly Lys Ser Ser Gly Ser Gly Ser Glu Ser Lys Ser Thr
    130                 135                 140

Gly Gly Ser Ser Tyr Glu Leu Thr Gln Pro Pro Ser Val Ser Val Ser
145                 150                 155                 160

Pro Gly Gln Thr Ala Ser Ile Thr Cys Ser Gly Asp Lys Leu Gly Asp
                165                 170                 175

Lys Phe Ala Ser Trp Tyr Gln Gln Lys Pro Gly Gln Ser Pro Val Leu
            180                 185                 190

Val Ile Phe Gln Asp Ser Lys Arg Pro Ser Gly Ile Pro Glu Arg Phe
        195                 200                 205

Ser Gly Ser Asn Ser Gly Asn Thr Ala Thr Leu Thr Ile Ser Gly Thr
    210                 215                 220

Gln Ala Met Asp Glu Ala Asp Tyr Phe Cys Gln Ala Trp Asp Ser Thr
225                 230                 235                 240

Thr Ala Trp Val Phe Gly Gly Gly Thr Lys Leu Thr Val Leu
                245                 250


<210> SEQ ID NO 119
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45

Asp Tyr Asp Gly Asp Ser Phe Leu Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Lys Lys Pro Gly Ala Ser Val Lys Val Ser Cys Lys Ala Ser Gly
                165                 170                 175

Tyr Thr Phe Thr Gly Tyr Trp Ile Glu Trp Val Arg Gln Arg Pro Gly
```

```
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Ala Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser
            260                 265


<210> SEQ ID NO 120
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45

Asp Tyr Glu Gly Asp Ser Phe Leu Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Lys Lys Pro Gly Ala Ser Val Lys Val Ser Cys Lys Ala Ser Gly
                165                 170                 175

Tyr Thr Phe Thr Gly Tyr Trp Ile Glu Trp Val Arg Gln Arg Pro Gly
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Ala Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser
            260                 265
```

<210> SEQ ID NO 121
<211> LENGTH: 267
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 121

Met Ala Trp Val Trp Thr Leu Leu Phe Leu Met Ala Ala Ala Gln Ser
1 5 10 15

Ile Gln Ala Asp Ile Val Leu Thr Gln Ser Pro Asp Ser Leu Ala Val
20 25 30

Ser Leu Gly Glu Arg Ala Thr Ile Asn Cys Lys Ala Ser Gln Ser Val
35 40 45

Asp Tyr Asp Gly Asp Ser Phe Leu Asn Trp Tyr Gln Gln Lys Pro Gly
50 55 60

Gln Pro Pro Lys Leu Leu Ile Tyr Ala Ala Ser Asn Leu Glu Ser Gly
65 70 75 80

Val Pro Asp Arg Phe Ser Gly Ser Gly Ser Gly Thr Asp Phe Thr Leu
85 90 95

Thr Ile Ser Ser Leu Gln Ala Glu Asp Val Ala Val Tyr Tyr Cys Gln
100 105 110

Gln Ser Asn Glu Asp Pro Leu Thr Phe Gly Gly Gly Thr Lys Val Glu
115 120 125

Ile Lys Gly Gly Ser Glu Gly Lys Ser Ser Gly Ser Gly Ser Glu Ser
130 135 140

Lys Ser Thr Gly Gly Ser Gln Val Gln Leu Val Gln Ser Gly Ala Glu
145 150 155 160

Val Lys Lys Pro Gly Ala Ser Val Lys Val Ser Cys Lys Ala Ser Gly
165 170 175

Tyr Thr Phe Thr Gly Tyr Trp Ile Glu Trp Val Arg Gln Arg Pro Gly
180 185 190

Gln Gly Leu Glu Trp Met Gly Glu Ile Leu Pro Gly Gly Gly Asp Thr
195 200 205

Asn Tyr Asn Gln Lys Phe Gln Gly Lys Val Thr Phe Thr Arg Asp Thr
210 215 220

Ser Thr Ser Thr Val Tyr Met Glu Leu Ser Ser Leu Arg Ser Glu Asp
225 230 235 240

Thr Ala Val Tyr Tyr Cys Ala Arg Arg Val Pro Val Tyr Phe Asp Tyr
245 250 255

Trp Gly Gln Gly Thr Leu Val Thr Val Ser Ser
260 265

<210> SEQ ID NO 122
<211> LENGTH: 267
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 122

Met Ala Trp Val Trp Thr Leu Leu Phe Leu Met Ala Ala Ala Gln Ser
1 5 10 15

Ile Gln Ala Asp Ile Val Leu Thr Gln Ser Pro Asp Ser Leu Ala Val
20 25 30

```
Ser Leu Gly Glu Arg Ala Thr Ile Asn Cys Lys Ala Ser Gln Ser Val
        35                  40                  45

Asp Tyr Glu Gly Asp Ser Phe Leu Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Lys Lys Pro Gly Ala Ser Val Lys Val Ser Cys Lys Ala Ser Gly
                165                 170                 175

Tyr Thr Phe Thr Gly Tyr Trp Ile Glu Trp Val Arg Gln Arg Pro Gly
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Val Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser
            260                 265


<210> SEQ ID NO 123
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45

Asp Tyr Glu Gly Asp Ser Phe Leu Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Ser Asn Glu Asp Pro Leu Thr Phe Gly Gly Gly Thr Lys Val Glu
        115                 120                 125
```

```
Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Lys Lys Pro Gly Ala Ser Val Lys Val Ser Cys Lys Ala Ser Gly
                165                 170                 175

Tyr Thr Phe Thr Gly Tyr Trp Ile Glu Trp Val Arg Gln Ala Pro Gly
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Ala Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser
            260                 265


<210> SEQ ID NO 124
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45

Asp Tyr Asp Gly Asp Ser Phe Leu Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Lys Lys Pro Gly Ala Ser Val Lys Val Ser Cys Lys Ala Ser Gly
                165                 170                 175

Tyr Thr Phe Thr Gly Tyr Trp Ile Glu Trp Val Arg Gln Ala Pro Gly
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
```

```
    210                 215                 220

Ser Thr Ser Thr Val Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser
            260                 265


<210> SEQ ID NO 125
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Ala Trp Val Trp Thr Leu Leu Phe Leu Met Ala Ala Ala Gln Ser
1               5                   10                  15

Ile Gln Ala Asp Ile Val Met Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45

Asp Tyr Asp Gly Asp Ser Phe Leu Asn Trp Tyr Gln Gln Lys Pro Gly
    50                  55                  60

Gln Pro Pro Lys Leu Phe Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Val Gln Ala Glu Asp Ala Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Met Lys Pro Gly Ala Ser Val Lys Ile Ser Cys Lys Ala Ser Gly
                165                 170                 175

Tyr Thr Phe Thr Gly Tyr Trp Ile Glu Trp Val Arg Gln Arg Pro Gly
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Val Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser
            260                 265


<210> SEQ ID NO 126
<211> LENGTH: 267
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 126

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45

Asp Tyr Lys Gly Asp Ser Phe Leu Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Met Lys Pro Gly Ala Ser Val Lys Ile Ser Cys Lys Ala Ser Gly
                165                 170                 175

Tyr Thr Phe Thr Gly Tyr Trp Ile Glu Trp Val Arg Gln Arg Pro Gly
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Val Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser
            260                 265

<210> SEQ ID NO 127
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Ala Trp Val Trp Thr Leu Leu Phe Leu Met Ala Ala Ala Gln Ser
1               5                   10                  15

Ile Gln Ala Ser Ser Glu Leu Thr Gln Asp Pro Ala Val Ser Val Ala
            20                  25                  30

Leu Gly Gln Thr Val Arg Ile Arg Cys Gln Gly Asp Ser Leu Arg Lys
        35                  40                  45

Tyr Tyr Gly Ser Trp Tyr Gln Gln Lys Pro Gly Gln Ala Pro Val Leu
    50                  55                  60

```
Val Ile Tyr Gly Glu Thr Asn Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Asn Ser Arg Asp Ser Ser
            100                 105                 110

Gly Lys His Val Val Phe Gly Gly Gly Thr Lys Leu Thr Val Leu Gly
        115                 120                 125

Gly Ser Glu Gly Lys Ser Ser Gly Ser Gly Ser Glu Ser Lys Ser Thr
    130                 135                 140

Gly Gly Ser Glu Val Gln Leu Gln Glu Ser Gly Pro Gly Leu Val Lys
145                 150                 155                 160

Pro Ser Glu Thr Leu Ser Leu Thr Cys Ser Val Ser Gly Gly Ser Ile
                165                 170                 175

Ser Gly Ser Ser Tyr Tyr Trp Gly Trp Ile Arg Gln Pro Pro Gly Lys
            180                 185                 190

Gly Leu Glu Trp Ile Gly Ser Ile Tyr Tyr Ser Gly Ser Thr Tyr Tyr
        195                 200                 205

Asn Pro Ser Leu Lys Ser Arg Val Thr Ile Ser Val Asp Thr Ser Lys
    210                 215                 220

Lys Gln Phe Ser Leu Lys Leu Arg Ser Val Thr Ala Ala Asp Thr Ala
225                 230                 235                 240

Val Tyr Tyr Cys Ala Arg Glu Glu Asp Ser Gly Ser Tyr Tyr Val Gly
                245                 250                 255

Ala Phe Asp Ile Trp Gly Gln Gly Thr Met Val Thr Val Ser Ser
            260                 265                 270


<210> SEQ ID NO 128
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Ala Trp Val Trp Thr Leu Leu Phe Leu Met Ala Ala Ala Gln Ser
1               5                   10                  15

Ile Gln Ala Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Asn
        35                  40                  45

Tyr Tyr Gly Ser Trp Tyr Gln Gln Lys Pro Gly Gln Ala Pro Val Leu
    50                  55                  60

Val Ile Tyr Gly Glu Lys Asn Arg Pro Ser Gly Ile Pro Asp Arg Phe
65                  70                  75                  80

Ser Gly Ser Ser Ser Gly Asn Thr Val Ser Leu Thr Ile Thr Gly Thr
                85                  90                  95

Gln Ala Glu Asp Glu Ala Asp Tyr Tyr Cys Asn Ser Arg Asp Ser Ser
            100                 105                 110

Gly Lys His Val Val Phe Gly Gly Gly Thr Lys Leu Thr Val Leu Gly
        115                 120                 125

Gly Ser Glu Gly Lys Ser Ser Gly Ser Gly Ser Glu Ser Lys Ser Thr
    130                 135                 140

Gly Gly Ser Gln Val Gln Leu Gln Glu Ser Gly Pro Gly Leu Val Lys
145                 150                 155                 160
```

```
Pro Ser Glu Thr Leu Ser Leu Thr Cys Ser Val Ser Gly Gly Ser Ile
                165                 170                 175

Arg Ser Ser Thr Tyr Tyr Trp Gly Trp Ile Arg Gln Pro Pro Gly Lys
            180                 185                 190

Gly Leu Glu Trp Ile Gly Ser Ile Tyr Tyr Ser Gly Ser Thr Tyr Ser
        195                 200                 205

Asn Pro Ser Leu Lys Ser Arg Val Thr Ile Ser Val Asp Thr Ser Lys
    210                 215                 220

Asn Gln Phe Ser Leu Lys Leu Ser Ser Val Thr Ala Ala Asp Thr Ala
225                 230                 235                 240

Ile Tyr Tyr Cys Ala Arg Glu Glu Asp Ser Gly Ser Tyr Tyr Val Gly
                245                 250                 255

Thr Phe Asp Ile Trp Gly Gln Gly Thr Met Val Thr Val Ser Ser
            260                 265                 270


<210> SEQ ID NO 129
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Ala Trp Val Trp Thr Leu Leu Phe Leu Met Ala Ala Ala Gln Ser
1               5                   10                  15

Ile Gln Ala Asp Val Val Met Thr Gln Ser Pro Leu Ser Leu Pro Val
            20                  25                  30

Thr Leu Gly Gln Pro Ala Ser Ile Ser Cys Arg Ser Ser Gln Ser Leu
        35                  40                  45

Val Tyr Ser Asp Gly Asn Thr Tyr Leu Ser Trp Phe Gln Gln Arg Pro
    50                  55                  60

Gly Gln Ser Pro Arg Arg Leu Ile Tyr Lys Val Ser Asn Arg Asp Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Met Gln Gly Thr His Trp Pro Pro Thr Phe Gly Gly Gly Thr Lys Val
        115                 120                 125

Glu Ile Lys Gly Gly Ser Glu Gly Lys Ser Ser Gly Ser Gly Ser Glu
    130                 135                 140

Ser Lys Ser Thr Gly Gly Ser Glu Val Gln Leu Val Glu Ser Gly Gly
145                 150                 155                 160

Gly Leu Val Gln Pro Gly Gly Ser Leu Arg Leu Ser Cys Ala Ala Ser
                165                 170                 175

Gly Phe Thr Leu Arg Asn Tyr Trp Met Ser Trp Val Arg Gln Ala Pro
            180                 185                 190

Gly Lys Gly Leu Glu Trp Val Ala Asn Ile Asn Gln Asp Gly Ser Glu
        195                 200                 205

Lys Tyr Tyr Val Asp Ser Val Glu Gly Arg Phe Thr Ile Ser Arg Asp
    210                 215                 220

Asn Ala Lys Lys Ser Leu Trp Leu Gln Met Ser Ser Leu Arg Val Glu
225                 230                 235                 240

Asp Thr Ala Val Tyr Tyr Cys Ala Arg Asp Pro Ile Glu Ser Arg Phe
```

```
            245                 250                 255

Asp Tyr Trp Gly Gln Gly Thr Leu Val Thr Val Ser Ser
            260                 265


<210> SEQ ID NO 130
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Ala Trp Val Trp Thr Leu Leu Phe Leu Met Ala Ala Ala Gln Ser
1               5                   10                  15

Ile Gln Ala Ser Ser Glu Leu Thr Gln Pro Pro Ser Val Ser Val Ser
            20                  25                  30

Pro Gly Gln Thr Ala Arg Ile Thr Cys Ser Gly Asp Ala Leu Pro Arg
        35                  40                  45

Lys Tyr Ala Tyr Trp Tyr Gln Gln Lys Ser Gly Gln Ala Pro Val Leu
    50                  55                  60

Val Ile Tyr Glu Asp Ser Lys Arg Pro Ser Gly Ile Pro Glu Arg Phe
65                  70                  75                  80

Ser Gly Ser Asn Ser Gly Thr Met Ala Thr Leu Thr Ile Ser Gly Ala
                85                  90                  95

Gln Val Glu Asp Glu Ala Ala Tyr Tyr Cys Tyr Ser Thr Asp Ser Ser
            100                 105                 110

Ala Asn His Arg Val Phe Gly Gly Gly Thr Lys Leu Thr Val Leu Gly
        115                 120                 125

Gly Ser Glu Gly Lys Ser Ser Gly Ser Gly Ser Glu Ser Lys Ser Thr
    130                 135                 140

Gly Gly Ser Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Thr Ile Tyr Ala Met Thr Trp Val Arg Gln Ala Pro Gly Lys Gly Leu
            180                 185                 190

Glu Trp Val Ser Gly Ile Ser Val Ser Gly Ile Arg Thr Tyr Tyr Ala
        195                 200                 205

Asp Ser Val Lys Gly Arg Phe Thr Ile Ser Arg Asp Asn Ser Lys Asn
    210                 215                 220

Thr Leu Phe Leu Gln Met Asn Ser Leu Ser Ala Glu Asp Thr Ala Val
225                 230                 235                 240

Tyr Tyr Cys Ala Lys Gly Leu Ser Ser Gly Asp Arg Asp Ala Ser Asp
                245                 250                 255

Ile Trp Gly Gln Gly Thr Met Val Thr Val Ser Ser
            260                 265


<210> SEQ ID NO 131
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Met Ala Trp Val Trp Thr Leu Leu Phe Leu Met Ala Ala Ala Gln Ser
```

```
1               5                   10                  15

Ile Gln Ala Glu Ile Val Met Thr Gln Ser Pro Leu Ser Leu Pro Val
            20                  25                  30

Thr Pro Gly Lys Pro Ala Ser Ile Ser Cys Arg Ser Ser Gln Ser Leu
        35                  40                  45

Glu Tyr Ser Asp Gly Asn Thr Tyr Leu Asn Trp Phe Gln Gln Arg Pro
    50                  55                  60

Gly Gln Ser Pro Arg Arg Leu Ile Tyr Lys Val Ser Asn Arg Asp Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Met Gln Gly Thr His Trp Pro Pro Thr Phe Gly Gly Gly Thr Lys Val
        115                 120                 125

Asp Ile Lys Gly Gly Ser Glu Gly Lys Ser Ser Gly Ser Gly Ser Glu
    130                 135                 140

Ser Lys Ser Thr Gly Gly Ser Glu Val Gln Leu Val Glu Ser Gly Gly
145                 150                 155                 160

Gly Leu Val Gln Pro Gly Gly Ser Leu Arg Leu Ser Cys Ala Ala Ser
                165                 170                 175

Gly Phe Ile Phe Ser Thr Tyr Trp Met Ser Trp Val Arg Gln Ala Pro
            180                 185                 190

Gly Lys Gly Leu Glu Trp Val Ala Asn Ile Asn Pro Asp Gly Asn Glu
        195                 200                 205

Lys Tyr Tyr Val Asp Ser Val Glu Gly Arg Phe Thr Ile Ser Arg Asp
    210                 215                 220

Asn Ala Gln Asp Ser Leu Tyr Leu Gln Met Asn Ser Leu Arg Ala Glu
225                 230                 235                 240

Asp Thr Ala Val Tyr Tyr Cys Ala Arg Asp Pro Ile Ser Ala Arg Phe
                245                 250                 255

Asp Phe Trp Gly Gln Gly Thr Leu Val Thr Val Ser Ser
            260                 265


<210> SEQ ID NO 132
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Ala Trp Val Trp Thr Leu Leu Phe Leu Met Ala Ala Ala Gln Ser
1               5                   10                  15

Ile Gln Ala Ser Tyr Glu Leu Thr Gln Pro Pro Ser Val Ser Val Ser
            20                  25                  30

Pro Gly Gln Thr Ala Ser Ile Thr Cys Ser Gly Asp Lys Leu Gly Asp
        35                  40                  45

Glu Phe Ala Ser Trp Tyr Gln Gln Lys Pro Gly Gln Ser Pro Val Val
    50                  55                  60

Val Ile Tyr Gln Asp Thr Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95
```

```
Gln Ala Met Asp Glu Ala Asp Tyr Tyr Cys Gln Ala Trp Asp Ser Asn
            100                 105                 110

Thr Ala Val Phe Gly Gly Gly Thr Lys Leu Thr Val Leu Gly Gly Ser
        115                 120                 125

Glu Gly Lys Ser Ser Gly Ser Gly Ser Glu Ser Lys Ser Thr Gly Gly
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Asn Trp Val Arg Gln Ala Pro Gly Lys Gly Leu Glu Trp
            180                 185                 190

Val Ser Thr Ile Ser Gly Ser Gly Gly Ser Ser Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Asn Pro Ser Gly Thr Phe Trp Asn Asp Ala Phe Asp Ile Trp
                245                 250                 255

Gly Gln Gly Thr Met Val Thr Val Ser Ser
            260                 265


<210> SEQ ID NO 133
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Ala Trp Val Trp Thr Leu Leu Phe Leu Met Ala Ala Ala Gln Ser
1               5                   10                  15

Ile Gln Ala Ser Tyr Glu Leu Thr Gln Pro Pro Ser Val Ser Val Ser
            20                  25                  30

Pro Gly Gln Thr Ala Arg Ile Thr Cys Ser Gly Asp Ala Leu Pro Lys
        35                  40                  45

Lys Tyr Ala Tyr Trp Tyr Gln Gln Lys Ser Gly Gln Ala Pro Val Leu
    50                  55                  60

Val Ile Tyr Glu Asp Ser Lys Arg Pro Ser Gly Ile Pro Glu Arg Phe
65                  70                  75                  80

Ser Ala Ser Ser Ser Gly Thr Met Ala Thr Leu Thr Ile Ser Gly Ala
                85                  90                  95

Gln Val Glu Asp Glu Ala Asp Tyr Tyr Cys Tyr Ser Ala Asp Ser Ser
            100                 105                 110

Gly Ser His Trp Val Phe Gly Gly Gly Thr Lys Leu Thr Val Leu Gly
        115                 120                 125

Gly Ser Glu Gly Lys Ser Ser Gly Ser Gly Ser Glu Ser Lys Ser Thr
    130                 135                 140

Gly Gly Ser Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Asn Asn Tyr Ala Met Asn Trp Val Arg Gln Ala Pro Gly Lys Gly Leu
            180                 185                 190
```

```
Glu Trp Val Ser Val Ile Ser Gly Asn Gly Gly Ser Ile His Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala Thr Pro Arg Gly Tyr Thr Gly Tyr Asp Gly Asp Ala
                245                 250                 255

Phe Asp Phe Trp Gly Gln Gly Thr Met Val Thr Val Ser Ser
            260                 265                 270


<210> SEQ ID NO 134
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Ala Trp Val Trp Thr Leu Leu Phe Leu Met Ala Ala Ala Gln Ser
1               5                   10                  15

Ile Gln Ala Ser Tyr Glu Leu Thr Gln Pro Pro Ser Val Ser Val Ser
            20                  25                  30

Pro Gly Gln Thr Ala Arg Ile Thr Cys Ser Gly Asp Ala Leu Pro Lys
        35                  40                  45

Lys Tyr Ala Tyr Trp Tyr Gln Lys Lys Ser Gly Gln Ala Pro Val Leu
    50                  55                  60

Val Ile His Glu Asp Ser Lys Arg Pro Ser Gly Ile Pro Glu Arg Phe
65                  70                  75                  80

Ser Gly Ser Ser Ser Gly Thr Met Ala Thr Leu Thr Ile Ser Gly Ala
                85                  90                  95

Gln Val Glu Asp Glu Ala Asp Tyr Tyr Cys Phe Ser Thr Asp Arg Ser
            100                 105                 110

Gly Asn His Val Val Phe Gly Gly Gly Thr Lys Leu Thr Val Leu Gly
        115                 120                 125

Gly Ser Glu Gly Lys Ser Ser Gly Ser Gly Ser Glu Ser Lys Ser Thr
    130                 135                 140

Gly Gly Ser Glu Val Gln Leu Val Glu Ser Gly Gly Asp Leu Val Gln
145                 150                 155                 160

Pro Gly Gly Ser Leu Arg Leu Ser Cys Glu Ala Ser Gly Phe Thr Phe
                165                 170                 175

Ser Asn Tyr Gly Met Asn Trp Val Arg Gln Ala Pro Gly Lys Gly Leu
            180                 185                 190

Glu Trp Val Ser Gly Ile Ser Gly Ser Gly Gly Thr Thr Tyr Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala Asn Leu Leu Leu Trp Leu Gly Tyr His Gly Asp Gly
                245                 250                 255

Phe Asp Leu Trp Gly Gln Gly Thr Met Val Thr Val Ser Ser
            260                 265                 270
```

<210> SEQ ID NO 135
<211> LENGTH: 268
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 135

Met Ala Trp Val Trp Thr Leu Leu Phe Leu Met Ala Ala Ala Gln Ser
1 5 10 15

Ile Gln Ala Gln Ser Ala Leu Thr Gln Pro Pro Ser Val Ser Glu Ala
20 25 30

Pro Arg Gln Arg Val Thr Ile Ser Cys Ser Gly Ser Ala Ser Asn Ile
35 40 45

Gly Asn Asn Gly Val Asn Trp Tyr Gln Gln Leu Pro Gly Lys Thr Pro
50 55 60

Lys Leu Leu Ile Tyr Asn Asp Asp Leu Leu Pro Ser Gly Val Ser Asp
65 70 75 80

Arg Phe Ser Gly Ser Lys Ser Gly Thr Ser Ala Ser Leu Ala Ile Ser
85 90 95

Gly Leu Gln Ser Glu Asp Glu Ala Asp Tyr Phe Cys Ala Ala Trp Asp
100 105 110

Asp Ser Leu Asn Gly Leu Val Phe Gly Gly Gly Thr Lys Leu Thr Val
115 120 125

Leu Gly Gly Ser Glu Gly Lys Ser Ser Gly Ser Gly Ser Glu Ser Lys
130 135 140

Ser Thr Gly Gly Ser Gln Val Gln Leu Gln Gln Ser Gly Pro Gly Leu
145 150 155 160

Val Lys Pro Ser Gln Thr Leu Ser Leu Thr Cys Ala Ile Ser Gly Asp
165 170 175

Ser Val Ser Ser Lys Ser Gly Ala Trp Asn Trp Ile Arg Gln Ser Pro
180 185 190

Ser Arg Gly Leu Glu Trp Leu Gly Arg Thr Tyr Tyr Arg Ser Lys Trp
195 200 205

Tyr Asn Glu Tyr Ala Val Ser Val Lys Ser Arg Ile Thr Ile Asn Pro
210 215 220

Asp Thr Ser Lys Asn Gln Phe Ser Leu Gln Leu Asn Ser Val Thr Pro
225 230 235 240

Glu Asp Thr Ala Val Tyr Tyr Cys Thr Arg Val Asp Thr Asp Phe Asp
245 250 255

Tyr Trp Gly Gln Gly Thr Leu Val Thr Val Ser Ser
260 265

<210> SEQ ID NO 136
<211> LENGTH: 268
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 136

Met Ala Trp Val Trp Thr Leu Leu Phe Leu Met Ala Ala Ala Gln Ser
1 5 10 15

Ile Gln Ala Ser Tyr Glu Leu Thr Gln Pro Pro Ser Val Ser Val Ser
20 25 30

Pro Gly Gln Thr Ala Ser Ile Thr Cys Ser Gly His Lys Leu Gly Asp 35 40 45

Lys Tyr Ala Ser Trp Tyr Gln Gln Lys Pro Gly Gln Ser Pro Val Leu
50 55 60

Val Ile Tyr Gln Asp Ser Lys Arg Pro Ser Gly Ile Pro Glu Arg Phe
65 70 75 80

Ser Gly Ser Asn Ser Gly Asn Thr Ala Thr Leu Thr Ile Ser Gly Thr
85 90 95

Gln Ala Met Asp Glu Ala Asp Tyr Tyr Cys Gln Ala Trp Asp Ser Ile
100 105 110

Thr Ala Trp Val Phe Gly Gly Gly Thr Lys Leu Thr Val Leu Gly Gly
115 120 125

Ser Glu Gly Lys Ser Ser Gly Ser Gly Ser Glu Ser Lys Ser Thr Gly
130 135 140

Gly Ser Glu Val Gln Leu Val Glu Ser Gly Gly Gly Leu Val Gln Pro
145 150 155 160

Gly Gly Ser Leu Arg Leu Ser Cys Ala Ala Ser Gly Phe Thr Phe Ser
165 170 175

Arg His Thr Met Asn Trp Val Arg Gln Ala Pro Gly Lys Gly Leu Glu
180 185 190

Trp Val Ser Ser Ile Ser Gly Ser Gly Gly Ser Thr Tyr Tyr Ala Asp
195 200 205

Ser Val Lys Gly Arg Phe Thr Val Ser Arg Asp Asn Ser Lys Asn Thr
210 215 220

Leu Tyr Leu Gln Met Asn Ser Leu Arg Ala Glu Asp Thr Ala Val Tyr
225 230 235 240

Tyr Cys Ala Lys Glu Ser Tyr Asp Ser Ser Gly Val Trp Tyr Phe Asp
245 250 255

Leu Trp Gly Arg Gly Thr Leu Val Thr Val Ser Ser
260 265

<210> SEQ ID NO 137
<211> LENGTH: 265
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

Met Ala Trp Val Trp Thr Leu Leu Phe Leu Met Ala Ala Ala Gln Ser
1 5 10 15

Ile Gln Ala Ser Tyr Glu Leu Met Gln Pro Pro Ser Val Ser Val Ser
20 25 30

Pro Gly Gln Thr Ala Arg Ile Thr Cys Ser Gly Asp Ala Leu Pro Arg
35 40 45

Gln Tyr Ala Tyr Trp Tyr Gln Gln Lys Pro Gly Gln Ala Pro Val Leu
50 55 60

Val Ile Tyr Lys Asp Ser Glu Arg Pro Ser Gly Ile Pro Glu Arg Phe
65 70 75 80

Ser Gly Ser Ser Ser Gly Thr Thr Val Thr Leu Thr Ile Ser Gly Val
85 90 95

Gln Ala Glu Asp Glu Ala Asp Tyr Tyr Cys Gln Ser Ala Asp Arg Thr
100 105 110

Gly Ile Tyr Val Leu Phe Gly Gly Gly Thr Lys Leu Thr Val Leu Gly
115 120 125

Gly Ser Glu Gly Lys Ser Ser Gly Ser Gly Ser Glu Ser Lys Ser Thr
130 135 140

Gly Gly Ser Gln Val Gln Leu Gln Glu Ser Gly Pro Gly Leu Val Lys
145 150 155 160

Pro Ser Glu Thr Leu Ser Leu Thr Cys Thr Val Ser Ser Gly Ser Ile
165 170 175

Ser Ser Tyr Tyr Trp Asn Trp Ile Arg Gln Pro Ala Gly Lys Gly Leu
180 185 190

Glu Trp Ile Gly Arg Ile Tyr Thr Ser Gly Thr Thr His Tyr Asn Pro
195 200 205

Ser Leu Lys Ser Arg Val Thr Met Ser Ile Asp Thr Ser Lys Asn Gln
210 215 220

Phe Ser Leu Lys Leu Ser Ser Val Thr Ala Ala Asp Thr Ala Val Tyr
225 230 235 240

Tyr Cys Ala Arg Glu Ile Arg Glu Leu Arg Gly Phe Asp Tyr Trp Gly
245 250 255

Gln Gly Thr Leu Val Thr Val Ser Ser
260 265

<210> SEQ ID NO 138
<211> LENGTH: 265
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 138

Met Ala Trp Val Trp Thr Leu Leu Phe Leu Met Ala Ala Ala Gln Ser
1 5 10 15

Ile Gln Ala Ser Tyr Glu Leu Thr Gln Pro Pro Ser Val Ser Val Ser
20 25 30

Pro Gly Gln Thr Ala Arg Ile Thr Cys Ser Gly Asp Ala Leu Pro Arg
35 40 45

Gln Tyr Ala Tyr Trp Tyr Gln Gln Lys Pro Gly Gln Ala Pro Val Leu
50 55 60

Val Ile Tyr Lys Asp Ser Glu Arg Pro Ser Gly Ile Pro Glu Arg Phe
65 70 75 80

Ser Gly Ser Ser Ser Gly Thr Thr Val Thr Leu Thr Ile Ser Gly Val
85 90 95

Gln Ala Glu Asp Glu Ala Asp Tyr Tyr Cys Gln Ser Ala Asp Arg Thr
100 105 110

Gly Ile Tyr Val Leu Phe Gly Gly Gly Thr Lys Leu Thr Val Leu Gly
115 120 125

Gly Ser Glu Gly Lys Ser Ser Gly Ser Gly Ser Glu Ser Lys Ser Thr
130 135 140

Gly Gly Ser Gln Val Gln Leu Gln Glu Ser Gly Pro Gly Leu Val Lys
145 150 155 160

Pro Ser Glu Thr Leu Ser Leu Thr Cys Thr Val Ser Ser Gly Ser Ile
165 170 175

Ser Ser Tyr Tyr Trp Asn Trp Ile Arg Gln Pro Ala Gly Lys Gly Leu
180 185 190

Glu Trp Ile Gly Arg Ile Tyr Thr Ser Gly Thr Thr His Tyr Asn Pro
195 200 205

Ser Leu Lys Ser Arg Val Thr Met Ser Ile Asp Thr Ser Lys Asn Gln
210 215 220

```
Phe Ser Leu Lys Leu Ser Ser Val Thr Ala Ala Asp Thr Ala Val Tyr
225                 230                 235                 240

Tyr Cys Ala Arg Glu Ile Arg Glu Leu Arg Gly Phe Asp Tyr Trp Gly
                245                 250                 255

Gln Gly Thr Leu Val Thr Val Ser Ser
            260                 265


<210> SEQ ID NO 139
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Ala Trp Val Trp Thr Leu Leu Phe Leu Met Ala Ala Ala Gln Ser
1               5                   10                  15

Ile Gln Ala Ser Tyr Glu Leu Thr Gln Pro Pro Ser Val Ser Val Ser
            20                  25                  30

Pro Gly Gln Thr Ala Ser Ile Thr Cys Ser Gly His Lys Leu Gly Asp
        35                  40                  45

Lys Tyr Ala Ser Trp Tyr Gln Gln Lys Pro Gly Gln Ser Pro Val Leu
    50                  55                  60

Val Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Ser Ile
            100                 105                 110

Thr Ala Trp Val Phe Gly Gly Gly Thr Lys Leu Thr Val Leu Gly Gly
        115                 120                 125

Ser Glu Gly Lys Ser Ser Gly Ser Gly Ser Glu Ser Lys Ser Thr Gly
    130                 135                 140

Gly Ser Glu Val Gln Leu Val Glu Ser Gly Gly Gly Leu Val Gln Pro
145                 150                 155                 160

Gly Gly Ser Leu Arg Leu Ser Cys Ala Ala Ser Gly Phe Thr Phe Ser
                165                 170                 175

Arg His Thr Met Asn Trp Val Arg Gln Ala Pro Gly Lys Gly Leu Glu
            180                 185                 190

Trp Val Ser Ser Ile Ser Gly Ser Gly Gly Ser Thr Tyr Tyr Ala Asp
        195                 200                 205

Ser Val Lys Gly Arg Phe Thr Val Ser Arg Asp Asn Ser Lys Asn Thr
    210                 215                 220

Leu Tyr Leu Gln Met Asn Ser Leu Arg Ala Glu Asp Thr Ala Val Tyr
225                 230                 235                 240

Tyr Cys Ala Lys Glu Ser Tyr Asp Ser Ser Gly Val Trp Tyr Phe Asp
                245                 250                 255

Leu Trp Gly Lys Gly Thr Thr Val Thr Val Ser Ser
            260                 265


<210> SEQ ID NO 140
<211> LENGTH: 273
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 140

Met Ala Trp Val Trp Thr Leu Leu Phe Leu Met Ala Ala Ala Gln Ser
1 5 10 15

Ile Gln Ala Ser Tyr Glu Leu Thr Gln Pro Pro Ser Val Ser Val Ser
20 25 30

Pro Gly Gln Thr Ala Ser Ile Thr Cys Ser Gly Asp Lys Leu Gly Asp
35 40 45

Lys Phe Ala Ser Trp Tyr Gln Gln Lys Pro Gly Gln Ser Pro Val Leu
50 55 60

Val Ile Phe Gln Asp Ser Lys Arg Pro Ser Gly Ile Pro Glu Arg Phe
65 70 75 80

Ser Gly Ser Asn Ser Gly Asn Thr Ala Thr Leu Thr Ile Ser Gly Thr
85 90 95

Gln Ala Met Asp Glu Ala Asp Tyr Phe Cys Gln Ala Trp Asp Ser Thr
100 105 110

Thr Ala Trp Val Phe Gly Gly Gly Thr Lys Leu Thr Val Leu Gly Gly
115 120 125

Ser Glu Gly Lys Ser Ser Gly Ser Gly Ser Glu Ser Lys Ser Thr Gly
130 135 140

Gly Ser Glu Val Gln Leu Val Glu Ser Gly Gly Gly Leu Val Gln Pro
145 150 155 160

Gly Gly Ser Leu Arg Leu Ser Cys Ala Ala Ser Gly Phe Thr Phe Asn
165 170 175

Ser Tyr Asn Met Asn Trp Val Arg Gln Ala Pro Gly Lys Gly Leu Glu
180 185 190

Trp Val Ser Tyr Ile Ser Ser Ser Gly Tyr Thr Ile Tyr Tyr Ala Asp
195 200 205

Ser Val Glu Gly Arg Phe Thr Ile Ser Arg Asp Asn Ala Lys Asn Ser
210 215 220

Leu Tyr Leu Gln Met Asp Ser Leu Arg Asp Glu Asp Thr Ala Ile Tyr
225 230 235 240

Tyr Cys Ala Arg Asp Arg Tyr Asn Tyr Asp Asn Gly Gly Tyr His Tyr
245 250 255

Tyr Thr Gly Met Asp Val Trp Gly Gln Gly Thr Met Val Thr Val Ser
260 265 270

Ser

<210> SEQ ID NO 141
<211> LENGTH: 267
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 141

Met Ala Trp Val Trp Thr Leu Leu Phe Leu Met Ala Ala Ala Gln Ser
1 5 10 15

Ile Gln Ala Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Gly Tyr Trp Ile Glu Trp Val Arg Gln Arg Pro Gly Gln Gly Leu
50 55 60

Glu Trp Met Gly Glu Ile Leu Pro Gly Gly Gly Asp Thr Asn Tyr Asn
65 70 75 80

Gln Lys Phe Gln Gly Lys Val Thr Phe Thr Arg Asp Thr Ser Thr Ser
85 90 95

Thr Ala Tyr Met Glu Leu Ser Ser Leu Arg Ser Glu Asp Thr Ala Val
100 105 110

Tyr Tyr Cys Ala Arg Arg Val Pro Val Tyr Phe Asp Tyr Trp Gly Gln
115 120 125

Gly Thr Leu Val Thr Val Ser Ser Gly Gly Ser Glu Gly Lys Ser Ser
130 135 140

Gly Ser Gly Ser Glu Ser Lys Ser Thr Gly Gly Ser Asp Ile Val Leu
145 150 155 160

Thr Gln Ser Pro Asp Ser Leu Ala Val Ser Leu Gly Glu Arg Ala Thr
165 170 175

Ile Asn Cys Lys Ala Ser Gln Ser Val Asp Tyr Asp Gly Asp Ser Phe
180 185 190

Leu Asn Trp Tyr Gln Gln Lys Pro Gly Gln Pro Pro Lys Leu Leu Ile
195 200 205

Tyr Ala Ala Ser Asn Leu Glu Ser Gly Val Pro Asp Arg Phe Ser Gly
210 215 220

Ser Gly Ser Gly Thr Asp Phe Thr Leu Thr Ile Ser Ser Leu Gln Ala
225 230 235 240

Glu Asp Val Ala Val Tyr Tyr Cys Gln Gln Ser Asn Glu Asp Pro Leu
245 250 255

Thr Phe Gly Gly Gly Thr Lys Val Glu Ile Lys
260 265

<210> SEQ ID NO 142
<211> LENGTH: 267
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 142

Met Ala Trp Val Trp Thr Leu Leu Phe Leu Met Ala Ala Ala Gln Ser
1 5 10 15

Ile Gln Ala Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Gly Tyr Trp Ile Glu Trp Val Arg Gln Arg Pro Gly Gln Gly Leu
50 55 60

Glu Trp Met Gly Glu Ile Leu Pro Gly Gly Gly Asp Thr Asn Tyr Asn
65 70 75 80

Gln Lys Phe Gln Gly Lys Val Thr Phe Thr Arg Asp Thr Ser Thr Ser
85 90 95

Thr Ala Tyr Met Glu Leu Ser Ser Leu Arg Ser Glu Asp Thr Ala Val
100 105 110

Tyr Tyr Cys Ala Arg Arg Val Pro Val Tyr Phe Asp Tyr Trp Gly Gln
115 120 125

Gly Thr Leu Val Thr Val Ser Ser Gly Gly Ser Glu Gly Lys Ser Ser
130 135 140

Gly Ser Gly Ser Glu Ser Lys Ser Thr Gly Gly Ser Asp Ile Val Leu

```
145                 150                 155                 160

Thr Gln Ser Pro Asp Ser Leu Ala Val Ser Leu Gly Glu Arg Ala Thr
                165                 170                 175

Ile Asn Cys Lys Ala Ser Gln Ser Val Asp Tyr Glu Gly Asp Ser Phe
            180                 185                 190

Leu Asn Trp Tyr Gln Gln Lys Pro Gly Gln Pro Pro Lys Leu Leu Ile
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Gln Gln Ser Asn Glu Asp Pro Leu
                245                 250                 255

Thr Phe Gly Gly Gly Thr Lys Val Glu Ile Lys
            260                 265


<210> SEQ ID NO 143
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Trp Ile Glu Trp Val Arg Gln Arg Pro Gly Gln Gly Leu
    50                  55                  60

Glu Trp Met Gly Glu Ile Leu Pro Gly Gly Gly Asp Thr Asn Tyr Asn
65                  70                  75                  80

Gln Lys Phe Gln Gly Lys Val Thr Phe Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Gln Ser Val Asp Tyr Asp Gly Asp Ser Phe
            180                 185                 190

Leu Asn Trp Tyr Gln Gln Lys Pro Gly Gln Pro Pro Lys Leu Leu Ile
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240
```

Glu Asp Val Ala Val Tyr Tyr Cys Gln Gln Ser Asn Glu Asp Pro Leu
                245                 250                 255

Thr Phe Gly Gly Gly Thr Lys Val Glu Ile Lys
            260                 265

<210> SEQ ID NO 144
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Trp Ile Glu Trp Val Arg Gln Arg Pro Gly Gln Gly Leu
    50                  55                  60

Glu Trp Met Gly Glu Ile Leu Pro Gly Gly Gly Asp Thr Asn Tyr Asn
65                  70                  75                  80

Gln Lys Phe Gln Gly Lys Val Thr Phe Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Gln Ser Val Asp Tyr Glu Gly Asp Ser Phe
            180                 185                 190

Leu Asn Trp Tyr Gln Gln Lys Pro Gly Gln Pro Pro Lys Leu Leu Ile
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Gln Gln Ser Asn Glu Asp Pro Leu
                245                 250                 255

Thr Phe Gly Gly Gly Thr Lys Val Glu Ile Lys
            260                 265

<210> SEQ ID NO 145
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Ala Trp Val Trp Thr Leu Leu Phe Leu Met Ala Ala Ala Gln Ser
1 5 10 15

Ile Gln Ala Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Gly Tyr Trp Ile Glu Trp Val Arg Gln Ala Pro Gly Gln Gly Leu
50 55 60

Glu Trp Met Gly Glu Ile Leu Pro Gly Gly Gly Asp Thr Asn Tyr Asn
65 70 75 80

Gln Lys Phe Gln Gly Lys Val Thr Phe Thr Arg Asp Thr Ser Thr Ser
85 90 95

Thr Ala Tyr Met Glu Leu Ser Ser Leu Arg Ser Glu Asp Thr Ala Val
100 105 110

Tyr Tyr Cys Ala Arg Arg Val Pro Val Tyr Phe Asp Tyr Trp Gly Gln
115 120 125

Gly Thr Leu Val Thr Val Ser Ser Gly Gly Ser Glu Gly Lys Ser Ser
130 135 140

Gly Ser Gly Ser Glu Ser Lys Ser Thr Gly Gly Ser Asp Ile Val Leu
145 150 155 160

Thr Gln Ser Pro Asp Ser Leu Ala Val Ser Leu Gly Glu Arg Ala Thr
165 170 175

Ile Asn Cys Lys Ala Ser Gln Ser Val Asp Tyr Glu Gly Asp Ser Phe
180 185 190

Leu Asn Trp Tyr Gln Gln Lys Pro Gly Gln Pro Pro Lys Leu Leu Ile
195 200 205

Tyr Ala Ala Ser Asn Leu Glu Ser Gly Val Pro Asp Arg Phe Ser Gly
210 215 220

Ser Gly Ser Gly Thr Asp Phe Thr Leu Thr Ile Ser Ser Leu Gln Ala
225 230 235 240

Glu Asp Val Ala Val Tyr Tyr Cys Gln Gln Ser Asn Glu Asp Pro Leu
245 250 255

Thr Phe Gly Gly Gly Thr Lys Val Glu Ile Lys
260 265

<210> SEQ ID NO 146
<211> LENGTH: 267
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 146

Met Ala Trp Val Trp Thr Leu Leu Phe Leu Met Ala Ala Ala Gln Ser
1 5 10 15

Ile Gln Ala Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Gly Tyr Trp Ile Glu Trp Val Arg Gln Ala Pro Gly Gln Gly Leu
50 55 60

Glu Trp Met Gly Glu Ile Leu Pro Gly Gly Gly Asp Thr Asn Tyr Asn
65 70 75 80

Gln Lys Phe Gln Gly Lys Val Thr Phe Thr Arg Asp Thr Ser Thr Ser
85 90 95

```
Thr Val Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Gln Ser Val Asp Tyr Asp Gly Asp Ser Phe
            180                 185                 190

Leu Asn Trp Tyr Gln Gln Lys Pro Gly Gln Pro Pro Lys Leu Leu Ile
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Gln Gln Ser Asn Glu Asp Pro Leu
                245                 250                 255

Thr Phe Gly Gly Gly Thr Lys Val Glu Ile Lys
            260                 265
```

<210> SEQ ID NO 147
<211> LENGTH: 267
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 147

```
Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Met Lys
            20                  25                  30

Pro Gly Ala Ser Val Lys Ile Ser Cys Lys Ala Ser Gly Tyr Thr Phe
        35                  40                  45

Thr Gly Tyr Trp Ile Glu Trp Val Arg Gln Arg Pro Gly Gln Gly Leu
    50                  55                  60

Glu Trp Met Gly Glu Ile Leu Pro Gly Gly Gly Asp Thr Asn Tyr Asn
65                  70                  75                  80

Gln Lys Phe Gln Gly Lys Val Thr Phe Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Met
145                 150                 155                 160

Thr Gln Ser Pro Asp Ser Leu Ala Val Ser Leu Gly Glu Arg Ala Thr
                165                 170                 175

Ile Asn Cys Lys Ala Ser Gln Ser Val Asp Tyr Asp Gly Asp Ser Phe
```

```
            180                 185                 190

Leu Asn Trp Tyr Gln Gln Lys Pro Gly Gln Pro Pro Lys Leu Phe Ile
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Val Gln Ala
225                 230                 235                 240

Glu Asp Ala Ala Val Tyr Tyr Cys Gln Gln Ser Asn Glu Asp Pro Leu
                245                 250                 255

Thr Phe Gly Gly Gly Thr Lys Val Glu Ile Lys
            260                 265


<210> SEQ ID NO 148
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Met Lys
            20                  25                  30

Pro Gly Ala Ser Val Lys Ile Ser Cys Lys Ala Ser Gly Tyr Thr Phe
        35                  40                  45

Thr Gly Tyr Trp Ile Glu Trp Val Arg Gln Arg Pro Gly Gln Gly Leu
    50                  55                  60

Glu Trp Met Gly Glu Ile Leu Pro Gly Gly Gly Asp Thr Asn Tyr Asn
65                  70                  75                  80

Gln Lys Phe Gln Gly Lys Val Thr Phe Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Gln Ser Val Asp Tyr Lys Gly Asp Ser Phe
            180                 185                 190

Leu Asn Trp Tyr Gln Gln Lys Pro Gly Gln Pro Pro Lys Leu Leu Ile
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Gln Gln Ser Asn Glu Asp Pro Leu
                245                 250                 255

Thr Phe Gly Gly Gly Thr Lys Val Glu Ile Lys
            260                 265
```

<210> SEQ ID NO 149
<211> LENGTH: 271
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 149

Met Ala Trp Val Trp Thr Leu Leu Phe Leu Met Ala Ala Ala Gln Ser
1 5 10 15

Ile Gln Ala Glu Val Gln Leu Gln Glu Ser Gly Pro Gly Leu Val Lys
20 25 30

Pro Ser Glu Thr Leu Ser Leu Thr Cys Ser Val Ser Gly Gly Ser Ile
35 40 45

Ser Gly Ser Ser Tyr Tyr Trp Gly Trp Ile Arg Gln Pro Pro Gly Lys
50 55 60

Gly Leu Glu Trp Ile Gly Ser Ile Tyr Tyr Ser Gly Ser Thr Tyr Tyr
65 70 75 80

Asn Pro Ser Leu Lys Ser Arg Val Thr Ile Ser Val Asp Thr Ser Lys
85 90 95

Lys Gln Phe Ser Leu Lys Leu Arg Ser Val Thr Ala Ala Asp Thr Ala
100 105 110

Val Tyr Tyr Cys Ala Arg Glu Glu Asp Ser Gly Ser Tyr Tyr Val Gly
115 120 125

Ala Phe Asp Ile Trp Gly Gln Gly Thr Met Val Thr Val Ser Ser Gly
130 135 140

Gly Ser Glu Gly Lys Ser Ser Gly Ser Gly Ser Glu Ser Lys Ser Thr
145 150 155 160

Gly Gly Ser Ser Ser Glu Leu Thr Gln Asp Pro Ala Val Ser Val Ala
165 170 175

Leu Gly Gln Thr Val Arg Ile Arg Cys Gln Gly Asp Ser Leu Arg Lys
180 185 190

Tyr Tyr Gly Ser Trp Tyr Gln Gln Lys Pro Gly Gln Ala Pro Val Leu
195 200 205

Val Ile Tyr Gly Glu Thr Asn Arg Pro Ser Gly Ile Pro Asp Arg Phe
210 215 220

Ser Gly Ser Ser Ser Gly Asn Thr Ala Ser Leu Thr Ile Thr Gly Ala
225 230 235 240

Gln Ala Glu Asp Glu Ala Asp Tyr Tyr Cys Asn Ser Arg Asp Ser Ser
245 250 255

Gly Lys His Val Val Phe Gly Gly Gly Thr Lys Leu Thr Val Leu
260 265 270

<210> SEQ ID NO 150
<211> LENGTH: 271
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 150

Met Ala Trp Val Trp Thr Leu Leu Phe Leu Met Ala Ala Ala Gln Ser
1 5 10 15

Ile Gln Ala Gln Val Gln Leu Gln Glu Ser Gly Pro Gly Leu Val Lys
20 25 30

```
Pro Ser Glu Thr Leu Ser Leu Thr Cys Ser Val Ser Gly Gly Ser Ile
        35                  40                  45

Arg Ser Ser Thr Tyr Tyr Trp Gly Trp Ile Arg Gln Pro Pro Gly Lys
    50                  55                  60

Gly Leu Glu Trp Ile Gly Ser Ile Tyr Tyr Ser Gly Ser Thr Tyr Ser
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Ile Tyr Tyr Cys Ala Arg Glu Glu Asp Ser Gly Ser Tyr Tyr Val Gly
        115                 120                 125

Thr Phe Asp Ile Trp Gly Gln Gly Thr Met Val Thr Val Ser Ser Gly
    130                 135                 140

Gly Ser Glu Gly Lys Ser Ser Gly Ser Gly Ser Glu Ser Lys Ser Thr
145                 150                 155                 160

Gly Gly Ser Ser Ser Glu Leu Thr Gln Asp Pro Ala Val Ser Val Ala
                165                 170                 175

Leu Gly Gln Thr Val Arg Ile Thr Cys Gln Gly Asp Ser Leu Arg Asn
            180                 185                 190

Tyr Tyr Gly Ser Trp Tyr Gln Gln Lys Pro Gly Gln Ala Pro Val Leu
        195                 200                 205

Val Ile Tyr Gly Glu Lys Asn Arg Pro Ser Gly Ile Pro Asp Arg Phe
    210                 215                 220

Ser Gly Ser Ser Ser Gly Asn Thr Val Ser Leu Thr Ile Thr Gly Thr
225                 230                 235                 240

Gln Ala Glu Asp Glu Ala Asp Tyr Tyr Cys Asn Ser Arg Asp Ser Ser
                245                 250                 255

Gly Lys His Val Val Phe Gly Gly Gly Thr Lys Leu Thr Val Leu
            260                 265                 270


<210> SEQ ID NO 151
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Ala Trp Val Trp Thr Leu Leu Phe Leu Met Ala Ala Ala Gln Ser
1               5                   10                  15

Ile Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Leu
        35                  40                  45

Arg Asn Tyr Trp Met Ser Trp Val Arg Gln Ala Pro Gly Lys Gly Leu
    50                  55                  60

Glu Trp Val Ala Asn Ile Asn Gln Asp Gly Ser Glu Lys Tyr Tyr Val
65                  70                  75                  80

Asp Ser Val Glu Gly Arg Phe Thr Ile Ser Arg Asp Asn Ala Lys Lys
                85                  90                  95

Ser Leu Trp Leu Gln Met Ser Ser Leu Arg Val Glu Asp Thr Ala Val
            100                 105                 110

Tyr Tyr Cys Ala Arg Asp Pro Ile Glu Ser Arg Phe Asp Tyr Trp Gly
        115                 120                 125
```

```
Gln Gly Thr Leu Val Thr Val Ser Ser Gly Gly Ser Glu Gly Lys Ser
    130                 135                 140

Ser Gly Ser Gly Ser Glu Ser Lys Ser Thr Gly Gly Ser Asp Val Val
145                 150                 155                 160

Met Thr Gln Ser Pro Leu Ser Leu Pro Val Thr Leu Gly Gln Pro Ala
                165                 170                 175

Ser Ile Ser Cys Arg Ser Ser Gln Ser Leu Val Tyr Ser Asp Gly Asn
            180                 185                 190

Thr Tyr Leu Ser Trp Phe Gln Gln Arg Pro Gly Gln Ser Pro Arg Arg
        195                 200                 205

Leu Ile Tyr Lys Val Ser Asn Arg Asp Ser Gly Val Pro Asp Arg Phe
    210                 215                 220

Ser Gly Ser Gly Ser Gly Thr Asp Phe Thr Leu Lys Ile Ser Arg Val
225                 230                 235                 240

Glu Ala Glu Asp Val Gly Val Tyr Tyr Cys Met Gln Gly Thr His Trp
                245                 250                 255

Pro Pro Thr Phe Gly Gly Gly Thr Lys Val Glu Ile Lys
            260                 265


<210> SEQ ID NO 152
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Ala Trp Val Trp Thr Leu Leu Phe Leu Met Ala Ala Ala Gln Ser
1               5                   10                  15

Ile Gln Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Ile Tyr Ala Met Thr Trp Val Arg Gln Ala Pro Gly Lys Gly Leu
    50                  55                  60

Glu Trp Val Ser Gly Ile Ser Val Ser Gly Ile Arg Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Ser Ala Glu Asp Thr Ala Val
            100                 105                 110

Tyr Tyr Cys Ala Lys Gly Leu Ser Ser Gly Asp Arg Asp Ala Ser Asp
        115                 120                 125

Ile Trp Gly Gln Gly Thr Met Val Thr Val Ser Ser Gly Gly Ser Glu
    130                 135                 140

Gly Lys Ser Ser Gly Ser Gly Ser Glu Ser Lys Ser Thr Gly Gly Ser
145                 150                 155                 160

Ser Ser Glu Leu Thr Gln Pro Pro Ser Val Ser Val Ser Pro Gly Gln
                165                 170                 175

Thr Ala Arg Ile Thr Cys Ser Gly Asp Ala Leu Pro Arg Lys Tyr Ala
            180                 185                 190

Tyr Trp Tyr Gln Gln Lys Ser Gly Gln Ala Pro Val Leu Val Ile Tyr
        195                 200                 205

Glu Asp Ser Lys Arg Pro Ser Gly Ile Pro Glu Arg Phe Ser Gly Ser
```

210 215 220

Asn Ser Gly Thr Met Ala Thr Leu Thr Ile Ser Gly Ala Gln Val Glu
225 230 235 240

Asp Glu Ala Ala Tyr Tyr Cys Tyr Ser Thr Asp Ser Ser Ala Asn His
245 250 255

Arg Val Phe Gly Gly Gly Thr Lys Leu Thr Val Leu
260 265

<210> SEQ ID NO 153
<211> LENGTH: 269
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 153

Met Ala Trp Val Trp Thr Leu Leu Phe Leu Met Ala Ala Ala Gln Ser
1 5 10 15

Ile Gln Ala Glu Val Gln Leu Val Glu Ser Gly Gly Gly Leu Val Gln
20 25 30

Pro Gly Gly Ser Leu Arg Leu Ser Cys Ala Ala Ser Gly Phe Ile Phe
35 40 45

Ser Thr Tyr Trp Met Ser Trp Val Arg Gln Ala Pro Gly Lys Gly Leu
50 55 60

Glu Trp Val Ala Asn Ile Asn Pro Asp Gly Asn Glu Lys Tyr Tyr Val
65 70 75 80

Asp Ser Val Glu Gly Arg Phe Thr Ile Ser Arg Asp Asn Ala Gln Asp
85 90 95

Ser Leu Tyr Leu Gln Met Asn Ser Leu Arg Ala Glu Asp Thr Ala Val
100 105 110

Tyr Tyr Cys Ala Arg Asp Pro Ile Ser Ala Arg Phe Asp Phe Trp Gly
115 120 125

Gln Gly Thr Leu Val Thr Val Ser Ser Gly Gly Ser Glu Gly Lys Ser
130 135 140

Ser Gly Ser Gly Ser Glu Ser Lys Ser Thr Gly Gly Ser Glu Ile Val
145 150 155 160

Met Thr Gln Ser Pro Leu Ser Leu Pro Val Thr Pro Gly Lys Pro Ala
165 170 175

Ser Ile Ser Cys Arg Ser Ser Gln Ser Leu Glu Tyr Ser Asp Gly Asn
180 185 190

Thr Tyr Leu Asn Trp Phe Gln Gln Arg Pro Gly Gln Ser Pro Arg Arg
195 200 205

Leu Ile Tyr Lys Val Ser Asn Arg Asp Ser Gly Val Pro Asp Arg Phe
210 215 220

Ser Gly Ser Gly Ser Gly Thr Asp Phe Thr Leu Lys Ile Ser Arg Val
225 230 235 240

Glu Ala Glu Asp Val Gly Val Tyr Tyr Cys Met Gln Gly Thr His Trp
245 250 255

Pro Pro Thr Phe Gly Gly Gly Thr Lys Val Asp Ile Lys
260 265

<210> SEQ ID NO 154
<211> LENGTH: 266
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 154

Met Ala Trp Val Trp Thr Leu Leu Phe Leu Met Ala Ala Ala Gln Ser
1 5 10 15

Ile Gln Ala Glu Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Ser Ser Tyr Ala Met Asn Trp Val Arg Gln Ala Pro Gly Lys Gly Leu
50 55 60

Glu Trp Val Ser Thr Ile Ser Gly Ser Gly Gly Ser Ser Tyr Tyr Ala
65 70 75 80

Asp Ser Val Lys Gly Arg Phe Thr Ile Ser Arg Asp Asn Ser Lys Asn
85 90 95

Thr Leu Tyr Leu Gln Met Asn Ser Leu Arg Ala Glu Asp Thr Ala Val
100 105 110

Tyr Tyr Cys Ala Asn Pro Ser Gly Thr Phe Trp Asn Asp Ala Phe Asp
115 120 125

Ile Trp Gly Gln Gly Thr Met Val Thr Val Ser Ser Gly Gly Ser Glu
130 135 140

Gly Lys Ser Ser Gly Ser Gly Ser Glu Ser Lys Ser Thr Gly Gly Ser
145 150 155 160

Ser Tyr Glu Leu Thr Gln Pro Pro Ser Val Ser Val Ser Pro Gly Gln
165 170 175

Thr Ala Ser Ile Thr Cys Ser Gly Asp Lys Leu Gly Asp Glu Phe Ala
180 185 190

Ser Trp Tyr Gln Gln Lys Pro Gly Gln Ser Pro Val Val Val Ile Tyr
195 200 205

Gln Asp Thr Lys Arg Pro Ser Gly Ile Pro Glu Arg Phe Ser Gly Ser
210 215 220

Asn Ser Gly Asn Thr Ala Thr Leu Thr Ile Ser Gly Thr Gln Ala Met
225 230 235 240

Asp Glu Ala Asp Tyr Tyr Cys Gln Ala Trp Asp Ser Asn Thr Ala Val
245 250 255

Phe Gly Gly Gly Thr Lys Leu Thr Val Leu
260 265

<210> SEQ ID NO 155
<211> LENGTH: 270
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 155

Met Ala Trp Val Trp Thr Leu Leu Phe Leu Met Ala Ala Ala Gln Ser
1 5 10 15

Ile Gln Ala Glu Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Asn Asn Tyr Ala Met Asn Trp Val Arg Gln Ala Pro Gly Lys Gly Leu
50 55 60

```
Glu Trp Val Ser Val Ile Ser Gly Asn Gly Gly Ser Ile His Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Thr Pro Arg Gly Tyr Thr Gly Tyr Asp Gly Asp Ala
        115                 120                 125

Phe Asp Phe Trp Gly Gln Gly Thr Met Val Thr Val Ser Ser Gly Gly
    130                 135                 140

Ser Glu Gly Lys Ser Ser Gly Ser Gly Ser Glu Ser Lys Ser Thr Gly
145                 150                 155                 160

Gly Ser Ser Tyr Glu Leu Thr Gln Pro Pro Ser Val Ser Val Ser Pro
                165                 170                 175

Gly Gln Thr Ala Arg Ile Thr Cys Ser Gly Asp Ala Leu Pro Lys Lys
            180                 185                 190

Tyr Ala Tyr Trp Tyr Gln Gln Lys Ser Gly Gln Ala Pro Val Leu Val
        195                 200                 205

Ile Tyr Glu Asp Ser Lys Arg Pro Ser Gly Ile Pro Glu Arg Phe Ser
    210                 215                 220

Ala Ser Ser Ser Gly Thr Met Ala Thr Leu Thr Ile Ser Gly Ala Gln
225                 230                 235                 240

Val Glu Asp Glu Ala Asp Tyr Tyr Cys Tyr Ser Ala Asp Ser Ser Gly
                245                 250                 255

Ser His Trp Val Phe Gly Gly Gly Thr Lys Leu Thr Val Leu
            260                 265                 270
```

<210> SEQ ID NO 156
<211> LENGTH: 270
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

```
Met Ala Trp Val Trp Thr Leu Leu Phe Leu Met Ala Ala Ala Gln Ser
1               5                   10                  15

Ile Gln Ala Glu Val Gln Leu Val Glu Ser Gly Gly Asp Leu Val Gln
            20                  25                  30

Pro Gly Gly Ser Leu Arg Leu Ser Cys Glu Ala Ser Gly Phe Thr Phe
        35                  40                  45

Ser Asn Tyr Gly Met Asn Trp Val Arg Gln Ala Pro Gly Lys Gly Leu
    50                  55                  60

Glu Trp Val Ser Gly Ile Ser Gly Ser Gly Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Asn Leu Leu Leu Trp Leu Gly Tyr His Gly Asp Gly
        115                 120                 125

Phe Asp Leu Trp Gly Gln Gly Thr Met Val Thr Val Ser Ser Gly Gly
    130                 135                 140

Ser Glu Gly Lys Ser Ser Gly Ser Gly Ser Glu Ser Lys Ser Thr Gly
145                 150                 155                 160
```

```
Gly Ser Ser Tyr Glu Leu Thr Gln Pro Pro Ser Val Ser Val Ser Pro
                165                 170                 175

Gly Gln Thr Ala Arg Ile Thr Cys Ser Gly Asp Ala Leu Pro Lys Lys
            180                 185                 190

Tyr Ala Tyr Trp Tyr Gln Lys Lys Ser Gly Gln Ala Pro Val Leu Val
        195                 200                 205

Ile His Glu Asp Ser Lys Arg Pro Ser Gly Ile Pro Glu Arg Phe Ser
    210                 215                 220

Gly Ser Ser Ser Gly Thr Met Ala Thr Leu Thr Ile Ser Gly Ala Gln
225                 230                 235                 240

Val Glu Asp Glu Ala Asp Tyr Tyr Cys Phe Ser Thr Asp Arg Ser Gly
                245                 250                 255

Asn His Val Val Phe Gly Gly Gly Thr Lys Leu Thr Val Leu
            260                 265                 270


<210> SEQ ID NO 157
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Ala Trp Val Trp Thr Leu Leu Phe Leu Met Ala Ala Ala Gln Ser
1               5                   10                  15

Ile Gln Ala Gln Val Gln Leu Gln Gln Ser Gly Pro Gly Leu Val Lys
            20                  25                  30

Pro Ser Gln Thr Leu Ser Leu Thr Cys Ala Ile Ser Gly Asp Ser Val
        35                  40                  45

Ser Ser Lys Ser Gly Ala Trp Asn Trp Ile Arg Gln Ser Pro Ser Arg
    50                  55                  60

Gly Leu Glu Trp Leu Gly Arg Thr Tyr Tyr Arg Ser Lys Trp Tyr Asn
65                  70                  75                  80

Glu Tyr Ala Val Ser Val Lys Ser Arg Ile Thr Ile Asn Pro Asp Thr
                85                  90                  95

Ser Lys Asn Gln Phe Ser Leu Gln Leu Asn Ser Val Thr Pro Glu Asp
            100                 105                 110

Thr Ala Val Tyr Tyr Cys Thr Arg Val Asp Thr Asp Phe Asp Tyr Trp
        115                 120                 125

Gly Gln Gly Thr Leu Val Thr Val Ser Ser Gly Gly Ser Glu Gly Lys
    130                 135                 140

Ser Ser Gly Ser Gly Ser Glu Ser Lys Ser Thr Gly Gly Ser Gln Ser
145                 150                 155                 160

Ala Leu Thr Gln Pro Pro Ser Val Ser Glu Ala Pro Arg Gln Arg Val
                165                 170                 175

Thr Ile Ser Cys Ser Gly Ser Ala Ser Asn Ile Gly Asn Asn Gly Val
            180                 185                 190

Asn Trp Tyr Gln Gln Leu Pro Gly Lys Thr Pro Lys Leu Leu Ile Tyr
        195                 200                 205

Asn Asp Asp Leu Leu Pro Ser Gly Val Ser Asp Arg Phe Ser Gly Ser
    210                 215                 220

Lys Ser Gly Thr Ser Ala Ser Leu Ala Ile Ser Gly Leu Gln Ser Glu
225                 230                 235                 240

Asp Glu Ala Asp Tyr Phe Cys Ala Ala Trp Asp Asp Ser Leu Asn Gly
```

```
                245                 250                 255

Leu Val Phe Gly Gly Gly Thr Lys Leu Thr Val Leu
            260                 265


<210> SEQ ID NO 158
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Ala Trp Val Trp Thr Leu Leu Phe Leu Met Ala Ala Ala Gln Ser
1               5                   10                  15

Ile Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg His Thr Met Asn Trp Val Arg Gln Ala Pro Gly Lys Gly Leu
    50                  55                  60

Glu Trp Val Ser Ser Ile Ser Gly Ser Gly Gly Ser Thr Tyr Tyr Ala
65                  70                  75                  80

Asp Ser Val Lys Gly Arg Phe Thr Val Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Ser Tyr Asp Ser Ser Gly Val Trp Tyr Phe
        115                 120                 125

Asp Leu Trp Gly Arg Gly Thr Leu Val Thr Val Ser Ser Gly Gly Ser
    130                 135                 140

Glu Gly Lys Ser Ser Gly Ser Gly Ser Glu Ser Lys Ser Thr Gly Gly
145                 150                 155                 160

Ser Ser Tyr Glu Leu Thr Gln Pro Pro Ser Val Ser Val Ser Pro Gly
                165                 170                 175

Gln Thr Ala Ser Ile Thr Cys Ser Gly His Lys Leu Gly Asp Lys Tyr
            180                 185                 190

Ala Ser Trp Tyr Gln Gln Lys Pro Gly Gln Ser Pro Val Leu Val Ile
        195                 200                 205

Tyr Gln Asp Ser Lys Arg Pro Ser Gly Ile Pro Glu Arg Phe Ser Gly
    210                 215                 220

Ser Asn Ser Gly Asn Thr Ala Thr Leu Thr Ile Ser Gly Thr Gln Ala
225                 230                 235                 240

Met Asp Glu Ala Asp Tyr Tyr Cys Gln Ala Trp Asp Ser Ile Thr Ala
                245                 250                 255

Trp Val Phe Gly Gly Gly Thr Lys Leu Thr Val Leu
            260                 265


<210> SEQ ID NO 159
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Ala Trp Val Trp Thr Leu Leu Phe Leu Met Ala Ala Ala Gln Ser
```

1 5 10 15

Ile Gln Ala Gln Val Gln Leu Gln Glu Ser Gly Pro Gly Leu Val Lys
20 25 30

Pro Ser Glu Thr Leu Ser Leu Thr Cys Thr Val Ser Ser Gly Ser Ile
35 40 45

Ser Ser Tyr Tyr Trp Asn Trp Ile Arg Gln Pro Ala Gly Lys Gly Leu
50 55 60

Glu Trp Ile Gly Arg Ile Tyr Thr Ser Gly Thr Thr His Tyr Asn Pro
65 70 75 80

Ser Leu Lys Ser Arg Val Thr Met Ser Ile Asp Thr Ser Lys Asn Gln
85 90 95

Phe Ser Leu Lys Leu Ser Ser Val Thr Ala Ala Asp Thr Ala Val Tyr
100 105 110

Tyr Cys Ala Arg Glu Ile Arg Glu Leu Arg Gly Phe Asp Tyr Trp Gly
115 120 125

Gln Gly Thr Leu Val Thr Val Ser Ser Gly Gly Ser Glu Gly Lys Ser
130 135 140

Ser Gly Ser Gly Ser Glu Ser Lys Ser Thr Gly Gly Ser Ser Tyr Glu
145 150 155 160

Leu Met Gln Pro Pro Ser Val Ser Val Ser Pro Gly Gln Thr Ala Arg
165 170 175

Ile Thr Cys Ser Gly Asp Ala Leu Pro Arg Gln Tyr Ala Tyr Trp Tyr
180 185 190

Gln Gln Lys Pro Gly Gln Ala Pro Val Leu Val Ile Tyr Lys Asp Ser
195 200 205

Glu Arg Pro Ser Gly Ile Pro Glu Arg Phe Ser Gly Ser Ser Ser Gly
210 215 220

Thr Thr Val Thr Leu Thr Ile Ser Gly Val Gln Ala Glu Asp Glu Ala
225 230 235 240

Asp Tyr Tyr Cys Gln Ser Ala Asp Arg Thr Gly Ile Tyr Val Leu Phe
245 250 255

Gly Gly Gly Thr Lys Leu Thr Val Leu
260 265

<210> SEQ ID NO 160
<211> LENGTH: 265
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 160

Met Ala Trp Val Trp Thr Leu Leu Phe Leu Met Ala Ala Ala Gln Ser
1 5 10 15

Ile Gln Ala Gln Val Gln Leu Gln Glu Ser Gly Pro Gly Leu Val Lys
20 25 30

Pro Ser Glu Thr Leu Ser Leu Thr Cys Thr Val Ser Ser Gly Ser Ile
35 40 45

Ser Ser Tyr Tyr Trp Asn Trp Ile Arg Gln Pro Ala Gly Lys Gly Leu
50 55 60

Glu Trp Ile Gly Arg Ile Tyr Thr Ser Gly Thr Thr His Tyr Asn Pro
65 70 75 80

Ser Leu Lys Ser Arg Val Thr Met Ser Ile Asp Thr Ser Lys Asn Gln
85 90 95

```
Phe Ser Leu Lys Leu Ser Ser Val Thr Ala Ala Asp Thr Ala Val Tyr
            100                 105                 110

Tyr Cys Ala Arg Glu Ile Arg Glu Leu Arg Gly Phe Asp Tyr Trp Gly
        115                 120                 125

Gln Gly Thr Leu Val Thr Val Ser Ser Gly Gly Ser Glu Gly Lys Ser
    130                 135                 140

Ser Gly Ser Gly Ser Glu Ser Lys Ser Thr Gly Gly Ser Ser Tyr Glu
145                 150                 155                 160

Leu Thr Gln Pro Pro Ser Val Ser Val Ser Pro Gly Gln Thr Ala Arg
                165                 170                 175

Ile Thr Cys Ser Gly Asp Ala Leu Pro Arg Gln Tyr Ala Tyr Trp Tyr
            180                 185                 190

Gln Gln Lys Pro Gly Gln Ala Pro Val Leu Val Ile Tyr Lys Asp Ser
        195                 200                 205

Glu Arg Pro Ser Gly Ile Pro Glu Arg Phe Ser Gly Ser Ser Ser Gly
    210                 215                 220

Thr Thr Val Thr Leu Thr Ile Ser Gly Val Gln Ala Glu Asp Glu Ala
225                 230                 235                 240

Asp Tyr Tyr Cys Gln Ser Ala Asp Arg Thr Gly Ile Tyr Val Leu Phe
                245                 250                 255

Gly Gly Gly Thr Lys Leu Thr Val Leu
            260                 265


<210> SEQ ID NO 161
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Ala Trp Val Trp Thr Leu Leu Phe Leu Met Ala Ala Ala Gln Ser
1               5                   10                  15

Ile Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg His Thr Met Asn Trp Val Arg Gln Ala Pro Gly Lys Gly Leu
    50                  55                  60

Glu Trp Val Ser Ser Ile Ser Gly Ser Gly Gly Ser Thr Tyr Tyr Ala
65                  70                  75                  80

Asp Ser Val Lys Gly Arg Phe Thr Val Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Ser Tyr Asp Ser Ser Gly Val Trp Tyr Phe
        115                 120                 125

Asp Leu Trp Gly Lys Gly Thr Thr Val Thr Val Ser Ser Gly Gly Ser
    130                 135                 140

Glu Gly Lys Ser Ser Gly Ser Gly Ser Glu Ser Lys Ser Thr Gly Gly
145                 150                 155                 160

Ser Ser Tyr Glu Leu Thr Gln Pro Pro Ser Val Ser Val Ser Pro Gly
                165                 170                 175

Gln Thr Ala Ser Ile Thr Cys Ser Gly His Lys Leu Gly Asp Lys Tyr
            180                 185                 190
```

```
Ala Ser Trp Tyr Gln Gln Lys Pro Gly Gln Ser Pro Val Leu Val Ile
        195                 200                 205

Tyr Gln Asp Ser Lys Arg Pro Ser Gly Ile Pro Glu Arg Phe Ser Gly
    210                 215                 220

Ser Asn Ser Gly Asn Thr Ala Thr Leu Thr Ile Ser Gly Thr Gln Ala
225                 230                 235                 240

Met Asp Glu Ala Asp Tyr Tyr Cys Gln Ala Trp Asp Ser Ile Thr Ala
                245                 250                 255

Trp Val Phe Gly Gly Gly Thr Lys Leu Thr Val Leu
            260                 265


<210> SEQ ID NO 162
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Met Ala Trp Val Trp Thr Leu Leu Phe Leu Met Ala Ala Ala Gln Ser
1               5                   10                  15

Ile Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Asn Ser Tyr Asn Met Asn Trp Val Arg Gln Ala Pro Gly Lys Gly Leu
    50                  55                  60

Glu Trp Val Ser Tyr Ile Ser Ser Ser Gly Tyr Thr Ile Tyr Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asp Ser Leu Arg Asp Glu Asp Thr Ala Ile
            100                 105                 110

Tyr Tyr Cys Ala Arg Asp Arg Tyr Asn Tyr Asp Asn Gly Gly Tyr His
        115                 120                 125

Tyr Tyr Thr Gly Met Asp Val Trp Gly Gln Gly Thr Met Val Thr Val
    130                 135                 140

Ser Ser Gly Gly Ser Glu Gly Lys Ser Ser Gly Ser Gly Ser Glu Ser
145                 150                 155                 160

Lys Ser Thr Gly Gly Ser Ser Tyr Glu Leu Thr Gln Pro Pro Ser Val
                165                 170                 175

Ser Val Ser Pro Gly Gln Thr Ala Ser Ile Thr Cys Ser Gly Asp Lys
            180                 185                 190

Leu Gly Asp Lys Phe Ala Ser Trp Tyr Gln Gln Lys Pro Gly Gln Ser
        195                 200                 205

Pro Val Leu Val Ile Phe Gln Asp Ser Lys Arg Pro Ser Gly Ile Pro
    210                 215                 220

Glu Arg Phe Ser Gly Ser Asn Ser Gly Asn Thr Ala Thr Leu Thr Ile
225                 230                 235                 240

Ser Gly Thr Gln Ala Met Asp Glu Ala Asp Tyr Phe Cys Gln Ala Trp
                245                 250                 255

Asp Ser Thr Thr Ala Trp Val Phe Gly Gly Gly Thr Lys Leu Thr Val
            260                 265                 270

Leu
```

<210> SEQ ID NO 163
<211> LENGTH: 154
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 163

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys Phe Ser Arg
        35                  40                  45

Ser Ala Asp Ala Pro Ala Tyr Lys Gln Gly Gln Asn Gln Leu Tyr Asn
    50                  55                  60

Glu Leu Asn Leu Gly Arg Arg Glu Glu Tyr Asp Val Leu Asp Lys Arg
65                  70                  75                  80

Arg Gly Arg Asp Pro Glu Met Gly Gly Lys Pro Arg Arg Lys Asn Pro
                85                  90                  95

Gln Glu Gly Leu Tyr Asn Glu Leu Gln Lys Asp Lys Met Ala Glu Ala
            100                 105                 110

Tyr Ser Glu Ile Gly Met Lys Gly Glu Arg Arg Arg Gly Lys Gly His
        115                 120                 125

Asp Gly Leu Tyr Gln Gly Leu Ser Thr Ala Thr Lys Asp Thr Tyr Asp
    130                 135                 140

Ala Leu His Met Gln Ala Leu Pro Pro Arg
145                 150
```

<210> SEQ ID NO 164
<211> LENGTH: 490
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

```
Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45

Asp Tyr Asp Gly Asp Ser Phe Leu Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140
```

Lys Ser Thr Gly Gly Ser Gln Val Gln Leu Val Gln Ser Gly Ala Glu
145 150 155 160

Val Lys Lys Pro Gly Ala Ser Val Lys Val Ser Cys Lys Ala Ser Gly
165 170 175

Tyr Thr Phe Thr Gly Tyr Trp Ile Glu Trp Val Arg Gln Arg Pro Gly
180 185 190

Gln Gly Leu Glu Trp Met Gly Glu Ile Leu Pro Gly Gly Gly Asp Thr
195 200 205

Asn Tyr Asn Gln Lys Phe Gln Gly Lys Val Thr Phe Thr Arg Asp Thr
210 215 220

Ser Thr Ser Thr Ala Tyr Met Glu Leu Ser Ser Leu Arg Ser Glu Asp
225 230 235 240

Thr Ala Val Tyr Tyr Cys Ala Arg Arg Val Pro Val Tyr Phe Asp Tyr
245 250 255

Trp Gly Gln Gly Thr Leu Val Thr Val Ser Ser Thr Ser Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr
290 295 300

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

Lys Arg Gly Arg Lys Lys Leu Leu Tyr Ile Phe Lys Gln Pro Phe Met
340 345 350

Arg Pro Val Gln Thr Thr Gln Glu Glu Asp Gly Cys Ser Cys Arg Phe
355 360 365

Pro Glu Glu Glu Glu Gly Gly Cys Glu Leu Arg Val Lys Phe Ser Arg
370 375 380

Ser Ala Asp Ala Pro Ala Tyr Lys Gln Gly Gln Asn Gln Leu Tyr Asn
385 390 395 400

Glu Leu Asn Leu Gly Arg Arg Glu Glu Tyr Asp Val Leu Asp Lys Arg
405 410 415

Arg Gly Arg Asp Pro Glu Met Gly Gly Lys Pro Arg Arg Lys Asn Pro
420 425 430

Gln Glu Gly Leu Tyr Asn Glu Leu Gln Lys Asp Lys Met Ala Glu Ala
435 440 445

Tyr Ser Glu Ile Gly Met Lys Gly Glu Arg Arg Arg Gly Lys Gly His
450 455 460

Asp Gly Leu Tyr Gln Gly Leu Ser Thr Ala Thr Lys Asp Thr Tyr Asp
465 470 475 480

Ala Leu His Met Gln Ala Leu Pro Pro Arg
485 490

<210> SEQ ID NO 165
<211> LENGTH: 490
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 165

Met Ala Trp Val Trp Thr Leu Leu Phe Leu Met Ala Ala Ala Gln Ser

-continued 1 5 10 15

Ile Gln Ala Asp Ile Val Leu Thr Gln Ser Pro Asp Ser Leu Ala Val
20 25 30

Ser Leu Gly Glu Arg Ala Thr Ile Asn Cys Lys Ala Ser Gln Ser Val
35 40 45

Asp Tyr Glu Gly Asp Ser Phe Leu Asn Trp Tyr Gln Gln Lys Pro Gly
50 55 60

Gln Pro Pro Lys Leu Leu Ile Tyr Ala Ala Ser Asn Leu Glu Ser Gly
65 70 75 80

Val Pro Asp Arg Phe Ser Gly Ser Gly Ser Gly Thr Asp Phe Thr Leu
85 90 95

Thr Ile Ser Ser Leu Gln Ala Glu Asp Val Ala Val Tyr Tyr Cys Gln
100 105 110

Gln Ser Asn Glu Asp Pro Leu Thr Phe Gly Gly Gly Thr Lys Val Glu
115 120 125

Ile Lys Gly Gly Ser Glu Gly Lys Ser Ser Gly Ser Gly Ser Glu Ser
130 135 140

Lys Ser Thr Gly Gly Ser Gln Val Gln Leu Val Gln Ser Gly Ala Glu
145 150 155 160

Val Lys Lys Pro Gly Ala Ser Val Lys Val Ser Cys Lys Ala Ser Gly
165 170 175

Tyr Thr Phe Thr Gly Tyr Trp Ile Glu Trp Val Arg Gln Arg Pro Gly
180 185 190

Gln Gly Leu Glu Trp Met Gly Glu Ile Leu Pro Gly Gly Gly Asp Thr
195 200 205

Asn Tyr Asn Gln Lys Phe Gln Gly Lys Val Thr Phe Thr Arg Asp Thr
210 215 220

Ser Thr Ser Thr Ala Tyr Met Glu Leu Ser Ser Leu Arg Ser Glu Asp
225 230 235 240

Thr Ala Val Tyr Tyr Cys Ala Arg Arg Val Pro Val Tyr Phe Asp Tyr
245 250 255

Trp Gly Gln Gly Thr Leu Val Thr Val Ser Ser Thr Ser Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr
290 295 300

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

Lys Arg Gly Arg Lys Lys Leu Leu Tyr Ile Phe Lys Gln Pro Phe Met
340 345 350

Arg Pro Val Gln Thr Thr Gln Glu Glu Asp Gly Cys Ser Cys Arg Phe
355 360 365

Pro Glu Glu Glu Glu Gly Gly Cys Glu Leu Arg Val Lys Phe Ser Arg
370 375 380

Ser Ala Asp Ala Pro Ala Tyr Lys Gln Gly Gln Asn Gln Leu Tyr Asn
385 390 395 400

Glu Leu Asn Leu Gly Arg Arg Glu Glu Tyr Asp Val Leu Asp Lys Arg
405 410 415

Arg Gly Arg Asp Pro Glu Met Gly Gly Lys Pro Arg Arg Lys Asn Pro
420 425 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 166
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45

Asp Tyr Asp Gly Asp Ser Phe Leu Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Lys Lys Pro Gly Ala Ser Val Lys Val Ser Cys Lys Ala Ser Gly
                165                 170                 175

Tyr Thr Phe Thr Gly Tyr Trp Ile Glu Trp Val Arg Gln Arg Pro Gly
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Val Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr 290 295 300

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

Lys Arg Gly Arg Lys Lys Leu Leu Tyr Ile Phe Lys Gln Pro Phe Met
340 345 350

Arg Pro Val Gln Thr Thr Gln Glu Glu Asp Gly Cys Ser Cys Arg Phe
355 360 365

Pro Glu Glu Glu Glu Gly Gly Cys Glu Leu Arg Val Lys Phe Ser Arg
370 375 380

Ser Ala Asp Ala Pro Ala Tyr Lys Gln Gly Gln Asn Gln Leu Tyr Asn
385 390 395 400

Glu Leu Asn Leu Gly Arg Arg Glu Glu Tyr Asp Val Leu Asp Lys Arg
405 410 415

Arg Gly Arg Asp Pro Glu Met Gly Gly Lys Pro Arg Arg Lys Asn Pro
420 425 430

Gln Glu Gly Leu Tyr Asn Glu Leu Gln Lys Asp Lys Met Ala Glu Ala
435 440 445

Tyr Ser Glu Ile Gly Met Lys Gly Glu Arg Arg Arg Gly Lys Gly His
450 455 460

Asp Gly Leu Tyr Gln Gly Leu Ser Thr Ala Thr Lys Asp Thr Tyr Asp
465 470 475 480

Ala Leu His Met Gln Ala Leu Pro Pro Arg
485 490

<210> SEQ ID NO 167
<211> LENGTH: 490
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 167

Met Ala Trp Val Trp Thr Leu Leu Phe Leu Met Ala Ala Ala Gln Ser
1 5 10 15

Ile Gln Ala Asp Ile Val Leu Thr Gln Ser Pro Asp Ser Leu Ala Val
20 25 30

Ser Leu Gly Glu Arg Ala Thr Ile Asn Cys Lys Ala Ser Gln Ser Val
35 40 45

Asp Tyr Glu Gly Asp Ser Phe Leu Asn Trp Tyr Gln Gln Lys Pro Gly
50 55 60

Gln Pro Pro Lys Leu Leu Ile Tyr Ala Ala Ser Asn Leu Glu Ser Gly
65 70 75 80

Val Pro Asp Arg Phe Ser Gly Ser Gly Ser Gly Thr Asp Phe Thr Leu
85 90 95

Thr Ile Ser Ser Leu Gln Ala Glu Asp Val Ala Val Tyr Tyr Cys Gln
100 105 110

Gln Ser Asn Glu Asp Pro Leu Thr Phe Gly Gly Gly Thr Lys Val Glu
115 120 125

Ile Lys Gly Gly Ser Glu Gly Lys Ser Ser Gly Ser Gly Ser Glu Ser
130 135 140

Lys Ser Thr Gly Gly Ser Gln Val Gln Leu Val Gln Ser Gly Ala Glu
145 150 155 160

```
Val Lys Lys Pro Gly Ala Ser Val Lys Val Ser Cys Lys Ala Ser Gly
                165                 170                 175

Tyr Thr Phe Thr Gly Tyr Trp Ile Glu Trp Val Arg Gln Arg Pro Gly
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Val Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 168
<211> LENGTH: 490
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 168

```
Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30
```

```
Ser Leu Gly Glu Arg Ala Thr Ile Asn Cys Lys Ala Ser Gln Ser Val
        35                  40                  45

Asp Tyr Glu Gly Asp Ser Phe Leu Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Lys Lys Pro Gly Ala Ser Val Lys Val Ser Cys Lys Ala Ser Gly
                165                 170                 175

Tyr Thr Phe Thr Gly Tyr Trp Ile Glu Trp Val Arg Gln Ala Pro Gly
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Ala Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445
```

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 169
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45

Asp Tyr Asp Gly Asp Ser Phe Leu Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Lys Lys Pro Gly Ala Ser Val Lys Val Ser Cys Lys Ala Ser Gly
                165                 170                 175

Tyr Thr Phe Thr Gly Tyr Trp Ile Glu Trp Val Arg Gln Ala Pro Gly
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Val Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

```
Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 170
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

```
Met Ala Trp Val Trp Thr Leu Leu Phe Leu Met Ala Ala Ala Gln Ser
1               5                   10                  15

Ile Gln Ala Asp Ile Val Met Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45

Asp Tyr Asp Gly Asp Ser Phe Leu Asn Trp Tyr Gln Gln Lys Pro Gly
    50                  55                  60

Gln Pro Pro Lys Leu Phe Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Val Gln Ala Glu Asp Ala Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Met Lys Pro Gly Ala Ser Val Lys Ile Ser Cys Lys Ala Ser Gly
                165                 170                 175

Tyr Thr Phe Thr Gly Tyr Trp Ile Glu Trp Val Arg Gln Arg Pro Gly
```

```
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Val Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 171
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45
```

```
Asp Tyr Lys Gly Asp Ser Phe Leu Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Ser Asn Glu Asp Pro Leu Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Val Gln Ser Gly Ala Glu
145                 150                 155                 160

Val Met Lys Pro Gly Ala Ser Val Lys Ile Ser Cys Lys Ala Ser Gly
                165                 170                 175

Tyr Thr Phe Thr Gly Tyr Trp Ile Glu Trp Val Arg Gln Arg Pro Gly
            180                 185                 190

Gln Gly Leu Glu Trp Met Gly Glu Ile Leu Pro Gly Gly Gly Asp Thr
        195                 200                 205

Asn Tyr Asn Gln Lys Phe Gln Gly Lys Val Thr Phe Thr Arg Asp Thr
    210                 215                 220

Ser Thr Ser Thr Val Tyr Met Glu Leu Ser Ser Leu Arg Ser Glu Asp
225                 230                 235                 240

Thr Ala Val Tyr Tyr Cys Ala Arg Arg Val Pro Val Tyr Phe Asp Tyr
                245                 250                 255

Trp Gly Gln Gly Thr Leu Val Thr Val Ser Ser Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
```

465 470 475 480

Ala Leu His Met Gln Ala Leu Pro Pro Arg
485 490

<210> SEQ ID NO 172
<211> LENGTH: 494
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

Met Ala Trp Val Trp Thr Leu Leu Phe Leu Met Ala Ala Ala Gln Ser
1 5 10 15

Ile Gln Ala Ser Ser Glu Leu Thr Gln Asp Pro Ala Val Ser Val Ala
20 25 30

Leu Gly Gln Thr Val Arg Ile Arg Cys Gln Gly Asp Ser Leu Arg Lys
35 40 45

Tyr Tyr Gly Ser Trp Tyr Gln Gln Lys Pro Gly Gln Ala Pro Val Leu
50 55 60

Val Ile Tyr Gly Glu Thr Asn Arg Pro Ser Gly Ile Pro Asp Arg Phe
65 70 75 80

Ser Gly Ser Ser Ser Gly Asn Thr Ala Ser Leu Thr Ile Thr Gly Ala
85 90 95

Gln Ala Glu Asp Glu Ala Asp Tyr Tyr Cys Asn Ser Arg Asp Ser Ser
100 105 110

Gly Lys His Val Val Phe Gly Gly Gly Thr Lys Leu Thr Val Leu Gly
115 120 125

Gly Ser Glu Gly Lys Ser Ser Gly Ser Gly Ser Glu Ser Lys Ser Thr
130 135 140

Gly Gly Ser Glu Val Gln Leu Gln Glu Ser Gly Pro Gly Leu Val Lys
145 150 155 160

Pro Ser Glu Thr Leu Ser Leu Thr Cys Ser Val Ser Gly Gly Ser Ile
165 170 175

Ser Gly Ser Ser Tyr Tyr Trp Gly Trp Ile Arg Gln Pro Pro Gly Lys
180 185 190

Gly Leu Glu Trp Ile Gly Ser Ile Tyr Tyr Ser Gly Ser Thr Tyr Tyr
195 200 205

Asn Pro Ser Leu Lys Ser Arg Val Thr Ile Ser Val Asp Thr Ser Lys
210 215 220

Lys Gln Phe Ser Leu Lys Leu Arg Ser Val Thr Ala Ala Asp Thr Ala
225 230 235 240

Val Tyr Tyr Cys Ala Arg Glu Glu Asp Ser Gly Ser Tyr Tyr Val Gly
245 250 255

Ala Phe Asp Ile Trp Gly Gln Gly Thr Met Val Thr Val Ser Ser Thr
260 265 270

Ser Thr Pro Ala Pro Arg Pro Pro Thr Pro Ala Pro Thr Ile Ala Ser
275 280 285

Gln Pro Leu Ser Leu Arg Pro Glu Ala Cys Arg Pro Ala Ala Gly Gly
290 295 300

Ala Val His Thr Arg Gly Leu Asp Phe Ala Cys Asp Ile Tyr Ile Trp
305 310 315 320

Ala Pro Leu Ala Gly Thr Cys Gly Val Leu Leu Leu Ser Leu Val Ile
325 330 335

```
Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490


<210> SEQ ID NO 173
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Met Ala Trp Val Trp Thr Leu Leu Phe Leu Met Ala Ala Ala Gln Ser
1               5                   10                  15

Ile Gln Ala Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Asn
        35                  40                  45

Tyr Tyr Gly Ser Trp Tyr Gln Gln Lys Pro Gly Gln Ala Pro Val Leu
    50                  55                  60

Val Ile Tyr Gly Glu Lys Asn Arg Pro Ser Gly Ile Pro Asp Arg Phe
65                  70                  75                  80

Ser Gly Ser Ser Ser Gly Asn Thr Val Ser Leu Thr Ile Thr Gly Thr
                85                  90                  95

Gln Ala Glu Asp Glu Ala Asp Tyr Tyr Cys Asn Ser Arg Asp Ser Ser
            100                 105                 110

Gly Lys His Val Val Phe Gly Gly Gly Thr Lys Leu Thr Val Leu Gly
        115                 120                 125

Gly Ser Glu Gly Lys Ser Ser Gly Ser Gly Ser Glu Ser Lys Ser Thr
    130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Ser Val Ser Gly Gly Ser Ile
                165                 170                 175

Arg Ser Ser Thr Tyr Tyr Trp Gly Trp Ile Arg Gln Pro Pro Gly Lys
            180                 185                 190

Gly Leu Glu Trp Ile Gly Ser Ile Tyr Tyr Ser Gly Ser Thr Tyr Ser
        195                 200                 205
```

Asn Pro Ser Leu Lys Ser Arg Val Thr Ile Ser Val Asp Thr Ser Lys
    210                 215                 220

Asn Gln Phe Ser Leu Lys Leu Ser Ser Val Thr Ala Ala Asp Thr Ala
225                 230                 235                 240

Ile Tyr Tyr Cys Ala Arg Glu Glu Asp Ser Gly Ser Tyr Tyr Val Gly
                245                 250                 255

Thr Phe Asp Ile Trp Gly Gln Gly Thr Met Val Thr Val Ser Ser Thr
            260                 265                 270

Ser Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 174
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Met Ala Trp Val Trp Thr Leu Leu Phe Leu Met Ala Ala Ala Gln Ser
1               5                   10                  15

Ile Gln Ala Asp Val Val Met Thr Gln Ser Pro Leu Ser Leu Pro Val
            20                  25                  30

Thr Leu Gly Gln Pro Ala Ser Ile Ser Cys Arg Ser Ser Gln Ser Leu
        35                  40                  45

Val Tyr Ser Asp Gly Asn Thr Tyr Leu Ser Trp Phe Gln Gln Arg Pro
    50                  55                  60

Gly Gln Ser Pro Arg Arg Leu Ile Tyr Lys Val Ser Asn Arg Asp Ser

```
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Met Gln Gly Thr His Trp Pro Pro Thr Phe Gly Gly Gly Thr Lys Val
        115                 120                 125

Glu Ile Lys Gly Gly Ser Glu Gly Lys Ser Ser Gly Ser Gly Ser Glu
    130                 135                 140

Ser Lys Ser Thr Gly Gly Ser Glu Val Gln Leu Val Glu Ser Gly Gly
145                 150                 155                 160

Gly Leu Val Gln Pro Gly Gly Ser Leu Arg Leu Ser Cys Ala Ala Ser
                165                 170                 175

Gly Phe Thr Leu Arg Asn Tyr Trp Met Ser Trp Val Arg Gln Ala Pro
            180                 185                 190

Gly Lys Gly Leu Glu Trp Val Ala Asn Ile Asn Gln Asp Gly Ser Glu
        195                 200                 205

Lys Tyr Tyr Val Asp Ser Val Glu Gly Arg Phe Thr Ile Ser Arg Asp
    210                 215                 220

Asn Ala Lys Lys Ser Leu Trp Leu Gln Met Ser Ser Leu Arg Val Glu
225                 230                 235                 240

Asp Thr Ala Val Tyr Tyr Cys Ala Arg Asp Pro Ile Glu Ser Arg Phe
                245                 250                 255

Asp Tyr Trp Gly Gln Gly Thr Leu Val Thr Val Ser Ser Thr Ser Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 175
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

```
Met Ala Trp Val Trp Thr Leu Leu Phe Leu Met Ala Ala Ala Gln Ser
1               5                   10                  15

Ile Gln Ala Ser Ser Glu Leu Thr Gln Pro Pro Ser Val Ser Val Ser
            20                  25                  30

Pro Gly Gln Thr Ala Arg Ile Thr Cys Ser Gly Asp Ala Leu Pro Arg
        35                  40                  45

Lys Tyr Ala Tyr Trp Tyr Gln Gln Lys Ser Gly Gln Ala Pro Val Leu
    50                  55                  60

Val Ile Tyr Glu Asp Ser Lys Arg Pro Ser Gly Ile Pro Glu Arg Phe
65                  70                  75                  80

Ser Gly Ser Asn Ser Gly Thr Met Ala Thr Leu Thr Ile Ser Gly Ala
                85                  90                  95

Gln Val Glu Asp Glu Ala Ala Tyr Tyr Cys Tyr Ser Thr Asp Ser Ser
            100                 105                 110

Ala Asn His Arg Val Phe Gly Gly Gly Thr Lys Leu Thr Val Leu Gly
        115                 120                 125

Gly Ser Glu Gly Lys Ser Ser Gly Ser Gly Ser Glu Ser Lys Ser Thr
    130                 135                 140

Gly Gly Ser Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Thr Ile Tyr Ala Met Thr Trp Val Arg Gln Ala Pro Gly Lys Gly Leu
            180                 185                 190

Glu Trp Val Ser Gly Ile Ser Val Ser Gly Ile Arg Thr Tyr Tyr Ala
        195                 200                 205

Asp Ser Val Lys Gly Arg Phe Thr Ile Ser Arg Asp Asn Ser Lys Asn
    210                 215                 220

Thr Leu Phe Leu Gln Met Asn Ser Leu Ser Ala Glu Asp Thr Ala Val
225                 230                 235                 240

Tyr Tyr Cys Ala Lys Gly Leu Ser Ser Gly Asp Arg Asp Ala Ser Asp
                245                 250                 255

Ile Trp Gly Gln Gly Thr Met Val Thr Val Ser Ser Thr Ser Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
```

```
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 176
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Met Ala Trp Val Trp Thr Leu Leu Phe Leu Met Ala Ala Ala Gln Ser
1               5                   10                  15

Ile Gln Ala Glu Ile Val Met Thr Gln Ser Pro Leu Ser Leu Pro Val
            20                  25                  30

Thr Pro Gly Lys Pro Ala Ser Ile Ser Cys Arg Ser Ser Gln Ser Leu
        35                  40                  45

Glu Tyr Ser Asp Gly Asn Thr Tyr Leu Asn Trp Phe Gln Gln Arg Pro
    50                  55                  60

Gly Gln Ser Pro Arg Arg Leu Ile Tyr Lys Val Ser Asn Arg Asp Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Met Gln Gly Thr His Trp Pro Pro Thr Phe Gly Gly Gly Thr Lys Val
        115                 120                 125

Asp Ile Lys Gly Gly Ser Glu Gly Lys Ser Ser Gly Ser Gly Ser Glu
    130                 135                 140

Ser Lys Ser Thr Gly Gly Ser Glu Val Gln Leu Val Glu Ser Gly Gly
145                 150                 155                 160

Gly Leu Val Gln Pro Gly Gly Ser Leu Arg Leu Ser Cys Ala Ala Ser
                165                 170                 175

Gly Phe Ile Phe Ser Thr Tyr Trp Met Ser Trp Val Arg Gln Ala Pro
            180                 185                 190

Gly Lys Gly Leu Glu Trp Val Ala Asn Ile Asn Pro Asp Gly Asn Glu
        195                 200                 205

Lys Tyr Tyr Val Asp Ser Val Glu Gly Arg Phe Thr Ile Ser Arg Asp
    210                 215                 220
```

```
Asn Ala Gln Asp Ser Leu Tyr Leu Gln Met Asn Ser Leu Arg Ala Glu
225                 230                 235                 240

Asp Thr Ala Val Tyr Tyr Cys Ala Arg Asp Pro Ile Ser Ala Arg Phe
                245                 250                 255

Asp Phe Trp Gly Gln Gly Thr Leu Val Thr Val Ser Ser Thr Ser Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 177
<211> LENGTH: 489
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 177

```
Met Ala Trp Val Trp Thr Leu Leu Phe Leu Met Ala Ala Ala Gln Ser
1               5                   10                  15

Ile Gln Ala Ser Tyr Glu Leu Thr Gln Pro Pro Ser Val Ser Val Ser
            20                  25                  30

Pro Gly Gln Thr Ala Ser Ile Thr Cys Ser Gly Asp Lys Leu Gly Asp
        35                  40                  45

Glu Phe Ala Ser Trp Tyr Gln Gln Lys Pro Gly Gln Ser Pro Val Val
    50                  55                  60

Val Ile Tyr Gln Asp Thr Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95
```

```
Gln Ala Met Asp Glu Ala Asp Tyr Tyr Cys Gln Ala Trp Asp Ser Asn
            100                 105                 110

Thr Ala Val Phe Gly Gly Gly Thr Lys Leu Thr Val Leu Gly Gly Ser
        115                 120                 125

Glu Gly Lys Ser Ser Gly Ser Gly Ser Glu Ser Lys Ser Thr Gly Gly
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Asn Trp Val Arg Gln Ala Pro Gly Lys Gly Leu Glu Trp
            180                 185                 190

Val Ser Thr Ile Ser Gly Ser Gly Gly Ser Ser Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Asn Pro Ser Gly Thr Phe Trp Asn Asp Ala Phe Asp Ile Trp
                245                 250                 255

Gly Gln Gly Thr Met Val Thr Val Ser Ser Thr Ser Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Lys Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 178
<211> LENGTH: 493

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 178

Met Ala Trp Val Trp Thr Leu Leu Phe Leu Met Ala Ala Ala Gln Ser
1 5 10 15

Ile Gln Ala Ser Tyr Glu Leu Thr Gln Pro Pro Ser Val Ser Val Ser
20 25 30

Pro Gly Gln Thr Ala Arg Ile Thr Cys Ser Gly Asp Ala Leu Pro Lys
35 40 45

Lys Tyr Ala Tyr Trp Tyr Gln Gln Lys Ser Gly Gln Ala Pro Val Leu
50 55 60

Val Ile Tyr Glu Asp Ser Lys Arg Pro Ser Gly Ile Pro Glu Arg Phe
65 70 75 80

Ser Ala Ser Ser Ser Gly Thr Met Ala Thr Leu Thr Ile Ser Gly Ala
85 90 95

Gln Val Glu Asp Glu Ala Asp Tyr Tyr Cys Tyr Ser Ala Asp Ser Ser
100 105 110

Gly Ser His Trp Val Phe Gly Gly Gly Thr Lys Leu Thr Val Leu Gly
115 120 125

Gly Ser Glu Gly Lys Ser Ser Gly Ser Gly Ser Glu Ser Lys Ser Thr
130 135 140

Gly Gly Ser Glu Val Gln Leu Val Glu Ser Gly Gly Gly Leu Val Gln
145 150 155 160

Pro Gly Gly Ser Leu Arg Leu Ser Cys Ala Ala Ser Gly Phe Thr Phe
165 170 175

Asn Asn Tyr Ala Met Asn Trp Val Arg Gln Ala Pro Gly Lys Gly Leu
180 185 190

Glu Trp Val Ser Val Ile Ser Gly Asn Gly Gly Ser Ile His Tyr Ala
195 200 205

Asp Ser Val Lys Gly Arg Phe Thr Ile Ser Arg Asp Asn Ser Lys Asn
210 215 220

Thr Leu Tyr Leu Gln Met Asn Ser Leu Arg Ala Glu Asp Thr Ala Val
225 230 235 240

Tyr Tyr Cys Ala Thr Pro Arg Gly Tyr Thr Gly Tyr Asp Gly Asp Ala
245 250 255

Phe Asp Phe Trp Gly Gln Gly Thr Met Val Thr Val Ser Ser Thr Ser
260 265 270

Thr Pro Ala Pro Arg Pro Pro Thr Pro Ala Pro Thr Ile Ala Ser Gln
275 280 285

Pro Leu Ser Leu Arg Pro Glu Ala Cys Arg Pro Ala Ala Gly Gly Ala
290 295 300

Val His Thr Arg Gly Leu Asp Phe Ala Cys Asp Ile Tyr Ile Trp Ala
305 310 315 320

Pro Leu Ala Gly Thr Cys Gly Val Leu Leu Leu Ser Leu Val Ile Thr
325 330 335

Leu Tyr Cys Lys Arg Gly Arg Lys Lys Leu Leu Tyr Ile Phe Lys Gln
340 345 350

Pro Phe Met Arg Pro Val Gln Thr Thr Gln Glu Glu Asp Gly Cys Ser
355 360 365

Cys Arg Phe Pro Glu Glu Glu Glu Gly Gly Cys Glu Leu Arg Val Lys
370 375 380

Phe Ser Arg Ser Ala Asp Ala Pro Ala Tyr Lys Gln Gly Gln Asn Gln
385 390 395 400

Leu Tyr Asn Glu Leu Asn Leu Gly Arg Arg Glu Glu Tyr Asp Val Leu
405 410 415

Asp Lys Arg Arg Gly Arg Asp Pro Glu Met Gly Gly Lys Pro Arg Arg
420 425 430

Lys Asn Pro Gln Glu Gly Leu Tyr Asn Glu Leu Gln Lys Asp Lys Met
435 440 445

Ala Glu Ala Tyr Ser Glu Ile Gly Met Lys Gly Glu Arg Arg Arg Gly
450 455 460

Lys Gly His Asp Gly Leu Tyr Gln Gly Leu Ser Thr Ala Thr Lys Asp
465 470 475 480

Thr Tyr Asp Ala Leu His Met Gln Ala Leu Pro Pro Arg
485 490

<210> SEQ ID NO 179
<211> LENGTH: 493
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

Met Ala Trp Val Trp Thr Leu Leu Phe Leu Met Ala Ala Ala Gln Ser
1 5 10 15

Ile Gln Ala Ser Tyr Glu Leu Thr Gln Pro Pro Ser Val Ser Val Ser
20 25 30

Pro Gly Gln Thr Ala Arg Ile Thr Cys Ser Gly Asp Ala Leu Pro Lys
35 40 45

Lys Tyr Ala Tyr Trp Tyr Gln Lys Lys Ser Gly Gln Ala Pro Val Leu
50 55 60

Val Ile His Glu Asp Ser Lys Arg Pro Ser Gly Ile Pro Glu Arg Phe
65 70 75 80

Ser Gly Ser Ser Ser Gly Thr Met Ala Thr Leu Thr Ile Ser Gly Ala
85 90 95

Gln Val Glu Asp Glu Ala Asp Tyr Tyr Cys Phe Ser Thr Asp Arg Ser
100 105 110

Gly Asn His Val Val Phe Gly Gly Gly Thr Lys Leu Thr Val Leu Gly
115 120 125

Gly Ser Glu Gly Lys Ser Ser Gly Ser Gly Ser Glu Ser Lys Ser Thr
130 135 140

Gly Gly Ser Glu Val Gln Leu Val Glu Ser Gly Gly Asp Leu Val Gln
145 150 155 160

Pro Gly Gly Ser Leu Arg Leu Ser Cys Glu Ala Ser Gly Phe Thr Phe
165 170 175

Ser Asn Tyr Gly Met Asn Trp Val Arg Gln Ala Pro Gly Lys Gly Leu
180 185 190

Glu Trp Val Ser Gly Ile Ser Gly Ser Gly Gly Thr Thr Tyr Tyr Ala
195 200 205

Asp Ser Val Lys Gly Arg Phe Thr Ile Ser Arg Asp Asn Ser Lys Asn
210 215 220

Thr Leu Tyr Leu Gln Met Asn Ser Leu Arg Ala Glu Asp Thr Ala Val
225 230 235 240

Tyr Tyr Cys Ala Asn Leu Leu Leu Trp Leu Gly Tyr His Gly Asp Gly 245 250 255

Phe Asp Leu Trp Gly Gln Gly Thr Met Val Thr Val Ser Ser Thr Ser
260 265 270

Thr Pro Ala Pro Arg Pro Pro Thr Pro Ala Pro Thr Ile Ala Ser Gln
275 280 285

Pro Leu Ser Leu Arg Pro Glu Ala Cys Arg Pro Ala Ala Gly Gly Ala
290 295 300

Val His Thr Arg Gly Leu Asp Phe Ala Cys Asp Ile Tyr Ile Trp Ala
305 310 315 320

Pro Leu Ala Gly Thr Cys Gly Val Leu Leu Leu Ser Leu Val Ile Thr
325 330 335

Leu Tyr Cys Lys Arg Gly Arg Lys Lys Leu Leu Tyr Ile Phe Lys Gln
340 345 350

Pro Phe Met Arg Pro Val Gln Thr Thr Gln Glu Glu Asp Gly Cys Ser
355 360 365

Cys Arg Phe Pro Glu Glu Glu Glu Gly Gly Cys Glu Leu Arg Val Lys
370 375 380

Phe Ser Arg Ser Ala Asp Ala Pro Ala Tyr Lys Gln Gly Gln Asn Gln
385 390 395 400

Leu Tyr Asn Glu Leu Asn Leu Gly Arg Arg Glu Glu Tyr Asp Val Leu
405 410 415

Asp Lys Arg Arg Gly Arg Asp Pro Glu Met Gly Gly Lys Pro Arg Arg
420 425 430

Lys Asn Pro Gln Glu Gly Leu Tyr Asn Glu Leu Gln Lys Asp Lys Met
435 440 445

Ala Glu Ala Tyr Ser Glu Ile Gly Met Lys Gly Glu Arg Arg Arg Gly
450 455 460

Lys Gly His Asp Gly Leu Tyr Gln Gly Leu Ser Thr Ala Thr Lys Asp
465 470 475 480

Thr Tyr Asp Ala Leu His Met Gln Ala Leu Pro Pro Arg
485 490

<210> SEQ ID NO 180
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

Met Ala Trp Val Trp Thr Leu Leu Phe Leu Met Ala Ala Ala Gln Ser
1 5 10 15

Ile Gln Ala Gln Ser Ala Leu Thr Gln Pro Pro Ser Val Ser Glu Ala
20 25 30

Pro Arg Gln Arg Val Thr Ile Ser Cys Ser Gly Ser Ala Ser Asn Ile
35 40 45

Gly Asn Asn Gly Val Asn Trp Tyr Gln Gln Leu Pro Gly Lys Thr Pro
50 55 60

Lys Leu Leu Ile Tyr Asn Asp Asp Leu Leu Pro Ser Gly Val Ser Asp
65 70 75 80

Arg Phe Ser Gly Ser Lys Ser Gly Thr Ser Ala Ser Leu Ala Ile Ser
85 90 95

Gly Leu Gln Ser Glu Asp Glu Ala Asp Tyr Phe Cys Ala Ala Trp Asp
100 105 110

```
Asp Ser Leu Asn Gly Leu Val Phe Gly Gly Gly Thr Lys Leu Thr Val
        115                 120                 125

Leu Gly Gly Ser Glu Gly Lys Ser Ser Gly Ser Gly Ser Glu Ser Lys
    130                 135                 140

Ser Thr Gly Gly Ser Gln Val Gln Leu Gln Gln Ser Gly Pro Gly Leu
145                 150                 155                 160

Val Lys Pro Ser Gln Thr Leu Ser Leu Thr Cys Ala Ile Ser Gly Asp
                165                 170                 175

Ser Val Ser Ser Lys Ser Gly Ala Trp Asn Trp Ile Arg Gln Ser Pro
            180                 185                 190

Ser Arg Gly Leu Glu Trp Leu Gly Arg Thr Tyr Tyr Arg Ser Lys Trp
        195                 200                 205

Tyr Asn Glu Tyr Ala Val Ser Val Lys Ser Arg Ile Thr Ile Asn Pro
    210                 215                 220

Asp Thr Ser Lys Asn Gln Phe Ser Leu Gln Leu Asn Ser Val Thr Pro
225                 230                 235                 240

Glu Asp Thr Ala Val Tyr Tyr Cys Thr Arg Val Asp Thr Asp Phe Asp
                245                 250                 255

Tyr Trp Gly Gln Gly Thr Leu Val Thr Val Ser Ser Thr Ser Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 181
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 181

```
Met Ala Trp Val Trp Thr Leu Leu Phe Leu Met Ala Ala Ala Gln Ser
1               5                   10                  15

Ile Gln Ala Ser Tyr Glu Leu Thr Gln Pro Pro Ser Val Ser Val Ser
            20                  25                  30

Pro Gly Gln Thr Ala Ser Ile Thr Cys Ser Gly His Lys Leu Gly Asp
        35                  40                  45

Lys Tyr Ala Ser Trp Tyr Gln Gln Lys Pro Gly Gln Ser Pro Val Leu
    50                  55                  60

Val Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Ser Ile
            100                 105                 110

Thr Ala Trp Val Phe Gly Gly Gly Thr Lys Leu Thr Val Leu Gly Gly
        115                 120                 125

Ser Glu Gly Lys Ser Ser Gly Ser Gly Ser Glu Ser Lys Ser Thr Gly
    130                 135                 140

Gly Ser Glu Val Gln Leu Val Glu Ser Gly Gly Gly Leu Val Gln Pro
145                 150                 155                 160

Gly Gly Ser Leu Arg Leu Ser Cys Ala Ala Ser Gly Phe Thr Phe Ser
                165                 170                 175

Arg His Thr Met Asn Trp Val Arg Gln Ala Pro Gly Lys Gly Leu Glu
            180                 185                 190

Trp Val Ser Ser Ile Ser Gly Ser Gly Gly Ser Thr Tyr Tyr Ala Asp
        195                 200                 205

Ser Val Lys Gly Arg Phe Thr Val Ser Arg Asp Asn Ser Lys Asn Thr
    210                 215                 220

Leu Tyr Leu Gln Met Asn Ser Leu Arg Ala Glu Asp Thr Ala Val Tyr
225                 230                 235                 240

Tyr Cys Ala Lys Glu Ser Tyr Asp Ser Ser Gly Val Trp Tyr Phe Asp
                245                 250                 255

Leu Trp Gly Arg Gly Thr Leu Val Thr Val Ser Ser Thr Ser Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400
```

```
Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 182
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Met Ala Trp Val Trp Thr Leu Leu Phe Leu Met Ala Ala Ala Gln Ser
1               5                   10                  15

Ile Gln Ala Ser Tyr Glu Leu Met Gln Pro Pro Ser Val Ser Val Ser
            20                  25                  30

Pro Gly Gln Thr Ala Arg Ile Thr Cys Ser Gly Asp Ala Leu Pro Arg
        35                  40                  45

Gln Tyr Ala Tyr Trp Tyr Gln Gln Lys Pro Gly Gln Ala Pro Val Leu
    50                  55                  60

Val Ile Tyr Lys Asp Ser Glu Arg Pro Ser Gly Ile Pro Glu Arg Phe
65                  70                  75                  80

Ser Gly Ser Ser Ser Gly Thr Thr Val Thr Leu Thr Ile Ser Gly Val
                85                  90                  95

Gln Ala Glu Asp Glu Ala Asp Tyr Tyr Cys Gln Ser Ala Asp Arg Thr
            100                 105                 110

Gly Ile Tyr Val Leu Phe Gly Gly Gly Thr Lys Leu Thr Val Leu Gly
        115                 120                 125

Gly Ser Glu Gly Lys Ser Ser Gly Ser Gly Ser Glu Ser Lys Ser Thr
    130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Ser Gly Ser Ile
                165                 170                 175

Ser Ser Tyr Tyr Trp Asn Trp Ile Arg Gln Pro Ala Gly Lys Gly Leu
            180                 185                 190

Glu Trp Ile Gly Arg Ile Tyr Thr Ser Gly Thr Thr His Tyr Asn Pro
        195                 200                 205

Ser Leu Lys Ser Arg Val Thr Met Ser Ile Asp Thr Ser Lys Asn Gln
    210                 215                 220

Phe Ser Leu Lys Leu Ser Ser Val Thr Ala Ala Asp Thr Ala Val Tyr
225                 230                 235                 240

Tyr Cys Ala Arg Glu Ile Arg Glu Leu Arg Gly Phe Asp Tyr Trp Gly
                245                 250                 255

Gln Gly Thr Leu Val Thr Val Ser Ser Thr Ser Thr Pro Ala Pro Arg
            260                 265                 270
```

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 183
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Met Ala Trp Val Trp Thr Leu Leu Phe Leu Met Ala Ala Ala Gln Ser
1               5                   10                  15

Ile Gln Ala Ser Tyr Glu Leu Thr Gln Pro Pro Ser Val Ser Val Ser
            20                  25                  30

Pro Gly Gln Thr Ala Arg Ile Thr Cys Ser Gly Asp Ala Leu Pro Arg
        35                  40                  45

Gln Tyr Ala Tyr Trp Tyr Gln Gln Lys Pro Gly Gln Ala Pro Val Leu
    50                  55                  60

Val Ile Tyr Lys Asp Ser Glu Arg Pro Ser Gly Ile Pro Glu Arg Phe
65                  70                  75                  80

Ser Gly Ser Ser Ser Gly Thr Thr Val Thr Leu Thr Ile Ser Gly Val
                85                  90                  95

Gln Ala Glu Asp Glu Ala Asp Tyr Tyr Cys Gln Ser Ala Asp Arg Thr
            100                 105                 110

Gly Ile Tyr Val Leu Phe Gly Gly Gly Thr Lys Leu Thr Val Leu Gly
        115                 120                 125

Gly Ser Glu Gly Lys Ser Ser Gly Ser Gly Ser Glu Ser Lys Ser Thr

```
130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Ser Gly Ser Ile
                165                 170                 175

Ser Ser Tyr Tyr Trp Asn Trp Ile Arg Gln Pro Ala Gly Lys Gly Leu
            180                 185                 190

Glu Trp Ile Gly Arg Ile Tyr Thr Ser Gly Thr Thr His Tyr Asn Pro
        195                 200                 205

Ser Leu Lys Ser Arg Val Thr Met Ser Ile Asp Thr Ser Lys Asn Gln
    210                 215                 220

Phe Ser Leu Lys Leu Ser Ser Val Thr Ala Ala Asp Thr Ala Val Tyr
225                 230                 235                 240

Tyr Cys Ala Arg Glu Ile Arg Glu Leu Arg Gly Phe Asp Tyr Trp Gly
                245                 250                 255

Gln Gly Thr Leu Val Thr Val Ser Ser Thr Ser Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485
```

<210> SEQ ID NO 184
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

-continued

Met Ala Trp Val Trp Thr Leu Leu Phe Leu Met Ala Ala Ala Gln Ser
1               5                   10                  15

Ile Gln Ala Ser Tyr Glu Leu Thr Gln Pro Pro Ser Val Ser Val Ser
            20                  25                  30

Pro Gly Gln Thr Ala Ser Ile Thr Cys Ser Gly His Lys Leu Gly Asp
        35                  40                  45

Lys Tyr Ala Ser Trp Tyr Gln Gln Lys Pro Gly Gln Ser Pro Val Leu
    50                  55                  60

Val Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Ser Ile
            100                 105                 110

Thr Ala Trp Val Phe Gly Gly Gly Thr Lys Leu Thr Val Leu Gly Gly
        115                 120                 125

Ser Glu Gly Lys Ser Ser Gly Ser Gly Ser Glu Ser Lys Ser Thr Gly
    130                 135                 140

Gly Ser Glu Val Gln Leu Val Glu Ser Gly Gly Gly Leu Val Gln Pro
145                 150                 155                 160

Gly Gly Ser Leu Arg Leu Ser Cys Ala Ala Ser Gly Phe Thr Phe Ser
                165                 170                 175

Arg His Thr Met Asn Trp Val Arg Gln Ala Pro Gly Lys Gly Leu Glu
            180                 185                 190

Trp Val Ser Ser Ile Ser Gly Ser Gly Gly Ser Thr Tyr Tyr Ala Asp
        195                 200                 205

Ser Val Lys Gly Arg Phe Thr Val Ser Arg Asp Asn Ser Lys Asn Thr
    210                 215                 220

Leu Tyr Leu Gln Met Asn Ser Leu Arg Ala Glu Asp Thr Ala Val Tyr
225                 230                 235                 240

Tyr Cys Ala Lys Glu Ser Tyr Asp Ser Ser Gly Val Trp Tyr Phe Asp
                245                 250                 255

Leu Trp Gly Lys Gly Thr Thr Val Thr Val Ser Ser Thr Ser Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn

```
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 185
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Ala Trp Val Trp Thr Leu Leu Phe Leu Met Ala Ala Ala Gln Ser
1               5                   10                  15

Ile Gln Ala Ser Tyr Glu Leu Thr Gln Pro Pro Ser Val Ser Val Ser
            20                  25                  30

Pro Gly Gln Thr Ala Ser Ile Thr Cys Ser Gly Asp Lys Leu Gly Asp
        35                  40                  45

Lys Phe Ala Ser Trp Tyr Gln Gln Lys Pro Gly Gln Ser Pro Val Leu
    50                  55                  60

Val Ile Phe Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Phe Cys Gln Ala Trp Asp Ser Thr
            100                 105                 110

Thr Ala Trp Val Phe Gly Gly Gly Thr Lys Leu Thr Val Leu Gly Gly
        115                 120                 125

Ser Glu Gly Lys Ser Ser Gly Ser Gly Ser Glu Ser Lys Ser Thr Gly
    130                 135                 140

Gly Ser Glu Val Gln Leu Val Glu Ser Gly Gly Gly Leu Val Gln Pro
145                 150                 155                 160

Gly Gly Ser Leu Arg Leu Ser Cys Ala Ala Ser Gly Phe Thr Phe Asn
                165                 170                 175

Ser Tyr Asn Met Asn Trp Val Arg Gln Ala Pro Gly Lys Gly Leu Glu
            180                 185                 190

Trp Val Ser Tyr Ile Ser Ser Ser Gly Tyr Thr Ile Tyr Tyr Ala Asp
        195                 200                 205

Ser Val Glu Gly Arg Phe Thr Ile Ser Arg Asp Asn Ala Lys Asn Ser
    210                 215                 220

Leu Tyr Leu Gln Met Asp Ser Leu Arg Asp Glu Asp Thr Ala Ile Tyr
225                 230                 235                 240

Tyr Cys Ala Arg Asp Arg Tyr Asn Tyr Asp Asn Gly Gly Tyr His Tyr
                245                 250                 255

Tyr Thr Gly Met Asp Val Trp Gly Gln Gly Thr Met Val Thr Val Ser
            260                 265                 270

Ser Thr Ser Thr Pro Ala Pro Arg Pro Pro Thr Pro Ala Pro Thr Ile
        275                 280                 285
```

```
Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Lys Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495
```

<210> SEQ ID NO 186
<211> LENGTH: 490
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 186

```
Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Trp Ile Glu Trp Val Arg Gln Arg Pro Gly Gln Gly Leu
    50                  55                  60

Glu Trp Met Gly Glu Ile Leu Pro Gly Gly Gly Asp Thr Asn Tyr Asn
65                  70                  75                  80

Gln Lys Phe Gln Gly Lys Val Thr Phe Thr Arg Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160
```

Thr Gln Ser Pro Asp Ser Leu Ala Val Ser Leu Gly Glu Arg Ala Thr
165 170 175

Ile Asn Cys Lys Ala Ser Gln Ser Val Asp Tyr Asp Gly Asp Ser Phe
180 185 190

Leu Asn Trp Tyr Gln Gln Lys Pro Gly Gln Pro Pro Lys Leu Leu Ile
195 200 205

Tyr Ala Ala Ser Asn Leu Glu Ser Gly Val Pro Asp Arg Phe Ser Gly
210 215 220

Ser Gly Ser Gly Thr Asp Phe Thr Leu Thr Ile Ser Ser Leu Gln Ala
225 230 235 240

Glu Asp Val Ala Val Tyr Tyr Cys Gln Gln Ser Asn Glu Asp Pro Leu
245 250 255

Thr Phe Gly Gly Gly Thr Lys Val Glu Ile Lys Thr Ser Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr
290 295 300

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

Lys Arg Gly Arg Lys Lys Leu Leu Tyr Ile Phe Lys Gln Pro Phe Met
340 345 350

Arg Pro Val Gln Thr Thr Gln Glu Glu Asp Gly Cys Ser Cys Arg Phe
355 360 365

Pro Glu Glu Glu Glu Gly Gly Cys Glu Leu Arg Val Lys Phe Ser Arg
370 375 380

Ser Ala Asp Ala Pro Ala Tyr Lys Gln Gly Gln Asn Gln Leu Tyr Asn
385 390 395 400

Glu Leu Asn Leu Gly Arg Arg Glu Glu Tyr Asp Val Leu Asp Lys Arg
405 410 415

Arg Gly Arg Asp Pro Glu Met Gly Gly Lys Pro Arg Arg Lys Asn Pro
420 425 430

Gln Glu Gly Leu Tyr Asn Glu Leu Gln Lys Asp Lys Met Ala Glu Ala
435 440 445

Tyr Ser Glu Ile Gly Met Lys Gly Glu Arg Arg Arg Gly Lys Gly His
450 455 460

Asp Gly Leu Tyr Gln Gly Leu Ser Thr Ala Thr Lys Asp Thr Tyr Asp
465 470 475 480

Ala Leu His Met Gln Ala Leu Pro Pro Arg
485 490

<210> SEQ ID NO 187
<211> LENGTH: 490
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

Met Ala Trp Val Trp Thr Leu Leu Phe Leu Met Ala Ala Ala Gln Ser
1 5 10 15

Ile Gln Ala Gln Val Gln Leu Val Gln Ser Gly Ala Glu Val Lys Lys

```
            20                  25                  30

Pro Gly Ala Ser Val Lys Val Ser Cys Lys Ala Ser Gly Tyr Thr Phe
        35                  40                  45

Thr Gly Tyr Trp Ile Glu Trp Val Arg Gln Arg Pro Gly Gln Gly Leu
    50                  55                  60

Glu Trp Met Gly Glu Ile Leu Pro Gly Gly Gly Asp Thr Asn Tyr Asn
65                  70                  75                  80

Gln Lys Phe Gln Gly Lys Val Thr Phe Thr Arg Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Gln Ser Val Asp Tyr Glu Gly Asp Ser Phe
            180                 185                 190

Leu Asn Trp Tyr Gln Gln Lys Pro Gly Gln Pro Pro Lys Leu Leu Ile
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Gln Gln Ser Asn Glu Asp Pro Leu
                245                 250                 255

Thr Phe Gly Gly Gly Thr Lys Val Glu Ile Lys Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445
```

```
Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 188
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Trp Ile Glu Trp Val Arg Gln Arg Pro Gly Gln Gly Leu
    50                  55                  60

Glu Trp Met Gly Glu Ile Leu Pro Gly Gly Gly Asp Thr Asn Tyr Asn
65                  70                  75                  80

Gln Lys Phe Gln Gly Lys Val Thr Phe Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Gln Ser Val Asp Tyr Asp Gly Asp Ser Phe
            180                 185                 190

Leu Asn Trp Tyr Gln Gln Lys Pro Gly Gln Pro Pro Lys Leu Leu Ile
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Gln Gln Ser Asn Glu Asp Pro Leu
                245                 250                 255

Thr Phe Gly Gly Gly Thr Lys Val Glu Ile Lys Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
```

```
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 189
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Trp Ile Glu Trp Val Arg Gln Arg Pro Gly Gln Gly Leu
    50                  55                  60

Glu Trp Met Gly Glu Ile Leu Pro Gly Gly Gly Asp Thr Asn Tyr Asn
65                  70                  75                  80

Gln Lys Phe Gln Gly Lys Val Thr Phe Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175
```

```
Ile Asn Cys Lys Ala Ser Gln Ser Val Asp Tyr Glu Gly Asp Ser Phe
            180                 185                 190

Leu Asn Trp Tyr Gln Gln Lys Pro Gly Gln Pro Pro Lys Leu Leu Ile
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Gln Gln Ser Asn Glu Asp Pro Leu
                245                 250                 255

Thr Phe Gly Gly Gly Thr Lys Val Glu Ile Lys Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 190
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45
```

```
Thr Gly Tyr Trp Ile Glu Trp Val Arg Gln Ala Pro Gly Gln Gly Leu
    50                  55                  60

Glu Trp Met Gly Glu Ile Leu Pro Gly Gly Gly Asp Thr Asn Tyr Asn
65                  70                  75                  80

Gln Lys Phe Gln Gly Lys Val Thr Phe Thr Arg Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Gln Ser Val Asp Tyr Glu Gly Asp Ser Phe
            180                 185                 190

Leu Asn Trp Tyr Gln Gln Lys Pro Gly Gln Pro Pro Lys Leu Leu Ile
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Gln Gln Ser Asn Glu Asp Pro Leu
                245                 250                 255

Thr Phe Gly Gly Gly Thr Lys Val Glu Ile Lys Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460
```

Asp Gly Leu Tyr Gln Gly Leu Ser Thr Ala Thr Lys Asp Thr Tyr Asp
465 470 475 480

Ala Leu His Met Gln Ala Leu Pro Pro Arg
485 490

<210> SEQ ID NO 191
<211> LENGTH: 490
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 191

Met Ala Trp Val Trp Thr Leu Leu Phe Leu Met Ala Ala Ala Gln Ser
1 5 10 15

Ile Gln Ala Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Gly Tyr Trp Ile Glu Trp Val Arg Gln Ala Pro Gly Gln Gly Leu
50 55 60

Glu Trp Met Gly Glu Ile Leu Pro Gly Gly Gly Asp Thr Asn Tyr Asn
65 70 75 80

Gln Lys Phe Gln Gly Lys Val Thr Phe Thr Arg Asp Thr Ser Thr Ser
85 90 95

Thr Val Tyr Met Glu Leu Ser Ser Leu Arg Ser Glu Asp Thr Ala Val
100 105 110

Tyr Tyr Cys Ala Arg Arg Val Pro Val Tyr Phe Asp Tyr Trp Gly Gln
115 120 125

Gly Thr Leu Val Thr Val Ser Ser Gly Gly Ser Glu Gly Lys Ser Ser
130 135 140

Gly Ser Gly Ser Glu Ser Lys Ser Thr Gly Gly Ser Asp Ile Val Leu
145 150 155 160

Thr Gln Ser Pro Asp Ser Leu Ala Val Ser Leu Gly Glu Arg Ala Thr
165 170 175

Ile Asn Cys Lys Ala Ser Gln Ser Val Asp Tyr Asp Gly Asp Ser Phe
180 185 190

Leu Asn Trp Tyr Gln Gln Lys Pro Gly Gln Pro Pro Lys Leu Leu Ile
195 200 205

Tyr Ala Ala Ser Asn Leu Glu Ser Gly Val Pro Asp Arg Phe Ser Gly
210 215 220

Ser Gly Ser Gly Thr Asp Phe Thr Leu Thr Ile Ser Ser Leu Gln Ala
225 230 235 240

Glu Asp Val Ala Val Tyr Tyr Cys Gln Gln Ser Asn Glu Asp Pro Leu
245 250 255

Thr Phe Gly Gly Gly Thr Lys Val Glu Ile Lys Thr Ser Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr
290 295 300

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

```
Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 192
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Met Lys
            20                  25                  30

Pro Gly Ala Ser Val Lys Ile Ser Cys Lys Ala Ser Gly Tyr Thr Phe
        35                  40                  45

Thr Gly Tyr Trp Ile Glu Trp Val Arg Gln Arg Pro Gly Gln Gly Leu
    50                  55                  60

Glu Trp Met Gly Glu Ile Leu Pro Gly Gly Gly Asp Thr Asn Tyr Asn
65                  70                  75                  80

Gln Lys Phe Gln Gly Lys Val Thr Phe Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Met
145                 150                 155                 160

Thr Gln Ser Pro Asp Ser Leu Ala Val Ser Leu Gly Glu Arg Ala Thr
                165                 170                 175

Ile Asn Cys Lys Ala Ser Gln Ser Val Asp Tyr Asp Gly Asp Ser Phe
            180                 185                 190

Leu Asn Trp Tyr Gln Gln Lys Pro Gly Gln Pro Pro Lys Leu Phe Ile
```

```
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Val Gln Ala
225                 230                 235                 240

Glu Asp Ala Ala Val Tyr Tyr Cys Gln Gln Ser Asn Glu Asp Pro Leu
                245                 250                 255

Thr Phe Gly Gly Gly Thr Lys Val Glu Ile Lys Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 193
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Met Lys
            20                  25                  30

Pro Gly Ala Ser Val Lys Ile Ser Cys Lys Ala Ser Gly Tyr Thr Phe
        35                  40                  45

Thr Gly Tyr Trp Ile Glu Trp Val Arg Gln Arg Pro Gly Gln Gly Leu
    50                  55                  60
```

```
Glu Trp Met Gly Glu Ile Leu Pro Gly Gly Gly Asp Thr Asn Tyr Asn
65                  70                  75                  80

Gln Lys Phe Gln Gly Lys Val Thr Phe Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Arg Val Pro Val Tyr Phe Asp Tyr Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Gln Ser Val Asp Tyr Lys Gly Asp Ser Phe
            180                 185                 190

Leu Asn Trp Tyr Gln Gln Lys Pro Gly Gln Pro Pro Lys Leu Leu Ile
        195                 200                 205

Tyr Ala Ala Ser Asn Leu Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Gln Gln Ser Asn Glu Asp Pro Leu
                245                 250                 255

Thr Phe Gly Gly Gly Thr Lys Val Glu Ile Lys Thr Ser Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
```

485 490

<210> SEQ ID NO 194
<211> LENGTH: 494
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 194

Met Ala Trp Val Trp Thr Leu Leu Phe Leu Met Ala Ala Ala Gln Ser
1 5 10 15

Ile Gln Ala Glu Val Gln Leu Gln Glu Ser Gly Pro Gly Leu Val Lys
20 25 30

Pro Ser Glu Thr Leu Ser Leu Thr Cys Ser Val Ser Gly Gly Ser Ile
35 40 45

Ser Gly Ser Ser Tyr Tyr Trp Gly Trp Ile Arg Gln Pro Pro Gly Lys
50 55 60

Gly Leu Glu Trp Ile Gly Ser Ile Tyr Tyr Ser Gly Ser Thr Tyr Tyr
65 70 75 80

Asn Pro Ser Leu Lys Ser Arg Val Thr Ile Ser Val Asp Thr Ser Lys
85 90 95

Lys Gln Phe Ser Leu Lys Leu Arg Ser Val Thr Ala Ala Asp Thr Ala
100 105 110

Val Tyr Tyr Cys Ala Arg Glu Glu Asp Ser Gly Ser Tyr Tyr Val Gly
115 120 125

Ala Phe Asp Ile Trp Gly Gln Gly Thr Met Val Thr Val Ser Ser Gly
130 135 140

Gly Ser Glu Gly Lys Ser Ser Gly Ser Gly Ser Glu Ser Lys Ser Thr
145 150 155 160

Gly Gly Ser Ser Ser Glu Leu Thr Gln Asp Pro Ala Val Ser Val Ala
165 170 175

Leu Gly Gln Thr Val Arg Ile Arg Cys Gln Gly Asp Ser Leu Arg Lys
180 185 190

Tyr Tyr Gly Ser Trp Tyr Gln Gln Lys Pro Gly Gln Ala Pro Val Leu
195 200 205

Val Ile Tyr Gly Glu Thr Asn Arg Pro Ser Gly Ile Pro Asp Arg Phe
210 215 220

Ser Gly Ser Ser Ser Gly Asn Thr Ala Ser Leu Thr Ile Thr Gly Ala
225 230 235 240

Gln Ala Glu Asp Glu Ala Asp Tyr Tyr Cys Asn Ser Arg Asp Ser Ser
245 250 255

Gly Lys His Val Val Phe Gly Gly Gly Thr Lys Leu Thr Val Leu Thr
260 265 270

Ser Thr Pro Ala Pro Arg Pro Pro Thr Pro Ala Pro Thr Ile Ala Ser
275 280 285

Gln Pro Leu Ser Leu Arg Pro Glu Ala Cys Arg Pro Ala Ala Gly Gly
290 295 300

Ala Val His Thr Arg Gly Leu Asp Phe Ala Cys Asp Ile Tyr Ile Trp
305 310 315 320

Ala Pro Leu Ala Gly Thr Cys Gly Val Leu Leu Leu Ser Leu Val Ile
325 330 335

Thr Leu Tyr Cys Lys Arg Gly Arg Lys Lys Leu Leu Tyr Ile Phe Lys
340 345 350

Gln Pro Phe Met Arg Pro Val Gln Thr Thr Gln Glu Glu Asp Gly Cys
355 360 365

Ser Cys Arg Phe Pro Glu Glu Glu Glu Gly Gly Cys Glu Leu Arg Val
370 375 380

Lys Phe Ser Arg Ser Ala Asp Ala Pro Ala Tyr Lys Gln Gly Gln Asn
385 390 395 400

Gln Leu Tyr Asn Glu Leu Asn Leu Gly Arg Arg Glu Glu Tyr Asp Val
405 410 415

Leu Asp Lys Arg Arg Gly Arg Asp Pro Glu Met Gly Gly Lys Pro Arg
420 425 430

Arg Lys Asn Pro Gln Glu Gly Leu Tyr Asn Glu Leu Gln Lys Asp Lys
435 440 445

Met Ala Glu Ala Tyr Ser Glu Ile Gly Met Lys Gly Glu Arg Arg Arg
450 455 460

Gly Lys Gly His Asp Gly Leu Tyr Gln Gly Leu Ser Thr Ala Thr Lys
465 470 475 480

Asp Thr Tyr Asp Ala Leu His Met Gln Ala Leu Pro Pro Arg
485 490

<210> SEQ ID NO 195
<211> LENGTH: 494
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 195

Met Ala Trp Val Trp Thr Leu Leu Phe Leu Met Ala Ala Ala Gln Ser
1 5 10 15

Ile Gln Ala Gln Val Gln Leu Gln Glu Ser Gly Pro Gly Leu Val Lys
20 25 30

Pro Ser Glu Thr Leu Ser Leu Thr Cys Ser Val Ser Gly Gly Ser Ile
35 40 45

Arg Ser Ser Thr Tyr Tyr Trp Gly Trp Ile Arg Gln Pro Pro Gly Lys
50 55 60

Gly Leu Glu Trp Ile Gly Ser Ile Tyr Tyr Ser Gly Ser Thr Tyr Ser
65 70 75 80

Asn Pro Ser Leu Lys Ser Arg Val Thr Ile Ser Val Asp Thr Ser Lys
85 90 95

Asn Gln Phe Ser Leu Lys Leu Ser Ser Val Thr Ala Ala Asp Thr Ala
100 105 110

Ile Tyr Tyr Cys Ala Arg Glu Glu Asp Ser Gly Ser Tyr Tyr Val Gly
115 120 125

Thr Phe Asp Ile Trp Gly Gln Gly Thr Met Val Thr Val Ser Ser Gly
130 135 140

Gly Ser Glu Gly Lys Ser Ser Gly Ser Gly Ser Glu Ser Lys Ser Thr
145 150 155 160

Gly Gly Ser Ser Ser Glu Leu Thr Gln Asp Pro Ala Val Ser Val Ala
165 170 175

Leu Gly Gln Thr Val Arg Ile Thr Cys Gln Gly Asp Ser Leu Arg Asn
180 185 190

Tyr Tyr Gly Ser Trp Tyr Gln Gln Lys Pro Gly Gln Ala Pro Val Leu
195 200 205

Val Ile Tyr Gly Glu Lys Asn Arg Pro Ser Gly Ile Pro Asp Arg Phe
210 215 220

Ser Gly Ser Ser Ser Gly Asn Thr Val Ser Leu Thr Ile Thr Gly Thr
225 230 235 240

Gln Ala Glu Asp Glu Ala Asp Tyr Tyr Cys Asn Ser Arg Asp Ser Ser
245 250 255

Gly Lys His Val Val Phe Gly Gly Gly Thr Lys Leu Thr Val Leu Thr
260 265 270

Ser Thr Pro Ala Pro Arg Pro Pro Thr Pro Ala Pro Thr Ile Ala Ser
275 280 285

Gln Pro Leu Ser Leu Arg Pro Glu Ala Cys Arg Pro Ala Ala Gly Gly
290 295 300

Ala Val His Thr Arg Gly Leu Asp Phe Ala Cys Asp Ile Tyr Ile Trp
305 310 315 320

Ala Pro Leu Ala Gly Thr Cys Gly Val Leu Leu Leu Ser Leu Val Ile
325 330 335

Thr Leu Tyr Cys Lys Arg Gly Arg Lys Lys Leu Leu Tyr Ile Phe Lys
340 345 350

Gln Pro Phe Met Arg Pro Val Gln Thr Thr Gln Glu Glu Asp Gly Cys
355 360 365

Ser Cys Arg Phe Pro Glu Glu Glu Glu Gly Gly Cys Glu Leu Arg Val
370 375 380

Lys Phe Ser Arg Ser Ala Asp Ala Pro Ala Tyr Lys Gln Gly Gln Asn
385 390 395 400

Gln Leu Tyr Asn Glu Leu Asn Leu Gly Arg Arg Glu Glu Tyr Asp Val
405 410 415

Leu Asp Lys Arg Arg Gly Arg Asp Pro Glu Met Gly Gly Lys Pro Arg
420 425 430

Arg Lys Asn Pro Gln Glu Gly Leu Tyr Asn Glu Leu Gln Lys Asp Lys
435 440 445

Met Ala Glu Ala Tyr Ser Glu Ile Gly Met Lys Gly Glu Arg Arg Arg
450 455 460

Gly Lys Gly His Asp Gly Leu Tyr Gln Gly Leu Ser Thr Ala Thr Lys
465 470 475 480

Asp Thr Tyr Asp Ala Leu His Met Gln Ala Leu Pro Pro Arg
485 490

<210> SEQ ID NO 196
<211> LENGTH: 492
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 196

Met Ala Trp Val Trp Thr Leu Leu Phe Leu Met Ala Ala Ala Gln Ser
1 5 10 15

Ile Gln Ala Glu Val Gln Leu Val Glu Ser Gly Gly Gly Leu Val Gln
20 25 30

Pro Gly Gly Ser Leu Arg Leu Ser Cys Ala Ala Ser Gly Phe Thr Leu
35 40 45

Arg Asn Tyr Trp Met Ser Trp Val Arg Gln Ala Pro Gly Lys Gly Leu
50 55 60

Glu Trp Val Ala Asn Ile Asn Gln Asp Gly Ser Glu Lys Tyr Tyr Val
65 70 75 80

Asp Ser Val Glu Gly Arg Phe Thr Ile Ser Arg Asp Asn Ala Lys Lys

```
                85                  90                  95

Ser Leu Trp Leu Gln Met Ser Ser Leu Arg Val Glu Asp Thr Ala Val
            100                 105                 110

Tyr Tyr Cys Ala Arg Asp Pro Ile Glu Ser Arg Phe Asp Tyr Trp Gly
        115                 120                 125

Gln Gly Thr Leu Val Thr Val Ser Ser Gly Gly Ser Glu Gly Lys Ser
    130                 135                 140

Ser Gly Ser Gly Ser Glu Ser Lys Ser Thr Gly Gly Ser Asp Val Val
145                 150                 155                 160

Met Thr Gln Ser Pro Leu Ser Leu Pro Val Thr Leu Gly Gln Pro Ala
                165                 170                 175

Ser Ile Ser Cys Arg Ser Ser Gln Ser Leu Val Tyr Ser Asp Gly Asn
            180                 185                 190

Thr Tyr Leu Ser Trp Phe Gln Gln Arg Pro Gly Gln Ser Pro Arg Arg
        195                 200                 205

Leu Ile Tyr Lys Val Ser Asn Arg Asp Ser Gly Val Pro Asp Arg Phe
    210                 215                 220

Ser Gly Ser Gly Ser Gly Thr Asp Phe Thr Leu Lys Ile Ser Arg Val
225                 230                 235                 240

Glu Ala Glu Asp Val Gly Val Tyr Tyr Cys Met Gln Gly Thr His Trp
                245                 250                 255

Pro Pro Thr Phe Gly Gly Gly Thr Lys Val Glu Ile Lys Thr Ser Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 197

<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 197

```
Met Ala Trp Val Trp Thr Leu Leu Phe Leu Met Ala Ala Ala Gln Ser
1               5                   10                  15

Ile Gln Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Ile Tyr Ala Met Thr Trp Val Arg Gln Ala Pro Gly Lys Gly Leu
    50                  55                  60

Glu Trp Val Ser Gly Ile Ser Val Ser Gly Ile Arg Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Ser Ala Glu Asp Thr Ala Val
            100                 105                 110

Tyr Tyr Cys Ala Lys Gly Leu Ser Ser Gly Asp Arg Asp Ala Ser Asp
        115                 120                 125

Ile Trp Gly Gln Gly Thr Met Val Thr Val Ser Ser Gly Gly Ser Glu
    130                 135                 140

Gly Lys Ser Ser Gly Ser Gly Ser Glu Ser Lys Ser Thr Gly Gly Ser
145                 150                 155                 160

Ser Ser Glu Leu Thr Gln Pro Pro Ser Val Ser Val Ser Pro Gly Gln
                165                 170                 175

Thr Ala Arg Ile Thr Cys Ser Gly Asp Ala Leu Pro Arg Lys Tyr Ala
            180                 185                 190

Tyr Trp Tyr Gln Gln Lys Ser Gly Gln Ala Pro Val Leu Val Ile Tyr
        195                 200                 205

Glu Asp Ser Lys Arg Pro Ser Gly Ile Pro Glu Arg Phe Ser Gly Ser
    210                 215                 220

Asn Ser Gly Thr Met Ala Thr Leu Thr Ile Ser Gly Ala Gln Val Glu
225                 230                 235                 240

Asp Glu Ala Ala Tyr Tyr Cys Tyr Ser Thr Asp Ser Ser Ala Asn His
                245                 250                 255

Arg Val Phe Gly Gly Gly Thr Lys Leu Thr Val Leu Thr Ser Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
```

```
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 198
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Met Ala Trp Val Trp Thr Leu Leu Phe Leu Met Ala Ala Ala Gln Ser
1               5                   10                  15

Ile Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ile Phe
        35                  40                  45

Ser Thr Tyr Trp Met Ser Trp Val Arg Gln Ala Pro Gly Lys Gly Leu
    50                  55                  60

Glu Trp Val Ala Asn Ile Asn Pro Asp Gly Asn Glu Lys Tyr Tyr Val
65                  70                  75                  80

Asp Ser Val Glu Gly Arg Phe Thr Ile Ser Arg Asp Asn Ala Gln Asp
                85                  90                  95

Ser Leu Tyr Leu Gln Met Asn Ser Leu Arg Ala Glu Asp Thr Ala Val
            100                 105                 110

Tyr Tyr Cys Ala Arg Asp Pro Ile Ser Ala Arg Phe Asp Phe Trp Gly
        115                 120                 125

Gln Gly Thr Leu Val Thr Val Ser Ser Gly Gly Ser Glu Gly Lys Ser
    130                 135                 140

Ser Gly Ser Gly Ser Glu Ser Lys Ser Thr Gly Gly Ser Glu Ile Val
145                 150                 155                 160

Met Thr Gln Ser Pro Leu Ser Leu Pro Val Thr Pro Gly Lys Pro Ala
                165                 170                 175

Ser Ile Ser Cys Arg Ser Ser Gln Ser Leu Glu Tyr Ser Asp Gly Asn
            180                 185                 190

Thr Tyr Leu Asn Trp Phe Gln Gln Arg Pro Gly Gln Ser Pro Arg Arg
        195                 200                 205

Leu Ile Tyr Lys Val Ser Asn Arg Asp Ser Gly Val Pro Asp Arg Phe
    210                 215                 220

Ser Gly Ser Gly Ser Gly Thr Asp Phe Thr Leu Lys Ile Ser Arg Val
225                 230                 235                 240
```

Glu Ala Glu Asp Val Gly Val Tyr Tyr Cys Met Gln Gly Thr His Trp
245 250 255

Pro Pro Thr Phe Gly Gly Gly Thr Lys Val Asp Ile Lys Thr Ser Thr
260 265 270

Pro Ala Pro Arg Pro Pro Thr Pro Ala Pro Thr Ile Ala Ser Gln Pro
275 280 285

Leu Ser Leu Arg Pro Glu Ala Cys Arg Pro Ala Ala Gly Gly Ala Val
290 295 300

His Thr Arg Gly Leu Asp Phe Ala Cys Asp Ile Tyr Ile Trp Ala Pro
305 310 315 320

Leu Ala Gly Thr Cys Gly Val Leu Leu Leu Ser Leu Val Ile Thr Leu
325 330 335

Tyr Cys Lys Arg Gly Arg Lys Lys Leu Leu Tyr Ile Phe Lys Gln Pro
340 345 350

Phe Met Arg Pro Val Gln Thr Thr Gln Glu Glu Asp Gly Cys Ser Cys
355 360 365

Arg Phe Pro Glu Glu Glu Glu Gly Gly Cys Glu Leu Arg Val Lys Phe
370 375 380

Ser Arg Ser Ala Asp Ala Pro Ala Tyr Lys Gln Gly Gln Asn Gln Leu
385 390 395 400

Tyr Asn Glu Leu Asn Leu Gly Arg Arg Glu Glu Tyr Asp Val Leu Asp
405 410 415

Lys Arg Arg Gly Arg Asp Pro Glu Met Gly Gly Lys Pro Arg Arg Lys
420 425 430

Asn Pro Gln Glu Gly Leu Tyr Asn Glu Leu Gln Lys Asp Lys Met Ala
435 440 445

Glu Ala Tyr Ser Glu Ile Gly Met Lys Gly Glu Arg Arg Arg Gly Lys
450 455 460

Gly His Asp Gly Leu Tyr Gln Gly Leu Ser Thr Ala Thr Lys Asp Thr
465 470 475 480

Tyr Asp Ala Leu His Met Gln Ala Leu Pro Pro Arg
485 490

<210> SEQ ID NO 199
<211> LENGTH: 489
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 199

Met Ala Trp Val Trp Thr Leu Leu Phe Leu Met Ala Ala Ala Gln Ser
1 5 10 15

Ile Gln Ala Glu Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Ser Ser Tyr Ala Met Asn Trp Val Arg Gln Ala Pro Gly Lys Gly Leu
50 55 60

Glu Trp Val Ser Thr Ile Ser Gly Ser Gly Gly Ser Ser Tyr Tyr Ala
65 70 75 80

Asp Ser Val Lys Gly Arg Phe Thr Ile Ser Arg Asp Asn Ser Lys Asn
85 90 95

Thr Leu Tyr Leu Gln Met Asn Ser Leu Arg Ala Glu Asp Thr Ala Val
100 105 110

```
Tyr Tyr Cys Ala Asn Pro Ser Gly Thr Phe Trp Asn Asp Ala Phe Asp
        115                 120                 125

Ile Trp Gly Gln Gly Thr Met Val Thr Val Ser Ser Gly Gly Ser Glu
    130                 135                 140

Gly Lys Ser Ser Gly Ser Gly Ser Glu Ser Lys Ser Thr Gly Gly Ser
145                 150                 155                 160

Ser Tyr Glu Leu Thr Gln Pro Pro Ser Val Ser Val Ser Pro Gly Gln
                165                 170                 175

Thr Ala Ser Ile Thr Cys Ser Gly Asp Lys Leu Gly Asp Glu Phe Ala
            180                 185                 190

Ser Trp Tyr Gln Gln Lys Pro Gly Gln Ser Pro Val Val Val Ile Tyr
        195                 200                 205

Gln Asp Thr Lys Arg Pro Ser Gly Ile Pro Glu Arg Phe Ser Gly Ser
    210                 215                 220

Asn Ser Gly Asn Thr Ala Thr Leu Thr Ile Ser Gly Thr Gln Ala Met
225                 230                 235                 240

Asp Glu Ala Asp Tyr Tyr Cys Gln Ala Trp Asp Ser Asn Thr Ala Val
                245                 250                 255

Phe Gly Gly Gly Thr Lys Leu Thr Val Leu Thr Ser Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Lys Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 200
<211> LENGTH: 493
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 200

```
Met Ala Trp Val Trp Thr Leu Leu Phe Leu Met Ala Ala Ala Gln Ser
1               5                   10                  15

Ile Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Asn Asn Tyr Ala Met Asn Trp Val Arg Gln Ala Pro Gly Lys Gly Leu
    50                  55                  60

Glu Trp Val Ser Val Ile Ser Gly Asn Gly Gly Ser Ile His Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Thr Pro Arg Gly Tyr Thr Gly Tyr Asp Gly Asp Ala
        115                 120                 125

Phe Asp Phe Trp Gly Gln Gly Thr Met Val Thr Val Ser Ser Gly Gly
    130                 135                 140

Ser Glu Gly Lys Ser Ser Gly Ser Gly Ser Glu Ser Lys Ser Thr Gly
145                 150                 155                 160

Gly Ser Ser Tyr Glu Leu Thr Gln Pro Pro Ser Val Ser Val Ser Pro
                165                 170                 175

Gly Gln Thr Ala Arg Ile Thr Cys Ser Gly Asp Ala Leu Pro Lys Lys
            180                 185                 190

Tyr Ala Tyr Trp Tyr Gln Gln Lys Ser Gly Gln Ala Pro Val Leu Val
        195                 200                 205

Ile Tyr Glu Asp Ser Lys Arg Pro Ser Gly Ile Pro Glu Arg Phe Ser
    210                 215                 220

Ala Ser Ser Ser Gly Thr Met Ala Thr Leu Thr Ile Ser Gly Ala Gln
225                 230                 235                 240

Val Glu Asp Glu Ala Asp Tyr Tyr Cys Tyr Ser Ala Asp Ser Ser Gly
                245                 250                 255

Ser His Trp Val Phe Gly Gly Gly Thr Lys Leu Thr Val Leu Thr Ser
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400
```

```
Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 201
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Met Ala Trp Val Trp Thr Leu Leu Phe Leu Met Ala Ala Ala Gln Ser
1               5                   10                  15

Ile Gln Ala Glu Val Gln Leu Val Glu Ser Gly Gly Asp Leu Val Gln
            20                  25                  30

Pro Gly Gly Ser Leu Arg Leu Ser Cys Glu Ala Ser Gly Phe Thr Phe
        35                  40                  45

Ser Asn Tyr Gly Met Asn Trp Val Arg Gln Ala Pro Gly Lys Gly Leu
    50                  55                  60

Glu Trp Val Ser Gly Ile Ser Gly Ser Gly Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Asn Leu Leu Leu Trp Leu Gly Tyr His Gly Asp Gly
        115                 120                 125

Phe Asp Leu Trp Gly Gln Gly Thr Met Val Thr Val Ser Ser Gly Gly
    130                 135                 140

Ser Glu Gly Lys Ser Ser Gly Ser Gly Ser Glu Ser Lys Ser Thr Gly
145                 150                 155                 160

Gly Ser Ser Tyr Glu Leu Thr Gln Pro Pro Ser Val Ser Val Ser Pro
                165                 170                 175

Gly Gln Thr Ala Arg Ile Thr Cys Ser Gly Asp Ala Leu Pro Lys Lys
            180                 185                 190

Tyr Ala Tyr Trp Tyr Gln Lys Lys Ser Gly Gln Ala Pro Val Leu Val
        195                 200                 205

Ile His Glu Asp Ser Lys Arg Pro Ser Gly Ile Pro Glu Arg Phe Ser
    210                 215                 220

Gly Ser Ser Ser Gly Thr Met Ala Thr Leu Thr Ile Ser Gly Ala Gln
225                 230                 235                 240

Val Glu Asp Glu Ala Asp Tyr Tyr Cys Phe Ser Thr Asp Arg Ser Gly
                245                 250                 255

Asn His Val Val Phe Gly Gly Gly Thr Lys Leu Thr Val Leu Thr Ser
```

```
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 202
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 202

```
Met Ala Trp Val Trp Thr Leu Leu Phe Leu Met Ala Ala Ala Gln Ser
1               5                   10                  15

Ile Gln Ala Gln Val Gln Leu Gln Gln Ser Gly Pro Gly Leu Val Lys
            20                  25                  30

Pro Ser Gln Thr Leu Ser Leu Thr Cys Ala Ile Ser Gly Asp Ser Val
        35                  40                  45

Ser Ser Lys Ser Gly Ala Trp Asn Trp Ile Arg Gln Ser Pro Ser Arg
    50                  55                  60

Gly Leu Glu Trp Leu Gly Arg Thr Tyr Tyr Arg Ser Lys Trp Tyr Asn
65                  70                  75                  80

Glu Tyr Ala Val Ser Val Lys Ser Arg Ile Thr Ile Asn Pro Asp Thr
                85                  90                  95

Ser Lys Asn Gln Phe Ser Leu Gln Leu Asn Ser Val Thr Pro Glu Asp
            100                 105                 110

Thr Ala Val Tyr Tyr Cys Thr Arg Val Asp Thr Asp Phe Asp Tyr Trp
        115                 120                 125
```

```
Gly Gln Gly Thr Leu Val Thr Val Ser Ser Gly Gly Ser Glu Gly Lys
    130                 135                 140

Ser Ser Gly Ser Gly Ser Glu Ser Lys Ser Thr Gly Gly Ser Gln Ser
145                 150                 155                 160

Ala Leu Thr Gln Pro Pro Ser Val Ser Glu Ala Pro Arg Gln Arg Val
                165                 170                 175

Thr Ile Ser Cys Ser Gly Ser Ala Ser Asn Ile Gly Asn Asn Gly Val
            180                 185                 190

Asn Trp Tyr Gln Gln Leu Pro Gly Lys Thr Pro Lys Leu Leu Ile Tyr
        195                 200                 205

Asn Asp Asp Leu Leu Pro Ser Gly Val Ser Asp Arg Phe Ser Gly Ser
    210                 215                 220

Lys Ser Gly Thr Ser Ala Ser Leu Ala Ile Ser Gly Leu Gln Ser Glu
225                 230                 235                 240

Asp Glu Ala Asp Tyr Phe Cys Ala Ala Trp Asp Asp Ser Leu Asn Gly
                245                 250                 255

Leu Val Phe Gly Gly Gly Thr Lys Leu Thr Val Leu Thr Ser Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 203
<211> LENGTH: 491
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 203

```
Met Ala Trp Val Trp Thr Leu Leu Phe Leu Met Ala Ala Ala Gln Ser
1               5                   10                  15

Ile Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg His Thr Met Asn Trp Val Arg Gln Ala Pro Gly Lys Gly Leu
    50                  55                  60

Glu Trp Val Ser Ser Ile Ser Gly Ser Gly Gly Ser Thr Tyr Tyr Ala
65                  70                  75                  80

Asp Ser Val Lys Gly Arg Phe Thr Val Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Ser Tyr Asp Ser Ser Gly Val Trp Tyr Phe
        115                 120                 125

Asp Leu Trp Gly Arg Gly Thr Leu Val Thr Val Ser Ser Gly Gly Ser
    130                 135                 140

Glu Gly Lys Ser Ser Gly Ser Gly Ser Glu Ser Lys Ser Thr Gly Gly
145                 150                 155                 160

Ser Ser Tyr Glu Leu Thr Gln Pro Pro Ser Val Ser Val Ser Pro Gly
                165                 170                 175

Gln Thr Ala Ser Ile Thr Cys Ser Gly His Lys Leu Gly Asp Lys Tyr
            180                 185                 190

Ala Ser Trp Tyr Gln Gln Lys Pro Gly Gln Ser Pro Val Leu Val Ile
        195                 200                 205

Tyr Gln Asp Ser Lys Arg Pro Ser Gly Ile Pro Glu Arg Phe Ser Gly
    210                 215                 220

Ser Asn Ser Gly Asn Thr Ala Thr Leu Thr Ile Ser Gly Thr Gln Ala
225                 230                 235                 240

Met Asp Glu Ala Asp Tyr Tyr Cys Gln Ala Trp Asp Ser Ile Thr Ala
                245                 250                 255

Trp Val Phe Gly Gly Gly Thr Lys Leu Thr Val Leu Thr Ser Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415
```

```
Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 204
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Met Ala Trp Val Trp Thr Leu Leu Phe Leu Met Ala Ala Ala Gln Ser
1               5                   10                  15

Ile Gln Ala Gln Val Gln Leu Gln Glu Ser Gly Pro Gly Leu Val Lys
            20                  25                  30

Pro Ser Glu Thr Leu Ser Leu Thr Cys Thr Val Ser Ser Gly Ser Ile
        35                  40                  45

Ser Ser Tyr Tyr Trp Asn Trp Ile Arg Gln Pro Ala Gly Lys Gly Leu
    50                  55                  60

Glu Trp Ile Gly Arg Ile Tyr Thr Ser Gly Thr Thr His Tyr Asn Pro
65                  70                  75                  80

Ser Leu Lys Ser Arg Val Thr Met Ser Ile Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Glu Ile Arg Glu Leu Arg Gly Phe Asp Tyr Trp Gly
        115                 120                 125

Gln Gly Thr Leu Val Thr Val Ser Ser Gly Gly Ser Glu Gly Lys Ser
    130                 135                 140

Ser Gly Ser Gly Ser Glu Ser Lys Ser Thr Gly Gly Ser Ser Tyr Glu
145                 150                 155                 160

Leu Met Gln Pro Pro Ser Val Ser Val Ser Pro Gly Gln Thr Ala Arg
                165                 170                 175

Ile Thr Cys Ser Gly Asp Ala Leu Pro Arg Gln Tyr Ala Tyr Trp Tyr
            180                 185                 190

Gln Gln Lys Pro Gly Gln Ala Pro Val Leu Val Ile Tyr Lys Asp Ser
        195                 200                 205

Glu Arg Pro Ser Gly Ile Pro Glu Arg Phe Ser Gly Ser Ser Ser Gly
    210                 215                 220

Thr Thr Val Thr Leu Thr Ile Ser Gly Val Gln Ala Glu Asp Glu Ala
225                 230                 235                 240

Asp Tyr Tyr Cys Gln Ser Ala Asp Arg Thr Gly Ile Tyr Val Leu Phe
                245                 250                 255

Gly Gly Gly Thr Lys Leu Thr Val Leu Thr Ser Thr Pro Ala Pro Arg
            260                 265                 270

Pro Pro Thr Pro Ala Pro Thr Ile Ala Ser Gln Pro Leu Ser Leu Arg
        275                 280                 285
```

Pro Glu Ala Cys Arg Pro Ala Ala Gly Gly Ala Val His Thr Arg Gly
290 295 300

Leu Asp Phe Ala Cys Asp Ile Tyr Ile Trp Ala Pro Leu Ala Gly Thr
305 310 315 320

Cys Gly Val Leu Leu Leu Ser Leu Val Ile Thr Leu Tyr Cys Lys Arg
325 330 335

Gly Arg Lys Lys Leu Leu Tyr Ile Phe Lys Gln Pro Phe Met Arg Pro
340 345 350

Val Gln Thr Thr Gln Glu Glu Asp Gly Cys Ser Cys Arg Phe Pro Glu
355 360 365

Glu Glu Glu Gly Gly Cys Glu Leu Arg Val Lys Phe Ser Arg Ser Ala
370 375 380

Asp Ala Pro Ala Tyr Lys Gln Gly Gln Asn Gln Leu Tyr Asn Glu Leu
385 390 395 400

Asn Leu Gly Arg Arg Glu Glu Tyr Asp Val Leu Asp Lys Arg Arg Gly
405 410 415

Arg Asp Pro Glu Met Gly Gly Lys Pro Arg Arg Lys Asn Pro Gln Glu
420 425 430

Gly Leu Tyr Asn Glu Leu Gln Lys Asp Lys Met Ala Glu Ala Tyr Ser
435 440 445

Glu Ile Gly Met Lys Gly Glu Arg Arg Arg Gly Lys Gly His Asp Gly
450 455 460

Leu Tyr Gln Gly Leu Ser Thr Ala Thr Lys Asp Thr Tyr Asp Ala Leu
465 470 475 480

His Met Gln Ala Leu Pro Pro Arg
485

<210> SEQ ID NO 205
<211> LENGTH: 488
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

Met Ala Trp Val Trp Thr Leu Leu Phe Leu Met Ala Ala Ala Gln Ser
1 5 10 15

Ile Gln Ala Gln Val Gln Leu Gln Glu Ser Gly Pro Gly Leu Val Lys
20 25 30

Pro Ser Glu Thr Leu Ser Leu Thr Cys Thr Val Ser Ser Gly Ser Ile
35 40 45

Ser Ser Tyr Tyr Trp Asn Trp Ile Arg Gln Pro Ala Gly Lys Gly Leu
50 55 60

Glu Trp Ile Gly Arg Ile Tyr Thr Ser Gly Thr Thr His Tyr Asn Pro
65 70 75 80

Ser Leu Lys Ser Arg Val Thr Met Ser Ile Asp Thr Ser Lys Asn Gln
85 90 95

Phe Ser Leu Lys Leu Ser Ser Val Thr Ala Ala Asp Thr Ala Val Tyr
100 105 110

Tyr Cys Ala Arg Glu Ile Arg Glu Leu Arg Gly Phe Asp Tyr Trp Gly
115 120 125

Gln Gly Thr Leu Val Thr Val Ser Ser Gly Gly Ser Glu Gly Lys Ser
130 135 140

Ser Gly Ser Gly Ser Glu Ser Lys Ser Thr Gly Gly Ser Ser Tyr Glu 145 150 155 160

Leu Thr Gln Pro Pro Ser Val Ser Val Ser Pro Gly Gln Thr Ala Arg
165 170 175

Ile Thr Cys Ser Gly Asp Ala Leu Pro Arg Gln Tyr Ala Tyr Trp Tyr
180 185 190

Gln Gln Lys Pro Gly Gln Ala Pro Val Leu Val Ile Tyr Lys Asp Ser
195 200 205

Glu Arg Pro Ser Gly Ile Pro Glu Arg Phe Ser Gly Ser Ser Ser Gly
210 215 220

Thr Thr Val Thr Leu Thr Ile Ser Gly Val Gln Ala Glu Asp Glu Ala
225 230 235 240

Asp Tyr Tyr Cys Gln Ser Ala Asp Arg Thr Gly Ile Tyr Val Leu Phe
245 250 255

Gly Gly Gly Thr Lys Leu Thr Val Leu Thr Ser Thr Pro Ala Pro Arg
260 265 270

Pro Pro Thr Pro Ala Pro Thr Ile Ala Ser Gln Pro Leu Ser Leu Arg
275 280 285

Pro Glu Ala Cys Arg Pro Ala Ala Gly Gly Ala Val His Thr Arg Gly
290 295 300

Leu Asp Phe Ala Cys Asp Ile Tyr Ile Trp Ala Pro Leu Ala Gly Thr
305 310 315 320

Cys Gly Val Leu Leu Leu Ser Leu Val Ile Thr Leu Tyr Cys Lys Arg
325 330 335

Gly Arg Lys Lys Leu Leu Tyr Ile Phe Lys Gln Pro Phe Met Arg Pro
340 345 350

Val Gln Thr Thr Gln Glu Glu Asp Gly Cys Ser Cys Arg Phe Pro Glu
355 360 365

Glu Glu Glu Gly Gly Cys Glu Leu Arg Val Lys Phe Ser Arg Ser Ala
370 375 380

Asp Ala Pro Ala Tyr Lys Gln Gly Gln Asn Gln Leu Tyr Asn Glu Leu
385 390 395 400

Asn Leu Gly Arg Arg Glu Glu Tyr Asp Val Leu Asp Lys Arg Arg Gly
405 410 415

Arg Asp Pro Glu Met Gly Gly Lys Pro Arg Arg Lys Asn Pro Gln Glu
420 425 430

Gly Leu Tyr Asn Glu Leu Gln Lys Asp Lys Met Ala Glu Ala Tyr Ser
435 440 445

Glu Ile Gly Met Lys Gly Glu Arg Arg Arg Gly Lys Gly His Asp Gly
450 455 460

Leu Tyr Gln Gly Leu Ser Thr Ala Thr Lys Asp Thr Tyr Asp Ala Leu
465 470 475 480

His Met Gln Ala Leu Pro Pro Arg
485

<210> SEQ ID NO 206
<211> LENGTH: 491
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 206

Met Ala Trp Val Trp Thr Leu Leu Phe Leu Met Ala Ala Ala Gln Ser
1 5 10 15

```
Ile Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg His Thr Met Asn Trp Val Arg Gln Ala Pro Gly Lys Gly Leu
    50                  55                  60

Glu Trp Val Ser Ser Ile Ser Gly Ser Gly Gly Ser Thr Tyr Tyr Ala
65                  70                  75                  80

Asp Ser Val Lys Gly Arg Phe Thr Val Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Ser Tyr Asp Ser Ser Gly Val Trp Tyr Phe
        115                 120                 125

Asp Leu Trp Gly Lys Gly Thr Thr Val Thr Val Ser Ser Gly Gly Ser
    130                 135                 140

Glu Gly Lys Ser Ser Gly Ser Gly Ser Glu Ser Lys Ser Thr Gly Gly
145                 150                 155                 160

Ser Ser Tyr Glu Leu Thr Gln Pro Pro Ser Val Ser Val Ser Pro Gly
                165                 170                 175

Gln Thr Ala Ser Ile Thr Cys Ser Gly His Lys Leu Gly Asp Lys Tyr
            180                 185                 190

Ala Ser Trp Tyr Gln Gln Lys Pro Gly Gln Ser Pro Val Leu Val Ile
        195                 200                 205

Tyr Gln Asp Ser Lys Arg Pro Ser Gly Ile Pro Glu Arg Phe Ser Gly
    210                 215                 220

Ser Asn Ser Gly Asn Thr Ala Thr Leu Thr Ile Ser Gly Thr Gln Ala
225                 230                 235                 240

Met Asp Glu Ala Asp Tyr Tyr Cys Gln Ala Trp Asp Ser Ile Thr Ala
                245                 250                 255

Trp Val Phe Gly Gly Gly Thr Lys Leu Thr Val Leu Thr Ser Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
```

```
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 207
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Met Ala Trp Val Trp Thr Leu Leu Phe Leu Met Ala Ala Ala Gln Ser
1               5                   10                  15

Ile Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Asn Ser Tyr Asn Met Asn Trp Val Arg Gln Ala Pro Gly Lys Gly Leu
    50                  55                  60

Glu Trp Val Ser Tyr Ile Ser Ser Ser Gly Tyr Thr Ile Tyr Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asp Ser Leu Arg Asp Glu Asp Thr Ala Ile
            100                 105                 110

Tyr Tyr Cys Ala Arg Asp Arg Tyr Asn Tyr Asp Asn Gly Gly Tyr His
        115                 120                 125

Tyr Tyr Thr Gly Met Asp Val Trp Gly Gln Gly Thr Met Val Thr Val
    130                 135                 140

Ser Ser Gly Gly Ser Glu Gly Lys Ser Ser Gly Ser Gly Ser Glu Ser
145                 150                 155                 160

Lys Ser Thr Gly Gly Ser Ser Tyr Glu Leu Thr Gln Pro Pro Ser Val
                165                 170                 175

Ser Val Ser Pro Gly Gln Thr Ala Ser Ile Thr Cys Ser Gly Asp Lys
            180                 185                 190

Leu Gly Asp Lys Phe Ala Ser Trp Tyr Gln Gln Lys Pro Gly Gln Ser
        195                 200                 205

Pro Val Leu Val Ile Phe Gln Asp Ser Lys Arg Pro Ser Gly Ile Pro
    210                 215                 220

Glu Arg Phe Ser Gly Ser Asn Ser Gly Asn Thr Ala Thr Leu Thr Ile
225                 230                 235                 240

Ser Gly Thr Gln Ala Met Asp Glu Ala Asp Tyr Phe Cys Gln Ala Trp
                245                 250                 255

Asp Ser Thr Thr Ala Trp Val Phe Gly Gly Gly Thr Lys Leu Thr Val
            260                 265                 270

Leu Thr Ser Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300
```

```
Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Lys Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495
```

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

```
Gly Tyr Thr Phe Thr Gly Tyr
1               5
```

<210> SEQ ID NO 209
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

```
Leu Pro Gly Gly Gly Asp
1               5
```

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

```
Arg Val Pro Val Tyr Phe Asp
1               5
```

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 211

Ser Gln Ser Val Asp Tyr Asp Gly Asp Ser Phe
1 5 10

<210> SEQ ID NO 212
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 212

Ala Ala Ser
1

<210> SEQ ID NO 213
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 213

Ser Asn Glu Asp Pro Leu
1 5

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 214

Ser Gln Ser Val Asp Tyr Glu Gly Asp Ser Phe
1 5 10

<210> SEQ ID NO 215
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Ser Gln Ser Val Asp Tyr Lys Gly Asp Ser Phe
1 5 10

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Gly Gly Ser Ile Ser Gly Ser Ser Tyr
1 5

<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 217

Tyr Tyr Ser Gly Ser
1 5

<210> SEQ ID NO 218
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Glu Glu Asp Ser Gly Ser Tyr Tyr Val Gly Ala Phe Asp
1 5 10

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 219

Asp Ser Leu Arg Lys Tyr Tyr
1 5

<210> SEQ ID NO 220
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 220

Gly Glu Thr
1

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Arg Asp Ser Ser Gly Lys His Val
1 5

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 222

Gly Phe Thr Leu Arg Asn Tyr
1 5

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 223

Asn Gln Asp Gly Ser Glu
1 5

<210> SEQ ID NO 224
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 224

Asp Pro Ile Glu Ser Arg Phe Asp
1 5

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 225

Ser Gln Ser Leu Val Tyr Ser Asp Gly Asn Thr Tyr
1 5 10

<210> SEQ ID NO 226
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 226

Lys Val Ser
1

<210> SEQ ID NO 227
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 227

Gly Thr His Trp Pro Pro
1 5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 228

Gly Gly Ser Ile Arg Ser Ser Thr Tyr
1 5

<210> SEQ ID NO 229
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 229

Glu Glu Asp Ser Gly Ser Tyr Tyr Val Gly Thr Phe Asp
1 5 10

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 230

Asp Ser Leu Arg Asn Tyr Tyr
1 5

<210> SEQ ID NO 231
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 231

Gly Glu Lys
1

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 232

Gly Phe Thr Phe Thr Ile Tyr
1 5

<210> SEQ ID NO 233
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 233

Ser Val Ser Gly Ile Arg
1               5

<210> SEQ ID NO 234
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Leu Ser Ser Gly Asp Arg Asp Ala Ser Asp
1               5                   10

<210> SEQ ID NO 235
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Asp Ala Leu Pro Arg Lys Tyr
1               5

<210> SEQ ID NO 236
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Glu Asp Ser
1

<210> SEQ ID NO 237
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Thr Asp Ser Ser Ala Asn His Arg
1               5

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Phe Ile Phe Ser Thr Tyr
1               5

<210> SEQ ID NO 239
<211> LENGTH: 6
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 239

Asn Pro Asp Gly Asn Glu
1               5

<210> SEQ ID NO 240
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Asp Pro Ile Ser Ala Arg Phe Asp
1               5

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ser Gln Ser Leu Glu Tyr Ser Asp Gly Asn Thr Tyr
1               5                   10

<210> SEQ ID NO 242
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Phe Thr Phe Ser Ser Tyr
1               5

<210> SEQ ID NO 243
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ser Gly Ser Gly Gly Ser
1               5

<210> SEQ ID NO 244
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Pro Ser Gly Thr Phe Trp Asn Asp Ala Phe Asp
1               5                   10

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 245

Asp Lys Leu Gly Asp Glu Phe
1 5

<210> SEQ ID NO 246
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 246

Gln Asp Thr
1

<210> SEQ ID NO 247
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 247

Trp Asp Ser Asn Thr Ala
1 5

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 248

Gly Phe Thr Phe Asn Asn Tyr
1 5

<210> SEQ ID NO 249
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 249

Ser Gly Asn Gly Gly Ser
1 5

<210> SEQ ID NO 250
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 250

Pro Arg Gly Tyr Thr Gly Tyr Asp Gly Asp Ala Phe Asp
1 5 10

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 251

Asp Ala Leu Pro Lys Lys Tyr
1 5

<210> SEQ ID NO 252
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 252

Ala Asp Ser Ser Gly Ser His Trp
1 5

<210> SEQ ID NO 253
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 253

Gly Phe Thr Phe Ser Asn Tyr
1 5

<210> SEQ ID NO 254
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 254

Ser Gly Ser Gly Gly Thr
1 5

<210> SEQ ID NO 255
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 255

Leu Leu Leu Trp Leu Gly Tyr His Gly Asp Gly Phe Asp
1 5 10

<210> SEQ ID NO 256
<211> LENGTH: 8

<212> TYPE: PRT
<213> ORGANISM: Artificial Sequence
<220> FEATURE:
<223> OTHER INFORMATION: Description of Artificial Sequence: Synthetic peptide

<400> SEQUENCE: 256

Thr Asp Arg Ser Gly Asn His Val
1 5

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

Gly Asp Ser Val Ser Ser Lys Ser Gly
1 5

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 258

Tyr Tyr Arg Ser Lys Trp Tyr
1 5

<210> SEQ ID NO 259
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 259

Val Asp Thr Asp Phe Asp
1 5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 260

Ser Ala Ser Asn Ile Gly Asn Asn Gly
1 5

<210> SEQ ID NO 261
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 261

Asn Asp Asp

1

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 262

Trp Asp Asp Ser Leu Asn Gly Leu
1 5

<210> SEQ ID NO 263
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 263

Gly Phe Thr Phe Ser Arg His
1 5

<210> SEQ ID NO 264
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 264

Glu Ser Tyr Asp Ser Ser Gly Val Trp Tyr Phe Asp
1 5 10

<210> SEQ ID NO 265
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 265

His Lys Leu Gly Asp Lys Tyr
1 5

<210> SEQ ID NO 266
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 266

Gln Asp Ser
1

<210> SEQ ID NO 267
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 267

Trp Asp Ser Ile Thr Ala Trp
1 5

<210> SEQ ID NO 268
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

Ser Gly Ser Ile Ser Ser Tyr
1 5

<210> SEQ ID NO 269
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 269

Tyr Thr Ser Gly Thr
1 5

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 270

Glu Ile Arg Glu Leu Arg Gly Phe Asp
1 5

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 271

Asp Ala Leu Pro Arg Gln Tyr
1 5

<210> SEQ ID NO 272
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 272

Lys Asp Ser
1

<210> SEQ ID NO 273

<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 273

Ala Asp Arg Thr Gly Ile Tyr Val
1 5

<210> SEQ ID NO 274
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 274

Gly Phe Thr Phe Asn Ser Tyr
1 5

<210> SEQ ID NO 275
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 275

Ser Ser Ser Gly Tyr Thr
1 5

<210> SEQ ID NO 276
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 276

Asp Arg Tyr Asn Tyr Asp Asn Gly Gly Tyr His Tyr Tyr Thr Gly Met
1 5 10 15

Asp

<210> SEQ ID NO 277
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 277

Asp Lys Leu Gly Asp Lys Phe
1 5

<210> SEQ ID NO 278
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 278

Trp Asp Ser Thr Thr Ala Trp
1 5

<210> SEQ ID NO 279
<211> LENGTH: 330
<212> TYPE: PRT
<213> ORGANISM: Homo sapiens

<400> SEQUENCE: 279

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 280
<211> LENGTH: 326

<212> TYPE: PRT
<213> ORGANISM: Homo sapiens

<400> SEQUENCE: 280

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 281
<211> LENGTH: 327
<212> TYPE: PRT
<213> ORGANISM: Homo sapiens

<400> SEQUENCE: 281

```
Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 282
<211> LENGTH: 229
<212> TYPE: PRT
<213> ORGANISM: Homo sapiens

<400> SEQUENCE: 282

Met Ala Arg Leu Ala Leu Ser Pro Val Pro Ser His Trp Met Val Ala
1 5 10 15

Leu Leu Leu Leu Leu Ser Ala Glu Pro Val Pro Ala Ala Arg Ser Glu
20 25 30

Asp Arg Tyr Arg Asn Pro Lys Gly Ser Ala Cys Ser Arg Ile Trp Gln
35 40 45

Ser Pro Arg Phe Ile Ala Arg Lys Arg Gly Phe Thr Val Lys Met His
50 55 60

Cys Tyr Met Asn Ser Ala Ser Gly Asn Val Ser Trp Leu Trp Lys Gln
65 70 75 80

Glu Met Asp Glu Asn Pro Gln Gln Leu Lys Leu Glu Lys Gly Arg Met
85 90 95

Glu Glu Ser Gln Asn Glu Ser Leu Ala Thr Leu Thr Ile Gln Gly Ile
100 105 110

Arg Phe Glu Asp Asn Gly Ile Tyr Phe Cys Gln Gln Lys Cys Asn Asn
115 120 125

Thr Ser Glu Val Tyr Gln Gly Cys Gly Thr Glu Leu Arg Val Met Gly
130 135 140

Phe Ser Thr Leu Ala Gln Leu Lys Gln Arg Asn Thr Leu Lys Asp Gly
145 150 155 160

Ile Ile Met Ile Gln Thr Leu Leu Ile Ile Leu Phe Ile Ile Val Pro
165 170 175

Ile Phe Leu Leu Leu Asp Lys Asp Asp Ser Lys Ala Gly Met Glu Glu
180 185 190

Asp His Thr Tyr Glu Gly Leu Asp Ile Asp Gln Thr Ala Thr Tyr Glu
195 200 205

Asp Ile Val Thr Leu Arg Thr Gly Glu Val Lys Trp Ser Val Gly Glu
210 215 220

His Pro Gly Gln Glu
225

<210> SEQ ID NO 283
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 283

Glu Val Gln Leu Gln Gln Ser Gly Ala Glu Leu Met Lys Pro Gly Ala
1 5 10 15

Ser Val Lys Ile Ser Cys Lys Ala Thr Gly Tyr Thr Phe Ser Ser Tyr
20 25 30

Trp Ile Glu Trp Val Lys Gln Arg Pro Gly His Gly Leu Glu Trp Ile
35 40 45

Gly Glu Ile Leu Pro Gly Gly Gly Asp Thr Asn Tyr Asn Glu Ile Phe
50 55 60

Lys Gly Lys Ala Thr Phe Thr Ala Asp Thr Ser Ser Asn Thr Ala Tyr
65 70 75 80

Met Gln Leu Ser Ser Leu Thr Ser Glu Asp Ser Ala Val Tyr Tyr Cys
85 90 95

Thr Arg Arg Val Pro Val Tyr Phe Asp Tyr Trp Gly Gln Gly Thr Ser
100 105 110

Val Thr Val Ser Ser
115

<210> SEQ ID NO 284
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 284

Asp Ile Val Leu Thr Gln Ser Pro Ala Ser Leu Ala Val Ser Leu Gly
1 5 10 15

Gln Arg Ala Thr Ile Ser Cys Lys Ala Ser Gln Ser Val Asp Tyr Asp
20 25 30

Gly Asp Ser Phe Leu Asn Trp Tyr Gln Gln Lys Pro Gly Gln Pro Pro
35 40 45

Lys Leu Phe Ile Tyr Ala Ala Ser Asn Leu Glu Ser Gly Ile Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Thr Tyr Tyr Cys Gln Gln Ser Asn
85 90 95

Glu Asp Pro Leu Thr Phe Gly Ala Gly Thr Glu Leu Glu Leu Lys
100 105 110

<210> SEQ ID NO 285
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

Glu Pro Lys Ser Cys Asp Lys Thr His Thr Cys Pro Pro Cys Pro
1 5 10 15

<210> SEQ ID NO 286
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 286

Glu Arg Lys Cys Cys Val Glu Cys Pro Pro Cys Pro
1 5 10

<210> SEQ ID NO 287
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 287

Glu Leu Lys Thr Pro Leu Gly Asp Thr Thr His Thr Cys Pro Arg Cys
1 5 10 15

Pro Glu Pro Lys Ser Cys Asp Thr Pro Pro Pro Cys Pro Arg Cys Pro
20 25 30

Glu Pro Lys Ser Cys Asp Thr Pro Pro Pro Cys Pro Arg Cys Pro Glu
35 40 45

Pro Lys Ser Cys Asp Thr Pro Pro Pro Cys Pro Arg Cys Pro
50 55 60

<210> SEQ ID NO 288
<211> LENGTH: 12
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 288

Glu Ser Lys Tyr Gly Pro Pro Cys Pro Ser Cys Pro
1               5                   10
```